United States Patent
Backes et al.

(10) Patent No.: US 11,111,259 B2
(45) Date of Patent: Sep. 7, 2021

(54) ACYLSULFONAMIDE DERIVATIVES FOR TREATING SENESCENCE-ASSOCIATED DISEASES AND DISORDERS

(71) Applicant: Unity Biotechnology, Inc., Brisbane, CA (US)

(72) Inventors: Bradley Backes, San Francisco, CA (US); Thomas W. von Geldern, Richmond, IL (US); Bing Chen, Shanghai (CN)

(73) Assignee: Unity Biotechnology, Inc., Brisbane, CA (US)

(*) Notice: Subject to any disclaimer, the term of this patent is extended or adjusted under 35 U.S.C. 154(b) by 503 days.

(21) Appl. No.: 16/063,135

(22) PCT Filed: Dec. 16, 2016

(86) PCT No.: PCT/CN2016/110309
§ 371 (c)(1),
(2) Date: Jun. 15, 2018

(87) PCT Pub. No.: WO2017/101851
PCT Pub. Date: Jun. 22, 2017

(65) Prior Publication Data
US 2020/0291050 A1  Sep. 17, 2020

Related U.S. Application Data

(60) Provisional application No. 62/269,869, filed on Dec. 18, 2015.

(51) Int. Cl.
| | | |
|---|---|---|
| C07F 9/6558 | (2006.01) | |
| A61P 43/00 | (2006.01) | |
| C07F 9/6509 | (2006.01) | |

(52) U.S. Cl.
CPC .......... C07F 9/65583 (2013.01); A61P 43/00 (2018.01); C07F 9/650952 (2013.01)

(58) Field of Classification Search
CPC .. A61P 11/00; A61P 17/00; A61P 1/00; A61P 27/00; A61P 35/00; A61P 37/00; A61P 3/00; A61P 43/00; C07F 9/650952; C07F 9/65583; C07F 9/657181
See application file for complete search history.

(56) References Cited

U.S. PATENT DOCUMENTS

| | | | |
|---|---|---|---|
| 5,807,846 | A | 9/1998 | Roark et al. |
| 6,720,338 | B2 | 4/2004 | Augeri et al. |
| 7,504,512 | B2 | 3/2009 | Augeri et al. |
| 7,767,684 | B2 | 8/2010 | Bruncko et al. |
| 8,354,404 | B2 | 1/2013 | Bruncko et al. |
| 8,518,913 | B2 | 8/2013 | Yuan et al. |
| 8,563,735 | B2 | 10/2013 | Bruncko et al. |
| 9,018,381 | B2 | 4/2015 | Diebold et al. |
| 9,248,140 | B2 | 2/2016 | Diebold et al. |
| 9,849,128 | B2 | 12/2017 | Laberge et al. |
| 9,901,080 | B2 | 2/2018 | Campisi et al. |
| 9,968,076 | B2 | 5/2018 | Kirkland et al. |
| 10,010,546 | B2 | 7/2018 | Laberge et al. |
| 10,195,213 | B2 | 2/2019 | David |
| 2012/0035134 | A1* | 2/2012 | Diebold ................ A61P 35/02 514/85 |
| 2016/0122758 | A1 | 5/2016 | Krizhanovsky et al. |
| 2017/0056421 | A1 | 5/2017 | Zhou et al. |
| 2017/0216286 | A1 | 8/2017 | Kirkland et al. |
| 2018/0000816 | A1 | 1/2018 | David et al. |

FOREIGN PATENT DOCUMENTS

| | | |
|---|---|---|
| WO | WO 2003000188 | 1/2003 |
| WO | WO 2004058267 | 7/2004 |
| WO | WO 2007040650 | 4/2007 |
| WO | WO 2010065865 | 6/2010 |
| WO | WO 2014113413 | 7/2014 |
| WO | WO 2015116740 | 8/2015 |
| WO | WO 2015153401 | 10/2015 |
| WO | WO 2017009321 | 1/2017 |

(Continued)

OTHER PUBLICATIONS

Bundgaard (Design of Prodrugs, 1985, chapter 1) (Year: 1985).*
Ashkenazi et al., (2017) "From basic apoptosis discoveries to advanced selective BCL-2 family inhibitors," Nature Reviews, 16: 273-284.
Baar et al. (2017) "Targeted Apoptosis of Senescent Cells Restores Tissue Homeostasis in Response to Chemotoxicity and Aging," Cell, 169(1): 132-147.
Bai et al., (2014) "BM-1197: A Novel and Specific Bcl-2/Bcl-xL Inhibitor Inducing Complete and Long-Lasting Tumor Regression In Vivo," PLOS ONE, 9(6): 1-13.

(Continued)

Primary Examiner — Umamaheswari Ramachandran
(74) Attorney, Agent, or Firm — Rudy J. Ng; Bozicevic, Field & Francis LLP

(57) ABSTRACT

Compounds represented by Formula (I) and (II) and salts thereof are described herein. The compounds or salts of Formula (I) and (II) may be used to treat senescence-associated diseases and disorders.

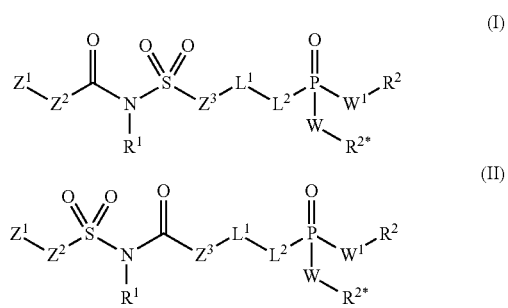

18 Claims, No Drawings

(56) References Cited

FOREIGN PATENT DOCUMENTS

WO    WO 2019001171    1/2019

OTHER PUBLICATIONS

Bajwa et al. (2012) "Inhibitors of the anti-apoptotic Bcl-2 proteins: a patent review," Expert Opin Ther Pat., 22(1): 37-55.
Baker et al. (2016) "Naturally occurring p16lnk4a-positive cells shorten healthy lifespan," Nature, 530 (7589): 184-189.
Blagosklonny et al. (2013) "Selective anti-cancer agents as anti-aging drugs," Cancer Biology & Therapy, 14(12): 1092-1097.
Campisi & Robert (2014) "Cell Senescence, Role in aging and age-related diseases," Interdiscip Top Gerontol, 39: 45-61.
Childs et al., (2017) "Senescent Cells: An Emerging Target for Diseases of Aging," Nat Rev Drug Discov., 16(10): 718-735.
Jeon et al., (2017) "Local Clearance of Senescent Cells Attenuates the Development of Post-Traumatic Osteoarthritis and Creates a Pro-Regenerative Environment," Nature Medicine, 1-9.
Kirkland & Tchkonia (2015) "Clinical Strategies and Animal Models for Developing Senolytic Agents," Exp Gerontol., 68: 19-25.
Wendt (2012) "The Discovery of Navitoclax, a Bcl-2 Family Inhibitor," Top Med Chem, 8: 231-258.
Yap et al., (2016) "Expanding the Cancer Arsenal with Targeted Therapies Disarmament of the Antiapoptotic Bcl-2 Proteins by Small Molecules," J. Med. Chem A-R 18 pages.
Yosef et al., (2015) "Directed Elimination of Senescent Cells by Inhibition of BCL-W and BCL-XL," Nature Communications, 1-11.
Zhou et al. (2012) "Design of Bcl-2 and Bcl-xL Inhibitors with Subnanomolar Binding Affinities Based upon a New Scaffold," J. Med. Chem. 55: 4664-4682.
Zhu et al., (2017) "New agents that Target Senescent Cells: the Flavone, Fisetin, and the BCL-XL Inhibitors, A1331852 and A1155463," Aging, 9: 1-9.
Braun et al., (2012) "Cellular Senescence Limits Regenerative Capacity and Allograft Survival," J. Am Soc Nephrol., 23(9): 1467-1473.
Breuer et al., (1990) "Stereoselectivity in Fragmentation and Rearrangement of α-Hydroxyimino-Phosphinates and -Phosphonates. A Synthetic Approach to Acylphosphon- and phosphor-amidates. Crystal Structures of Methyl (E)-α-Hydroxyimino-Benzylphenylphosphinate and Methyl Benzoylphenylphosphonamidate," J. Chem. Soc. Perkin Trans: 3263-3269.
Lee et al., (1998) "Inhibitors of ACYL-COA:Cholesterol O-Acyltransferase (ACAT) as Hypocholesterolemic Agents: Synthesis and Structure-Activity Relationships of Novel Series of Sulfonamides, Acylphosphonamides and Acylphosphoramidates," Bioorganic & Medicinal Chemistry Letters, 8: 289-294.

\* cited by examiner

ACYLSULFONAMIDE DERIVATIVES FOR TREATING SENESCENCE-ASSOCIATED DISEASES AND DISORDERS

CROSS REFERENCE TO RELATED APPLICATIONS

This application claims the benefit of U.S. Provisional Application No. 62/269,869, filed on Dec. 18, 2015, which is incorporated herein by reference in its entirety for all purposes.

BACKGROUND OF THE INVENTION

Aging is a risk factor for most chronic diseases, disabilities, and declining health. Senescent cells, which are cells in replicative arrest, accumulate as an individual ages and can contribute partially or significantly to cell and tissue deterioration that underlies aging and age related diseases. Cells can also become senescent after exposure to an environmental, chemical, or biological insult or as a result of a disease. Because senescent cells contribute to a variety of pathologies, there is currently a need for agents which selectively kill senescent cells over non-senescent cells.

Therapies that specifically target and kill senescent cells and thereby treat or prevent senescence-associated diseases and disorders are lacking. The present disclosure addresses this deficiency with compounds and compositions for use in killing senescent cells and treating senescence-associated diseases and disorders.

SUMMARY OF THE INVENTION

The present disclosure provides a compound represented by Formula (I) or (II):

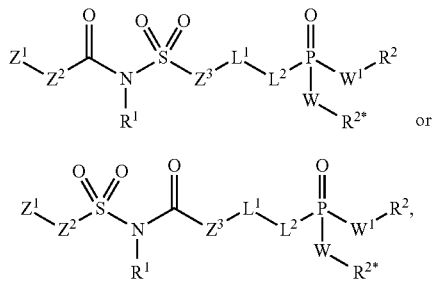

or a salt thereof, wherein:

$Z^1$ is $C_{3-12}$ carbocycle or 3- to 12-membered heterocycle, each of which is substituted with $-(C(R^6)_2)_n-X-(C(R^5)_2)_p-R^3$, $-X-C_{1-6}$alkyl-$R^3$, $-X-C_{2-6}$alkenyl-$R^3$, or $X-C_{2-6}$alkynyl-$R^3$ and $Z^1$ is further optionally substituted with one or more $R^6$;

$Z^2$ and $Z^3$ are each independently selected from $C_{3-12}$ carbocycle or 3- to 12-membered heterocycle, wherein each may be independently optionally substituted with one or more $R^6$;

$L^1$ is selected from a bond; alkylene, heteroalkylene, and Y, each of which is optionally substituted at each occurrence with one or more $R^6$;

$L^2$ is selected from a bond; alkylene, heteroalkylene, Y, Y-alkylene and Y-heteroalkylene each of which is optionally substituted at each occurrence with one or more $R^6$;

W and $W^1$ are independently selected from $-O-$, $-S-$ and $-NR^{10}-$;

X at each occurrence is independently selected from bond, $-O-$, $-S-$, $-N(R^4)-$, $-C(O)-$, $-C(O)O-$, $-OC(O)-$, $-OC(O)O-$, $-C(O)N(R^4)-$, $-C(O)N(R^4)C(O)-$, $-C(O)N(R^4)C(O)N(R^4)-$, $-N(R^4)C(O)-$, $-N(R^4)C(O)N(R^4)-$, $-N(R^4)C(O)O-$, $-OC(O)N(R^4)-$, $-C(NR^4)-$, $-N(R^4)C(NR^4)-$, $-C(NR^4)N(R^4)-$, $-N(R^4)C(NR^4)N(R^4)-$, $-S(O)_2-$, $-OS(O)-$, $-S(O)O-$, $-S(O)-$, $-OS(O)_2-$, $-S(O)_2O-$, $-N(R^4)S(O)_2-$, $-S(O)_2N(R^4)-$, $-N(R^4)S(O)-$, $-S(O)N(R^4)-$, $-N(R^4)S(O)_2N(R^4)-$, and $-N(R^4)S(O)N(R^4)-$;

Y is selected at each occurrence from X, $C_{3-12}$ carbocycle and 3- to 12-membered heterocycle;

$R^1$ is selected from $R^4$;

$R^2$ and $R^{2*}$ are independently selected from $R^7$, or $R^2$ and $R^{2*}$ are taken together with the atoms to which they are attached to form a heterocycle, optionally substituted with one or more $R^6$;

$R^3$ is $C_{3-12}$ carbocycle or 3- to 12-membered heterocycle, each of which is optionally substituted with one or more $R^6$;

$R^4$ is independently selected at each occurrence from hydrogen, $-C(O)R^{10}$, $-C(O)OR^{10}$ and $-C(O)N(R^4)-$; $C_{1-6}$ alkyl, $C_{2-6}$ alkenyl, and $C_{2-6}$ alkynyl, each of which is independently optionally substituted at each occurrence with one or more substituents selected from halogen, $-NO_2$, $-CN$, $-OR^{10}$, $-SR^{10}$, $-N(R^{10})_2$, $-S(=O)R^{10}$, $-S(=O)_2R^{10}$, $-S(=O)_2N(R^{10})_2$, $-NR^{10}S(=O)_2R^{10}$, $-C(O)R^{10}$, $-C(O)OR^{10}$, $-OC(O)R^{10}$, $-OC(O)OR^{10}$, $-OC(O)N(R^{10})_2$, $-NR^{10}C(O)R^{10}$, $-C(O)N(R^{10})_2$, $=O$, $=S$, $=N(R^{10})$, $-P(O)(OR^7)_2$, $-OP(O)(OR^7)_2$, $C_{3-10}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^4$ is independently optionally substituted with one or more substituents selected from halogen, $-NO_2$, $-CN$, $-OR^{10}$, $-SR^{10}$, $-N(R^{10})_2$, $-S(=O)R^{10}$, $-S(=O)_2R^{10}$, $-S(=O)_2N(R^{10})_2$, $-NR^{10}S(=O)_2R^{10}$, $-C(O)R^{10}$, $-C(O)OR^{10}$, $-OC(O)R^{10}$, $-OC(O)OR^{10}$, $-OC(O)N(R^{10})_2$, $-NR^{10}C(O)R^{10}$, $-C(O)N(R^{10})_2$, $=O$, $=S$, $=N(R^{10})$, $-P(O)(OR^7)_2$, $-OP(O)(OR^7)_2$, $C_{1-6}$ alkyl, $C_{1-6}$ haloalkyl, $C_{2-6}$ alkenyl, and $C_{2-6}$ alkynyl;

$R^5$ is independently selected at each occurrence from hydrogen, halogen, $-NO_2$, $-CN$, $-OR^{10}$, $-SR^{10}$, $-N(R^{10})_2$, $-S(=O)R^{10}$, $-S(=O)_2R^{10}$, $-S(=O)_2N(R^{10})_2$, $-NR^{10}S(=O)_2R^{10}$, $-C(O)R^{10}$, $-C(O)OR^{10}$, $-OC(O)R^{10}$, $-OC(O)OR^{10}$, $-OC(O)N(R^{10})_2$, $-NR^{10}C(O)R^{10}$, $-C(O)N(R^{10})_2$, $=O$, $=S$, $=N(R^{10})$, $-P(O)(OR^7)_2$, $-OP(O)(OR^7)_2$; $C_{1-10}$ alkyl, $C_{2-10}$ alkenyl, and $C_{2-10}$ alkynyl, each of which is independently optionally substituted at each occurrence with one or more substituents selected from halogen, $-NO_2$, $-CN$, $-OR^{10}$, $-SR^{10}$, $-N(R^{10})_2$, $-S(=O)R^{10}$, $-S(=O)_2R^{10}$, $-S(=O)_2N(R^{10})_2$, $-NR^{10}S(=O)_2R^{10}$, $-C(O)R^{10}$, $-C(O)OR^{10}$, $-OC(O)R^{10}$, $-OC(O)OR^{10}$, $-OC(O)N(R^{10})_2$, $-NR^{10}C(O)R^{10}$, $-C(O)N(R^{10})_2$, $=O$, $=S$, $=N(R^{10})$, $-P(O)(OR^7)_2$, $-OP(O)(OR^7)_2$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^5$ is independently optionally substituted with one or more substituents selected from halogen, $-NO_2$, $-CN$, $-OR^{10}$, $-SR^{10}$, $-N(R^{10})_2$, $-S(=O)R^{10}$, $-S(=O)_2R^{10}$, $-S(=O)_2N(R^{10})_2$, $-NR^{10}S(=O)_2R^{10}$, $-C(O)R^{10}$, $-C(O)OR^{10}$, $-OC(O)R^{10}$, $-OC(O)OR^{10}$, $-OC(O)N(R^{10})_2$, $-NR^{10}C(O)R^{10}$, $-C(O)N $(R^{10})_2$, =O, =S, =N($R^{10}$), —P(O)(O$R^7$)$_2$, —OP(O)(O$R^7$)$_2$, $C_{1-6}$ alkyl, $C_{1-6}$ haloalkyl, $C_{2-6}$ alkenyl, and $C_{2-6}$ alkynyl;

$R^6$ is independently selected at each occurrence from halogen, —NO$_2$, —CN, —O$R^{10}$, —S$R^{10}$, —N($R^{10}$)$_2$, —S(=O)$R^{10}$, —S(=O)$_2R^{10}$, —S(=O)$_2$N($R^{10}$)$_2$, —N$R^{10}$S(=O)$_2R^{10}$, —C(O)$R^{10}$, —C(O)O$R^{10}$, —OC(O)$R^{10}$, —OC(O)O$R^{10}$, —OC(O)N($R^{10}$)$_2$, —N$R^{10}$C(O)$R^{10}$, —C(O)N($R^{10}$)$_2$, =O, =S, =N($R^{10}$), —P(O)(O$R^7$)$_2$, —OP(O)(O$R^7$)$_2$; $C_{1-10}$ alkyl, $C_{2-10}$ alkenyl, and $C_{2-10}$ alkynyl, each of which is independently optionally substituted at each occurrence with one or more substituents selected from halogen, —NO$_2$, —CN, —O$R^{10}$, —S$R^{10}$, —N($R^{10}$)$_2$, —S(=O)$R^{10}$, —S(=O)$_2R^{10}$, —S(=O)$_2$N($R^{10}$)$_2$, —N$R^{10}$S(=O)$_2R^{10}$, —C(O)$R^{10}$, —C(O)O$R^{10}$, —OC(O)$R^{10}$, —OC(O)O$R^{10}$, —OC(O)N($R^{10}$)$_2$, —N$R^{10}$C(O)$R^{10}$, —C(O)N($R^{10}$)$_2$, =O, =S, =N($R^{10}$), —P(O)(O$R^{10}$)$_2$, —OP(O)(O$R^{10}$)$_2$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^6$ is independently optionally substituted with one or more substituents selected from halogen, —NO$_2$, —CN, —O$R^{10}$, —S$R^{10}$, —N($R^{10}$)$_2$, —S(=O)$R^{10}$, —S(=O)$_2R^{10}$, —S(=O)$_2$N($R^{10}$)$_2$, —N$R^{10}$S(=O)$_2R^{10}$, —C(O)$R^{10}$, —C(O)O$R^{10}$, —OC(O)$R^{10}$, —OC(O)O$R^{10}$, —OC(O)N($R^{10}$)$_2$, —N$R^{10}$C(O)$R^{10}$, —C(O)N($R^{10}$)$_2$, =O, =S, =N($R^{10}$), —P(O)(O$R^7$)$_2$, —OP(O)(O$R^7$)$_2$, $C_{1-6}$ alkyl, $C_{1-6}$ haloalkyl, $C_{2-6}$ alkenyl, and $C_{2-6}$ alkynyl;

$R^7$ is independently selected at each occurrence from hydrogen, —C(O)$R^{10}$, —C(O)O$R^{10}$ and —C(O)N($R^4$)—; $C_{1-6}$ alkyl, $C_{2-6}$ alkenyl, $C_{2-6}$ alkynyl, and $C_{3-12}$ carbocycle, each of which is independently optionally substituted at each occurrence with one or more substituents selected from halogen, —NO$_2$, —CN, —O$R^{10}$, —S$R^{10}$, —S—S—$R^{10}$, —N($R^{10}$)$_2$, —S(=O)$R^{10}$, —S(=O)$_2R^{10}$, —S(=O)$_2$N($R^{10}$)$_2$, —N$R^{10}$S(=O)$_2R^{10}$, —S—C(O)$R^{10}$, —C(O)$R^{10}$, —C(O)O$R^{10}$, —OC(O)$R^{10}$, —OC(O)O$R^{10}$, —OC(O)N($R^{10}$)$_2$, —N$R^{10}$C(O)$R^{10}$, —C(O)N($R^{10}$)$_2$, =O, =S, =N($R^{10}$), —P(O)(O$R^{10}$)$_2$, —OP(O)(O$R^{10}$)$_2$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^7$ is independently optionally substituted with one or more substituents selected from halogen, —NO$_2$, —CN, —O$R^{10}$, —S$R^{10}$, —N($R^{10}$)$_2$, —S(=O)$R^{10}$, —S(=O)$_2R^{10}$, —S(=O)$_2$N($R^{10}$)$_2$, —N$R^{10}$S(=O)$_2R^{10}$, —C(O)$R^{10}$, —C(O)O$R^{10}$, —OC(O)$R^{10}$, —OC(O)O$R^{10}$, —OC(O)N($R^{10}$)$_2$, —N$R^{10}$C(O)$R^{10}$, —C(O)N($R^{10}$)$_2$, =O, =S, =N($R^{10}$), —P(O)(O$R^{10}$)$_2$, —OP(O)(O$R^{10}$)$_2$, $C_{1-6}$ alkyl, $C_{1-6}$ haloalkyl, $C_{2-6}$ alkenyl, and $C_{2-6}$ alkynyl;

$R^{10}$ at each occurrence is independently selected from hydrogen; and $C_{1-20}$ alkyl, $C_{2-20}$ alkenyl, $C_{2-20}$ alkynyl, $C_{3-12}$ carbocycle and 3- to 12-membered heterocycle, each of which may be optionally substituted by halogen, —CN, —NO$_2$, —OH and —OCH$_3$;

n is 0, 1, 2, 3, or 4; and p is 0, 1, 2, 3, or 4, wherein for a compound or salt of Formula (I), when $L^2$ is Y-heteroalkylene and Y is piperidine, one of $R^2$ and $R^{2^*}$ is other than hydrogen.

In certain aspects, the present disclosure provides a compound represented by Formula (I):

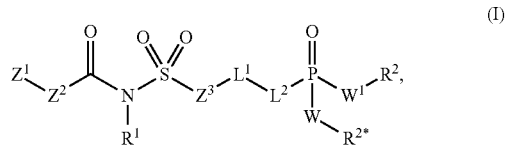

or a salt thereof.

In certain aspects, the present disclosure provides a compound represented by Formula (II):

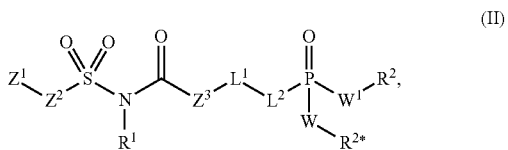

or a salt thereof.

For a compound of Formula (I) or (II), at least one of $R^2$ and $R^{2^*}$ may be selected from $C_{1-6}$ alkyl, $C_{2-6}$ alkenyl, and $C_{2-6}$ alkynyl, each of which may be independently optionally substituted at each occurrence with one or more substituents selected from halogen, —NO$_2$, —CN, —O$R^{10}$, —S$R^{10}$, —S—S—$R^{10}$, —N($R^{10}$)$_2$, —S(=O)$R^{10}$, —S(=O)$_2R^{10}$, —S(=O)$_2$N($R^{10}$)$_2$, —N$R^{10}$S(=O)$_2R^{10}$, —S—C(O)$R^{10}$, —C(O)$R^{10}$, —C(O)O$R^{10}$, —OC(O)$R^{10}$, —OC(O)O$R^{10}$, —OC(O)N($R^{10}$)$_2$, —N$R^{10}$C(O)$R^{10}$, —C(O)N($R^{10}$)$_2$, =O, =S, =N($R^{10}$), —P(O)(O$R^{10}$)$_2$, —OP(O)(O$R^{10}$)$_2$; and $C_{3-12}$ carbocycle and 3- to 12-membered heterocycle, each of which may be independently optionally substituted at each occurrence with one or more substituents selected from halogen, $C_{1-6}$ alkyl, —O$R^{10}$, —OC(O)$R^{10}$, —C(O)O$R^{10}$, and —C(O)$R^{10}$. In certain embodiments, $R^2$ and $R^{2^*}$ are independently selected from $C_{1-6}$ alkyl, $C_{2-6}$ alkenyl, and $C_{2-6}$ alkynyl, each of which is independently optionally substituted at each occurrence with one or more substituents selected from halogen, —NO$_2$, —CN, —O$R^{10}$, —S$R^{10}$, —S—S—$R^{10}$, —N($R^{10}$)$_2$, —S(=O)$R^{10}$, —S(=O)$_2R^{10}$, —S(=O)$_2$N($R^{10}$)$_2$, —N$R^{10}$S(=O)$_2R^{10}$, —S—C(O)$R^{10}$, —C(O)$R^{10}$, —C(O)O$R^{10}$, —OC(O)$R^{10}$, —OC(O)O$R^{10}$, —OC(O)N($R^{10}$)$_2$, —N$R^{10}$C(O)$R^{10}$, —C(O)N($R^{10}$)$_2$, =O, =S, =N($R^{10}$), —P(O)(O$R^{10}$)$_2$, —OP(O)(O$R^{10}$)$_2$; and $C_{3-12}$ carbocycle and 3- to 12-membered heterocycle, each of which is independently optionally substituted at each occurrence with one or more substituents selected from halogen, $C_{1-6}$ alkyl, —O$R^{10}$, —OC(O)$R^{10}$, —C(O)O$R^{10}$, and —C(O)$R^{10}$.

For a compound of Formula (I) or (II), $R^2$ and $R^{2^*}$ may independently be selected from $C_{1-6}$ alkyl substituted with one or more substituents selected from halogen, —OC(O)$R^{10}$, —OC(O)O$R^{10}$, —S—S—$R^{10}$, —S—C(O)$R^{10}$, —O$R^{10}$, and —P(O)(O$R^{10}$)$_2$. In certain embodiments, $R^2$ and $R^{2^*}$ are taken together with the atoms to which they are attached to form a heterocycle, optionally substituted with one or more $R^6$.

For a compound of Formula (I) or (II), W and $W^1$ may each be —O—. In certain embodiments, one of W and $W^1$ is —O— and the other one of W and $W^1$ is —N$R^{10}$—.

For a compound of Formula (I) or (II), $L^1$ may be heteroalkylene optionally substituted with one or more $R^6$. In certain embodiments, $L^1$ is selected from —(CH$_2$)$_s$—$X^{10}$—(CH$_2$)$_r$—, —(CH$_2$)$_r$—$X^{10}$—(CH$_2$)$_r$—$X^{10}$—(CH$_2$)$_r$—, and —(CH$_2$)$_r$—$X^{10}$—(CH$_2$)$_r$—$X^{10}$ —(CH$_2$)$_r$—X$^{10}$—(CH$_2$)$_r$—, wherein s is selected from 0 to 3, each r is independently selected from 1 to 4, each X$^{10}$ is selected from —O—, —S—, or —N(R$^4$)—, and L$^1$ may be optionally substituted with one or more R$^6$. In certain embodiments, L$^1$ is selected from —(CH$_2$)$_s$—X$^{10}$—(CH$_2$)$_r$—, wherein s is 0, r is selected from 1 to 3, X$^{10}$ is —N(R$^4$)—, and L$^1$ is optionally substituted with one or more R$^6$.

For a compound of Formula (I) or (II), L$^2$ may be a bond. In certain embodiments, L$^2$ selected from —Y-alkylene— optionally substituted with one or more R$^6$. In certain embodiments, Y of L$^2$ is selected from 3- to 12-membered heterocycle. In certain embodiments, Y of L$^2$ is selected from 5- and 6-membered heterocycles.

For a compound of Formula (I) or (II), Z$^3$ is 3- to 12-membered heterocycle, C$_3$-C$_{12}$ cycloalkane or C$_3$-C$_{12}$cycloalkene, any of which is optionally substituted with one or more R$^6$. In certain embodiments, Z$^3$ is selected from a heteroaryl group optionally substituted with one or more R$^6$. In certain embodiments, Z$^3$ is selected from:

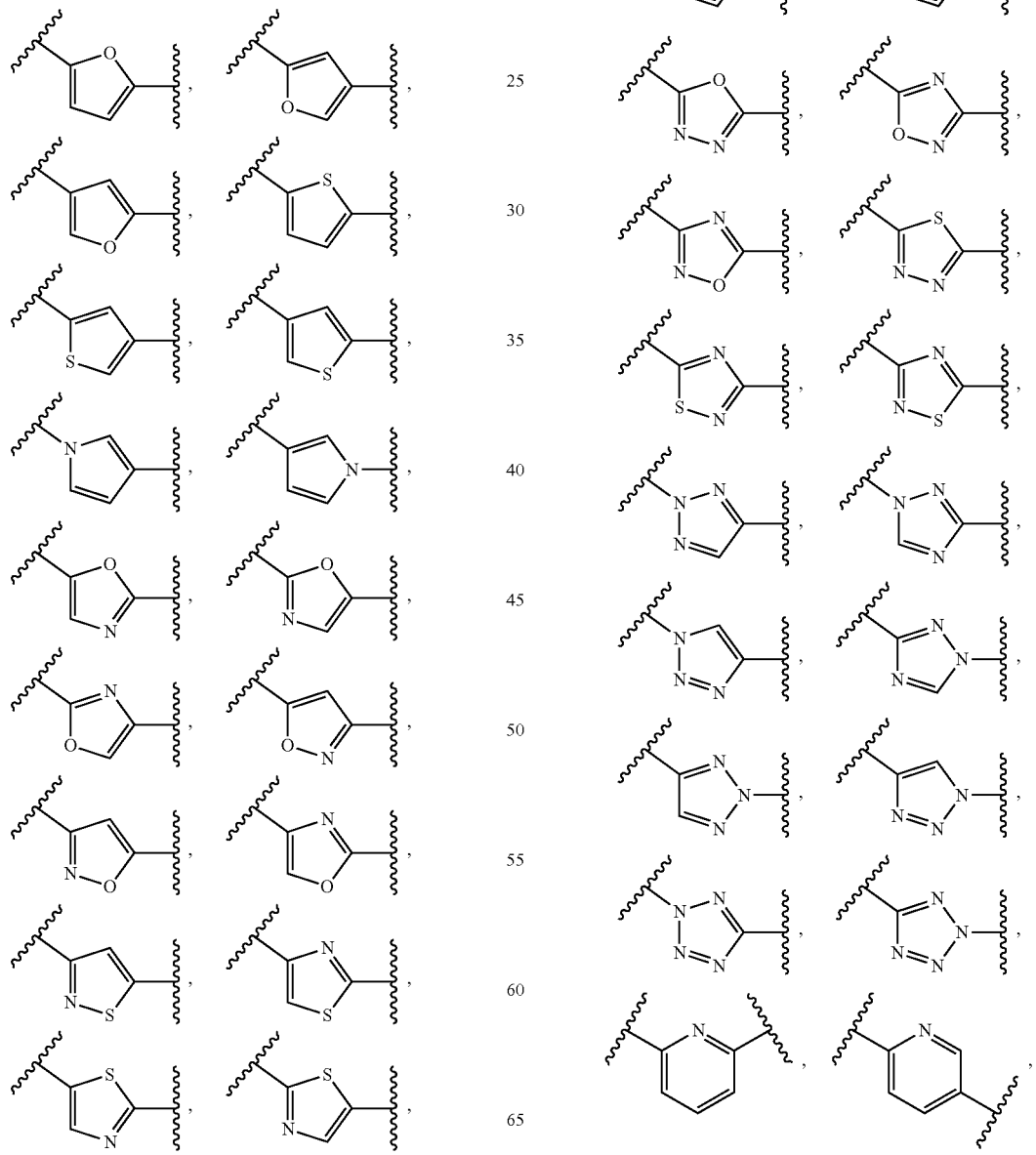

any one of which is optionally substituted with one or more R⁶. In certain embodiments, Z³ is selected from:

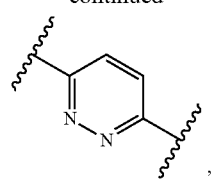

any one of which is optionally substituted with one or more $R^6$. In certain embodiments, $Z^3$ is phenyl optionally substituted with one or more $R^6$. In certain embodiments, $Z^3$ is

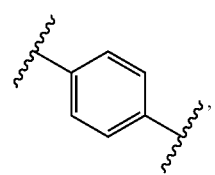 [SMILES: *c1ccc(*)cc1]

optionally substituted by one or more $R^6$. In certain embodiments, $Z^3$ is

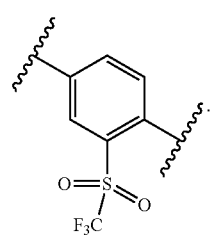 [SMILES: *c1ccc(*)c(S(=O)(=O)C(F)(F)F)c1]

For a compound of Formula (I) or (II), $Z^2$ may be 3- to 12-membered heterocycle, $C_{3-12}$ cycloalkane or $C_{3-12}$ cycloalkene, any one of which may optionally be substituted with one or more $R^6$. In certain embodiments, $Z^2$ is selected from a heterocycloalkyl and heterocycloalkenyl group, either of which is optionally substituted with one or more $R^6$. In certain embodiments, $Z^2$ is selected from azetidine, oxetane, thietane, pyrrolidine, pyrroline, tetrahydrofuran, dihydrofuran, thiolane, dihydrothiophene, imidazolidine, imidazoline, pyrazolidine, oxazolidine, oxazoline, isoxazolidine, isoxazoline, thiazolidine, thiazoline, isothiazolidine, dioxolane, piperazine, piperidine, morpholine, thiomorpholine, dioxane, dithiane, and dithiolane, any one of which is optionally substituted with one or more $R^6$. In certain embodiments, $Z^2$ is

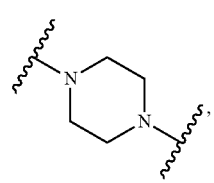 [SMILES: *N1CCN(*)CC1]

optionally substituted with one or more $R^6$. In certain embodiments, $Z^2$ is

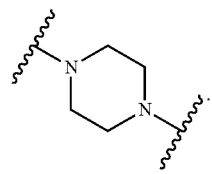

In certain embodiments, $Z^2$ is phenyl optionally substituted with one or more $R^6$. In certain embodiments, $Z^2$ is

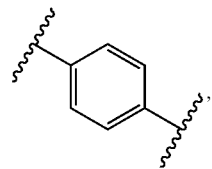 [SMILES: *c1ccc(*)cc1]

optionally substituted with one or more $R^6$. In certain embodiments, $Z^2$ is:

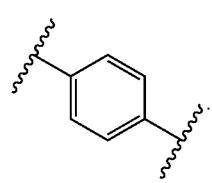

For a compound of Formula (I) or (II), $R^1$ may be selected from hydrogen; and $C_{1-6}$ alkyl, $C_{2-6}$ alkenyl, and $C_{2-6}$ alkynyl, each of which may be independently optionally substituted at each occurrence with one or more substituents selected from halogen, —$NO_2$, —CN, —$OR^{10}$, —$SR^{10}$, and —$N(R^{10})_2$. In certain embodiments, $R^1$ is hydrogen.

For a compound of Formula (I) or (II), $Z^1$ may be selected from 3- to 12-membered heterocycle. In certain embodiments, $Z^1$ is a heterocycloalkyl or heterocycloalkenyl group. In certain embodiments, $Z^1$ is selected from azetidine, oxetane, thietane, pyrrolidine, pyrroline, tetrahydrofuran, dihydrofuran, thiolane, dihydrothiophene, imidazolidine, imidazoline, pyrazolidine, oxazolidine, oxazoline, isoxazolidine, isoxazoline, thiazolidine, thiazoline, isothiazolidine, dioxolane, piperazine, piperidine, morpholine, thiomorpholine, dioxane, dithiane, and dithiolane, any one of which is optionally substituted with one or more $R^6$. In certain embodiments, $Z^1$ is selected from azetidine, oxetane, thietane, pyrrolidine, pyrroline, tetrahydrofuran, dihydrofuran, thiolane, dihydrothiophene, imidazolidine, imidazoline, pyrazolidine, oxazolidine, oxazoline, isoxazolidine, isoxazoline, thiazolidine, thiazoline, isothiazolidine, dioxolane, piperazine, morpholine, thiomorpholine, dioxane, dithiane, and dithiolane, any one of which is optionally substituted with one or more $R^6$. In certain embodiments, $Z^1$ is

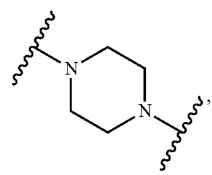 [SMILES: *N1CCN(*)CC1]

optionally substituted with one or more $R^6$. In certain embodiments, $Z^1$ is

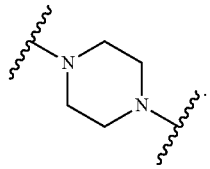 [SMILES: *N1CCN(*)CC1]

In certain embodiments, $Z^1$ is phenyl optionally substituted with one or more $R^6$. In certain embodiments, $Z^1$ is

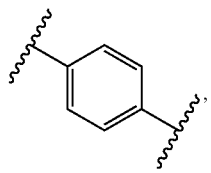 [SMILES: *c1ccc(*)cc1]

optionally substituted with one or more $R^6$. In certain embodiments, $Z^1$ is:

For a compound of Formula (I) or (II), $R^3$ may be $C_{3-10}$ carbocycle optionally substituted with one or more $R^6$. In certain embodiments. $R^3$ is selected from:

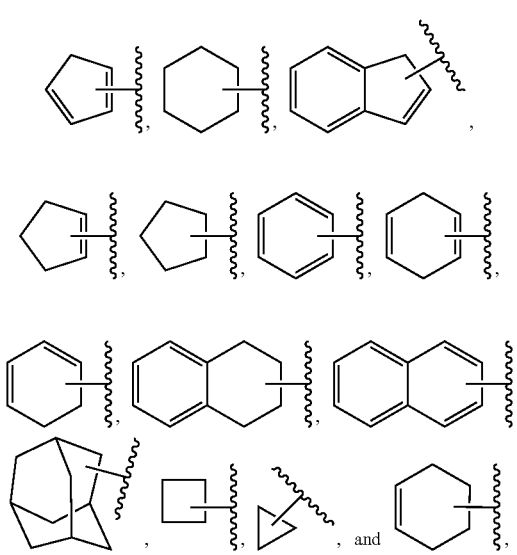

any one of which is optionally substituted with one or more $R^6$. In certain embodiments, $R^3$ is selected from:

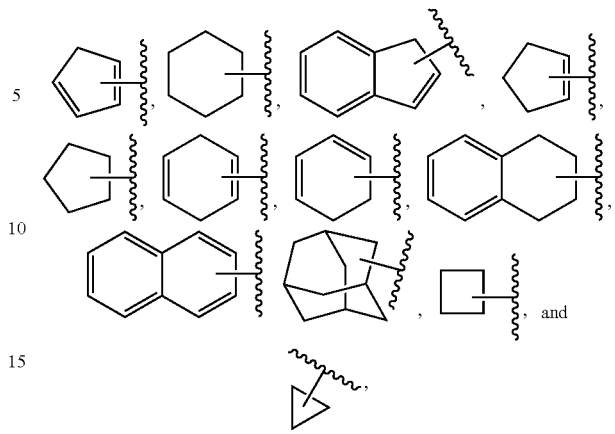

any one of which is optionally substituted with one or more $R^6$. In certain embodiments, $R^3$ is selected from heterocycloalkyl and heterocycloalkenyl, either of which is optionally substituted with one or more $R^6$. In certain embodiments, $R^3$ is selected from azetidine, oxetane, thietane, pyrrolidine, pyrroline, tetrahydrofuran, dihydrofuran, thiolane, dihydrothiophene, imidazolidine, imidazoline, pyrazolidine, oxazolidine, oxazoline, isoxazolidine, isoxazoline, thiazolidine, thiazoline, isothiazolidine, dioxolane, piperazine, piperidine, morpholine, thiomorpholine, dioxane, dithiane, and dithiolane, any one of which is optionally substituted with one or more $R^6$. In certain embodiments, $R^3$ is substituted with $C_{3-12}$ carbocycle or 3- to 12-membered heterocycle, wherein the $C_{3-12}$ carbocycle and 3- to 12-membered heterocycle are optionally substituted with one or more substituents selected from halogen, —$NO_2$, —CN, —$OR^{10}$, —$SR^{10}$, —$N(R^{10})_2$, —$S(=O)R^{10}$, —$S(=O)_2R^{10}$, —$S(=O)_2N(R^{10})_2$, —$NR^{10}S(=O)_2R^{10}$, —$C(O)R^{10}$, —$C(O)OR^{10}$, —$OC(O)R^{10}$, —$OC(O)OR^{10}$, —$OC(O)N(R^{10})_2$, —$NR^{10}C(O)R^{10}$, —$C(O)N(R^{10})_2$, =O, =S, =$N(R^{10})$, —$P(O)(OR^7)_2$, —$OP(O)(OR^7)_2$, $C_{1-6}$ alkyl, $C_{1-6}$ haloalkyl, $C_{2-6}$ alkenyl, and $C_{2-6}$ alkynyl and $R^3$ is further optionally substituted with one or more $R^6$. In certain embodiments, $R^3$ is substituted with phenyl optionally substituted with one or more substituents selected from halogen, —$NO_2$, —CN, —$OR^{10}$, —$SR^{10}$, —$N(R^{10})_2$, —$S(=O)R^{10}$, —$S(=O)_2R^{10}$, —$S(=O)_2N(R^{10})_2$, —$NR^{10}S(=O)_2R^{10}$, —$C(O)R^{10}$, —$C(O)OR^{10}$, —$OC(O)R^{10}$, —$OC(O)OR^{10}$, —$OC(O)N(R^{10})_2$, —$NR^{10}C(O)R^{10}$, —$C(O)N(R^{10})_2$, =O, =S, =$N(R^{10})$, —$P(O)(OR^7)_2$, —$OP(O)(OR^7)_2$, $C_{1-6}$ alkyl, $C_{1-6}$ haloalkyl, $C_{2-6}$ alkenyl, and $C_{2-6}$ alkynyl and $R^3$ is further optionally substituted with one or more $R^6$. In certain embodiments, $R^3$ is selected from

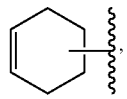

substituted with one or more $R^6$. In certain embodiments, $R^3$ is

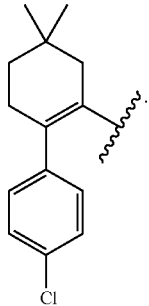 [SMILES: *C1=C(c2ccc(Cl)cc2)CCC(C)(C)C1]

In certain embodiments, $R^3$ is selected from

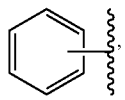

substituted with one or more $R^6$. In certain embodiments, $R^3$ is

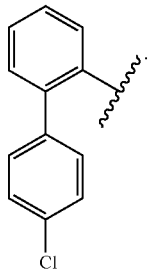 [SMILES: *c1ccccc1-c1ccc(Cl)cc1]

In certain aspects, the disclosure provides a pharmaceutical composition comprising a compound of Formula (I) or (II), or a salt thereof. In certain embodiments, a pharmaceutical composition further comprises one or more carriers or excipients. In certain aspects, the disclosure provides a pharmaceutical composition, comprising a compound or salt described herein and a pharmaceutically compatible excipient.

In certain aspects, the present disclosure provides a method of killing senescent cells, comprising contacting the cells with a compound or salt of Formula (I) or (II). In certain embodiments, the disclosure provides a method for treating a senescence-associated disease or disorder, comprising administering to a subject in need thereof a compound of Formula (I) or (II), or a salt thereof. In certain embodiments, the disclosure provides a compound or salt described herein for use in medicine. In certain embodiments, the disclosure provides a compound or salt of Formula (I) or (II) for use in treating a senescence-associated condition. In certain embodiments, the disclosure provides the use of a compound or salt described herein in the preparation of a medicament.

DETAILED DESCRIPTION OF THE INVENTION

The present disclosure provides compounds for killing senescent cells and treating senescence-associated diseases and disorders. In one aspect, the compounds of the disclosure have moieties that facilitate transport across cell membranes. In certain embodiments, compounds of the disclosure include a mono- or di-ester of a phosphonate, phosphinate or phosphate. The mono- or di-esters, described herein, may include one or more lipophilic moieties such that the compound is able to cross a cell membrane and localize inside the cell.

In one aspect, the esters of the disclosure are hydrolyzed or enzymatically cleaved within a cell to reveal an acidic moiety, e.g., a phosphonic acid moiety. The acidic moiety that is revealed once in the cell may provide advantageous properties such as the ability to interact with a basic residue in an active site or an aqueous pocket adjacent to the active site. The unveiling of an acidic moiety may also increase the cell residence of the compound by decreasing the lipophilicity and cell membrane permeability.

A. DEFINITIONS

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Alkyl" refers to a straight or branched hydrocarbon chain radical consisting solely of carbon and hydrogen atoms, containing no unsaturation, and preferably having from one to fifteen carbon atoms (i.e., $C_1$-$C_{15}$ alkyl). In certain embodiments, an alkyl comprises one to thirteen carbon atoms (i.e., $C_1$-$C_{13}$ alkyl). In certain embodiments, an alkyl comprises one to eight carbon atoms (i.e., $C_1$-$C_8$ alkyl). In other embodiments, an alkyl comprises one to five carbon atoms (i.e., $C_1$-$C_5$ alkyl). In other embodiments, an alkyl comprises one to four carbon atoms (i.e., $C_1$-$C_4$ alkyl). In other embodiments, an alkyl comprises one to three carbon atoms (i.e., $C_1$-$C_3$ alkyl). In other embodiments, an alkyl comprises one to two carbon atoms (i.e., $C_1$-$C_2$ alkyl). In other embodiments, an alkyl comprises one carbon atom (i.e., $C_1$ alkyl). In other embodiments, an alkyl comprises five to fifteen carbon atoms (i.e., $C_5$-$C_{15}$ alkyl). In other embodiments, an alkyl comprises five to eight carbon atoms (i.e., $C_5$-$C_8$ alkyl). In other embodiments, an alkyl comprises two to five carbon atoms (i.e., $C_2$-$C_5$ alkyl). In other embodiments, an alkyl comprises three to five carbon atoms (i.e., $C_3$-$C_5$ alkyl). In certain embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more substituents such as those substituents described herein.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and preferably having from two to twelve carbon atoms (i.e., $C_2$-$C_{12}$ alkenyl). In certain embodiments, an alkenyl comprises two to eight carbon atoms (i.e., $C_2$-$C_8$ alkenyl). In certain embodiments, an alkenyl comprises two to six carbon atoms (i.e., $C_2$-$C_6$ alkenyl). In other embodiments, an alkenyl comprises two to four carbon atoms (i.e., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents such as those substituents described herein.

"Alkynyl" refers to a straight or branched hydrocarbon chain radical group consisting solely of carbon and hydrogen atoms, containing at least one carbon-carbon triple bond, and preferably having from two to twelve carbon atoms (i.e., $C_2$-$C_{12}$ alkynyl). In certain embodiments, an alkynyl comprises two to eight carbon atoms (i.e., $C_2$-$C_8$ alkynyl). In other embodiments, an alkynyl comprises two to six carbon atoms (i.e., $C_2$-$C_6$ alkynyl). In other embodiments, an alkynyl comprises two to four carbon atoms (i.e., $C_2$-$C_4$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents such as those substituents described herein.

"Alkylene" or "alkylene chain" refers to a straight or branched divalent hydrocarbon chain linking the rest of the molecule to a radical group, consisting solely of carbon and hydrogen, containing no unsaturation, and preferably having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group may be through any two carbons within the chain. In certain embodiments, an alkylene comprises one to ten carbon atoms (i.e., $C_1$-$C_{10}$ alkylene). In certain embodiments, an alkylene comprises one to eight carbon atoms (i.e., $C_1$-$C_8$ alkylene). In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). In other embodiments, an alkylene comprises five to eight carbon atoms (i.e., $C_5$-$C_8$ alkylene). In other embodiments, an alkylene comprises two to five carbon atoms (i.e., $C_2$-$C_5$ alkylene). In other embodiments, an alkylene comprises three to five carbon atoms (i.e., $C_3$-$C_5$ alkylene). Unless stated otherwise specifically in the specification, an alkylene chain is optionally substituted by one or more substituents such as those substituents described herein.

"Alkenylene" or "alkenylene chain" refers to a straight or branched divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group may be through any two carbons within the chain. In certain embodiments, an alkenylene comprises two to ten carbon atoms (i.e., $C_2$-$C_{10}$ alkenylene). In certain embodiments, an alkenylene comprises two to eight carbon atoms (i.e., $C_2$-$C_8$ alkenylene). In other embodiments, an alkenylene comprises two to five carbon atoms (i.e., $C_2$-$C_5$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atom (i.e., $C_2$ alkenylene). In other embodiments, an alkenylene comprises five to eight carbon atoms (i.e., $C_5$-$C_8$ alkenylene). In other embodiments, an alkenylene comprises three to five carbon atoms (i.e., $C_3$-$C_5$ alkenylene). Unless stated otherwise specifically in the specification, an alkenylene chain is optionally substituted by one or more substituents such as those substituents described herein.

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group may be through any two carbons within the chain. In certain embodiments, an alkynylene comprises two to ten carbon atoms (i.e., $C_2$-$C_{10}$ alkynylene). In certain embodiments, an alkynylene comprises two to eight carbon atoms (i.e., $C_2$-$C_8$ alkynylene). In other embodiments, an alkynylene comprises two to five carbon atoms (i.e., $C_2$-$C_5$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atom (i.e., $C_2$ alkynylene). In other embodiments, an alkynylene comprises five to eight carbon atoms (i.e., $C_5$-$C_8$ alkynylene). In other embodiments, an alkynylene comprises three to five carbon atoms (i.e., $C_3$-$C_5$ alkynylene). Unless stated otherwise specifically in the specification, an alkynylene chain is optionally substituted by one or more substituents such as those substituents described herein.

"Aryl" refers to a radical derived from an aromatic monocyclic or aromatic multicyclic hydrocarbon ring system by removing a hydrogen atom from a ring carbon atom. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents such as those substituents described herein.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as described above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as described above for an alkynylene chain.

The term "$C_{x-y}$" or "$C_x-C_y$" when used in conjunction with a chemical moiety, such as alkyl, alkenyl, or alkynyl is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain. The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond respectively.

"Carbocycle" refers to a saturated, unsaturated or aromatic ring in which each atom of the ring is a carbon atom. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those substituents described herein.

"Cycloalkyl" refers to a stable fully saturated non-aromatic monocyclic or polycyclic hydrocarbon radical consisting solely of carbon and hydrogen atoms, which includes fused or bridged ring systems, and preferably having from three to twelve carbon atoms. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "cycloalkyl" is meant to include cycloalkyl radicals that are optionally substituted by one or more substituents such as those substituents described herein.

"Cycloalkenyl" refers to a stable unsaturated non-aromatic monocyclic or polycyclic hydrocarbon radical consisting solely of carbon and hydrogen atoms, which includes fused or bridged ring systems, preferably having from three to twelve carbon atoms and comprising at least one double bond. In certain embodiments, a cycloalkenyl comprises three to ten carbon atoms. In other embodiments, a cycloalkenyl comprises five to seven carbon atoms. The cycloalkenyl may be attached to the rest of the molecule by a single bond. Examples of monocyclic cycloalkenyls include, e.g., cyclopentenyl, cyclohexenyl, cycloheptenyl, and cyclooctenyl. Unless otherwise stated specifically in the specification, the term "cycloalkenyl" is meant to include cycloalkenyl radicals that are optionally substituted by one or more substituents such as those substituents described herein.

"Cycloalkylalkyl" refers to a radical of the formula —$R^c$-cycloalkyl where $R^c$ is an alkylene chain as described above. The alkylene chain and the cycloalkyl radical is optionally substituted as described herein.

"Heteroalkylene" or "heteroalkylene chain" refers to a straight or branched divalent hydrocarbon chain including at least one heteroatom in the chain linking the rest of the molecule to a radical group, containing no unsaturation, and preferably having from one to twelve carbon atoms and from one to 6 heteroatoms, e.g., —O—, —NH—, —S—. The heteroalkylene chain is attached to the rest of the molecule through a single bond and to the radical group through a single bond. The points of attachment of the heteroalkylene chain to the rest of the molecule and to the radical group may be through any two carbon atoms, heteroatoms or combinations thereof, within the chain. In certain embodiments, a heteroalkylene comprises one to ten carbon atoms and from one to four heteroatoms. In certain embodiments, a heteroalkylene comprises one to eight carbon atoms and from one to four heteroatoms. In other embodiments, a heteroalkylene comprises one to five carbon atoms and from one to three heteroatoms. In other embodiments, a heteroalkylene comprises one to four carbon atoms and from one to three heteroatoms. In other embodiments, a heteroalkylene comprises one to three carbon atoms and from one to two heteroatoms. In other embodiments, a heteroalkylene comprises one to two carbon atoms and from one to two heteroatoms. In other embodiments, a heteroalkylene comprises one carbon atom and from one to two heteroatoms. In other embodiments, a heteroalkylene comprises five to eight carbon atoms and from one to four heteroatoms. In other embodiments, a heteroalkylene comprises two to five carbon atoms and from one to three heteroatoms. In other embodiments, a heteroalkylene comprises three to five carbon atoms and from one to three heteroatoms. Unless stated otherwise specifically in the specification, a heteroalkylene chain is optionally substituted by one or more substituents such as those substituents described herein.

"Heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. In some embodiments, the heterocycle is a heteroaryl. In some embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene.

"Heterocycloalkyl" refers to a stable 3- to 12-membered non-aromatic ring radical that comprises two to twelve carbon atoms and at least one heteroatom wherein each heteroatom may be selected from N, O, Si, P, B, and S atoms. The heterocycloalkyl may be selected from monocyclic or bicyclic, and fused or bridged ring systems. The heteroatoms in the heterocycloalkyl radical are optionally oxidized. One or more nitrogen atoms, if present, are optionally quaternized. The heterocycloalkyl radical is partially or fully saturated. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents such as those substituents described herein.

"Heterocycloalkenyl" refers to a stable 3- to 12-membered non-aromatic ring radical that comprises two to twelve carbon atoms and at least one heteroatom, and at least one double bond, wherein each heteroatom may be selected from N, O, Si, P, B, and S atoms. The heterocycloalkenyl may be selected from monocyclic or bicyclic, and fused or bridged ring systems. The heteroatoms in the heterocycloalkyl radical are optionally oxidized. One or more nitrogen atoms, if present, are optionally quaternized. The heterocycloalkenyl is attached to the rest of the molecule through any atom of the heterocycloalkenyl, valence permitting, such as any carbon or nitrogen atoms of the heterocycloalkyl. Unless stated otherwise specifically in the specification, the term "heterocycloalkenyl" is meant to include heterocycloalkenyl radicals as defined above that are optionally substituted by one or more substituents such as those substituents described herein.

"Heterocycloalkylalkyl" refers to a radical of the formula —$R^c$-heterocycloalkyl where $R^c$ is an alkylene chain as defined above. If the heterocycloalkyl is a nitrogen-containing heterocycloalkyl, the heterocycloalkyl is optionally attached to the alkylene chain at the nitrogen atom. The alkylene chain of the heterocycloalkylalkyl radical is optionally substituted as described above for an alkylene chain. The heterocycloalkyl part of the heterocycloalkylalkyl radical is optionally substituted as described herein.

"Heteroaryl" refers to a 5- to 12-membered aromatic ring that comprises at least one heteroatom wherein each heteroatom may be independently selected from N, O, and S. As used herein, the heteroaryl ring may be selected from monocyclic or bicyclic and fused or bridged ring systems rings wherein at least one of the rings in the ring system is aromatic, i.e., it contains a cyclic, delocalized (4n+2) π-electron system in accordance with the Hückel theory. The heteroatom(s) in the heteroaryl may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryls as defined above which are optionally substituted by one or more substituents such as those substituents described herein.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkylene chain at the nitrogen atom. The alkylene chain of the heteroarylalkyl radical is optionally substituted as described above for an alkylene chain. The heteroaryl part of the heteroarylalkyl radical is optionally substituted as described herein.

Compounds of the present disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present invention, whether radioactive or not, are encompassed within the scope of the present invention. For example, hydrogen has three naturally occurring isotopes, denoted $^1$H (protium), $^2$H (deuterium), and $^3$H (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety. In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^{b-S(O)}{}_tOR^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, hydroxy, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

It will be understood by those skilled in the art that substituents can themselves be substituted, if appropriate. Unless specifically stated as "unsubstituted," references to chemical moieties herein are understood to include substituted variants. For example, reference to a "heteroaryl" group or moiety implicitly includes both substituted and unsubstituted variants.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intraderrnal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compostions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

A "senescent cell" is a cell that has a senescence-associated secretory phenotype (SASP). It can be identified by determining that the cell produces SASP related factors such as mmp-3 and IL-6, and/or determining endogenous senescence markers such as (p21, p16INK4a, and p53). Methods for producing and identifying senescent cells is provided in the examples below. A "senescent-associated" disease or condition is a clinical condition in which the presence and action of senescent cells contributes substantially to the pathophysiology of the condition.

The terms "treat," "treating" or "treatment," as used herein, may include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

B. COMPOUNDS OF THE DISCLOSURE

In some aspects, the present disclosure provides a phosphonate, phosphinate, or phosphate derivative of a compound or salt described in U.S. Pat. Nos. 8,563,735; 8,586,754; 9,018,381; 7,358,251; or 7,449,485, each of which is hereby incorporated by reference. In certain embodiments, the compound or salt described in U.S. Pat. Nos. 8,563,735; 8,586,754; 9,018,381; 7,358,251; or 7,449,485, comprises at least one phosphonate, phosphinate or phosphate moiety, in monoester, diester or diacid form. For example, a compound or salt described in U.S. Pat. Nos. 8,563,735; 8,586,754; 9,018,381; 7,358,251; or 7,449,485, may be substituted with a phosphonate monoester, such as —P(O)(OMe)(OH), a phosphonate diester, such as —P(O)(OMe)$_2$, or a phosphonic acid, such as —P(O)(OH)$_2$, or a combination of two or more thereof. In certain embodiments, a compound or salt described in U.S. Pat. Nos. 8,563,735; 8,586,754; 9,018,381; 7,358,251; or 7,449,485, includes a phosphonate, phosphinate, or phosphate prodrug such as those described in Pradere, U.; Garnier-Amblard, E. C.; Coats, S. J.; Amblard, F.; Schinazi, R. F. Chem. Rev. 2014, 114, 9154-9218; Pertusati, F.; Serpi, M.; McGuigan, C. *Antiviral Chemistry & Chemotherapy* 2012, 22, 181-203; and He, G.; Krise, J. P.; Oliyai, R. Prodrugs of Phosphonates, Phosphinates, and Phosphates, in *Prodrugs: Challenges and Rewards*; Stella, V. J.; et al. Eds; Springer: New York, 2007, Vol. 5, 923-964; each of which is hereby incorporated by reference.

In certain aspects, the present disclosure provides a compound of Formula (I) or (II):

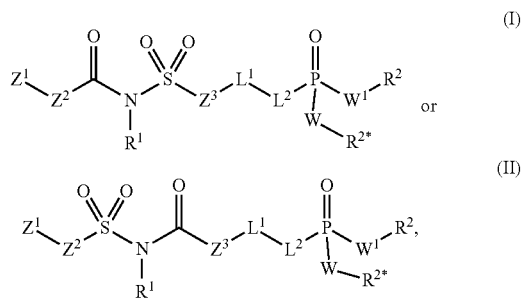

or a salt thereof, wherein:

$Z^1$ is $C_{3-12}$ carbocycle or 3- to 12-membered heterocycle, each of which is substituted with —$(C(R^5)_2)_n$—X—$(C(R^5)_2)_p$—$R^3$, —X—$C_{1-6}$ alkyl-$R^3$, —X—$C_{2-6}$ alkenyl-$R^3$, or —X—$C_{2-6}$ alkynyl-$R^3$ and $Z^1$ is further optionally substituted with one or more $R^6$;

$Z^2$ and $Z^3$ are each independently selected from $C_{3-12}$ carbocycle or 3- to 12-membered heterocycle, wherein each may be independently optionally substituted with one or more $R^6$;

$L^1$ is selected from a bond; alkylene, heteroalkylene, and Y, each of which is optionally substituted at each occurrence with one or more $R^6$;

$L^2$ is selected from a bond; alkylene, heteroalkylene, Y, Y-alkylene and Y-heteroalkylene, each of which is optionally substituted at each occurrence with one or more $R^6$;

W and $W^1$ are independently selected from —O—, —S— and —N($R^{10}$)—;

X at each occurrence is independently selected from bond, —O—, —S—, —N($R^4$)—, —C(O)—, —C(O)O—, —OC(O)—, —OC(O)O—, —C(O)N($R^4$)—, —C(O)N($R^4$)C(O)—, —C(O)N($R^4$)C(O)N($R^4$)—, —N($R^4$)C(O)—, —N($R^4$)C(O)N($R^4$)—, —N($R^4$)C(O)O—, —OC(O)N($R^4$)—, —C(N$R^4$)—, —N($R^4$)C(N$R^4$)—, —C(N$R^4$)N($R^4$)—, —N($R^4$)C(N$R^4$)N($R^4$)—, —S(O)$_2$-, —OS(O)—, —S(O)O—, —S(O)—, —OS(O)$_2$—, —S(O)$_2$O—, —N($R^4$)S(O)$_2$—, —S(O)$_2$N($R^4$)—, —N($R^4$)S(O)—, —S($R^4$)—, —N($R^4$)S(O)$_2$N($R^4$)—, and —N($R^4$)S(O)N($R^4$)—;

Y is selected at each occurrence from X, $C_{3-12}$ carbocycle and 3- to 12-membered heterocycle;

$R^1$ is selected from $R^4$;

$R^2$ and $R^{2*}$ are independently selected from $R^7$, or $R^2$ and $R^{2*}$ are taken together with the atoms to which they are attached to form a heterocycle, optionally substituted with one or more $R^6$;

R³ is C$_{3-12}$ carbocycle or 3- to 12-membered heterocycle, each of which is optionally substituted with one or more R⁶;

R⁴ is independently selected at each occurrence from hydrogen, —C(O)R¹⁰, —C(O)OR¹⁰ and —C(O)N(R⁴)—; C$_{1-6}$ alkyl, C$_{2-6}$ alkenyl, and C$_{2-6}$ alkynyl, each of which is independently optionally substituted at each occurrence with one or more substituents selected from halogen, —NO₂, —CN, —OR¹⁰, —SR¹⁰, —N(R¹⁰)₂, —S(=O)R¹⁰, —S(=O)₂R¹⁰, —S(=O)₂N(R¹⁰)₂, —NR¹⁰S(=O)₂R¹⁰, —C(O)R¹⁰, —C(O)OR¹⁰, —OC(O)R¹⁰, —OC(O)OR¹⁰, —OC(O)N(R¹⁰)₂, —NR¹⁰C(O)R¹⁰, —C(O)N(R¹⁰)₂, =O, =S, =N(R¹⁰), —P(O)(OR⁷)₂, —OP(O)(OR⁷)₂, C$_{3-10}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R⁴ is independently optionally substituted with one or more substituents selected from halogen, —NO₂, —CN, —OR¹⁰, —SR¹⁰, —N(R¹⁰)₂, —S(=O)R¹⁰, —S(=O)₂R¹⁰, —S(=O)₂N(R¹⁰)₂, —NR¹⁰S(=O)₂R¹⁰, —C(O)R¹⁰, —C(O)OR¹⁰, —OC(O)R¹⁰, —OC(O)OR¹⁰, —OC(O)N(R¹⁰)₂, —NR¹⁰C(O)R¹⁰, —C(O)N(R¹⁰)₂, =O, =S, =N(R¹⁰), —P(O)(OR⁷)₂, —OP(O)(OR⁷)₂, C$_{1-6}$ alkyl, C$_{1-6}$ haloalkyl, C$_{2-6}$ alkenyl, and C$_{2-6}$ alkynyl;

R⁵ is independently selected at each occurrence from hydrogen, halogen, —NO₂, —CN, —OR¹⁰, —SR¹⁰, —N(R¹⁰)₂, —S(=O)R¹⁰, —S(=O)₂R¹⁰, —S(=O)₂N(R¹⁰)₂, —NR¹⁰S(=O)₂R¹⁰, —C(O)R¹⁰, —C(O)OR¹⁰, —OC(O)R¹⁰, —OC(O)OR¹⁰, —OC(O)N(R¹⁰)₂, —NR¹⁰C(O)R¹⁰, —C(O)N(R¹⁰)₂, =O, =S, =N(R¹⁰), —P(O)(OR⁷)₂, —OP(O)(OR⁷)₂; C$_{1-10}$ alkyl, C$_{2-10}$ alkenyl, and C$_{2-10}$ alkynyl, each of which is independently optionally substituted at each occurrence with one or more substituents selected from halogen, —NO₂, —CN, —OR¹⁰, —SR¹⁰, —N(R¹⁰)₂, —S(=O)R¹⁰, —S(=O)₂R¹⁰, —S(=O)₂N(R¹⁰)₂, —NR¹⁰S(=O)₂R¹⁰, —C(O)R¹⁰, —C(O)OR¹⁰, —OC(O)R¹⁰, —OC(O)OR¹⁰, —OC(O)N(R¹⁰)₂, —NR¹⁰C(O)R¹⁰, —C(O)N(R¹⁰)₂, =O, =S, =N(R¹⁰), —P(O)(OR⁷)₂, —OP(O)(OR⁷)₂, C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R⁵ is independently optionally substituted with one or more substituents selected from halogen, —NO₂, —CN, —OR¹⁰, —SR¹⁰, —N(R¹⁰)₂, —S(=O)R¹⁰, —S(=O)₂R¹⁰, —S(=O)₂N(R¹⁰)₂, —NR¹⁰S(=O)₂R¹⁰, —C(O)R¹⁰, —C(O)OR¹⁰, —OC(O)R¹⁰, —OC(O)OR¹⁰, —OC(O)N(R¹⁰)₂, —NR¹⁰C(O)R¹⁰, —C(O)N(R¹⁰)₂, =O, =S, =N(R¹⁰), —P(O)(OR⁷)₂, —OP(O)(OR⁷)₂, C$_{1-6}$ alkyl, C$_{1-6}$ haloalkyl, C$_{2-6}$ alkenyl, and C$_{2-6}$ alkynyl;

R⁶ is independently selected at each occurrence from halogen, —NO₂, —CN, —OR¹⁰, —SR¹⁰, —N(R¹⁰)₂, —S(=O)R¹⁰, —S(=O)₂R¹⁰, —S(=O)₂N(R¹⁰)₂, —NR¹⁰S(=O)₂R¹⁰, —C(O)R¹⁰, —C(O)OR¹⁰, —OC(O)R¹⁰, —OC(O)OR¹⁰, —OC(O)N(R¹⁰)₂, —NR¹⁰C(O)R¹⁰, —C(O)N(R¹⁰)₂, =O, =S, =N(R¹⁰), —P(O)(OR⁷)₂, —OP(O)(OR⁷)₂; C$_{1-10}$ alkyl, C$_{2-10}$ alkenyl, and C$_{2-10}$ alkynyl, each of which is independently optionally substituted at each occurrence with one or more substituents selected from halogen, —NO₂, —CN, —OR¹⁰, —SR¹⁰, —N(R¹⁰)₂, —S(=O)R¹⁰, —S(=O)₂R¹⁰, —S(=O)₂N(R¹⁰)₂, —NR¹⁰S(=O)₂R¹⁰, —C(O)R¹⁰, —C(O)OR¹⁰, —OC(O)R¹⁰, —OC(O)OR¹⁰, —OC(O)N(R¹⁰)₂, —NR¹⁰C(O)R¹⁰, —C(O)N(R¹⁰)₂, =O, =S, =N(R¹⁰), —P(O)(OR⁷)₂, —OP(O)(OR⁷)₂, C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R⁶ is independently optionally substituted with one or more substituents selected from halogen, —NO₂, —CN, —OR¹⁰, —SR¹⁰, —N(R¹⁰)₂, —S(=O)R¹⁰, —S(=O)₂R¹⁰, —S(=O)₂N(R¹⁰)₂, —NR¹⁰S(=O)₂R¹⁰, —C(O)R¹⁰, —C(O)OR¹⁰, —OC(O)R¹⁰, —OC(O)OR¹⁰, —OC(O)N(R¹⁰)₂, —NR¹⁰C(O)R¹⁰, —C(O)N(R¹⁰)₂, =O, =S, =N(R¹⁰), —P(O)(OR⁷)₂, —OP(O)(OR⁷)₂, C$_{1-6}$ alkyl, C$_{1-6}$ haloalkyl, C$_{2-6}$ alkenyl, and C$_{2-6}$ alkynyl;

R⁷ is independently selected at each occurrence from hydrogen, —C(O)R¹⁰, —C(O)OR¹⁰ and —C(O)N(R⁴)—; C$_{1-6}$ alkyl, C$_{2-6}$ alkenyl, and C$_{2-6}$ alkynyl, each of which is independently optionally substituted at each occurrence with one or more substituents selected from halogen, —NO₂, —CN, —OR¹⁰, —SR¹⁰, —S—S—R¹⁰, —N(R¹⁰)₂, —S(=O)R¹⁰, —S(=O)₂R¹⁰, —S(=O)₂N(R¹⁰)₂, —NR¹⁰S(=O)₂R¹⁰, —S—C(O)R¹⁰, —C(O)R¹⁰, —C(O)OR¹⁰, —OC(O)R¹⁰, —OC(O)OR¹⁰, —OC(O)N(R¹⁰)₂, —NR¹⁰C(O)R¹⁰, —C(O)N(R¹⁰)₂, =O, =S, =N(R¹⁰), —P(O)(OR¹⁰)₂, —OP(O)(OR¹⁰)₂, C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R⁷ is independently optionally substituted with one or more substituents selected from halogen, —NO₂, —CN, —OR¹⁰, —SR¹⁰, —N(R¹⁰)₂, —S(=O)R¹⁰, —S(=O)₂R¹⁰, —S(=O)₂N(R¹⁰)₂, —NR¹⁰S(=O)₂R¹⁰, —C(O)R¹⁰, —C(O)OR¹⁰, —OC(O)R¹⁰, —OC(O)OR¹⁰, —OC(O)N(R¹⁰)₂, —NR¹⁰C(O)R¹⁰, —C(O)N(R¹⁰)₂, =O, =S, =N(R¹⁰), —P(O)(OR¹⁰)₂, —OP(O)(OR¹⁰)₂, C$_{1-6}$ alkyl, C$_{1-6}$ haloalkyl, C$_{2-6}$ alkenyl, and C$_{2-6}$ alkynyl;

R¹⁰ at each occurrence is independently selected from hydrogen; and C$_{1-6}$ alkyl, C$_{2-6}$ alkenyl, C$_{2-6}$ alkynyl, C$_{3-12}$ carbocycle and 3- to 12-membered heterocycle, each of which may be optionally substituted by halogen, —CN, —NO₂, —OH and —OCH₃;

n is 0, 1, 2, 3, or 4; and p is 0, 1, 2, 3, or 4, wherein for a compound or salt of Formula (I), when L² is Y-heteroalkylene and Y is piperidine, one of R² and R²* is other than hydrogen.

In some aspects, the present disclosure provides a compound of Formula (I):

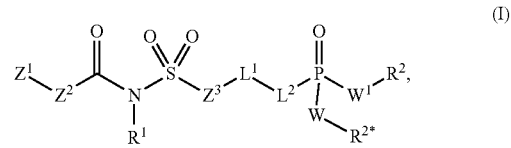

or a salt thereof.

In some aspects, the present disclosure provides a compound of Formula (II):

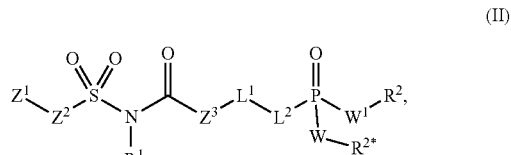

or a salt thereof.

In certain embodiments, for a compound of Formula (I) or (II), at least one of R² and R²* is selected from C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{10}$, —SR$^{10}$, —S—S—R$^{10}$, —N(R$^{10}$)$_2$, —S(=O)R$^{10}$, —S(=O)$_2$R$^{10}$, —S(=O)$_2$N(R$^{10}$)$_2$, —NR$^{10}$S(=O)$_2$R$^{10}$, —S—C(O)R$^{10}$, —C(O)R$^{10}$, —C(O)OR$^{10}$, —OC(O)R$^{10}$, —OC(O)OR$^{10}$, —OC(O)N(R$^{10}$)$_2$, —NR$^{10}$C(O)R$^{10}$, —C(O)N(R$^{10}$)$_2$, =O, =S, =N(R$^{10}$), —P(O)(OR$^{10}$)$_2$, —OP(O)(OR$^{10}$)$_2$; and C$_{3-12}$ carbocycle and 3- to 12-membered heterocycle, each of which is independently optionally substituted at each occurrence with one or more substituents selected from halogen, C$_{1-6}$ alkyl, —OR$^{10}$, —OC(O)R$^{10}$, and —C(O)R$^{10}$.

In certain embodiments, for a compound of Formula (I) or (II), R$^2$ and R$^{2^*}$ may be independently selected from C$_{1-6}$ alkyl, C$_{2-6}$ alkenyl, and C$_{2-6}$ alkynyl, each of which is independently optionally substituted at each occurrence with one or more substituents selected from halogen, —NO$_2$, —CN, —OR$^{10}$, —SR$^{10}$, —S—S—R$^{10}$, —N(R$^{10}$)$_2$, —S(=O)R$^{10}$, —S(=O)$_2$R$^{10}$, —S(=O)$_2$N(R$^{10}$)$_2$, —NR$^{10}$S(=O)$_2$R$^{10}$, —S—C(O)R$^{10}$, —C(O)R$^{10}$, —C(O)OR$^{10}$, —OC(O)R$^{10}$, —OC(O)OR$^{10}$, —OC(O)N(R$^{10}$)$_2$, —NR$^{10}$C(O)R$^{10}$, —C(O)N(R$^{10}$)$_2$, =O, =S, =N(R$^{10}$), —P(O)(OR$^{10}$)$_2$, —OP(O)(OR$^{10}$)$_2$; and C$_{3-12}$ carbocycle and 3- to 12-membered heterocycle, each of which is independently optionally substituted at each occurrence with one or more substituents selected from halogen, C$_{1-6}$ alkyl, —OR$^{10}$, —OC(O)R$^{10}$, and —C(O)R$^{10}$.

In certain embodiments, for a compound of Formula (I) or (II), R$^2$ and R$^{2^*}$ are independently selected from C$_{1-6}$ alkyl substituted with one or more substituents selected from halogen, —OC(O)R$^{10}$, —OC(O)OR$^{10}$, —S—S—R$^{10}$, —S—C(O)R$^{10}$, —OR$^{10}$, and —P(O)(OR$^{10}$)$_2$. In certain embodiments, R$^2$ and R$^{2^*}$ are independently selected from C$_{1-6}$ alkyl substituted with one or more substituents selected from —OC(O)R$^{10}$ and —OC(O)OR$^{10}$. In certain embodiments, R$^2$ and R$^{2^*}$ are independently selected from C$_1$ alkyl substituted with one or more substituents selected from —OC(O)R$^{10}$ and —OC(O)OR$^{10}$, wherein R$^{10}$ is C$_{1-6}$ alkyl. In certain embodiments, R$^2$ and R$^{2^*}$ are independently selected from —CH$_2$OC(O)C(CH$_3$)$_3$, —CH$_2$OC(O)OCH(CH$_3$)$_2$, and —CH$_2$OC(O)CH$_3$. In certain embodiments, R$^2$ and R$^{2^*}$ are each —CH$_2$OC(O)C(CH$_3$)$_3$. In certain embodiments, R$^2$ and R$^{2^*}$ are each —CH$_2$OC(O)OCH(CH$_3$)$_2$.

In certain embodiments, for a compound of Formula (I) or (II), R$^2$ and R$^{2^*}$ are independently selected from C$_{1-6}$ alkyl substituted with one or more substituents selected from —S—S—R$^{10}$, and —S—C(O)R$^{10}$. In certain embodiments, R$^2$ and R$^{2^*}$ are independently selected from —CH$_2$CH$_2$—S—S—(CH$_2$)$_2$OH and —CH$_2$CH$_2$—S—C(O)CH$_3$. In certain embodiments, R$^2$ and R$^{2^*}$ are each —CH$_2$CH$_2$—S—S—(CH$_2$)$_2$OH. In certain embodiments, R$^2$ and R$^{2^*}$ are each —CH$_2$CH$_2$—S—C(O)CH$_3$.

In certain embodiments, for a compound of Formula (I) or (II), R$^2$ and R$^{2^*}$ are independently selected from C$_{3-12}$ carbocycle, such as phenyl, wherein the C$_{3-12}$ carbocycle is optionally substituted with one or more substituents selected from halogen, C$_{1-6}$ alkyl, —OR$^{10}$, —OC(O)R$^{10}$, —C(O)OR$^{10}$, and C(O)R$^{10}$.

In certain embodiments, R$^2$ and R$^{2^*}$ are independently selected from phenyl, wherein the phenyl is optionally substituted with OR$^{10}$, such as phenyl substituted with OCH$_2$CH$_3$. In certain embodiments, one of R$^2$ and R$^{2^*}$ is selected from C$_{3-12}$ carbocycle, such as phenyl and benzyl, and the other of R$^2$ and R$^{2^*}$ is selected from C$_{1-6}$ alkyl substituted with one or more substituents selected from —OC(O)R$^{10}$, —C(O)OR$^{10}$, and —OC(O)OR$^{10}$, wherein R$^{10}$ is C$_{1-6}$ alkyl.

In certain embodiments, for a compound of Formula (I) or (II), R$^2$ and R$^{2^*}$ are independently selected from hydrogen and C$_{1-6}$ alkylene-OR$^{50}$, wherein R$^{50}$ at each occurrence is independently selected from C$_{7-20}$ alkyl and C$_{7-20}$ alkenyl. In certain embodiments, one of R$^2$ or R$^{2^*}$ is selected from C$_{1-3}$alkylene O—C$_{7-20}$alkyl and C$_{1-3}$alkylene O—C$_{7-20}$alkenyl, such as one of R$^2$ or R$^{2^*}$ is selected from hexadecyloxypropyl (—CH$_2$(CH$_2$)$_2$)(CH$_2$)$_{13}$CH$_3$), octadecyloxyethyl (—CH$_2$CH$_2$O(CH$_2$)$_{17}$CH$_3$), oleyoxyethyl (—CH$_2$CH$_2$O(CH$_2$)$_8$CH=CH(CH$_2$)$_7$CH$_3$), and oleyoxypropyl (—CH$_2$(CH$_2$)$_2$O(CH$_2$)$_8$CH=CH(CH$_2$)$_7$CH$_3$), and the other of R$^2$ and R$^{2^*}$ is hydrogen.

In certain embodiments, for a compound of Formula (I) or (II), R$^2$ and R$^{2^*}$ may be taken together with the atoms to which they are attached to form a heterocycle, optionally substituted with one or more R$^6$. In certain embodiments, the heterocycle is a 5- or 6-membered heterocycle. In certain embodiments, R$^2$ and R$^{2^*}$ are taken together with the atoms to which they are attached to form a heterocycle selected from:

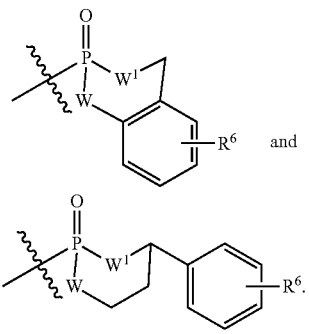

In certain embodiments, R$^6$ is a halogen.

In certain embodiments, for a compound of Formula (I) or (II), W and W$^1$ are each —O—. In certain embodiments, one of W and W$^1$ is —O— and the other one of W and W$^1$ is —N(R$^{10}$)—. In certain embodiments, at least one of —W—R$^{2^*}$ and W$^1$—R$^2$ comprises an amino acid or an amino acid ester, such as an L-alanine ester, e.g., —NHCH(CH$_3$)C(O)OCH(CH$_3$)$_2$ and —NHCH(CH$_3$)C(O)OCH$_2$CH$_3$. In certain embodiments, at least one of —W—R$^{2^*}$ and —W$^1$—R$^2$ comprises alanine, serine, phenylalanine, valine, or two or more thereof.

In certain embodiments, for a compound of Formula (I) or (II), —W—R$^{2^*}$ and —W$^1$—R$^2$ are independently selected from:
—OH, —O—CH$_3$, —O—CH$_2$CH$_3$, —O—CH$_2$— -Ph, —O-Ph,

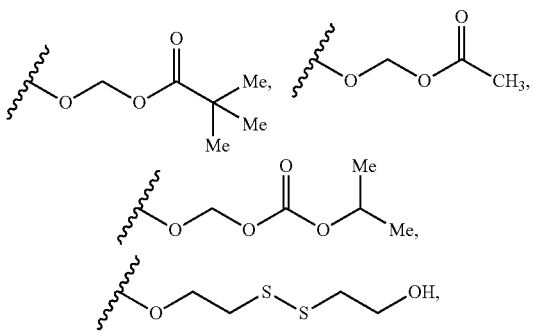

-continued

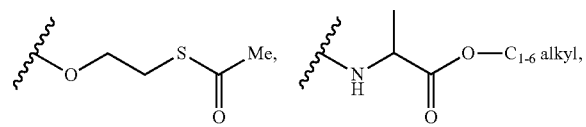

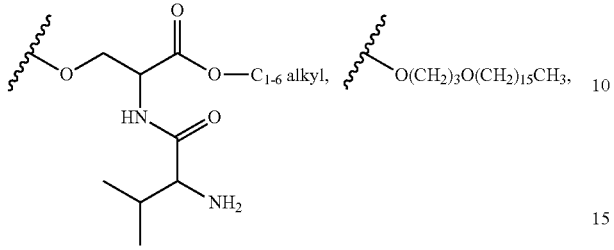

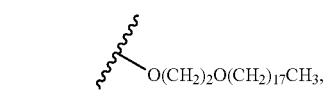

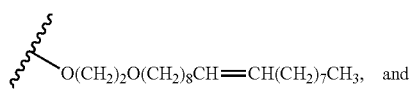

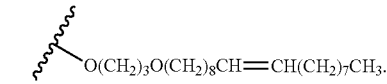

In certain embodiments, —W—R$^{2*}$ and W$^1$—R$^2$ are different, such as —W—R$^{2*}$ is —OH and —W$^1$—R$^2$ is —O(CH$_2$)$_3$O(CH$_2$)$_{15}$CH$_3$. In certain embodiments, one of —W—R$^{2*}$ and —W$^1$—R$^2$ is —OH, and the other one of —W—R$^{2*}$ and —W$^1$—R$^2$ is selected from

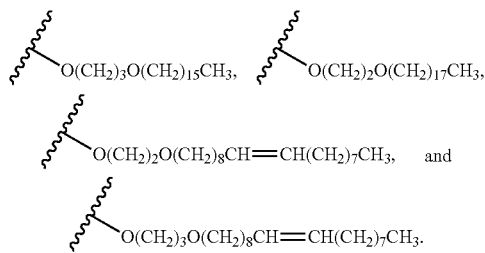

In certain embodiments, —W—R$^{2*}$ and —W$^1$—R$^2$ are selected from the same moieties, for example, —W—R$^{2*}$ is

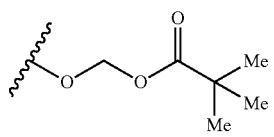 [SMILES: *OCOC(=O)C(C)(C)C]

and —W$^1$—R$^2$ is

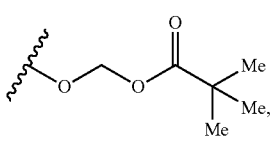 [SMILES: *OCOC(=O)C(C)(C)C]

or —W—R$^{2*}$ is

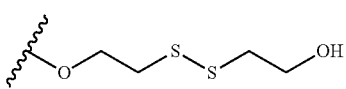 [SMILES: *OCCSSCCO]

and —W$^1$—R$^2$ is

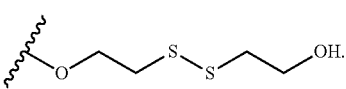 [SMILES: *OCCSSCCO]

In certain embodiments, —W—R$^{2*}$ and —W$^1$—R$^2$ are each —O—CH$_3$, —O—CH$_2$CH$_3$, —O—CH$_2$-Ph, —O-Ph,

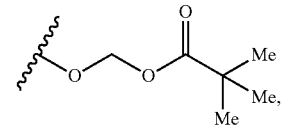

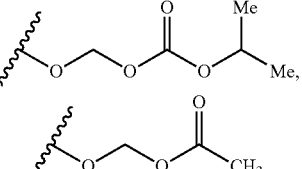

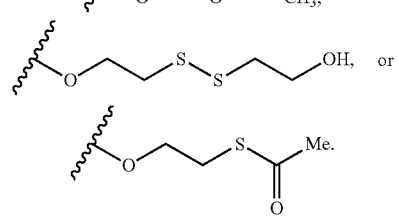

In certain embodiments, for a compound of Formula (I) or (II), L$^1$ is selected from heteroalkylene, for example, L$^1$ is selected from —(CH$_2$)$_s$—X$^{10}$—(CH$_2$)$_r$—, —(CH$_2$)$_r$—X$^{10}$—(CH$_2$)$_r$—X$^{10}$—(CH$_2$)$_r$—, and —(CH(CH$_2$)$_r$—X$^{10}$—(CH$_2$)$_r$—, —X$^{10}$—(CH$_2$)$_r$—X$^{10}$—(CH$_2$)$_r$—, wherein s is selected from 0 to 3, each r is selected from 1 to 4, each X$^{10}$ is selected from —O—, —S—, or —N(R$^4$)—, and L$^1$ may be optionally substituted with one or more R$^6$. In certain embodiments, L$^1$ is selected from —(CH$_2$)$_s$—X$^{10}$—(CH$_2$)$_r$— optionally substituted with R$^6$, wherein s is 0, X$^{10}$ is —O— or N(R$^4$)—, and r is 1, 2, or 3. In certain embodiments, L$^1$ is selected from —(CH$_2$)$_s$—X$^{10}$—(CH$_2$)$_r$—, wherein s is 0, r is selected from 1 to 3, X$^{10}$ is —N(R$^4$)—, and L$^1$ is optionally substituted with one or more R$^6$. In certain embodiments, L$^1$ is selected from N(R$^4$)—(CH$_2$)$_{1-4}$—, optionally substituted with one or more R$^6$. In certain embodiments, L$^1$ is selected from —N(R$^4$)—(CH$_2$)$_3$— optionally substituted with one or more R$^6$. In certain embodiments, L$^1$ is selected from —N(R$^4$)—(CH$_2$)$_3$—N(R$^4$)—(CH$_2$)$_2$— optionally substituted with R$^6$. In certain embodiments, L$^1$ is selected from:

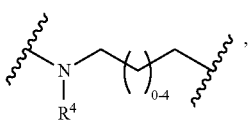

-continued

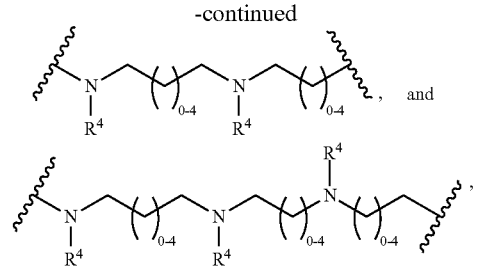

any one of which is optionally substituted by one or more $R^6$. In certain embodiments, $L^1$ is selected from:

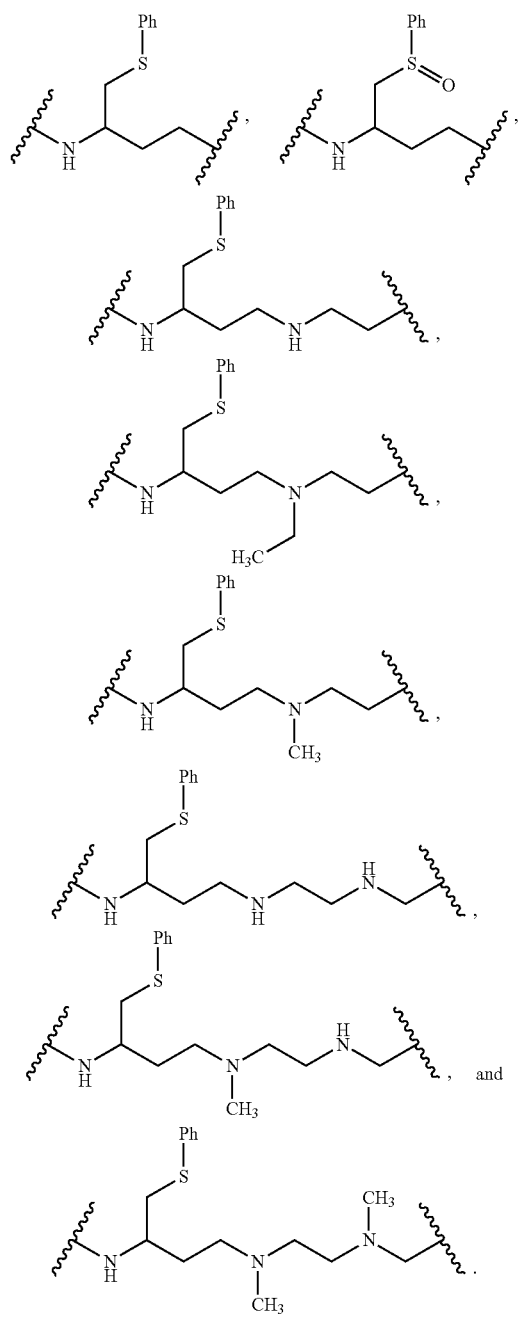

In certain embodiments, $L^1$ is selected from:

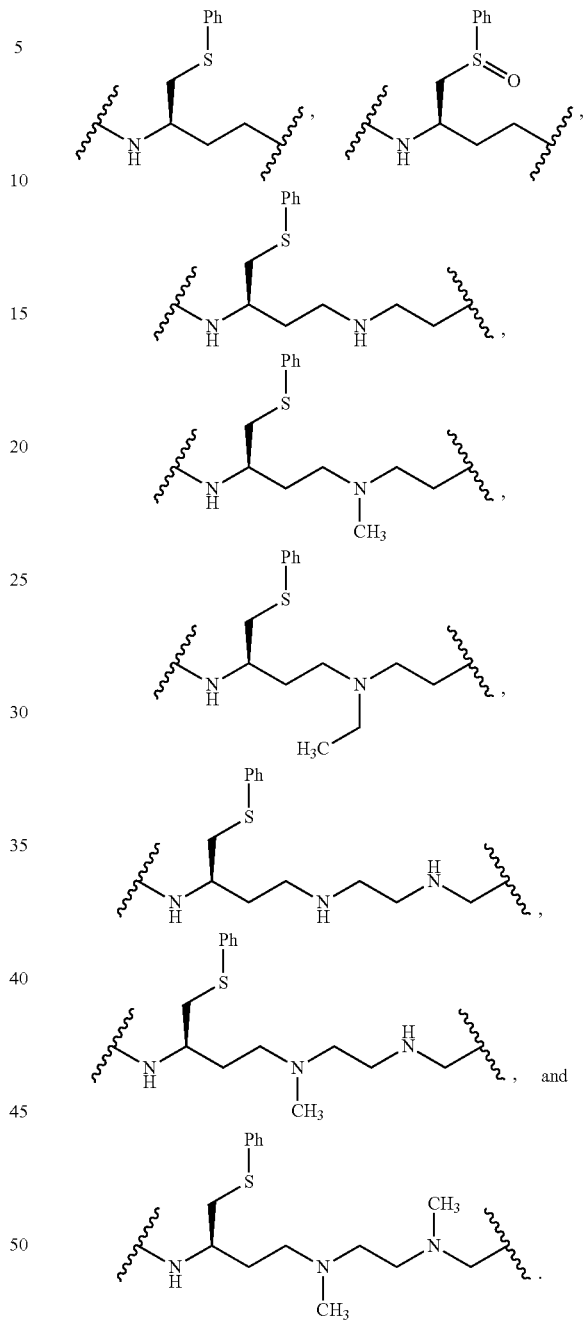

In certain embodiments, for a compound of Formula (I) or (II), $L^2$ is a bond. In certain embodiments, $L^2$ is selected from —Y-alkylene- and Y-heteroalkylene, either of which is optionally substituted with one or more $R^6$. In certain embodiments, Y of $L^2$ is selected from a 3- to 6-membered heterocycle optionally substituted with one or more $R^6$. In certain embodiments, Y of $L^2$ is selected from 5- and 6-membered heterocycles such as 5- and 6-membered saturated heterocycles. In certain embodiments, Y of $L^2$ is selected from piperidine, piperazine, morpholine, pyrrolidine, tetrahydrofuran, imidazolidine, and pyrazolidine. In certain embodiments, $L^2$ is selected from:

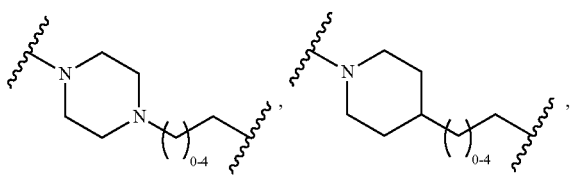

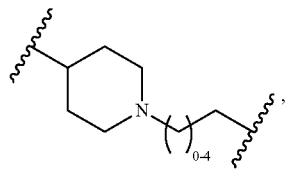

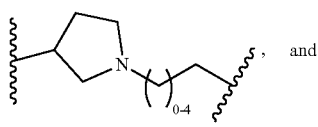

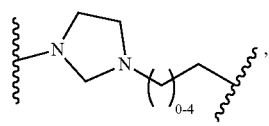

any one of which is optionally substituted by one or more $R^6$. In certain embodiments, for a compound of Formula (I) or (II), $L^2$ is a further selected from —Y-alkenylene- and —Y-heteroalkenylene, either of which is optionally substituted with one or more $R^6$. In certain embodiments, $L^2$ is selected from

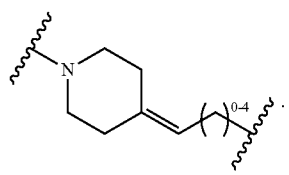

In certain embodiments, $L^2$ is selected from:

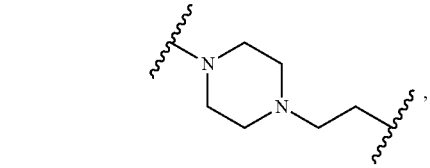

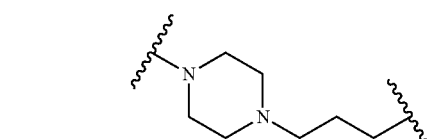

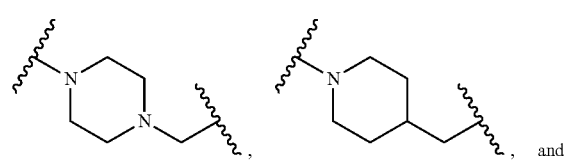

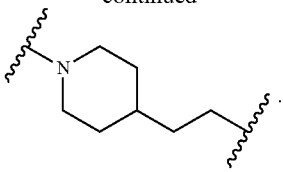

In certain embodiments, for a compound of Formula (I) or (II), $-L^1-L^2-$ is selected from:

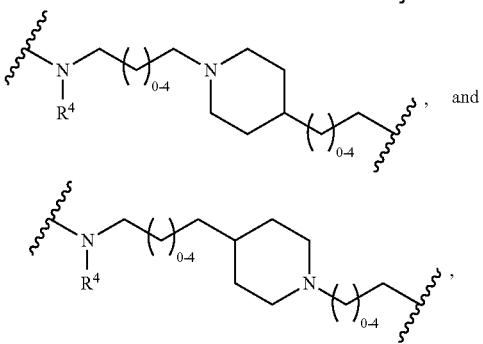

any one of which is optionally substituted by one or more $R^6$. In certain embodiments, for a compound of Formula (I) or (II), $-L^1-L^2-$ is selected from:

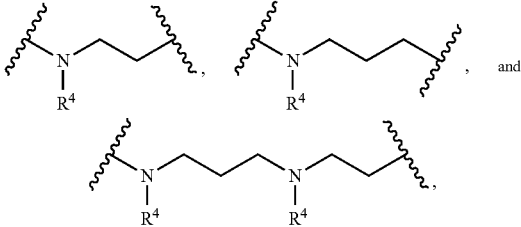

any one of which is optionally substituted by one or more $R^6$. In certain embodiments, $R^4$ at each occurrence is independently selected from hydrogen and $C_{1-6}$ alkyl, e.g., —$CH_3$. In certain embodiments, $-L^1-L^2-$ is selected from:

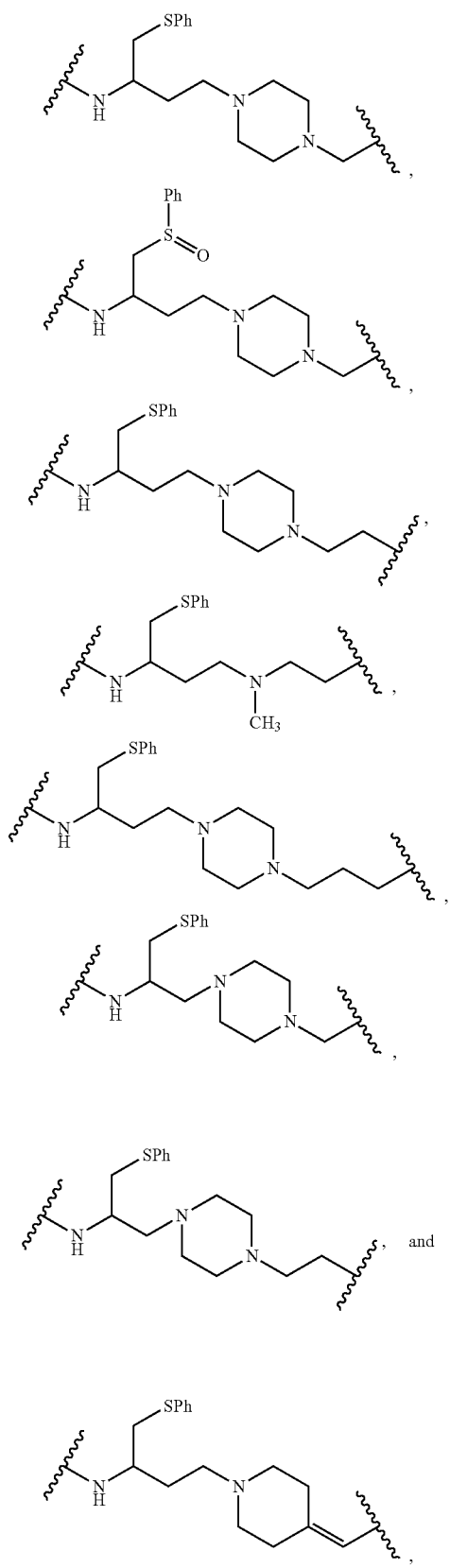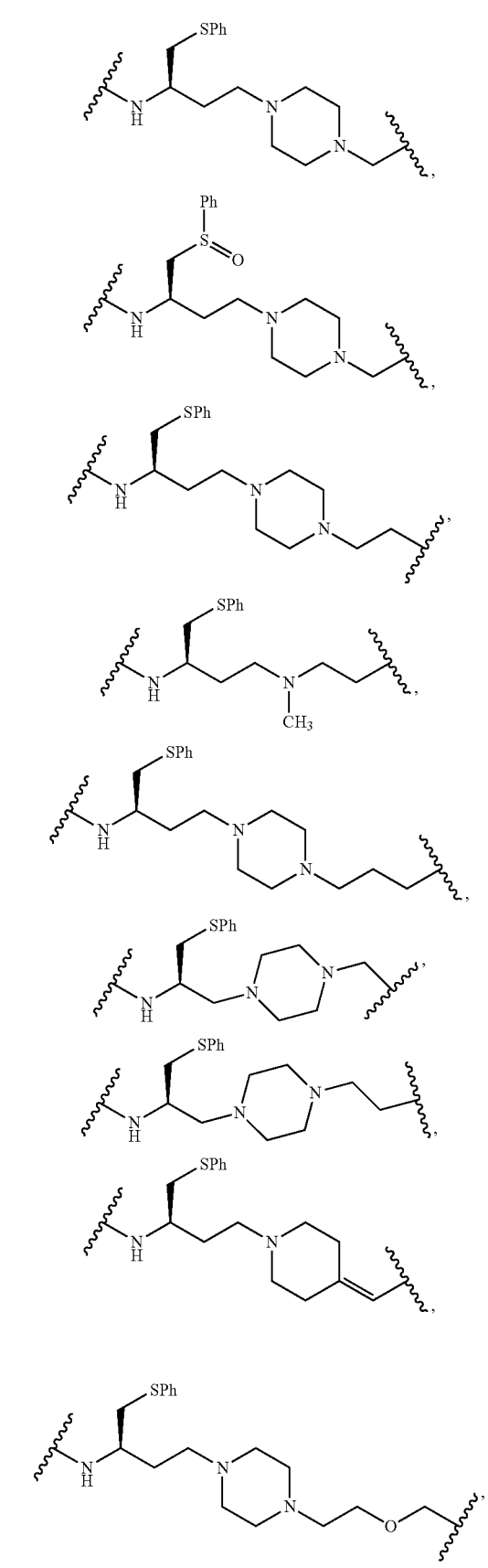
any one of which is optionally substituted by one or more $R^6$. In certain embodiments, -$L^1$-$L^2$- is selected from:

-continued

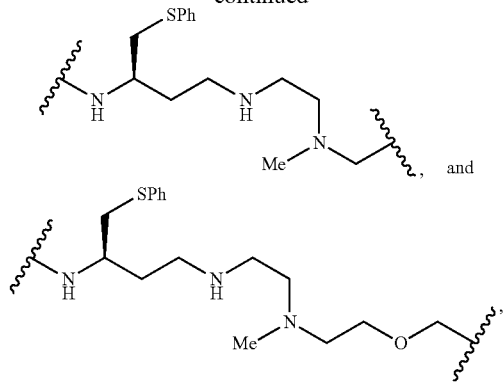

any one of which is optionally substituted by one or more $R^6$.

In certain embodiments, for a compound of Formula (I) or (II), $Z^3$ is a 3- to 12-membered heterocycle, $C_3$-$C_{12}$ cycloalkane or $C_3$-$C_{12}$cycloalkene, any of which is optionally substituted with one or more $R^6$. In certain embodiments, $Z^3$ is selected from a heteroaryl group optionally substituted with one or more $R^6$. In certain embodiments, $Z^3$ is selected from:

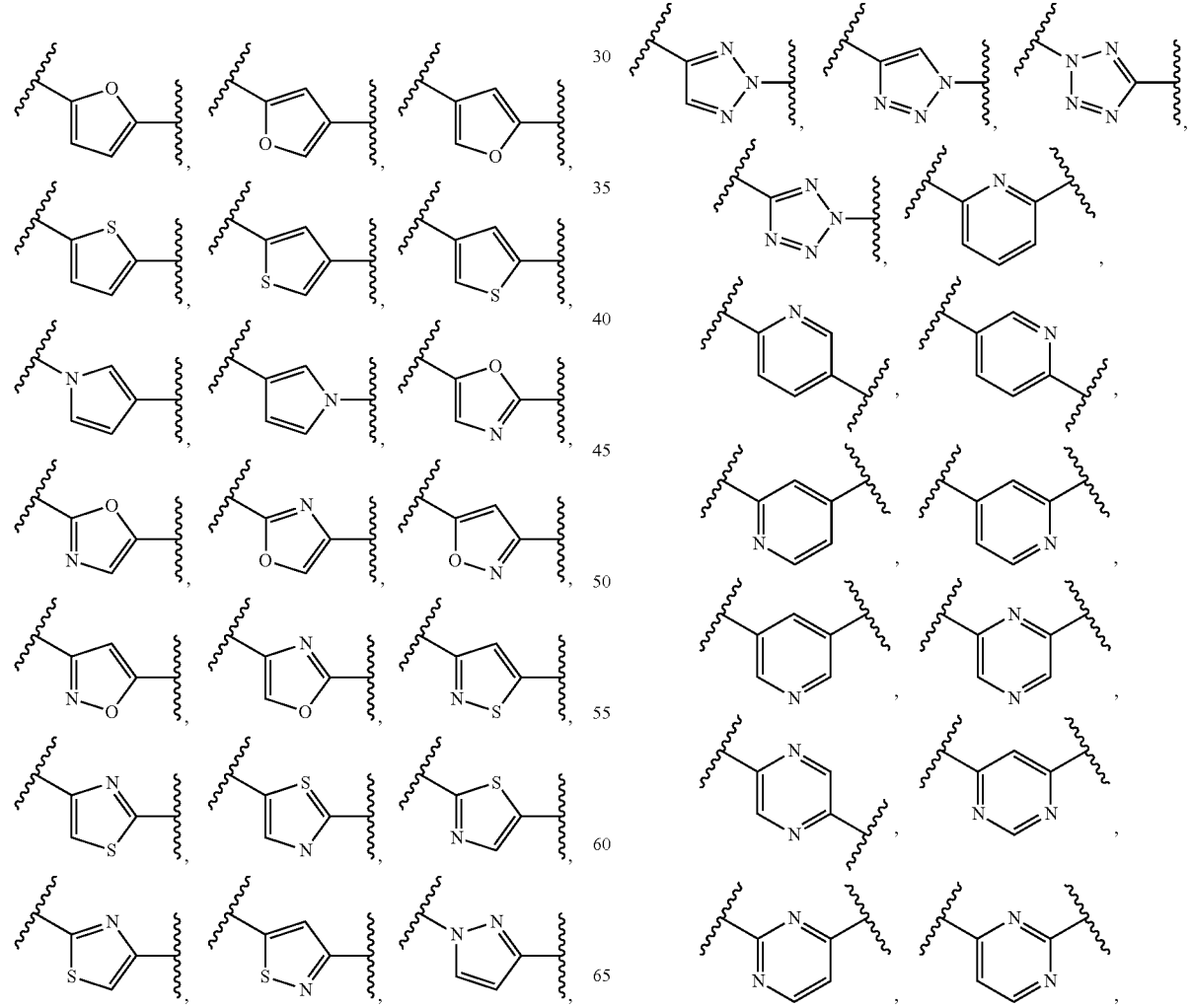

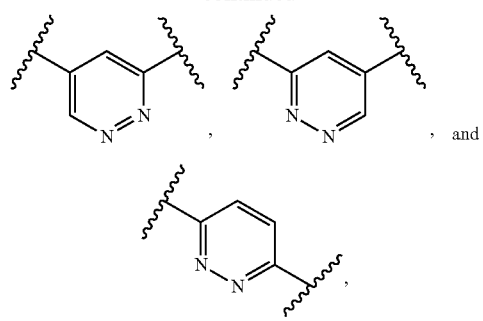

any one of which is optionally substituted with one or more $R^6$. In certain embodiments, $Z^3$ is selected from:

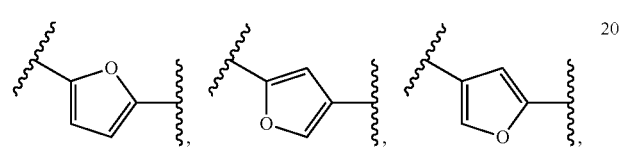

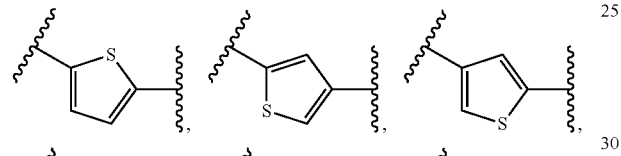

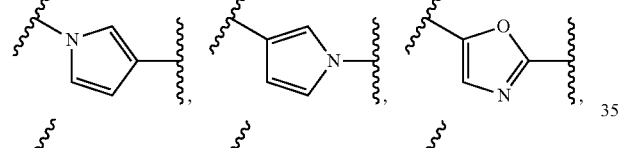

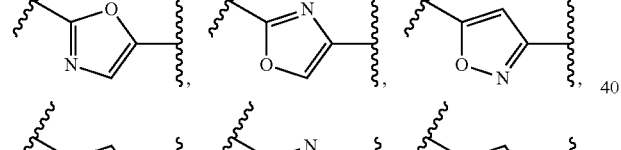

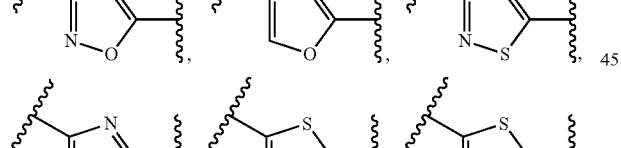

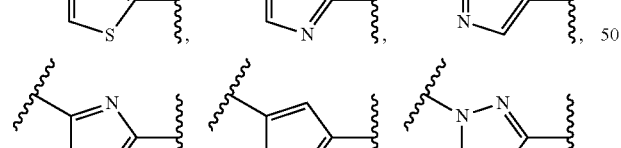

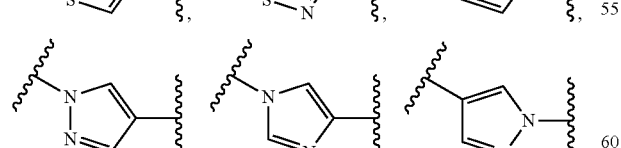

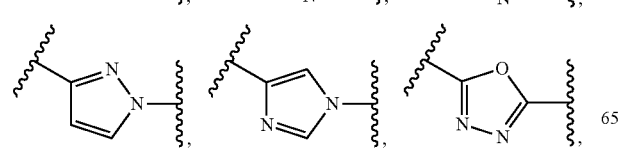

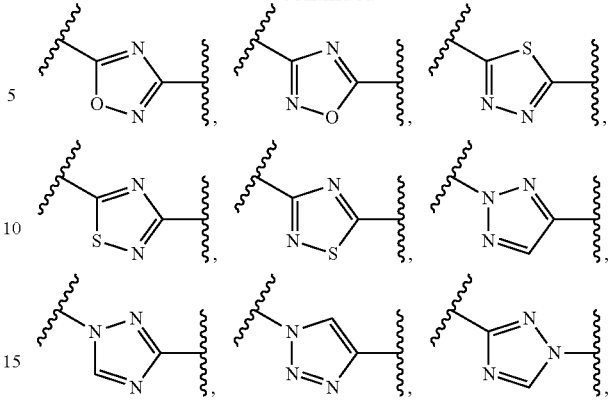

any one of which is optionally substituted with one or more $R^6$.

In certain embodiments, $Z^3$ is a $C_3$-$C_{12}$ cycloalkane or $C_3$-$C_{12}$ cycloalkene, any one of which is optionally substituted with one or more $R^6$. In certain embodiments, $Z^3$ is a $C_{3-10}$ cycloalkane such as a $C_{3-6}$ cycloalkane. In certain embodiments, $Z^3$ is a $C_3$-$C_{12}$ cycloalkene such as a $C_{3-6}$ cycloalkene. In certain embodiments, $Z^3$ is selected from:

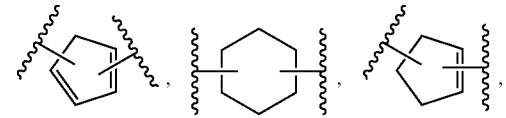

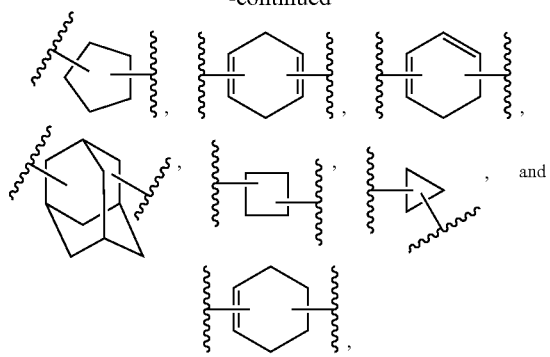

any one of which is optionally substituted with one or more $R^6$.

In certain embodiments, $Z^3$ is optionally substituted with one or more $R^6$. In certain embodiments, $Z^3$ is selected from:

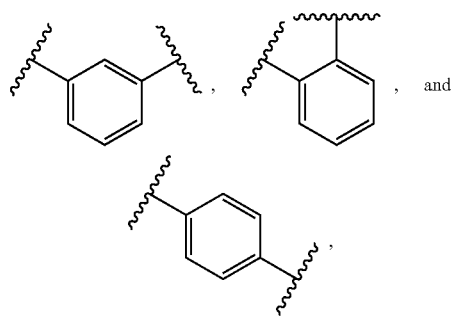

any one of which is optionally substituted by one or more $R^6$. In certain embodiments, $Z^3$ is

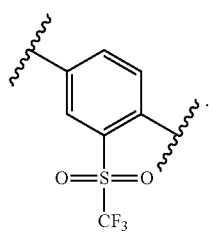 [SMILES: *c1ccc(*)c(S(=O)(=O)C(F)(F)F)c1]

In certain embodiments, for a compound of Formula (I) or (II), $Z^2$ is a 3- to 12-membered heterocycle, $C_3$-$C_{12}$ cycloalkane or $C_3$-$C_{12}$ cycloalkene, any one of which is optionally substituted with one or more $R^6$. In certain embodiments, $Z^2$ is selected from a heterocycloalkyl and heterocycloalkenyl group, such as azetidine, oxetane, thietane, pyrrolidine, pyrroline, tetrahydrofuran, dihydrofuran, thiolane, dihydrothiophene, imidazolidine, imidazoline, pyrazolidine, oxazolidine, oxazoline, isoxazolidine, isoxazoline, thiazolidine, thiazoline, isothiazolidine, dioxolane, piperazine, piperidine, morpholine, thiomorpholine, dioxane, dithiane, and dithiolane, any one of which is optionally substituted with one or more $R^6$. In certain embodiments, $Z^2$ is piperidine or piperazine, either of which is optionally substituted with one or more $R^6$.

In certain embodiments, for a compound of Formula (I) or (II), $Z^2$ is a $C_3$-$C_{12}$ cycloalkane or $C_3$-$C_{12}$ cycloalkene. In certain embodiments, $Z^2$ is a $C_{3-10}$ cycloalkane such as a $C_{3-6}$ cycloalkane. In certain embodiments, $Z^2$ is a $C_3$-$C_{12}$ cycloalkene such as a $C_{3-6}$ cycloalkene. In certain embodiments, $Z^2$ is selected from:

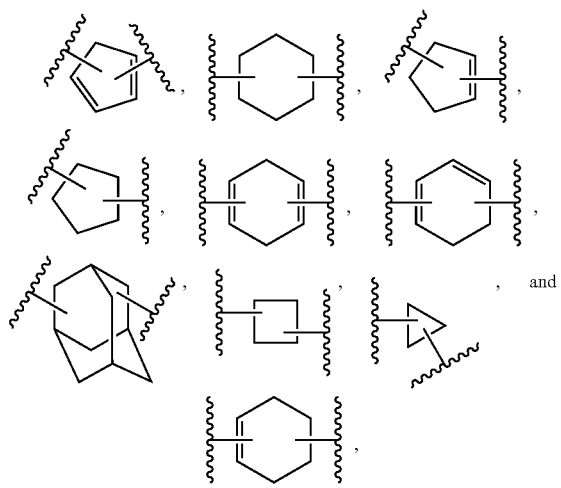

any one of which is optionally substituted with one or more $R^6$.

In certain embodiments, $Z^2$ is phenyl optionally substituted with one or more $R^6$. In certain embodiments, $Z^2$ is selected from:

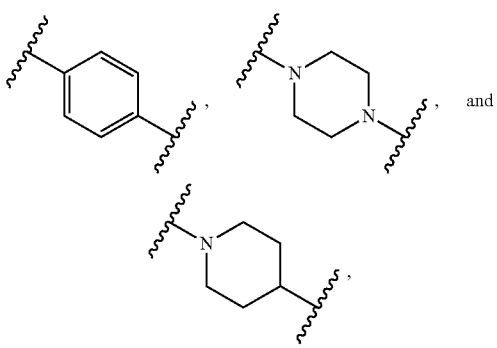

any one of which is optionally substituted with one or more $R^6$.

For a compound of Formula (II), $Z^2$ may be $C_{3-12}$ carbocycle or 3- to 12-membered heterocycle, each of which is optionally substituted with one or more $R^6$. In certain embodiments, $Z^2$ is phenyl optionally substituted with one or more $R^6$. For a compound of Formula (II), $Z^3$ may be $C_{3-12}$ carbocycle or 3- to 12-membered heterocycle, each of which is optionally substituted with one or more $R^6$. In certain embodiments, $Z^3$ is phenyl optionally substituted with one or more $R^6$.

In certain embodiments, for a compound of Formula (I) or (II), $R^1$ may be selected from hydrogen; and $C_{1-6}$ alkyl, $C_{2-6}$ alkenyl, and $C_{2-6}$ alkynyl, each of which is independently optionally substituted at each occurrence with one or more substituents selected from halogen, $-NO_2$, $-CN$, $-OR^{10}$, $-SR^{10}$, and $-N(R^{10})_2$. In certain embodiments, $R^1$ is hydrogen.

In certain embodiments, for a compound of Formula (I) or (II), $Z^1$ may be selected from 3- to 12-membered heterocycle. In certain embodiments, $Z^1$ is a heterocycloalkyl or heterocycloalkenyl group, such as azetidine, oxetane, thietane, pyrrolidine, pyrroline, tetrahydrofuran, dihydrofuran, thiolane, dihydrothiophene, imidazolidine, imidazoline, pyrazolidine, oxazolidine, oxazoline, isoxazolidine, isoxazoline, thiazolidine, thiazoline, isothiazolidine, dioxolane, piperazine, piperidine, morpholine, thiomorpholine, dioxane, dithiane, and dithiolane, any one of which is optionally substituted with one or more $R^6$. In certain embodiments, $Z^1$ is selected from azetidine, oxetane, thietane, pyrrolidine, pyrroline, tetrahydrofuran, dihydrofuran, thiolane, dihydrothiophene, imidazolidine, imidazoline, pyrazolidine, oxazolidine, oxazoline, isoxazolidine, isoxazoline, thiazolidine, thiazoline, isothiazolidine, dioxolane, piperazine, morpholine, thiomorpholine, dioxane, dithiane, and dithiolane, any one of which is optionally substituted with one or more $R^6$. In certain embodiments, $Z^1$ is piperidine optionally substituted with one or more $R^6$. In certain embodiments, $Z^1$ is phenyl optionally substituted with one or more $R^6$.

In certain embodiments, for a compound of Formula (I) or (II), $Z^1$ is 3- to 12-membered heterocycle substituted with a substituent selected from $-(C(R^5)_2)_n-X-(C(R^5)_2)_p-R^3$ and $-X-C_{1-6}$ alkyl-$R^3$, and $Z^1$ is further optionally substituted with one or more $R^6$. In certain embodiments, $Z^1$ is substituted with $-X-C_{1-6}$ alkyl-$R^3$, such as $Z^1$ is substituted with $-X-C_{1-2}$ alkyl-$R^3$, wherein X is a bond.

In certain embodiments, for a compound of Formula (I) or (II), $R^3$ may be carbocycle, such as $C_{3-10}$carbocycle, optionally substituted with one or more $R^6$, such as $R^3$ is selected from:

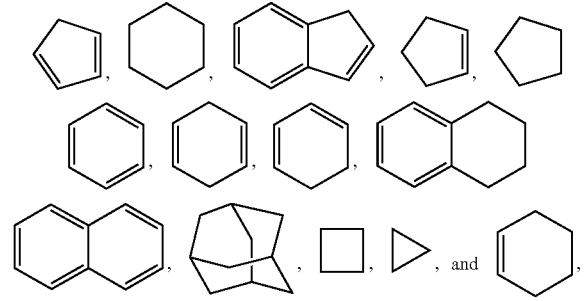

any one of which is optionally substituted with one or more $R^6$. In certain embodiments, for a compound of Formula (I) or (II), $R^3$ may be carbocycle optionally substituted with one or more $R^6$, such as $R^3$ is selected from:

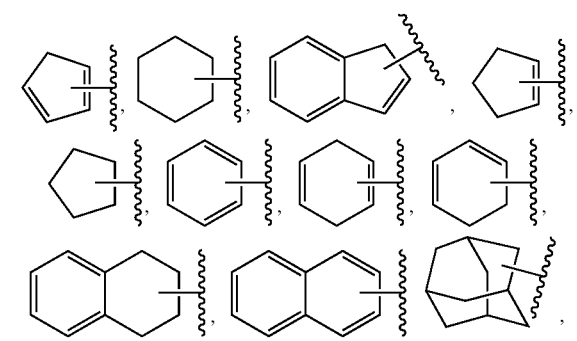

-continued

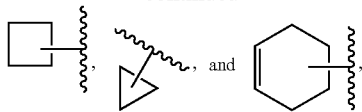

any one of which is optionally substituted with one or more $R^6$. In certain embodiments, $R^3$ is cyclohexene optionally substituted with one or more $R^6$.

In certain embodiments, for a compound of Formula (I) or (II), $R^3$ is selected from:

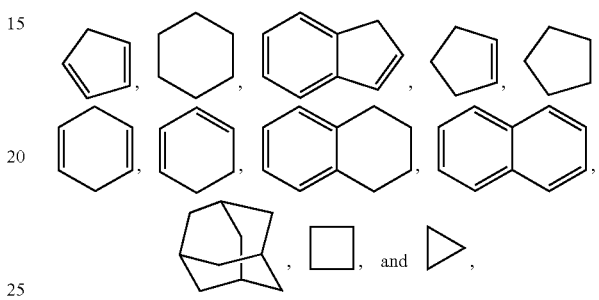

any one of which is optionally substituted with one or more $R^6$.

In certain embodiments, for a compound of Formula (I) or (II), $R^3$ is selected from:

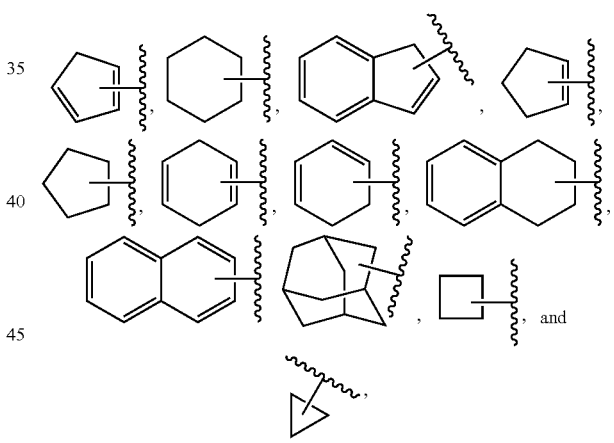

any one of which is optionally substituted with one or more $R^6$.

In certain embodiments, for a compound or salt of Formula (I) or (II), $R^3$ is selected from heterocycloalkyl and heterocycloalkenyl, such as azetidine, oxetane, thietane, pyrrolidine, pyrroline, tetrahydrofuran, dihydrofuran, thiolane, dihydrothiophene, imidazolidine, imidazoline, pyrazolidine, oxazolidine, oxazoline, isoxazolidine, isoxazoline, thiazolidine, thiazoline, isothiazolidine, dioxolane, piperazine, piperidine, morpholine, thiomorpholine, dioxane, dithiane, and dithiolane, any one of which is optionally substituted with one or more $R^6$. In certain embodiments, $R^3$ is substituted with $C_{3-12}$ carbocycle or 3- to 12-membered heterocycle, wherein the $C_{3-12}$ carbocycle and 3- to 12-membered heterocycle are optionally substituted with one or more substituents selected from halogen, $-NO_2$, $-CN$, $-OR^{10}$, $-SR^{10}$, $-N(R^{10})_2$, $-S(=O)R^{10}$, $-S(=O)_2R^{10}$, —S(=O)₂N(R¹⁰)₂, —NR¹⁰S(=O)₂R¹⁰, —C(O)R¹⁰, —C(O)OR¹⁰, —OC(O)R¹⁰, —OC(O)OR¹⁰, —OC(O)N (R¹⁰)₂, —NR¹⁰C(O)R¹⁰, —C(O)N(R¹⁰)₂, =O, =S, =N(R¹⁰), —P(O)(OR¹⁰)₂, —OP(O)(OR¹⁰)₂, C₁₋₆ alkyl, C₁₋₆haloalkyl, C₂₋₆ alkenyl, and C₂₋₆ alkynyl. In certain embodiments, R³ is C₃₋₁₂ carbocycle substituted with C₃₋₁₂ carbocycle.

In certain embodiments, for a compound or salt of Formula (I) or (II):

Z¹ is 3- to 12-membered heterocycle substituted with —X—C₁₋₆ alkyl-R³ and Z¹ is further optionally substituted with one or more R⁶;

Z² is C₃₋₁₂ carbocycle optionally substituted with one or more R⁶;

R¹ is hydrogen;

Z³ is C₃₋₁₂ carbocycle optionally substituted with one or more R⁶;

L¹ is heteroalkylene optionally substituted at each occurrence with one or more R⁶, such as L¹ is selected from —(CH₂)ₛ—X¹⁰—(CH₂)ᵣ—, —(CH₂)ᵣ—X¹⁰—(CH₂)ᵣ—X¹⁰—(CH₂)ᵣ—, and —(CH₂)ᵣ—X¹⁰—(CH₂)ᵣ—X¹⁰—(CH₂)ᵣ—X¹⁰—(CH₂)ᵣ—, wherein s is selected from 0 to 3, each r is selected from 1 to 4, each X¹⁰ is selected from —O—, —S—, or —N(R⁴)—, and L¹ may be optionally substituted with one or more R⁶;

L² is Y-alkylene;

Y is 3- to 12-membered heterocycle;

W and W¹ are independently selected from —O—, —S— and —NR¹⁰—;

R² and R²* are independently selected from R⁷, or R² and R²* are taken together with the atoms to which they are attached to form a heterocycle, optionally substituted with one or more R⁶; and R³, R⁶, R⁷, R¹⁰ and X are as described for Formula (I) and (II).

In certain embodiments, for a compound or salt of Formula (I) or (II):

Z¹ is 3- to 12-membered heterocycle substituted with —X—C₁₋₆ alkyl-R³ and Z¹ is further optionally substituted with one or more R⁶;

Z² is C₃₋₁₂ carbocycle optionally substituted with one or more R⁶;

R¹ is hydrogen;

Z³ is C₃₋₁₂ carbocycle optionally substituted with one or more R⁶;

L¹ is heteroalkylene optionally substituted at each occurrence with one or more R⁶, such as L¹ is selected from —(CH₂)ₛ—X¹⁰—(CH₂)ᵣ—, —(CH₂)ᵣ—X¹⁰—(CH₂)ᵣ—X¹⁰—(CH₂)ᵣ—, and —(CH₂)ᵣ—X¹⁰—(CH₂)ᵣ—X¹⁰—(CH₂)ᵣ—X¹⁰—(CH₂)ᵣ—, wherein s is selected from 0 to 3, each r is selected from 1 to 4, each X¹⁰ is selected from —O—, —S—, or —N(R⁴)—, and L¹ may be optionally substituted with one or more R⁶;

L² is Y-alkylene;

Y is 3- to 12-membered heterocycle;

W—R²* is selected from: —OH, —O—CH₃, —O—CH₂CH₃, —O—CH₂-Ph, —O-Ph,

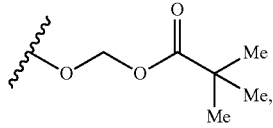

and W¹—R² is selected from —O—CH₃, —O—CH₂CH₃, —O—CH₂-Ph, —O-Ph,

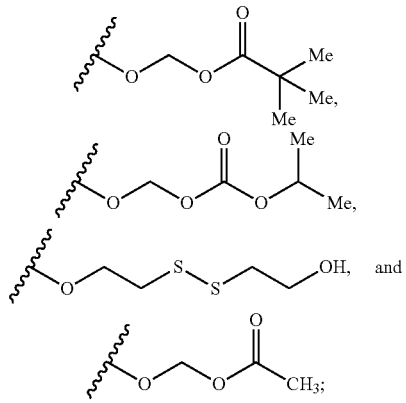

and

R³, R⁶, R⁷, R¹⁰ and X are as described for Formula (I) and (II).

In certain embodiments, for a compound or salt of Formula (II):

Z¹ is 3- to 12-membered heterocycle substituted with —X—C₁₋₆ alkyl-R³ and Z¹ is further optionally substituted with one or more R⁶;

Z² is C₃₋₁₂ carbocycle optionally substituted with one or more R⁶;

R¹ is hydrogen;

Z³ is C₃₋₁₂ carbocycle optionally substituted with one or more R⁶;

L¹ is heteroalkylene optionally substituted at each occurrence with one or more R⁶, such as L¹ is selected from —(CH₂)ₛ—X¹⁰—(CH₂)ᵣ—, —(CH₂)ᵣ—X¹⁰—(CH₂)ᵣ—X¹⁰—(CH₂)ᵣ—, and —(CH₂)ᵣ—X¹⁰—(CH₂)ᵣ—X¹⁰—(CH₂)ᵣ—X¹⁰—(CH₂)ᵣ—, wherein s is selected from 0 to 3, each r is selected from 1 to 4, each X¹⁰ is selected from —O—, —S—, or —N(R⁴)—, and L¹ may be optionally substituted with one or more R⁶;

L² is Y-alkylene;

Y is 3- to 12-membered heterocycle;

W—R²* is selected from: —OH, —O—CH₃, —O—CH₂CH₃, —O—CH₂-Ph, —O-Ph,

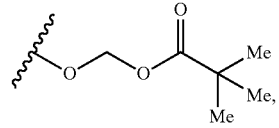

-continued

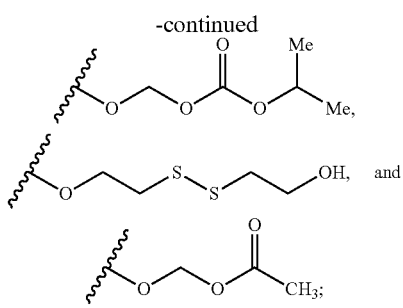

and $W^1$—$R^2$ is selected from —OH, —O—$CH_3$, —O—$CH_2CH_3$, —O—$CH_2$-Ph, —O-Ph,

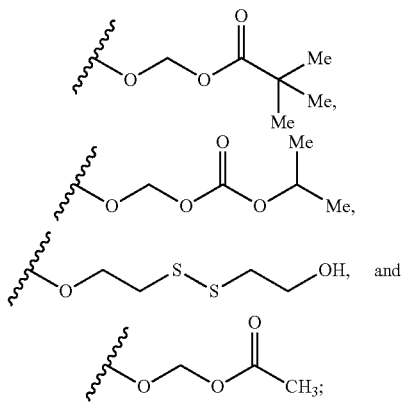

and $R^3$, $R^6$, $R^7$, $R^{10}$ and X are as described for Formula (II).

In certain embodiments, for a compound or salt of Formula (I) or (II):

$Z^1$ is 5- 6-membered heterocycle, substituted with —X—$C_{1-6}$ alkyl-$R^3$ and $Z^1$ is further optionally substituted with one or more $R^6$;

$Z^2$ is $C_{5-6}$ carbocycle optionally substituted with one or more $R^6$;

$R^1$ is hydrogen;

$Z^3$ is $C_{5-6}$ carbocycle optionally substituted with one or more $R^6$;

$L^1$ is heteroalkylene optionally substituted at each occurrence with one or more $R^6$, such as $L^1$ is selected from:

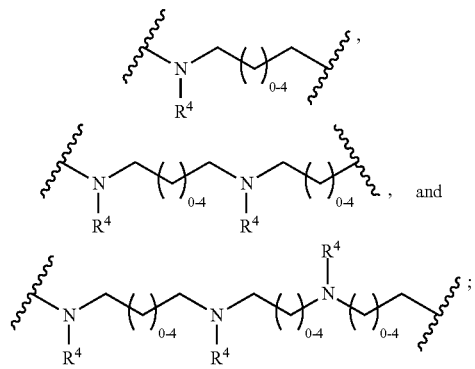

$L^2$ is Y-alkylene, such as $L^2$ is selected from:

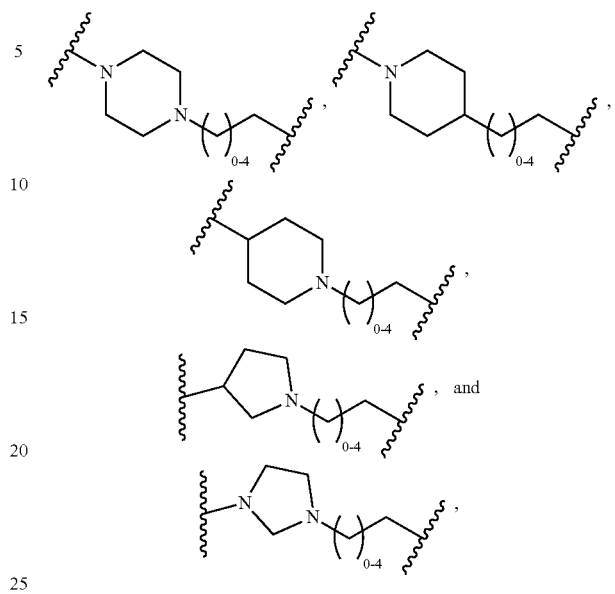

any one of which is optionally substituted by one or more $R^6$;

Y is 3- to 12-membered heterocycle;

W and $W^1$ are independently selected from —O—, —S— and —$NR^{10}$—;

$R^2$ and $R^{2*}$ are independently selected from $R^7$, or $R^2$ and $R^{2*}$ are taken together with the atoms to which they are attached to form a heterocycle, optionally substituted with one or more $R^6$; and $R^3$, $R^4$, $R^6$, $R^7$, $R^{10}$ and X are as described for Formula (I) and (II).

In certain embodiments, for a compound or salt of Formula (I) or (II):

$Z^1$ is piperazine, substituted with —X—$C_{1-6}$ alkyl-$R^3$ and $Z^1$ is further optionally substituted with one or more $R^6$;

X is a bond;

$R^3$ is $C_{5-6}$ carbocycle, such as cyclohexene, optionally substituted with one or more $R^6$;

$Z^2$ is phenyl optionally substituted with one or more $R^6$;

$R^1$ is hydrogen;

$Z^3$ is phenyl optionally substituted with one or more $R^6$;

$L^1$ is heteroalkylene optionally substituted at each occurrence with one or more $R^6$, such as $L^1$ is selected from:

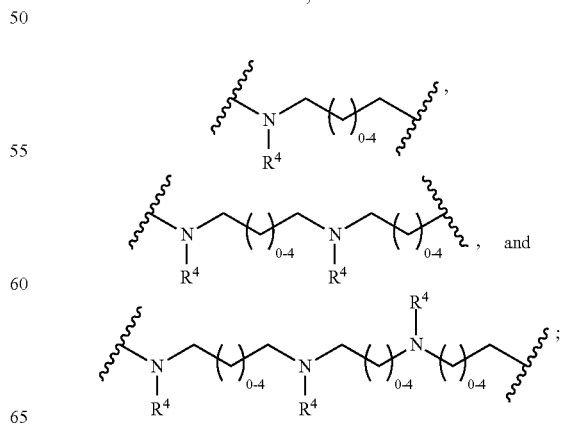

$L^2$ is Y-methylene, Y-ethylene, or Y-propylene;

Y is 5- to 6-membered heterocycle, such as piperidine or piperazine, optionally substituted with one or more $R^6$;

W and $W^1$ are independently selected from —O—, —S— and —NR$^{10}$—;

$R^2$ and $R^{2*}$ are independently selected from $R^7$, or $R^2$ and $R^{2*}$ are taken together with the atoms to which they are attached to form a heterocycle, optionally substituted with one or more $R^6$; and $R^4$, $R^6$, $R^7$, and $R^{10}$ are as described for Formula (I) and (II).

In certain embodiments, for a compound or salt of Formula (I) or (II):

$Z^1$ is piperazine, substituted with —X—$C_{1-6}$ alkyl-$R^3$ and $Z^1$ is further optionally substituted with one or more $R^6$;

X is a bond;

$R^3$ is $C_{5-6}$ carbocycle optionally substituted with one or more $R^6$;

$Z^2$ is phenyl optionally substituted with one or more $R^6$;

$R^1$ is hydrogen;

$Z^3$ is phenyl optionally substituted with one or more $R^6$;

$L^1$ is heteroalkylene optionally substituted at each occurrence with one or more $R^6$, such as $L^1$ is selected from:

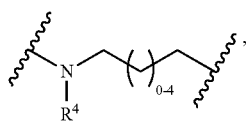

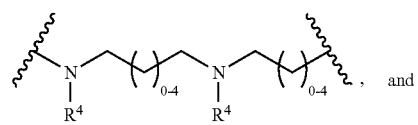

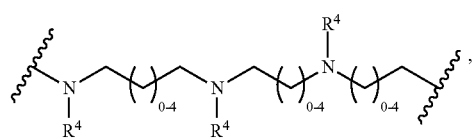

$L^2$ is a bond;

W and $W^1$ are independently selected from —O—, —S— and —NR$^{10}$—;

$R^2$ and $R^{2*}$ are independently selected from $R^7$, or $R^2$ and $R^{2*}$ are taken together with the atoms to which they are attached to form a heterocycle, optionally substituted with one or more $R^6$; and $R^4$, $R^6$, $R^7$, and $R^{10}$ are as described for Formula (I) and (II).

In certain embodiments, for a compound or salt of Formula (I) or (II):

$Z^1$ is piperazine, substituted with —X—$C_{1-6}$ alkyl-$R^3$ and $Z^1$ is further optionally substituted with one or more $R^6$;

X is a bond;

$R^3$ is $C_{5-6}$ carbocycle, such as cyclohexene, optionally substituted with one or more $R^6$;

$Z^2$ is phenyl optionally substituted with one or more $R^6$;

$R^1$ is hydrogen;

$Z^3$ is phenyl optionally substituted with one or more $R^6$;

$L^1$ is heteroalkylene optionally substituted at each occurrence with one or more $R^6$; such as $L^1$ is selected from:

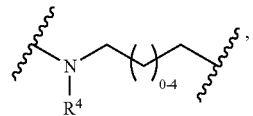

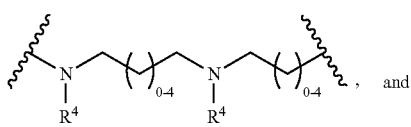

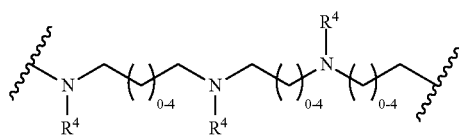

$L^2$ is a bond;

—W—$R^{2*}$ and $W^1$—$R^2$ are independently selected from:

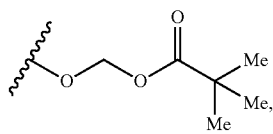

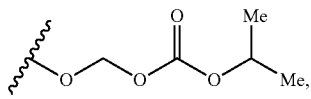

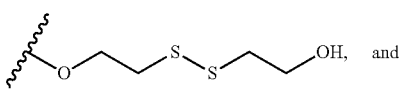

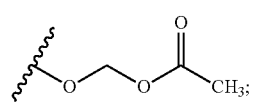

and $R^4$, $R^6$, $R^7$, and $R^{10}$ are as described for Formula (I) and (II).

In certain embodiments, a compound or salt of Formula (I) is represented by Formula (III):

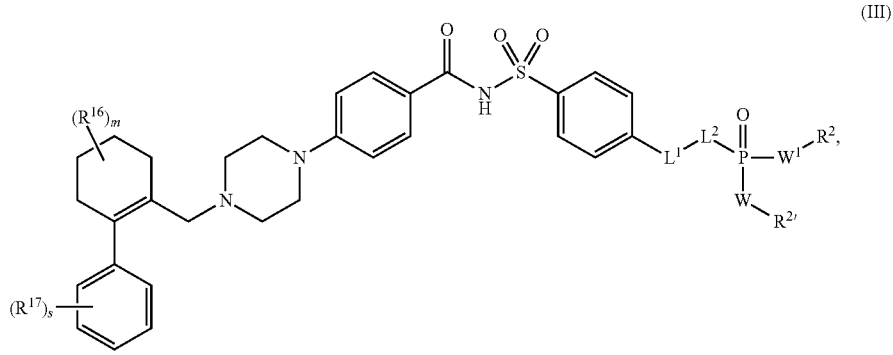

(III)

wherein:
$L^1$, $L^2$, W, $W^1$, $R^2$, and $R^{2*}$ are as defined for Formula (I);
$R^{16}$, $R^{17}$ and $R^{18}$ are independently selected at each occurrence from $R^6$; and m, s, and r are independently selected from 0 to 6.

In certain embodiments, a compound or salt of Formula (I) is represented by Formula (IV):

wherein:
$L^2$, W, $W^1$, $R^2$, and $R^{2*}$ are as defined for Formula (I);

$R^{16}$, $R^{17}$ and $R^{18}$ are independently selected at each occurrence from $R^6$;

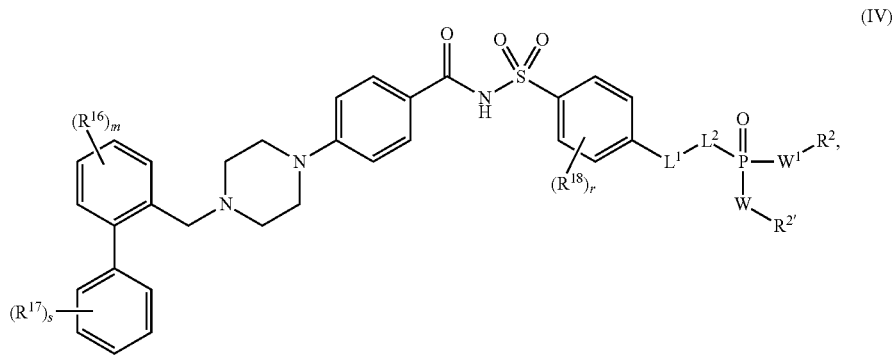

(IV)

wherein:
$L^1$, $L^2$, W, $W^1$, $R^2$, and $R^{2*}$ are as defined for Formula (I);
$R^{16}$, $R^{17}$ and $R^{18}$ are independently selected at each occurrence from $R^6$; and
m, s, and r are independently selected from 0 to 6.

In certain embodiments, a compound or salt of Formula (I) is represented by Formula (V):

$R^{19}$ is selected at each occurrence from hydrogen and $R^6$; and
m, s, and r are independently selected from 0 to 6.

In certain embodiments, a compound or salt of Formula (I) is represented by Formula (VI):

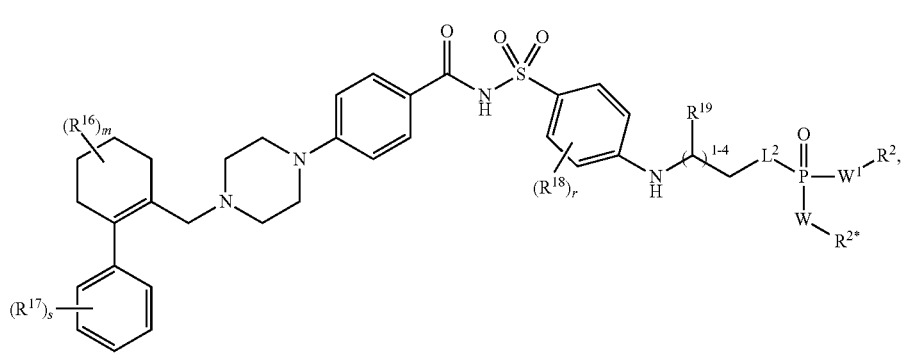

(V)

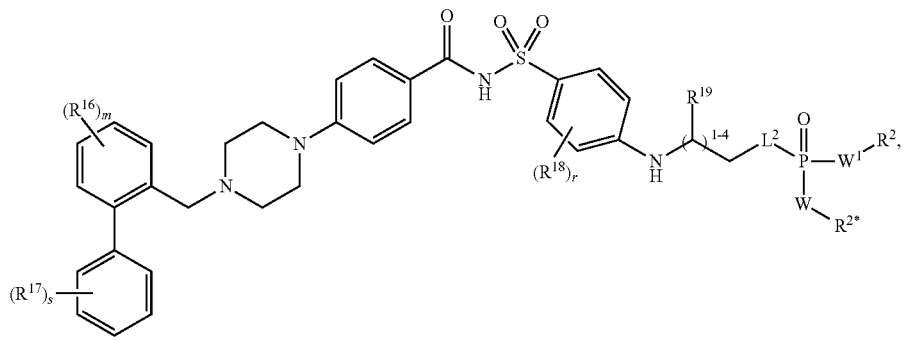

(VI)

wherein:

$L^2$, W, $W^1$, $R^2$, and $R^{2*}$ are as defined for Formula (I);

$R^{10}$, $R^{17}$ and $R^{18}$ are independently selected at each occurrence from $R^6$;

$R^{19}$ is selected at each occurrence from hydrogen and $R^6$; and m, s, and r are independently selected from 0 to 6.

In certain embodiments, the disclosure provides a compound or salt of Formula (III) or (IV), wherein $L^1$ is heteroalkylene optionally substituted at each occurrence with one or more $R^6$, such as $L^1$ is selected from:

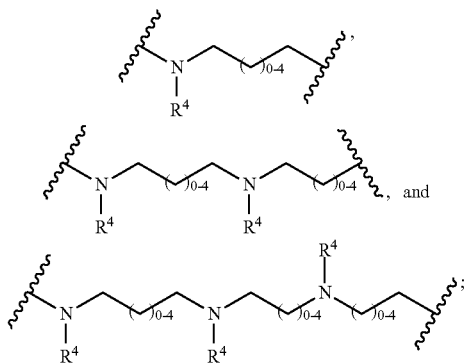

$L^2$ is a bond or Y-alkylene, such as Y-methylene, Y-ethylene, or Y-propylene; Y is 5- to 6-membered heterocycle, such as piperidine or piperazine, optionally substituted with one or more $R^6$; W and $W^1$ are independently selected from —O—, —S— and —$NR^{10}$—; $R^2$ and $R^{2*}$ are independently selected from $R^7$, or $R^2$ and $R^{2*}$ are taken together with the atoms to which they are attached to form a heterocycle, optionally substituted with one or more $R^6$.

In certain embodiments, the disclosure provides a compound or salt of Formula (V) or (VI), wherein $L^2$ is Y-alkylene, such as Y-methylene, Y-ethylene, or Y-propylene; Y is 5- to 6-membered heterocycle, such as piperidine or piperazine, optionally substituted with one or more $R^6$; W and $W^1$ are independently selected from —O—, —S— and —$NR^{10}$—; $R^2$ and $R^{2*}$ are independently selected from $R^7$, or $R^2$ and $R^{2*}$ are taken together with the atoms to which they are attached to form a heterocycle, optionally substituted with one or more $R^6$.

Any combination of the groups described above for the various variables is contemplated herein. Throughout the specification, groups and substituents thereof can be chosen to provide stable moieties and compounds.

In some other embodiments, exemplary compounds may include, but are not limited to, a compound or salt of any one of compounds:

(6)

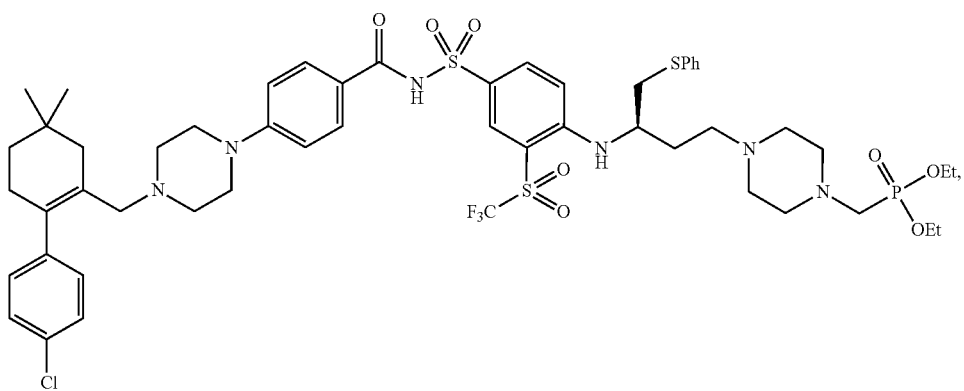

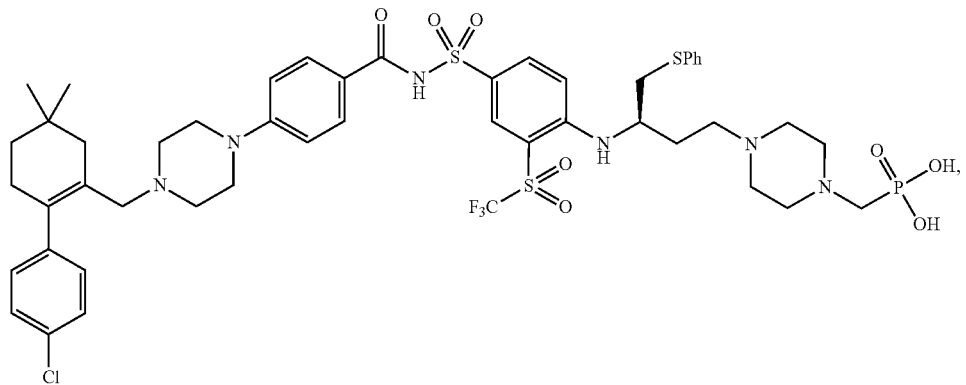
(7)
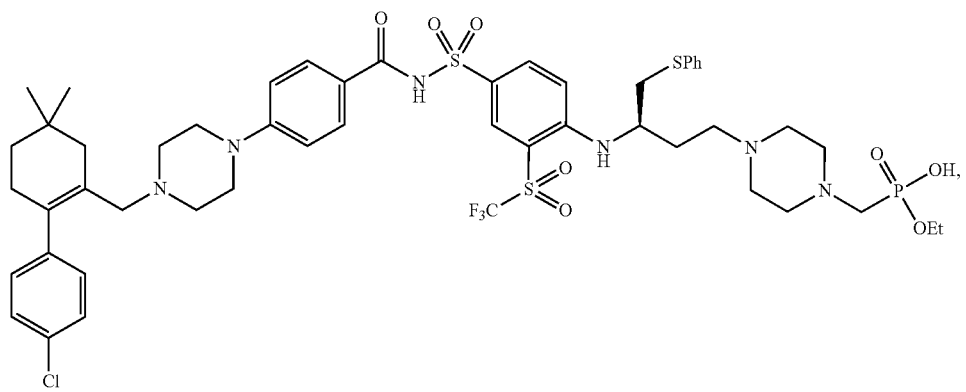
(8)
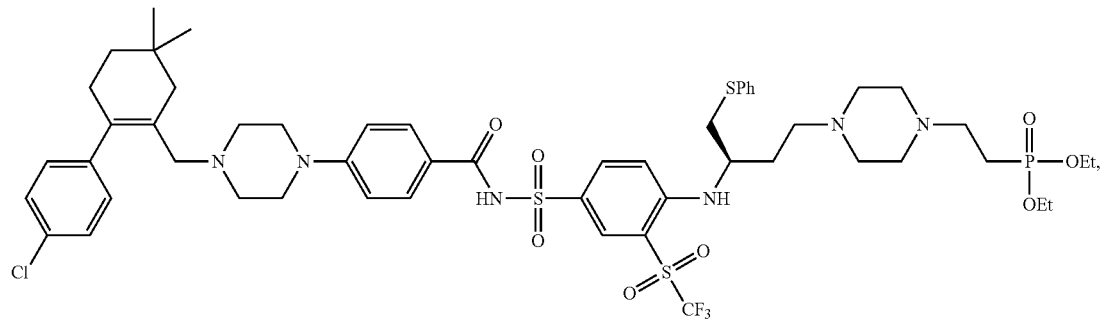
(9)
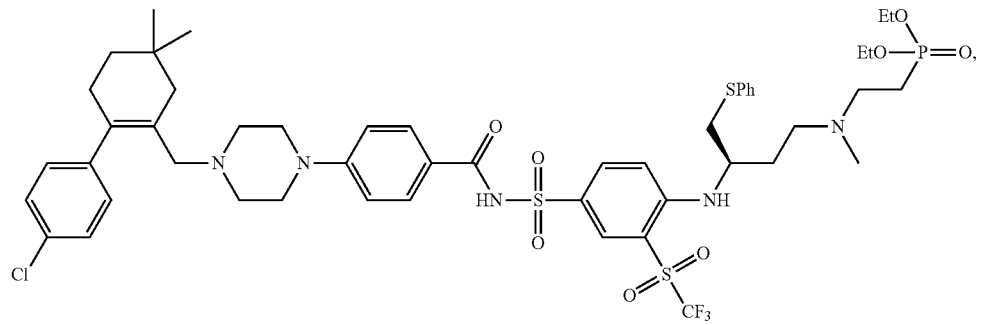
(10)

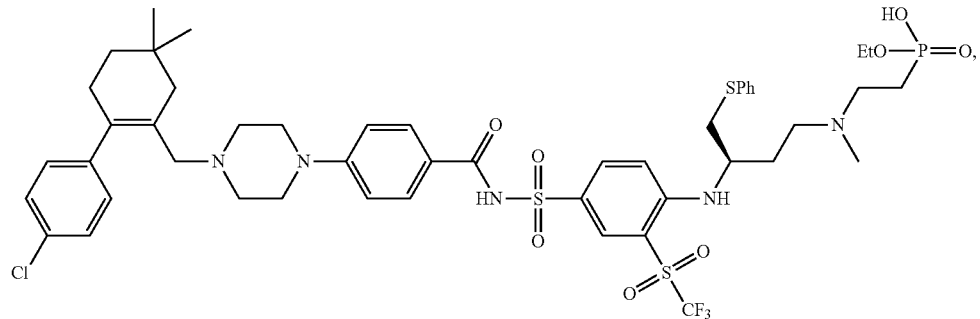
(11)
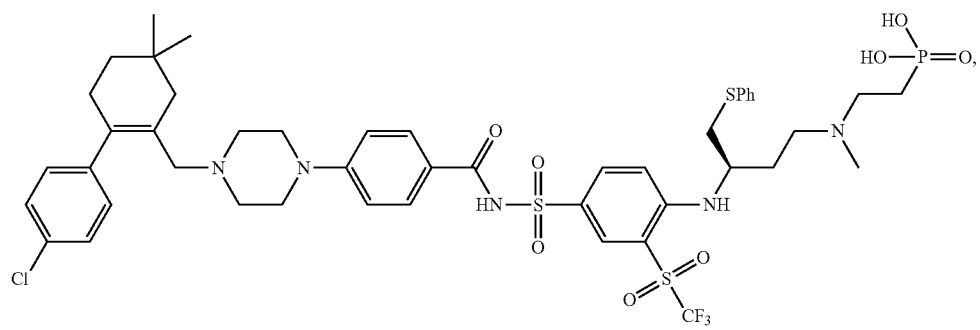
(12)
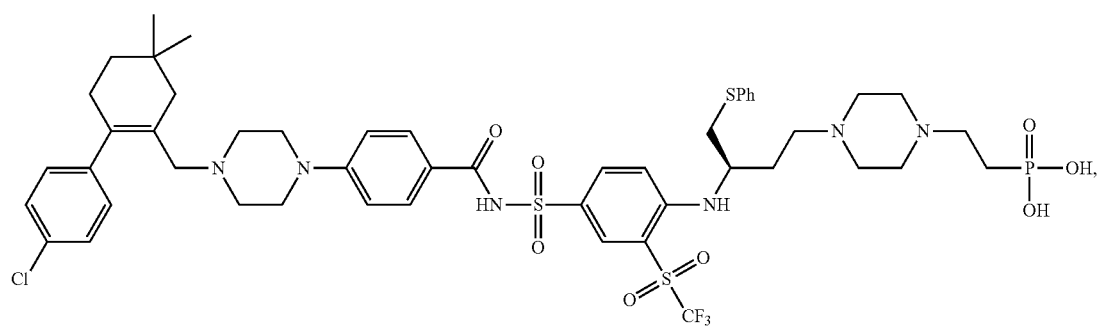
(13)
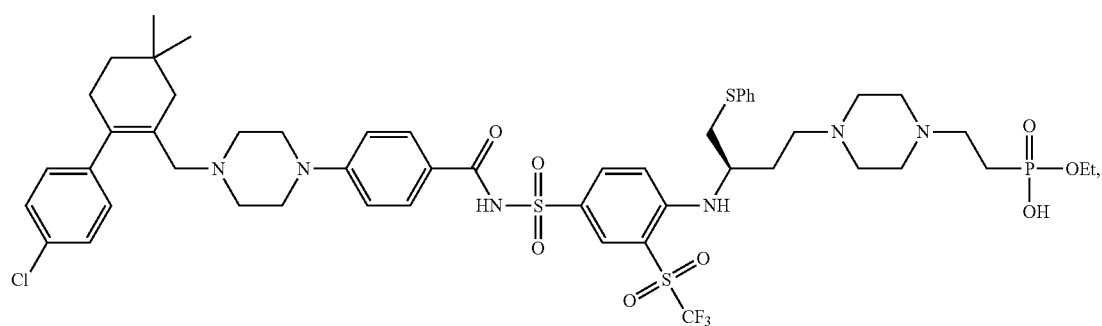
(14)

-continued
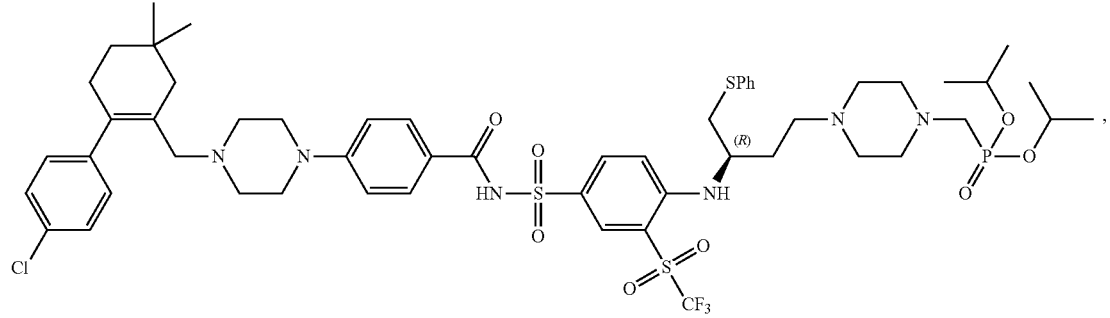
(15)
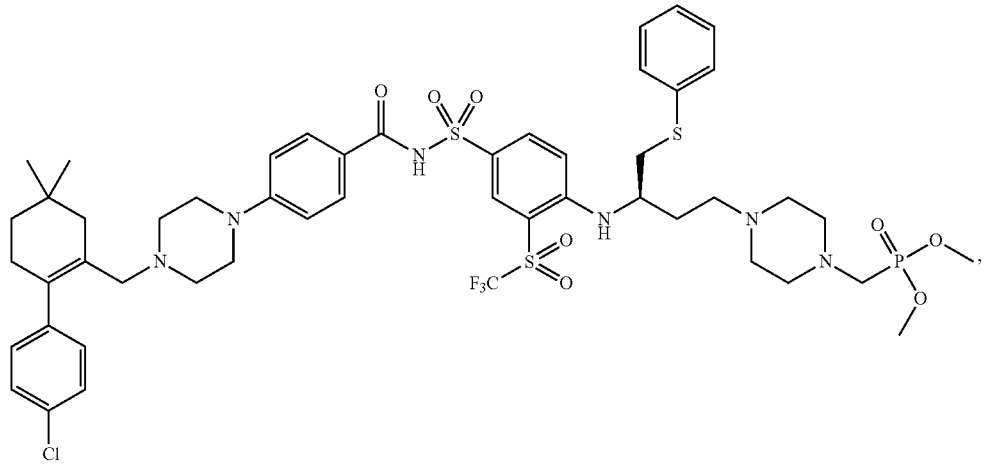
(16)
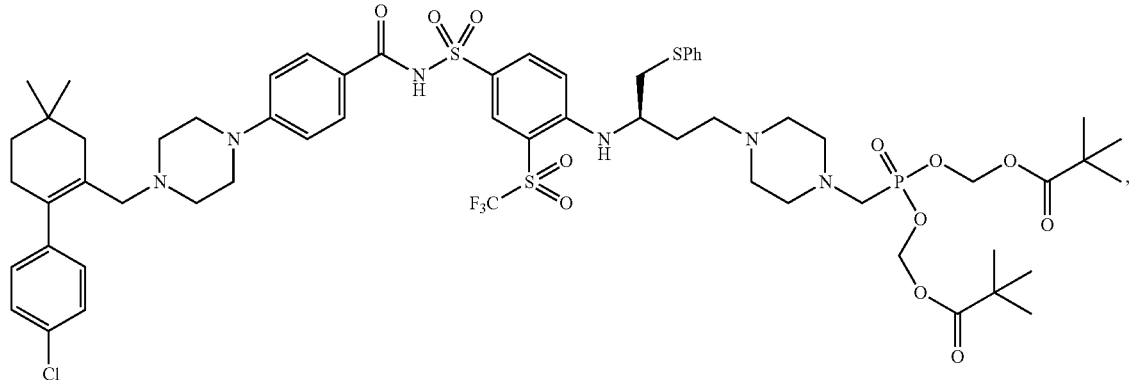
(17)
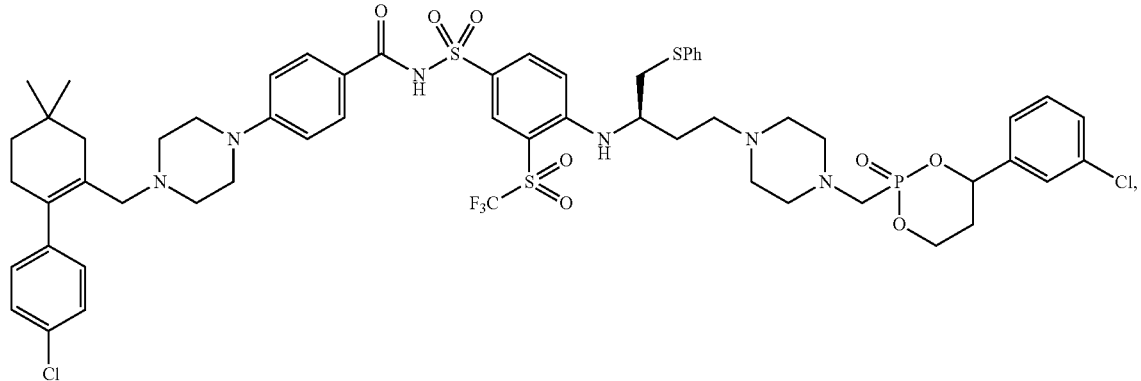
(18)

-continued
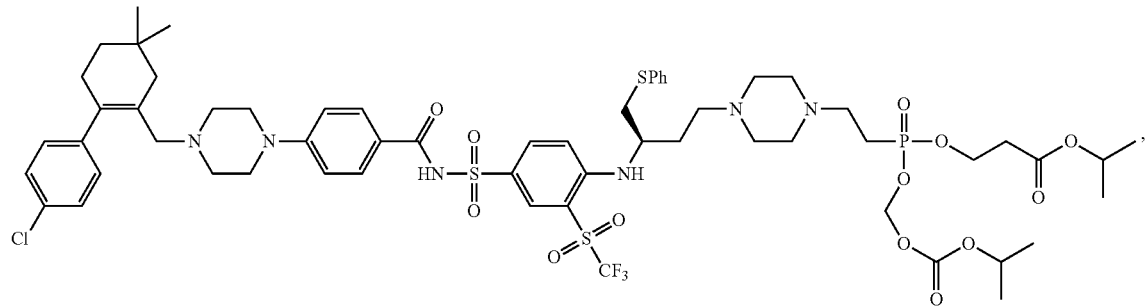
(19)
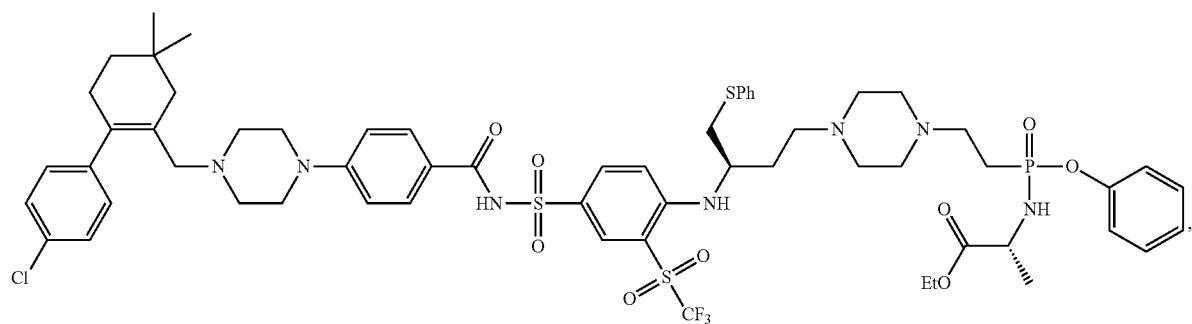
(20)
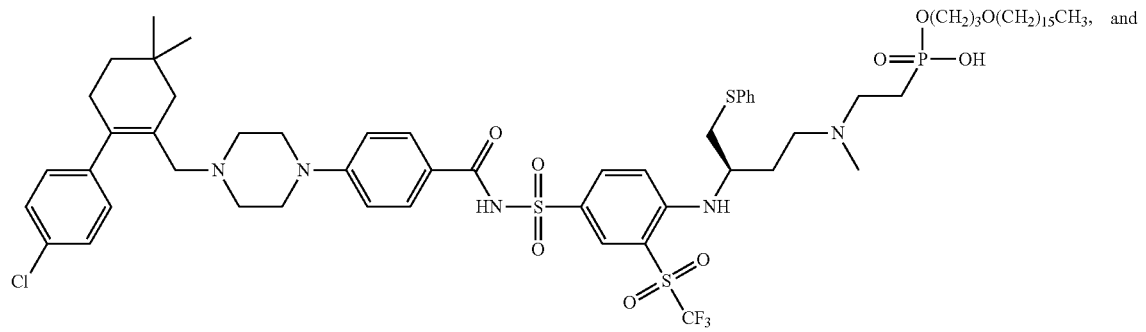
(21)
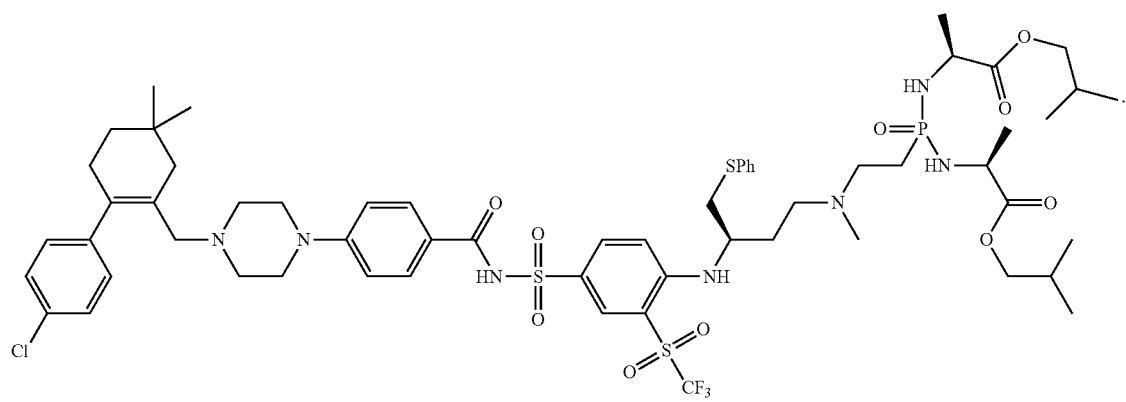
(22)

In some other embodiments, exemplary compounds may include, but are not limited to, a compound or salt of any one of compounds:
(23)
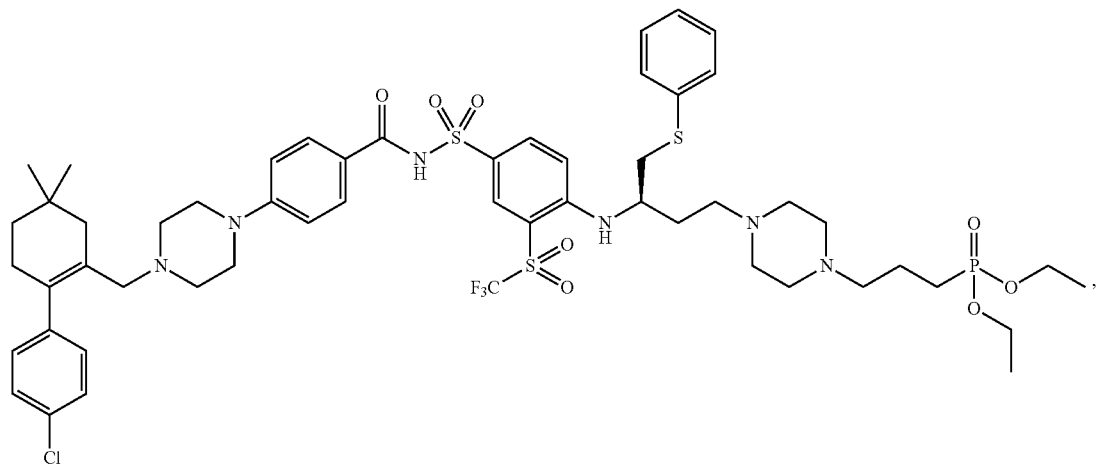
(24)
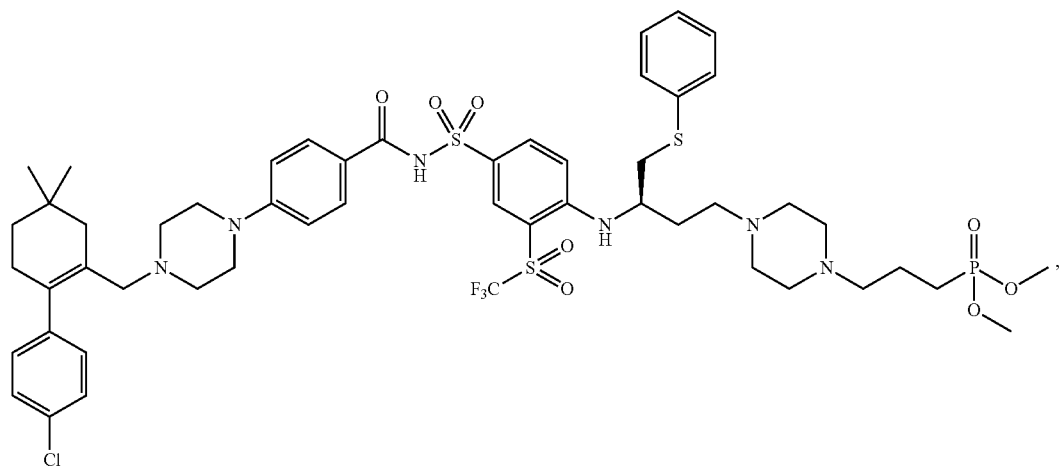
(25)
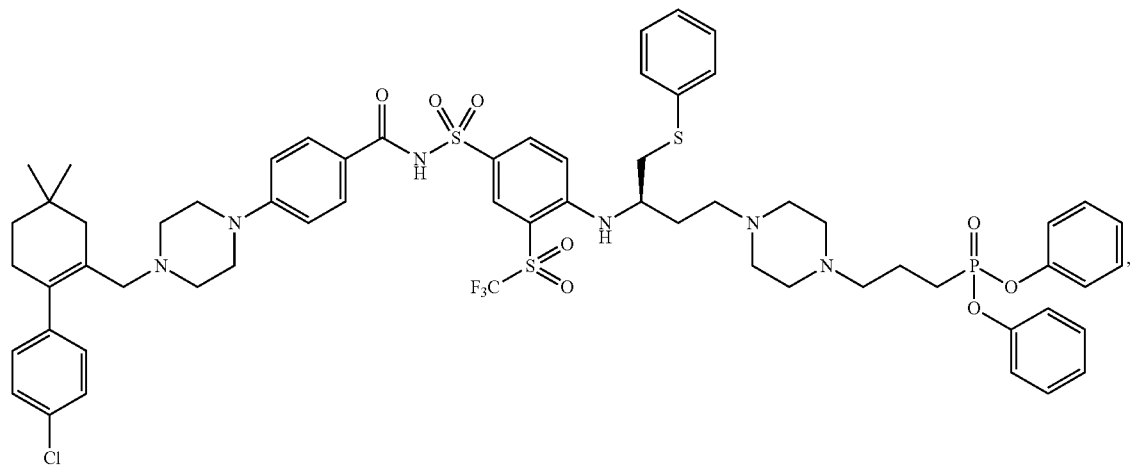

(26)
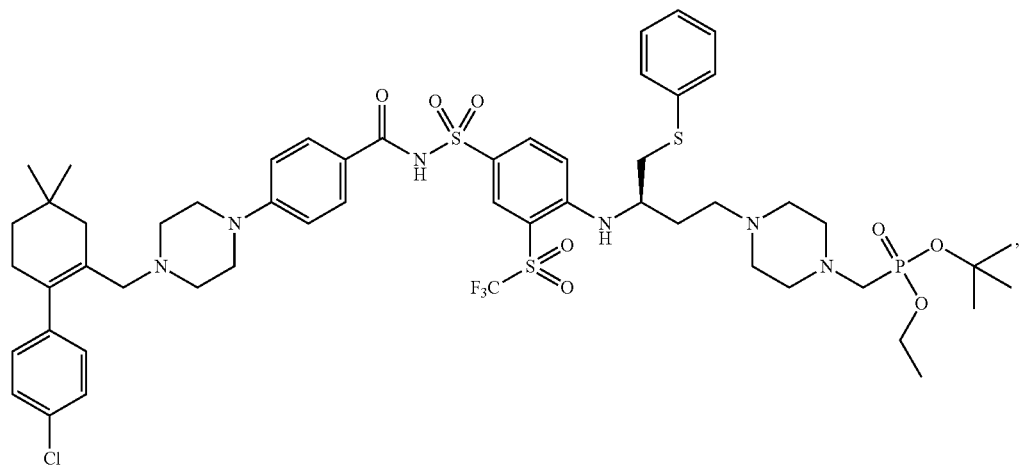
(27)
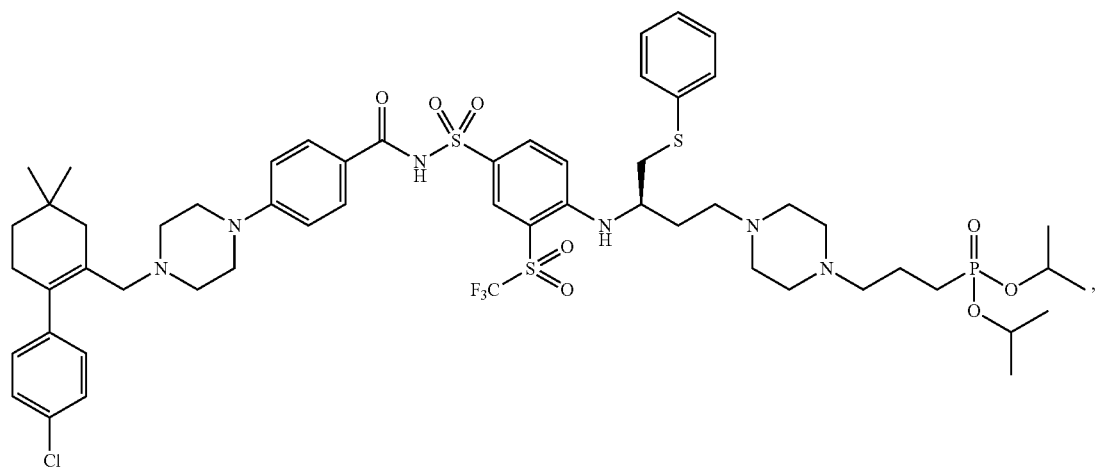
(28)
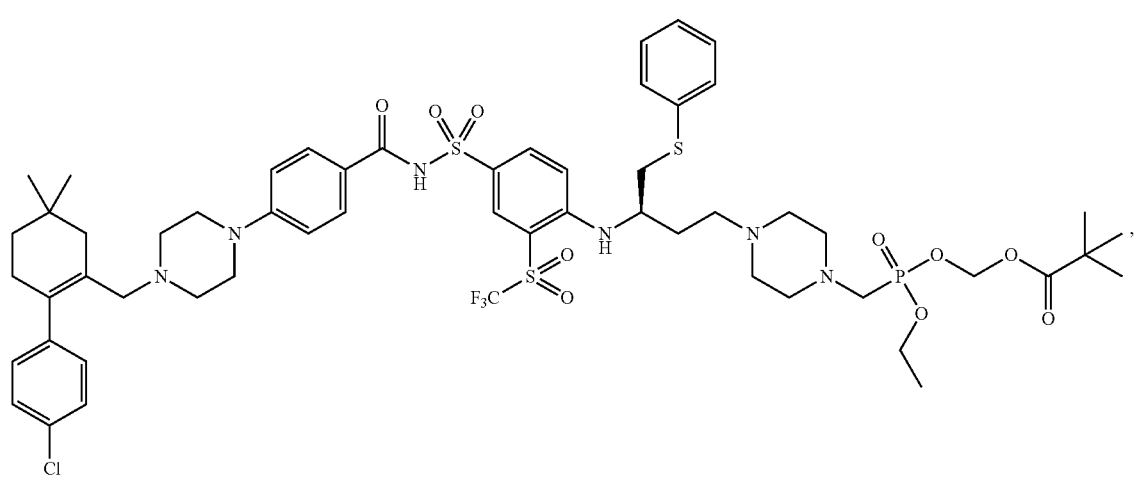

(29)
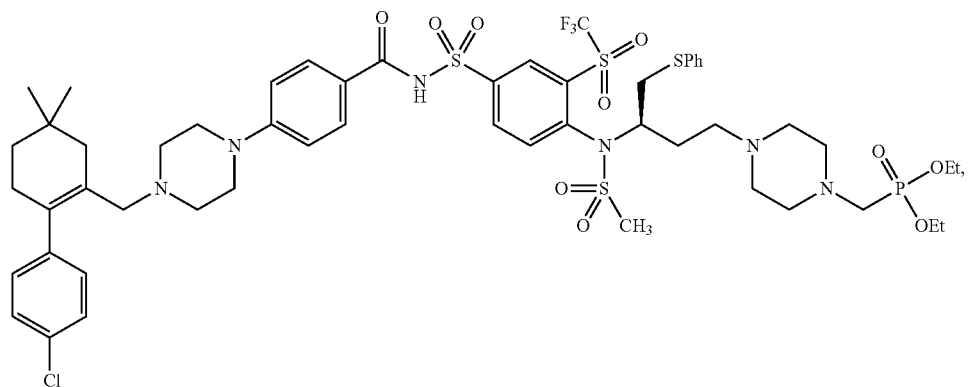
(30)
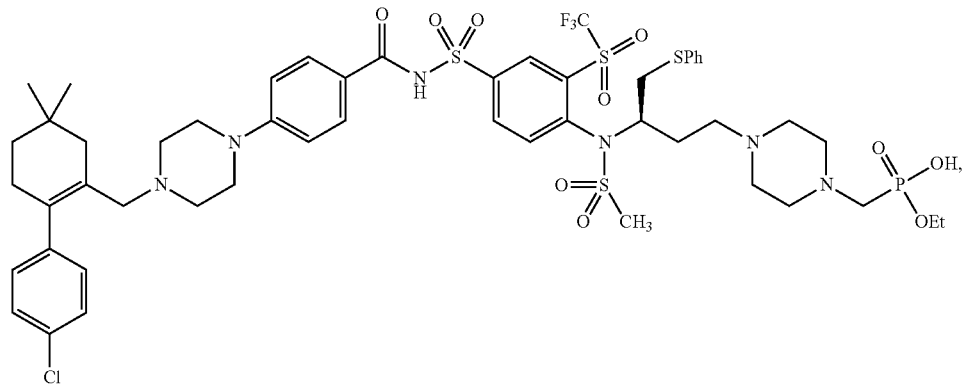
(31)
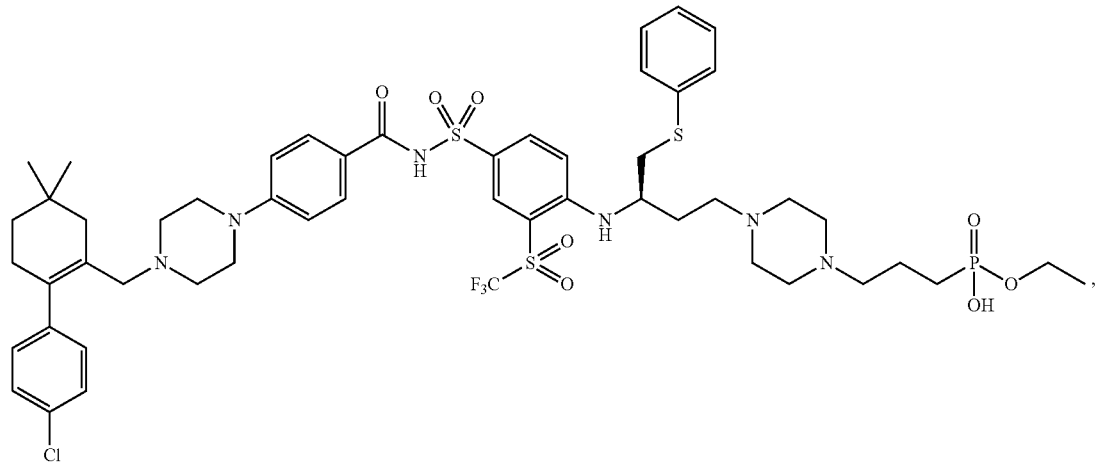

(32)
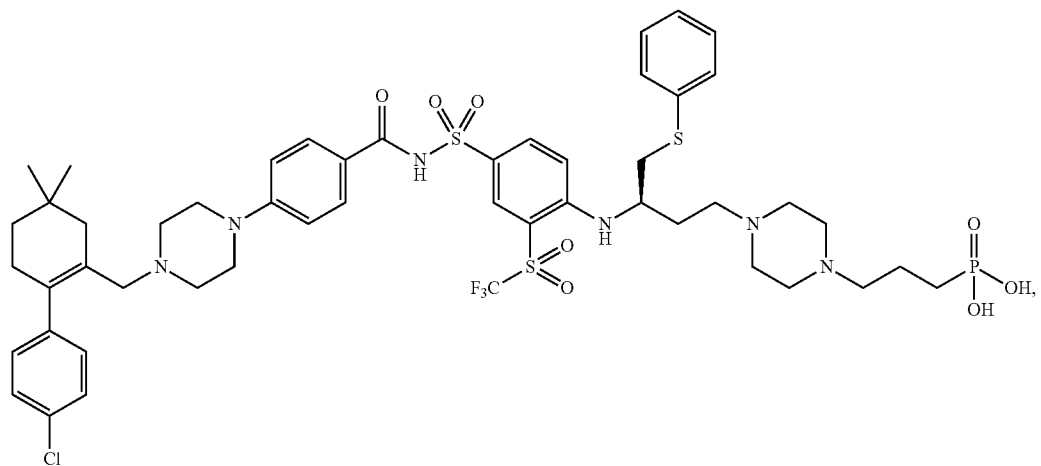
(33)
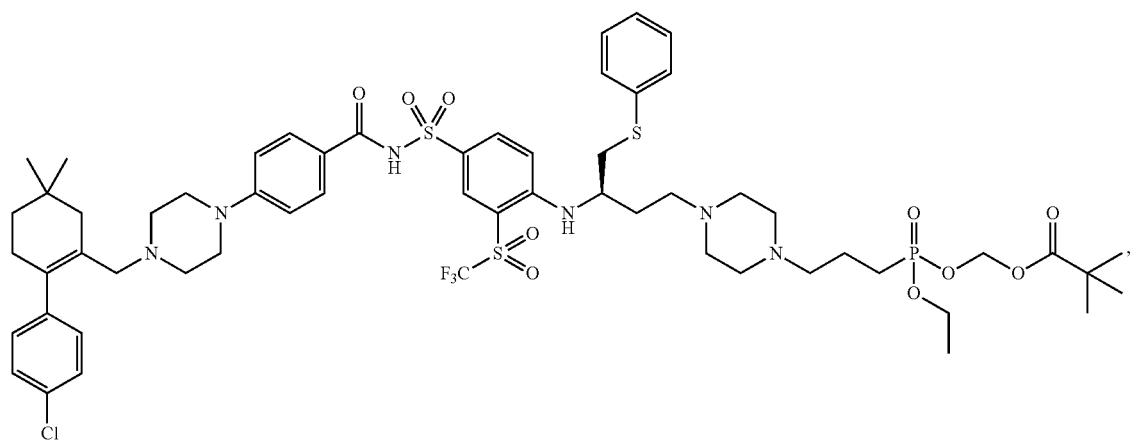
(34)
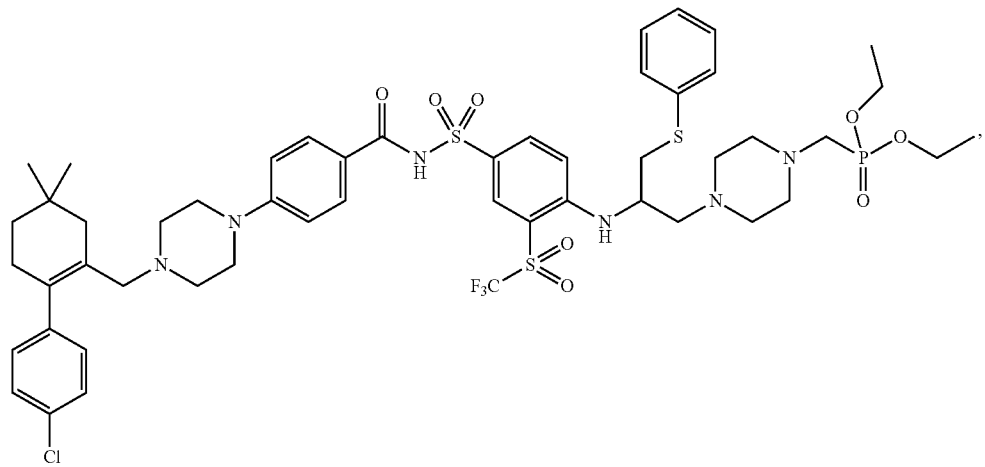

-continued
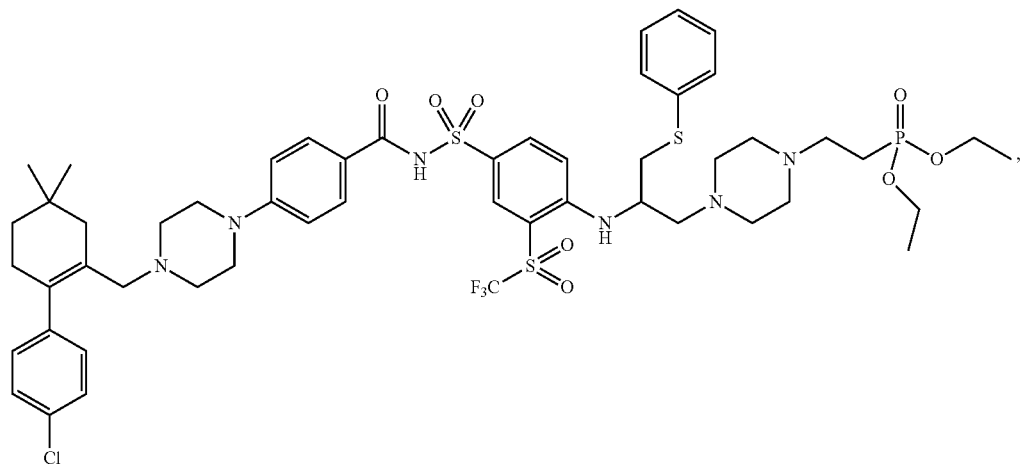
(35)
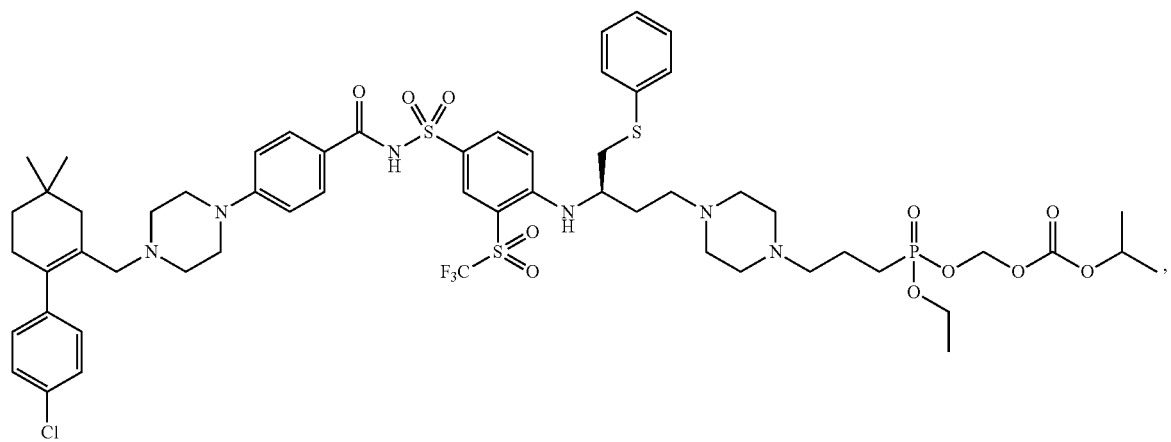
(36)
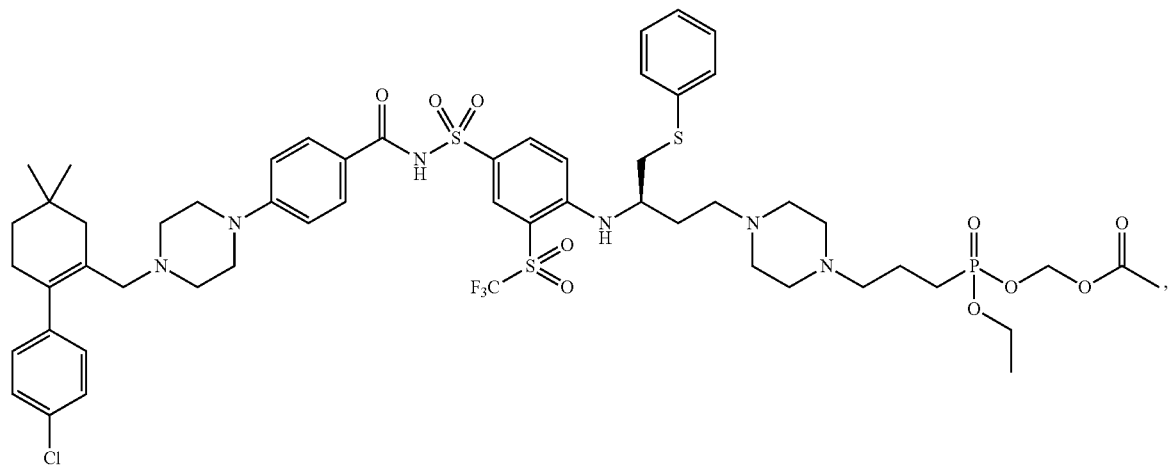
(37)

(38)
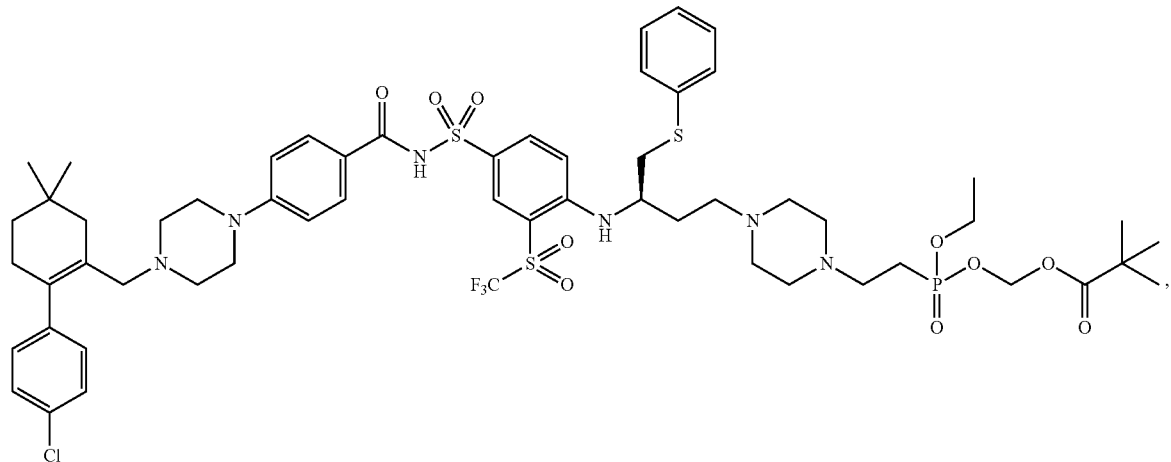
(39)
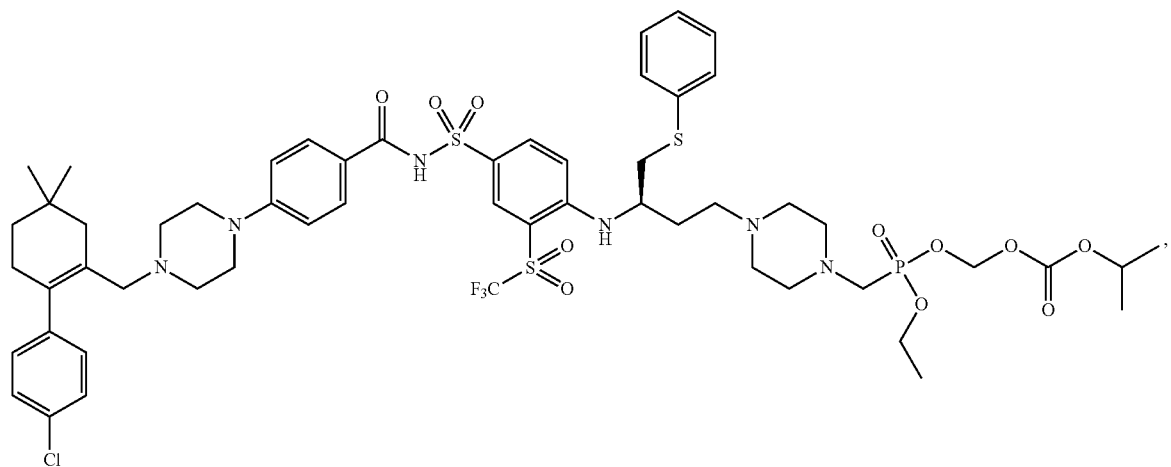
(40)
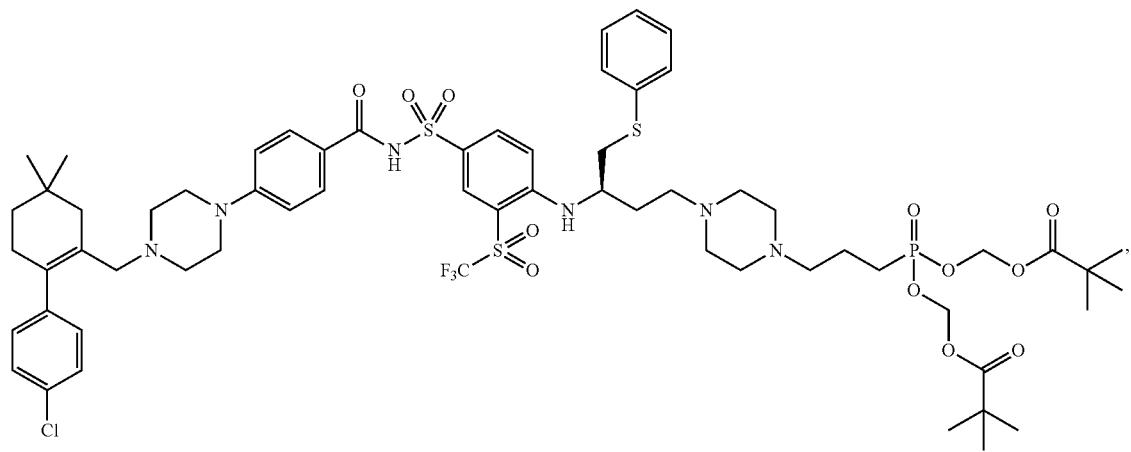

(41)
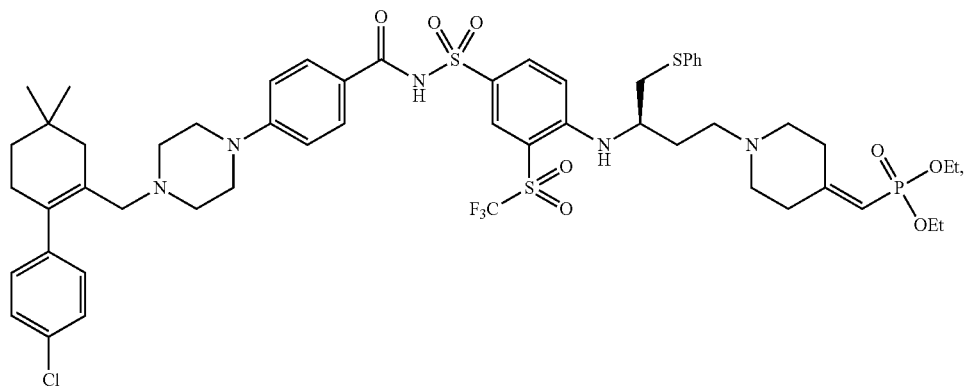
(42)
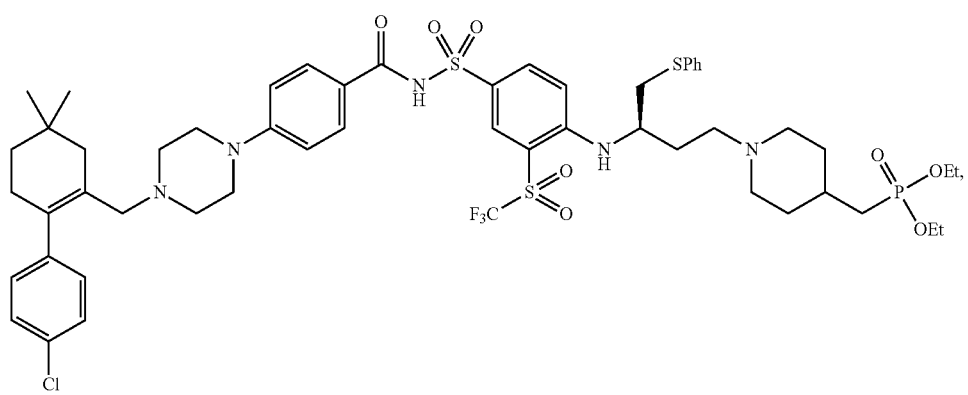
(43)
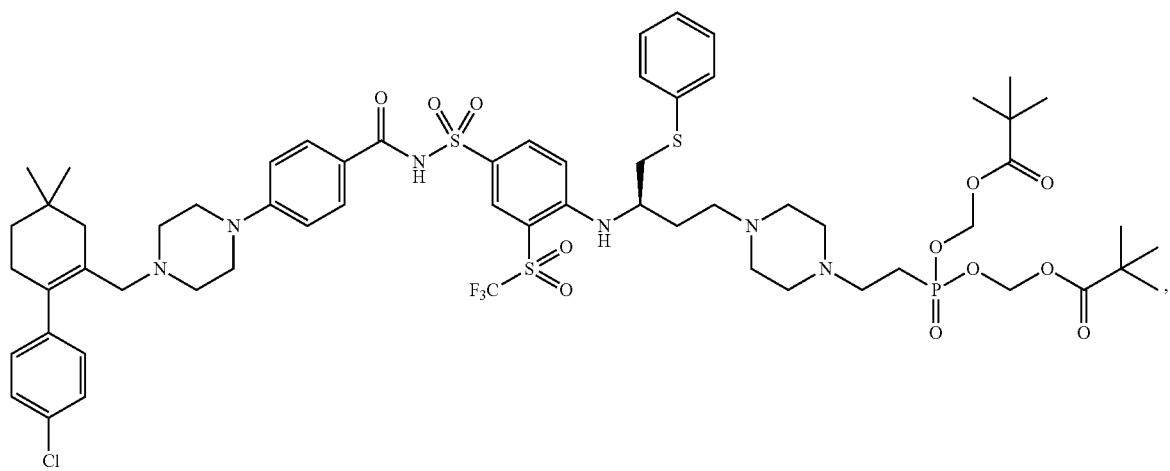

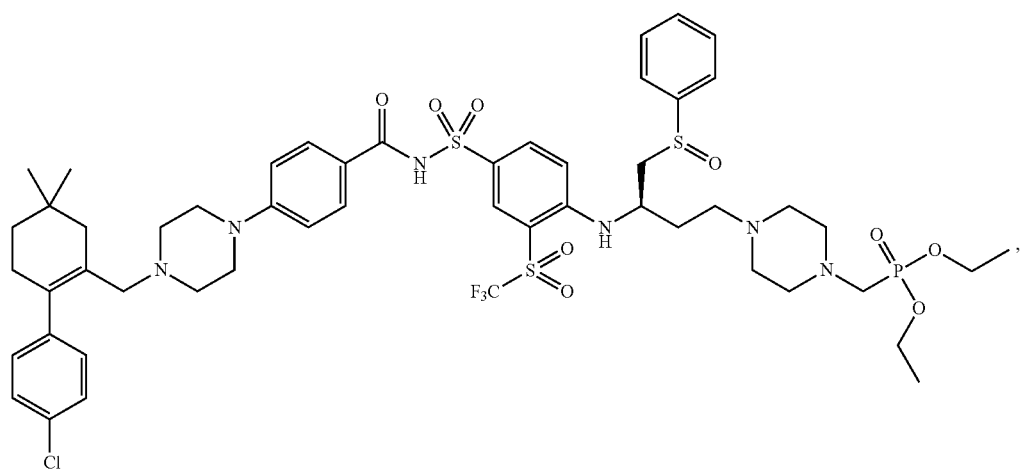
(44)
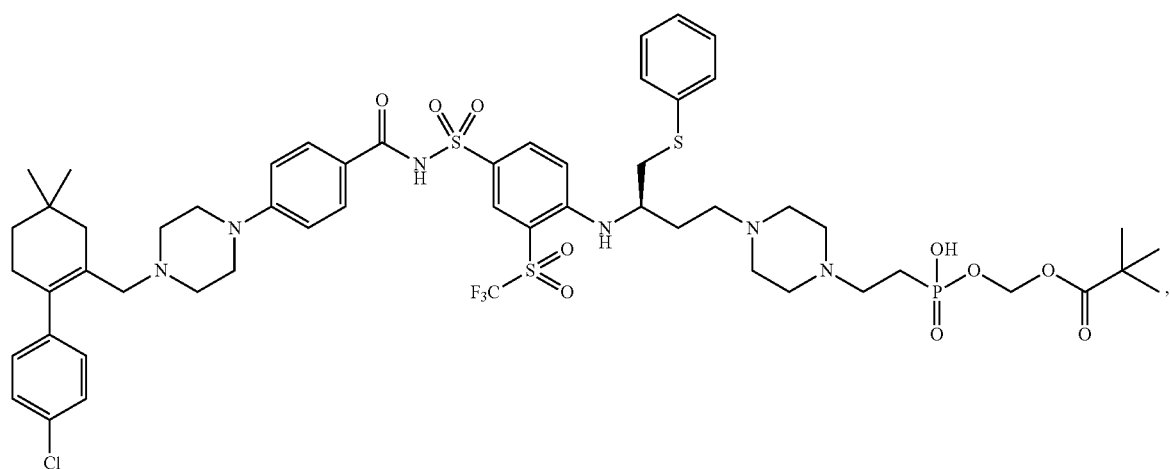
(45)
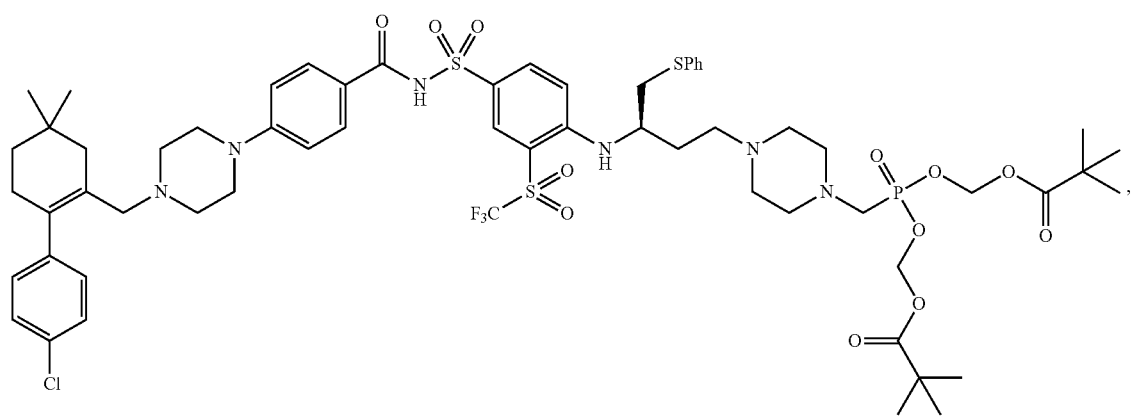
(46)

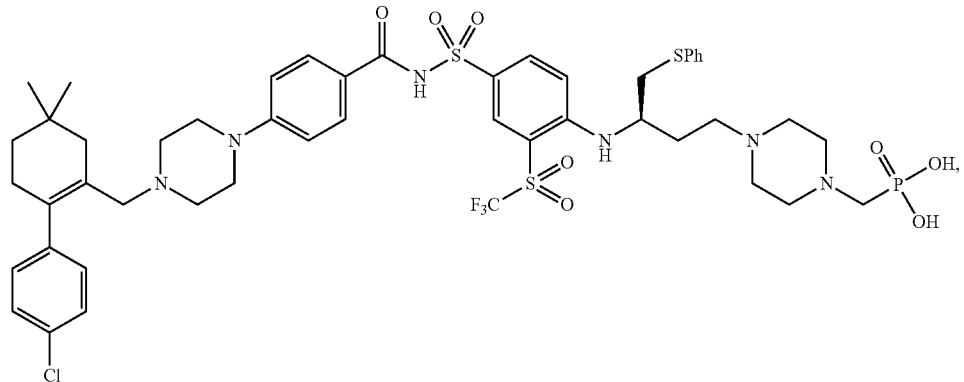
(47)
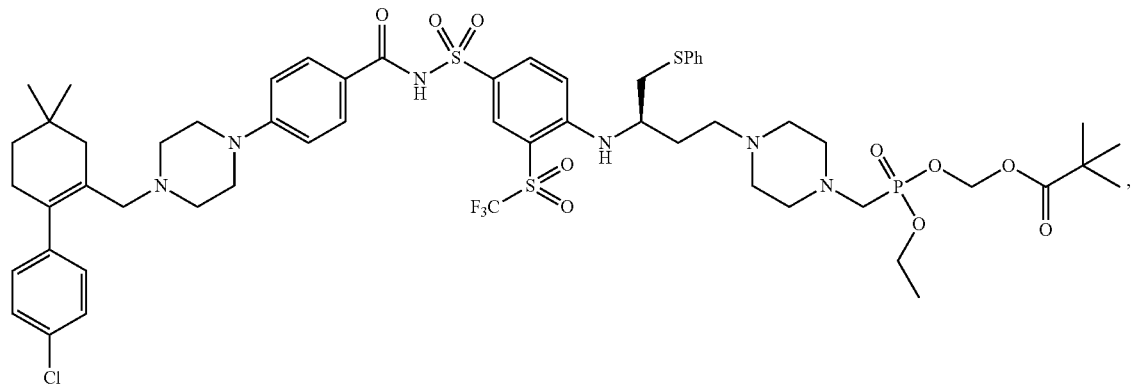
(48)
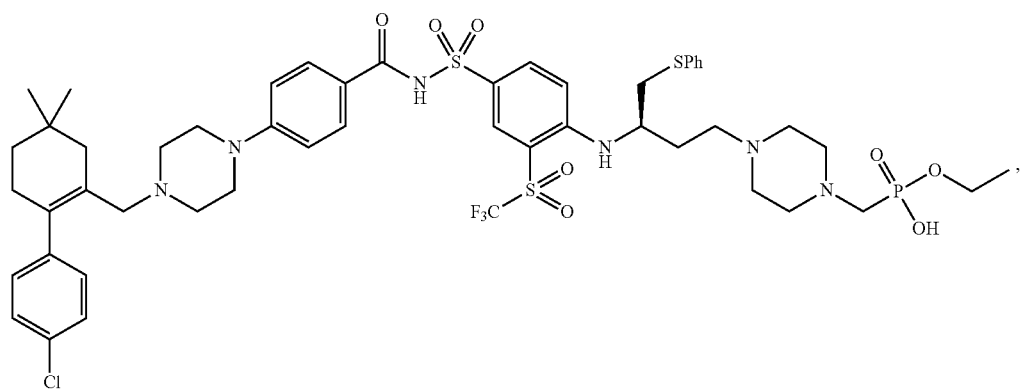
(49)
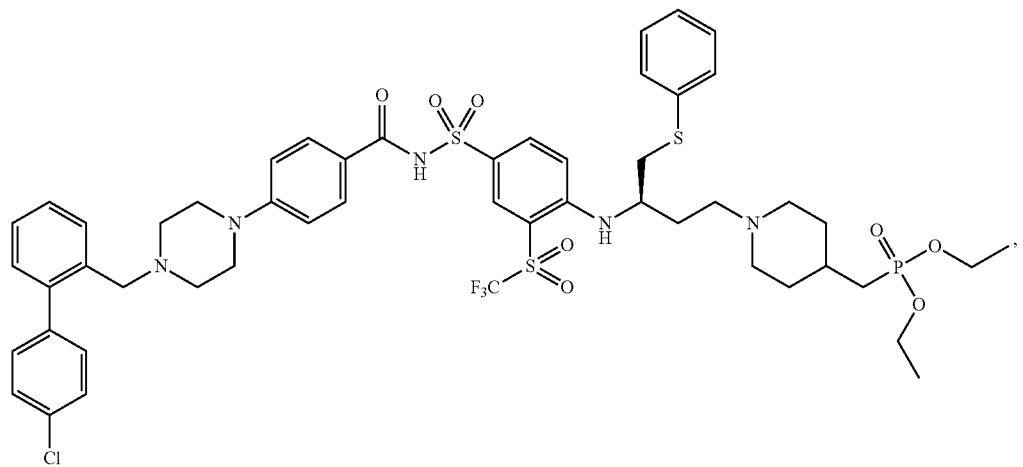
(50)

(51)
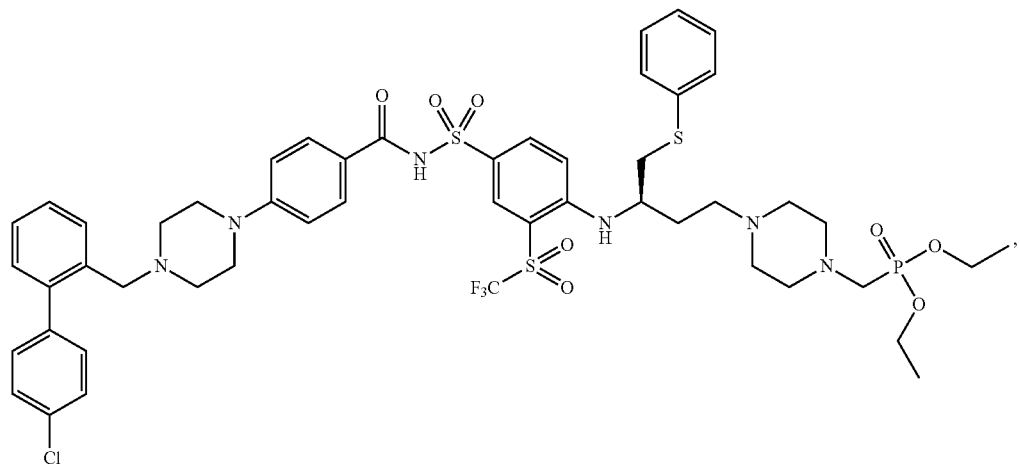
(52)
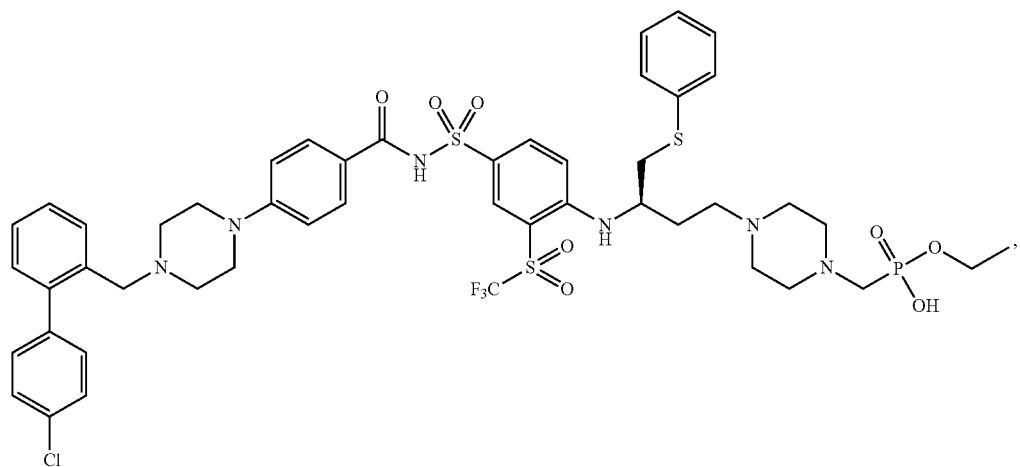
(53)
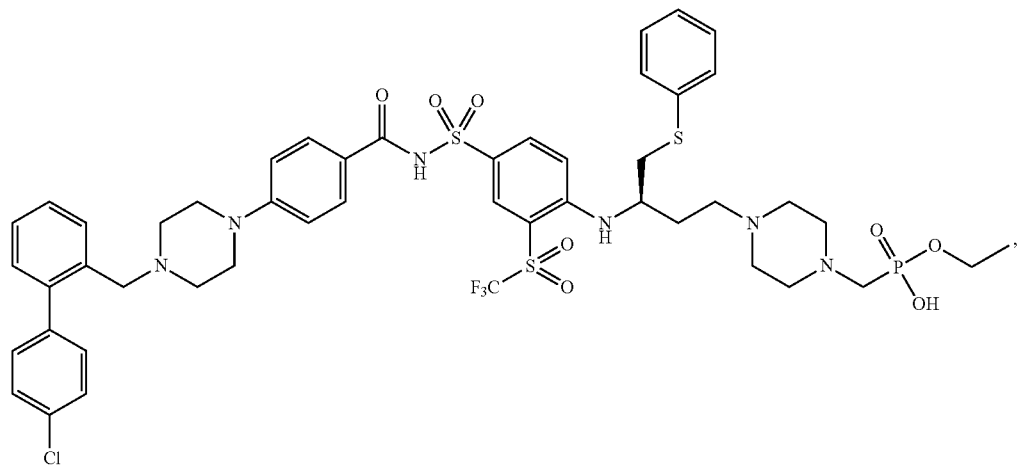

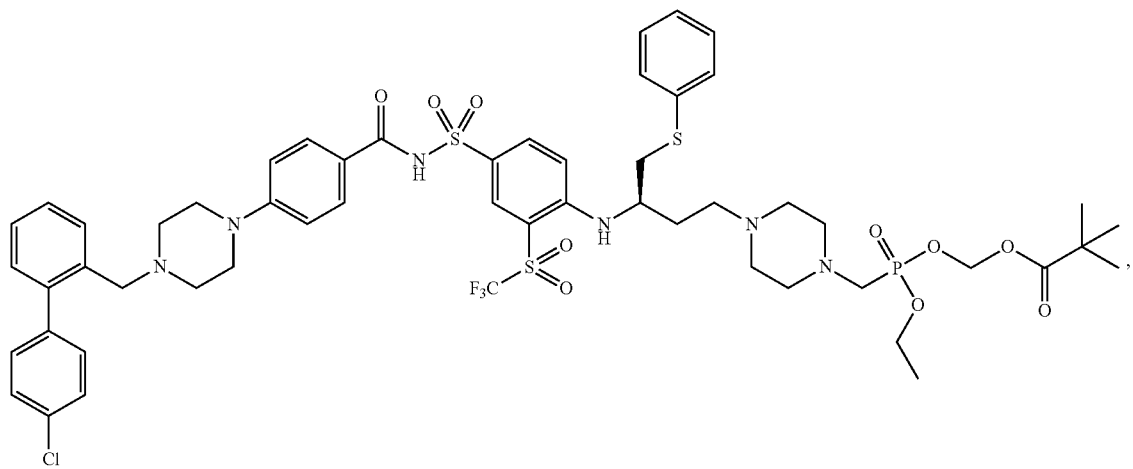
(54)
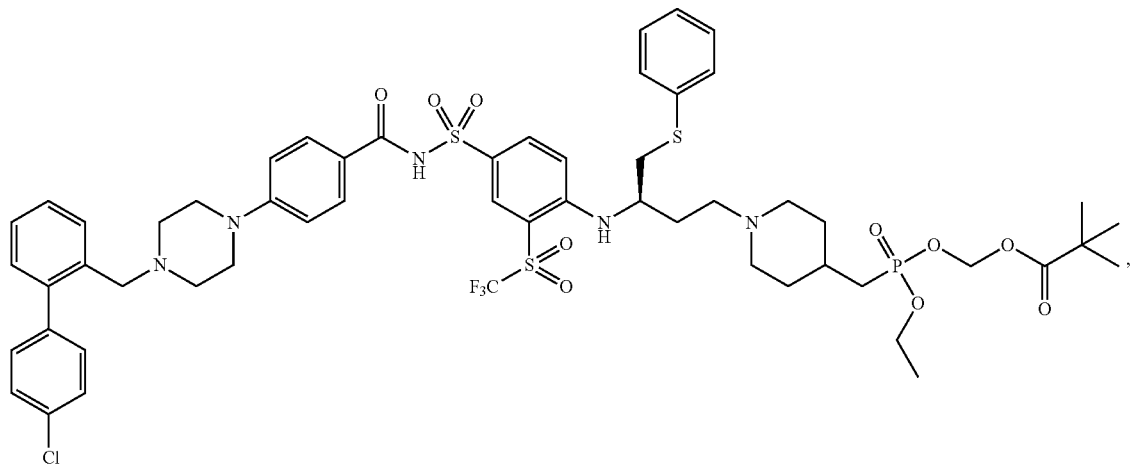
(55)
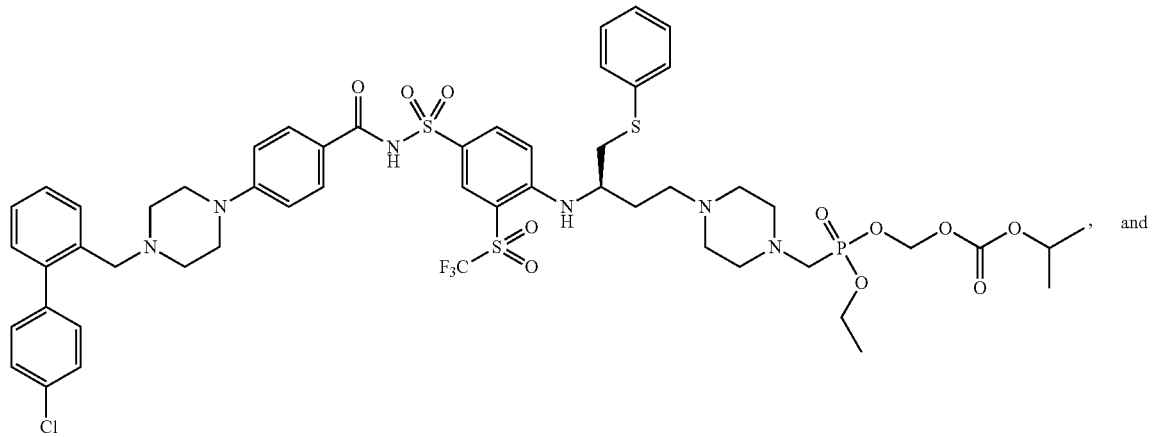
(56)

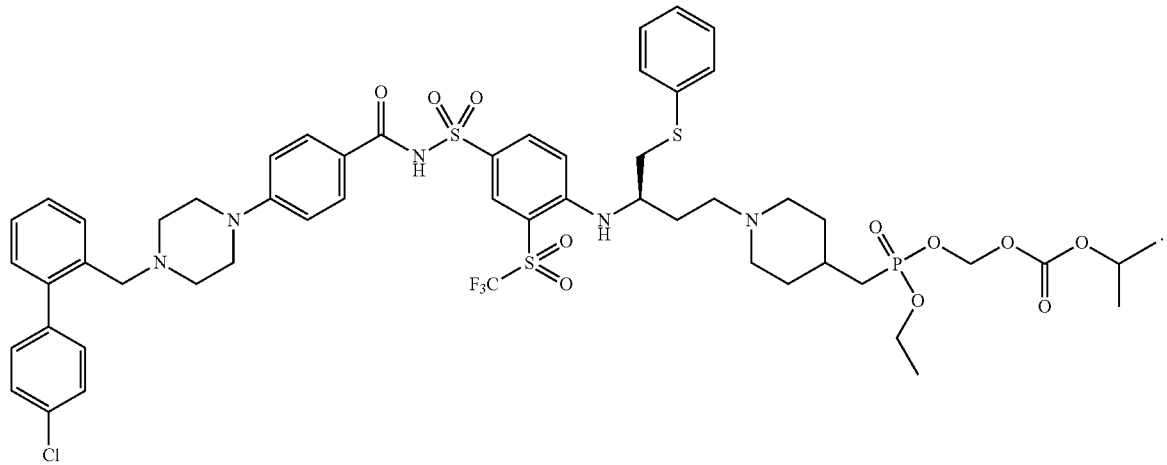

(57)

Included in the present disclosure are salts, particularly pharmaceutically acceptable salts, of the compounds described herein. The compounds of the present disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compounds or salts of the compounds of Formula (I) or (H) may be prodrugs, e.g., wherein a phosphonic acid in the parent compound is presented as an ester, or carboxylic acid present in the parent compound is presented as an ester. The term "prodrug" is intended to encompass compounds which, under physiologic conditions, are converted into pharmaceutical agents, i.e., parent compound, of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. For example, the prodrug may have improved cell permeability over the parent compound. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In particular embodiments, a prodrug of the disclosure, such as a compound or salt of Formula (I), (II), (III), (IV), (V) or (VI), wherein at least one of $R^2$ and $R^{2^*}$ is other than hydrogen, is converted to the acid parent compound, i.e., wherein each of $R^2$ and $R^{2^*}$ are hydrogen, after it has passed through the cell membrane into a cell. In certain embodiments, the parent compound, such as a compound or salt of Formula (I), (II), (III), (IV), (V) or (VI), wherein each of $R^2$ and $R^{2^*}$ is hydrogen, has diminished cell membrane permeability properties relative to the prodrug, such as decreased lipophilicity and increased hydrophilicity, thereby increasing the retention time of the parent compound within the cell.

For example, a prodrug such as compound (VII):

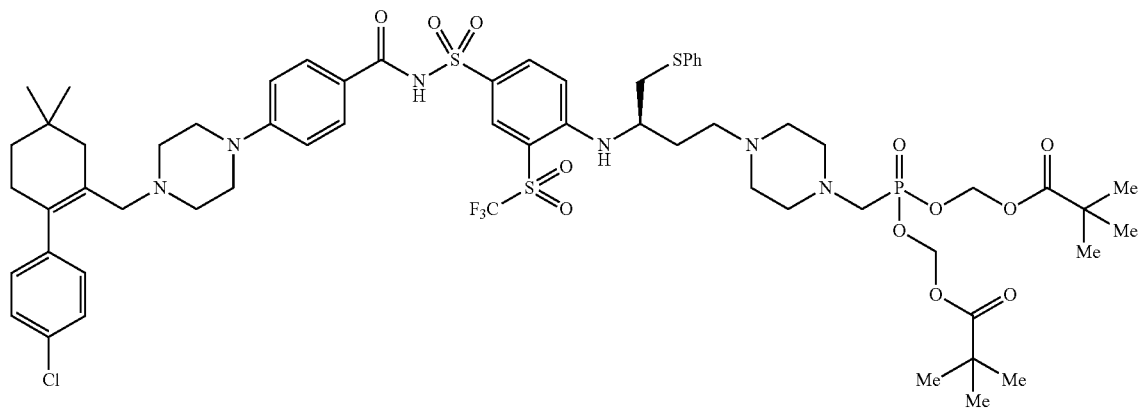

may be converted within the cell to parent compound (VIIa):

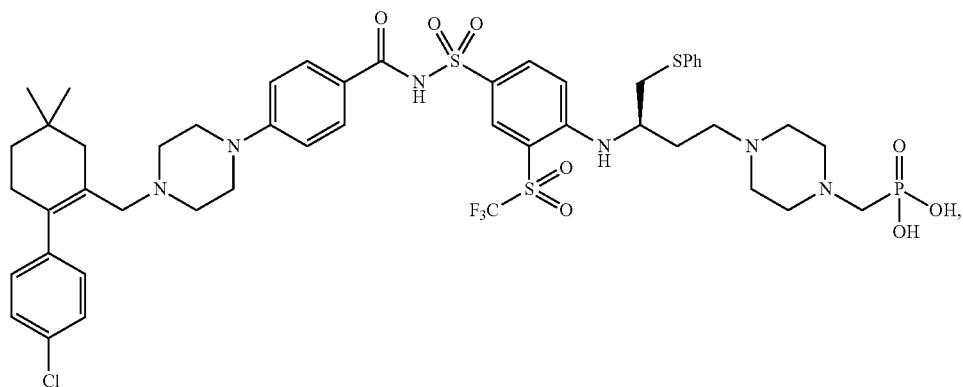

which may be retained within the cell for a longer duration than the prodrug.

Not wishing to be bound by any theory, a prodrug, e.g., compound (VII), may be sufficiently lipophilic and/or hydrophobic to permit membrane permeability. Once the prodrug has crossed the cell membrane into the cell, it may be chemically or enzymatically converted to a parent compound, e.g., compound (VIIa) which is generally more hydrophilic and/or lipophobic than the prodrug precursor. The decreased membrane permeability of the parent compound relative to the prodrug precursor may reduce the passive diffusion of the parent compound out of the cell, thereby allowing the active compound to accumulate inside the cell. While the acidic moieties described herein are depicted in their protonated states, the acidic moieties are likely deprotonated under physiological conditions.

Membrane permeability may be assessed in cell culture by measuring the activity of a compound in an appropriate cellular assay. The measured activity may be compared to the affinity with which the compound binds a particular protein. For example, compound (VIIa) may bind Bcl-2 with high affinity, but may have low membrane permeability as evidenced by an $EC_{50}$ value for senolytic cells of greater than 10 μM. A prodrug of compound (VIIa), e.g., compound (VII), may permit membrane permeability and may be converted in a cell to the parent compound, e.g., compound (VIIa), as evidenced by an $EC_{50}$ value for senolytic cells of less than 10 μM. Not wishing to be bound by any theory, an $EC_{50}$ value for senolytic cells of less than 10 μM for a particular prodrug may indicate that the prodrug is both cell permeable and readily converted to the parent compound at the site of action. A prodrug having an $EC_{50}$ value for senolytic cells of greater than 10 μM may have low membrane permeability and/or may not be readily converted to the parent compound at the site of action.

The parent compound, such as a compound or salt of Formula (I), (II), (III), (IV), (V) or (VI) with a phosphonic acid moiety, may be retained within the cell, i.e., drug residence, for 10% or longer, such as 15% or longer, such as 20% or longer, such as 25% or longer, such as 30% or longer, such as 35% or longer, such as 40% or longer such as 45% or longer, such as 50% or longer, such as 55% or longer, such as 60% or longer, such as 65% or longer, such as 70% or longer, such as 75% or longer, such as 80% or longer, such as 85% or longer, or even 90% or longer relative to the same compound without the phosphonic acid moiety.

In some embodiments, the design of a prodrug increases the lipophilicity of the pharmaceutical agent. In some embodiments, the design of a prodrug increases the effective water solubility. See, e.g., Fedorak et al., *Am. J. PhysioL,* 269:G210-218 (1995); McLoed et al., *Gastroenterol,* 106: 405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J. Pharmaceutics,*

47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis*, 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

C. PHARMACEUTICAL COMPOSITIONS

Provided herein, in certain embodiments, are compositions comprising a therapeutically effective amount of any compound or salt of Formula (I), (II), (III), (IV), (V) or (VI) (also referred to herein as "the pharmaceutical agent").

Pharmaceutical compositions may be formulated using one or more physiologically acceptable carriers including excipients and auxiliaries which facilitate processing of the pharmaceutical agent into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa., Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

D. EXEMPLARY TARGETS

The pharmaceutical agents described herein may alter (i.e., interfere with, affect) one or more cellular pathways that are activated during the senescence process of a cell. Pharmaceutical agents may alter either a cell survival signaling pathway, e.g., Akt pathway, or an inflammatory pathway or alter both a cell survival signaling pathway and an inflammatory pathway in a senescent cell. Activation of certain cellular pathways during senescence decreases or inhibits the cell's capability to induce, and ultimately undergo apoptosis. Without wishing to be bound by theory, the mechanism by which a pharmaceutical agent selectively kills senescent cells is by inducing, activating, stimulating, or removing inhibition of, an apoptotic pathway that leads to cell death. A pharmaceutical agent may alter one or more signaling pathways in a senescent cell by interacting with one, two, or more target proteins in the one or more pathways, which results in removing or reducing suppression of a cell death pathway, such as an apoptotic pathway. Contacting or exposing a senescent cell to a pharmaceutical agent described here to alter one, two, or more cellular pathways in the senescent cell, may restore the cell's mechanisms and pathways for initiating apoptosis. In certain embodiments, a pharmaceutical agent is an agent that alters a signaling pathway in a senescent cell, which in turn inhibits secretion and/or expression of one or more gene products important for survival of a senescent cell. The pharmaceutical agent may inhibit a biological activity of the gene product(s) important for survival of the senescent cell. Alternatively, the decrease or reduction of the level of the gene product(s) in the senescent cell may alter the biological activity of another cellular component, which triggers, initiates, activates, or stimulates an apoptotic pathway or removes or reduces suppression of the apoptotic pathway. The pharmaceutical agents described herein are biologically active agents capable of selectively killing senescent cells in the absence of linkage or conjugation to a cytotoxic moiety (e.g., a toxin or cytotoxic peptide or cytotoxic nucleic acid). The pharmaceutical agents are also active in selectively killing senescent cells in the absence of linkage or conjugation to a targeting moiety (e.g., an antibody or antigen-binding fragment thereof; cell binding peptide) that selectively binds senescent cells.

Two alternative modes of cell death can be distinguished, apoptosis and necrosis. Apoptosis is typically characterized by the rounding of the cell, chromatin condensation (pyknosis), nuclear fragmentation (karyorhexis), and engulfment by neighboring cells (see, e.g., Kroemer et al., *Cell Death Differ.* 16:3-11 (2009)). Several molecular assays have been developed and are used in the art; however, the morphological changes, which are detected by light and electron microscopy, are viewed in the art as the optimal techniques to differentiate the two distinct modes of cell death (see, e.g., Kroemer et al., supra). Alternative cell death modes, such as caspase-independent apoptosis-like programmed cell death (PCD), autophagy, necrosis-like PCD, and mitotic catastrophe, have also been characterized (see, e.g., Golstein, *Biochem. Sci.* 32:37-43 (2007); Leist et al., *Nat. Rev. Mol. Cell Biol.* 2:589-98 (2001)). See, e.g., Caruso et al., *Rare Tumors* 5(2): 68-71 (2013); published online 2013 Jun. 7. doi: 10.3081/rt.2013.e18. Techniques and methods routinely practiced in the art and described herein (e.g., TUNEL) may be used to show that apoptotic cell death results from contact with the pharmaceutical agents described herein.

In certain embodiment, a method is provided for treating a senescence-associated disease or disorder comprising inhibiting the activity of any one or more of MDM2, BCL-2 and Akt with a pharmaceutical agent of the disclosure. In certain embodiments, the pharmaceutical agent of the disclosure is a BCL-2 inhibitor such as a BCL-2/BCL-xL inhibitor, a BCL-2/BCL-xL/BCL-w inhibitor, or a BCL-xL selective inhibitor.

The following examples are given for the purpose of illustrating various embodiments of the disclosure and are not meant to limit the present disclosure in any fashion. The present examples, along with the methods and compositions described herein, are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

E. EXAMPLES

Example 1

Chemical Syntheses

Example 1.1: Synthesis of Compound 1.6.

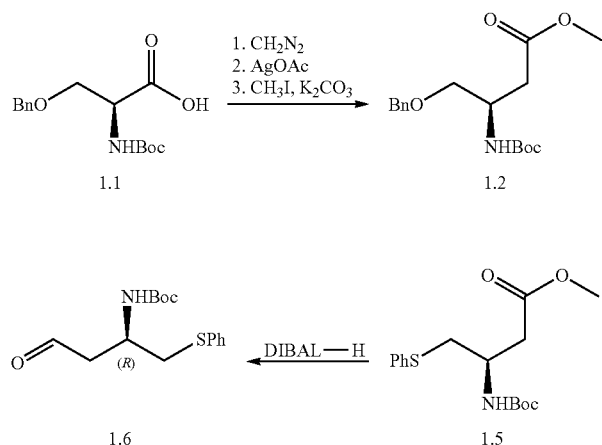
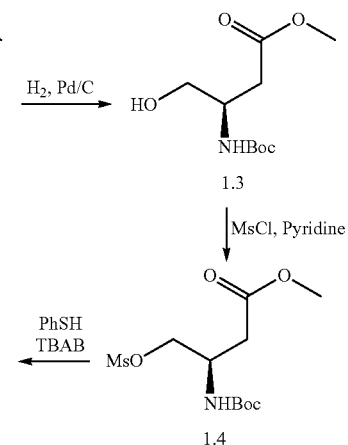

Step A: Synthesis of methyl (R)-4-(benzyloxy)-3-((tert-butoxycarbonyl)amino) butanoate (1.2). To a solution of propanoic acid derivative 1.1 (15.0 g, 50.79 mmol) in THF (200 mL) precooled to −15° C. were added 4-methylmorpholine (5.65 g, 55.87 mmol) and ClCO$_2$Et (6.06 g, 55.87 mmol) sequentially over 30 min. CH$_2$N$_2$ (2.14 g, 50.79 mmol) in Et$_2$O (50 mL) was added and the reaction mixture was stirred at r.t. for 2 h. The mixture was then poured into 10% AcOH (200 mL), and the two phases were separated. The aqueous phase was extracted with EtOAc (30 mL×3). The combined organic phases were washed with NaHCO$_3$ (300 mL×2), dried over anhydrous Na$_2$SO$_4$, and concentrated to afford tert-butyl N-[(1 R)-1-(benzyloxymethyl)-3-diazenyl-2-oxo-propyl]carbamate (15.00 g, 46.68 mmol, 92% yield), which was used in the next step without further purification.

To a solution of tert-butyl N-[(1R)-1-(benzyloxymethyl)-3-diazenyl-2-oxo-propyl]carbamate (38.00 g, 118.24 mmol) in THF (200 mL) and H$_2$O (20 mL) was added AgOAc (8.21 g, 59.12 mmol). The reaction mixture was heated at 40° C. for 5 h, and then concentrated directly. The residue was poured into a mixture of acetone (100 mL) and H$_2$O (200 mL). The resulting mixture was adjusted to pH=8~9 and extracted with ether (300 mL×3). The aqueous phase was adjusted to pH=3-4 and extracted with AcOEt (300 mL×3). The combined EtOAc phases were dried over anhydrous MgSO$_4$ and concentrated to afford (3R)-4-benzyloxy-3-(tert-butoxycarbonylamino) butanoic acid (~30 g, 96.97 mmol, ~82% yield).

To a solution of (3R)-4-benzyloxy-3-(tert-butoxycarbonylamino)butanoic acid (30 g, 96.97 mmol) in DMF (300.00 mL) were added K$_2$CO$_3$ (40.21 g, 290.91 mmol) and MeI (20.65 g, 145.46 mmol). The reaction mixture was stirred at r.t. for 2 h. The mixture was poured into water (2.5 L) and the resulting solution was extracted with EtOAc (300 mL×3). The combined organic phases were washed with brine (300 mL×3), dried over anhydrous Na$_2$SO$_4$, and concentrated to afford 1.2 (31.0 g, 95.86 mmol, quantitative), which was used in the next step without further purification. MS (ESI) m/z=345[M+Na]$^+$. $^1$H NMR (400 MHz, CDCl$_3$): δ 7.29 (m, 5H), 5.15 (br, 1H), 4.51 (s, 2H), 4.15 (m, 1H), 3.65 (s, 3H), 3.53 (m, 2H), 2.63 (m, 2H), 1.44 (s, 9H).

Step B: Synthesis of ethyl (R)-3-((tert-butoxycarbonyl)amino)-4-hydroxybutanoate (1.3). To a solution of 1.2 (5.00 g, 15.46 mmol) in MeOH (100 mL) was added 10% Pd/C (1.00 g). The reaction mixture was stirred at room temperature overnight under H$_2$ atmosphere. The reaction mixture was filtered over celite and the filtrate was concentrated in vacuum. The residue was purified by flash column chromatography on silica gel (Petroleum Ether:EtOAc=2:1) to afford 1.3 (2.50 g, 10.72 mmol, 69% yield). MS (ESI) m/z=256[M+Na]$^+$. $^1$H NMR (400 MHz, CDCl$_3$): δ 5.22, (br, 1H), 3.99 (m, 1H), 3.72~3.70 (m, 5H), 2.64 (d, J=6.0 Hz, 2H), 1.44 (s, 9H).

Step C: Synthesis of methyl (R)-3-((tert-butoxycarbonyl)amino)-4-((methylsulfonyl)oxy)butanoate (1.4). A solution of 1.3 (330 mg, 1.41 mmol) in pyridine (10 mL) was stirred at 0° C. for about 15 min and then MsCl (323.03 mg, 2.82 mmol) was added slowly. The reaction mixture was stirred at r.t. for about 30 min. The mixture was poured into water (40 mL) and extracted with EtOAc (40 mL×3). The combined organic phases were washed with 1N HCl (40 mL×3). The organic phases were dried over anhydrous MgSO$_4$ and concentrated. The residue was purified by flash column chromatography on silica gel (Petroleum Ether:EtOAc=1:1) to afford 1.4 (360.00 mg, 1.16 mmol, ~82% yield). MS (ESI) m/z=334[M+Na]$^+$. $^1$H NMR (400 MHz, CDCl$_3$): δ 5.22 (br, 1H), 4.36~4.25 (m, 3H), 3.72 (s, 3H), 3.03 (s, 3H), 2.67 (d, J=6.0 Hz, 2H), 1.45 (s, 9H).

Step D: Synthesis of methyl (R)-3-((tert-butoxycarbonyl)amino)-4-(phenylthio)butanoate (1.5). To a solution of 1.4 (5.94 g, 19.08 mmol) in toluene (50 mL) were added benzenethiol (3.15 g, 28.62 mmol), tetrabutylammonium bromide (545.84 mg, 1.91 mmol), and potassium carbonate (5.27 g, 38.16 mmol) sequentially. The reaction mixture was heated at 50° C. overnight. The mixture was directly subjected to flash column chromatography on silica gel (Petroelum Ether:EtOAc=10:1) to afford 1.5 (5.40 g, 16.59 mmol, 87% yield). MS (ESI) m/z=326[M+H]$^+$. $^1$H NMR (400 MHz, CDCl$_3$): δ 7.41 (m, 2H), 7.29 (m, 2H), 7.20 (m, 1H), 5.20 (br, 1H), 4.11 (m, 1H), 3.65 (s, 3H), 3.23 (m, 1H), 3.10 (m, 1H), 2.74 (m, 1H), 2.63 (m, 1H), 1.42 (s, 9H).

Step E: Synthesis of 1.6: To a solution of 1.5 (1.00 g, 3.07 mmol) in toluene (40.00 mL) was added DIBAL-H (433.93 mg, 3.07 mmol) slowly at −78° C. The reaction mixture was stirred at the same temperature for about 1 hr, then quenched with MeOH. An excess of solvent was concentrated and the residue diluted with AcOEt (100 mL) and washed with brine (20 mL). The organic layer was dried over anhydrous MgSO$_4$ and concentrated. The residue was purified by flash chromatography on silica gel (Pentane:AcOEt=10:1) to afford 1.6 (420.00 mg, 1.42 mmol, ~46% yield). MS (ESI) m/z=318[M+Na]$^+$. $^1$H NMR (400 MHz, CDCl$_3$): δ 9.68 (s, 1H), 7.42 (m, 2H), 7.37 (m, 2H), 7.21 (m, 1H), 4.97 (br, 1H), 4.20 (m, 1H), 3.23 (m, 1H), 3.09 (m, 1H), 2.81 (m, 2H), 1.42 (s, 9H).

Example 1.2: Synthesis of Compound 2.4.

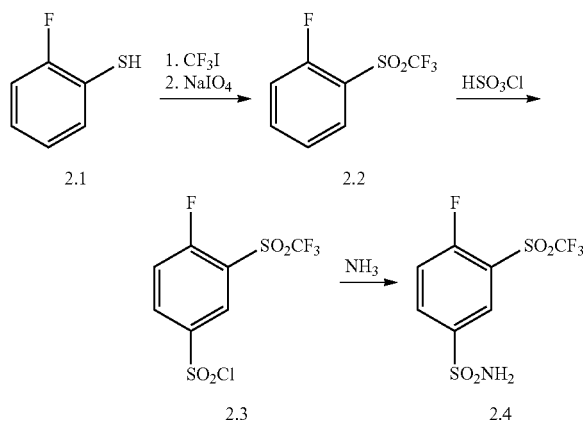

Step A: Synthesis of 1-Fluoro-2-((trifluoromethyl)sulfonyl)benzene (2.2). A suspension of methyl viologen dichloride (120.37 mg, 468.00 μmol) in DMF (30.00 mL) was saturated with CF$_3$I (3.67 g, 18.72 mmol) at −20° C. The mixture was stirred for 20 min, and then 2-fluorobenzenethiol (1.20 g, 9.36 mmol) and Et$_3$N (1.42 g, 14.04 mmol) were added sequentially. The reaction mixture was stirred at room temperature overnight. The mixture was then poured into water (100 mL), and the two phases were separated. The aqueous phase was extracted with DCM (120 mL). The organic phases were combined and extracted with 1N aqueous NaOH (150 mL) and saturated NH$_4$Cl (150 mL). The organic layer was dried over anhydrous Na$_2$SO$_4$ and concentrated to afford crude 1-fluoro-2-(trifluoromethylsulfanyl)benzene (1.40 g, 7.14 mmol, 76% yield), which was used directly in the next step without further purification. GCMS m/z=196. $^1$H NMR (400 MHz, CDCl$_3$): δ 7.63 (m, 1H), 7.42 (m, 1H), 7.28 (m, 2H).

To a mixture of crude 1-fluoro-2-(trifluoromethylsulfanyl)benzene (10.00 g, 50.98 mmol) in H$_2$O (1.00 L) and MeCN (100 mL) cooled by ice-batch was added a mixture of RuCl$_3$ (2.04 mg, 2.05 mmol) and NaIO$_4$ (109.03 g, 50.98 mmol) in H$_2$O (100 mL). The reaction mixture was stirred at r.t. for 3 h. The mixture was then filtered and the filtrate was extracted with EtOAc (80 mL×2). The combined organic layers were washed with saturated Na$_2$S$_2$O$_3$ (100 mL×2), dried over anhydrous Na$_2$SO$_4$ and concentrated. The residue was purified by flash chromatography (Hexane/EtOAc=100:1) to afford 2.2 (4.00 g, 17.53 mmol, 34% yield). $^1$H NMR (400 MHz, DMSO-d6): δ 8.14 (m, 2H), 7.78 (m, 1H), 7.68 (m, 1H).

Step B: Synthesis of 4-Fluoro-3-((trifluoromethyl)sulfonyl)benzenesulfonyl chloride (2.3). A solution of 2.2 (10.00 g, 43.83 mmol) in HClSC$_3$ (35.00 mL) was heated at 120° C. for 5 h. The mixture was then poured into a mixture of crushed ice (100 g) in water (300 mL). The resulting mixture was extracted with DCM (80 mL×2), and the combined organic phases were washed with water (200 mL×2), dried over anhydrous Na$_2$SO$_4$ and concentrated to afford 2.3 (12.60 g, 38.57 mmol, 88% yield), which was directly used in the next step without further purification. MS (ESI) m/z=307[M−Cl+OH−H]$^−$. $^1$H NMR (400 MHz, DMSO-d6): δ 8.25 (m, 1H), 8.15 (m, 1H), 7.73 (m, 1H).

Step C: Synthesis of 2.4: To a solution of 2.3 (7.00 g, 21.43 mmol) in propan-2-ol (100 mL) precooled to −60° C. was added NH$_3$.H$_2$O (1.88 g, 53.57 mmol) dropwise. The reaction mixture was stirred at the same temperature for another hour. The mixture was then concentrated and purified by flash chromatography on silica gel (Hexane/EtOAc=2:1) to afford 2.4 (3.60 g, 11.72 mmol, 55% yield). MS (ESI) m/z=306[M−H]$^−$. $^1$H NMR (400 MHz, DMSO-d6): δ 8.45~8.41 (m, 2H), 7.98 (m, 1H), 7.81 (br, 2H).

Example 1.3: Synthesis of Compound 3.7.

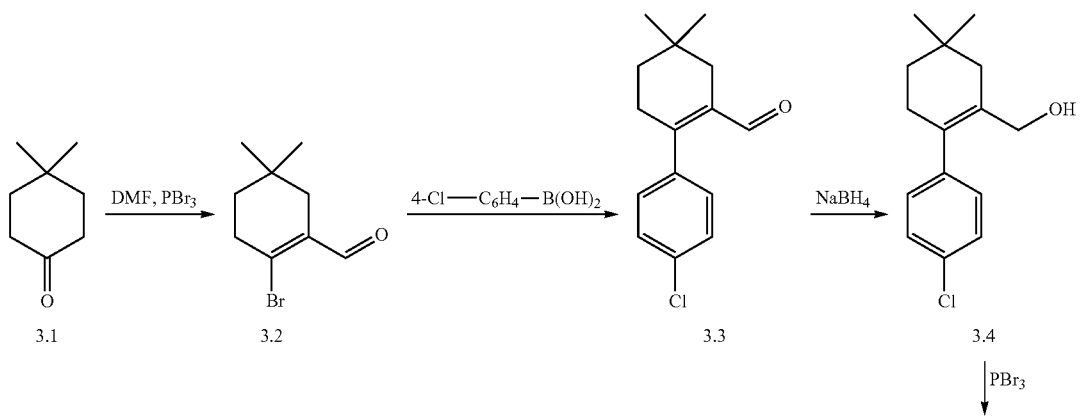

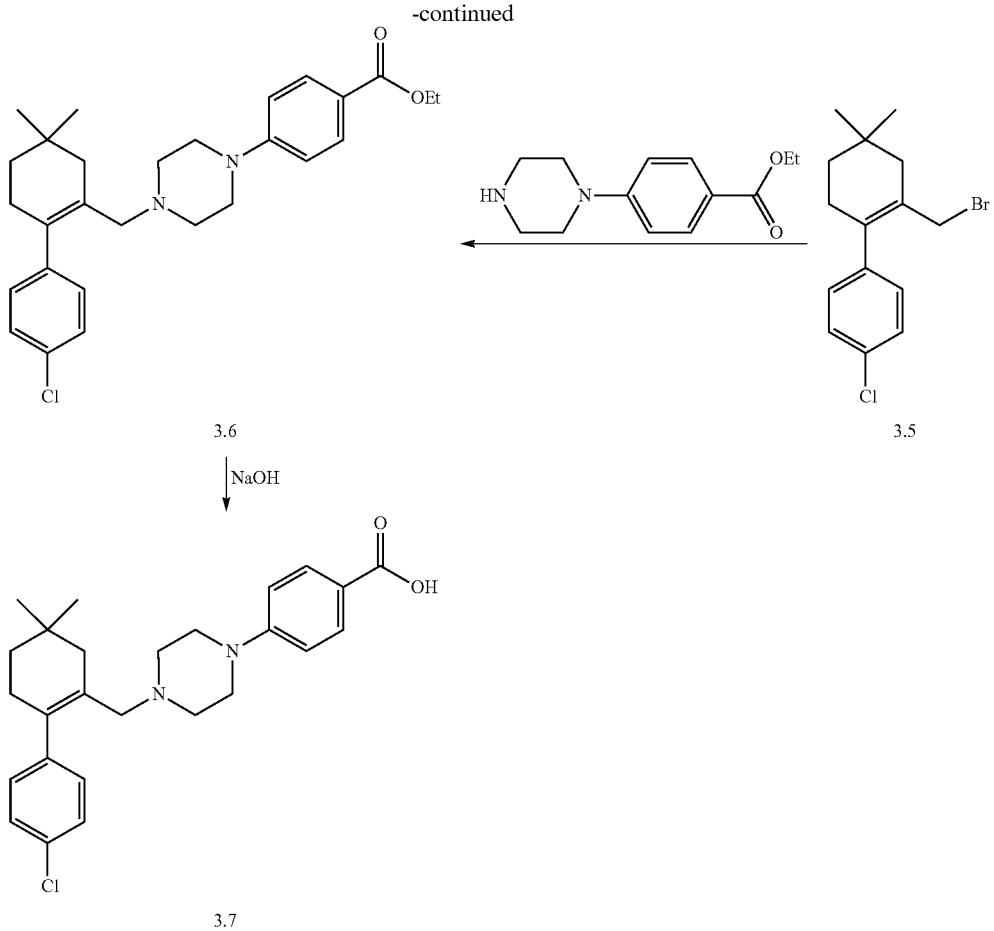

Step A: Synthesis of 2-Bromo-5,5-dimethylcyclohex-1-ene-1-carbaldehyde (3.2). To a solution of 4,4-dimethylcyclohexanone (50.40 g, 399.37 mmol) in PBr$_3$ (103.07 mL) was added DMF (88.34 mL) at 0° C. The mixture was stirred for 20 min and then PBr$_3$ (103.07 mL) was added at 0° C. The reaction mixture was stirred at the same temperature for 10 min and then heated at 60° C. overnight. The mixture was then poured into ice water (1 L), and the resulting mixture was extracted with DCM (3×500 mL). The combined organic phases were dried over anhydrous Na$_2$SO$_4$, filtered and concentrated to afford crude 3.2 (65.50 g, 301.70 mmol, 76% yield), which was used in the next step without further purification. $^1$H NMR (400 M, CDCl$_3$), δ 10.03 (s, 1H), 2.76 (m, 2H), 2.09 (m, 2H), 1.54 (m, 2H), 0.95 (s, 6H).

Step B: Synthesis of 4'-Chloro-4,4-dimethyl-3,4,5,6-tetrahydro-[1,1'-biphenyl]-2-carbaldehyde (3.3). To a solution of 3.2 (67.00 g, 308.61 mmol) and (4-chlorophenyl)boronic acid (72.39 g, 462.92 mmol) in 1,4-Dioxane (700.00 mL) and H$_2$O (7.00 mL) were added KOAc (90.86 g, 925.83 mmol) and Pd(dppf)Cl$_2$ (6.70 g, 308.61 mmol) under N$_2$ atmosphere. The reaction mixture was stirred at 90° C. for 3 h, and then quenched with H$_2$O (2 L). The resulting mixture was extracted with EtOAc (2×1 L). The combined phases were washed with brine (2×800 mL), dried over anhydrous Na$_2$SO$_4$, filtered and concentrated. The residue was purified by flash column chromatography on silica gel (neat petroleum ether) to afford 3.3 (45.00 g, 180.90 mmol, 59% yield). MS (ESI) m/z=250[M+H]$^+$. $^1$H NMR (400 M, CDCl$_3$), δ 9.49 (s, 1H), 7.36 (m, 2H), 7.18 (m, 2H), 2.55 (m, 2H), 2.14 (m, 2H), 1.53 (t, 2H, J=6.4 Hz), 0.99 (s, 6H).

Step C: Synthesis of (4'-Chloro-4,4-dimethyl-3,4,5,6-tetrahydro-[1,1'-biphenyl]-2-yl)methanol (3.4). To a solution of 3.3 (43.00 g, 172.86 mmol) in THF (100.00 mL) and H$_2$O (100.00 mL) was added NaBH$_4$ (9.81 g, 259.29 mmol) slowly at room temperature. The reaction mixture was stirred at room temperature for 1 h and then directly extracted with DCM (3×300 mL). The combined organic phases were dried over anhydrous MgSO$_4$, filtered and concentrated to afford the crude 3.4 (43.00 g, 171.48 mmol, quantitative), which was used in the next step without further purification. MS (ESI) m/z=233[M−H$_2$O+H]+. $^1$H NMR (400 M, CDCl$_3$), δ 7.28 (m, 2H), 7.08 (m, 2H), 3.91 (s, 2H), 2.28 (m, 2H), 2.04 (m, 2H), 1.46 (m, 2H), 1.00 (s, 6H).

Step D: Synthesis of 6-(Bromomethyl)-4'-chloro-4,4-dimethyl-2,3,4,5-tetrahydro-1,1'-biphenyl (3.5). To a solution of 3.4 (43.00 g, 171.48 mmol) in DCM (300.00 mL) was added PBr$_3$ (34.81 g, 128.61 mmol) at −10° C. The reaction mixture was stirred at 0° C. for 0.5 h and then quenched with saturated Na$_2$CO$_3$ (500 mL). The resulting mixture was extracted with DCM (3×400 mL) and the combined organic phases were dried over anhydrous Na$_2$SO$_4$, filtered and concentrated to afford the crude 3.5 (50.60 g, 161.32 mmol, 94% yield), which was used in the next step without further purification. $^1$H NMR (400 M, CDCl$_3$), δ 7.32 (m, 2H), 7.18 (m, 2H), 3.82 (s, 2H), 2.28 (m, 2H), 2.07 (m, 2H), 1.48 (m, 2H), 1.00 (s, 6H).

Step E: Synthesis of ethyl 4-(4-((4'-chloro-4,4-dimethyl-3,4,5,6-tetrahydro-[1,1'-biphenyl]-2-yl)methyl) piperazin-1-yl) benzoate (3.6). To a solution of ethyl 4-fluorobenzoate (50.00 g, 297.34 mmol) in DMSO (500.00 mL) were added piperazine (76.84 g, 892.02 mmol) and $K_2CO_3$ (82.19 g, 594.68 mmol). The reaction mixture was stirred at 100° C. overnight. The mixture was then poured into $H_2O$ (2 L) and the resulting mixture was extracted with EtOAc (3×500 mL). The combined organic phases were washed with brine (2×800 mL), dried over anhydrous $MgSO_4$, filtered and concentrated to afford the crude ethyl 4-piperazin-1-ylbenzoate (43.00 g, 183.53 mmol, 62% yield), which was pure enough to be used in the next step without further purification. MS (ESI) m/z=235[M+H]$^+$. $^1$H NMR (400 M, CDCl$_3$), δ 7.92 (m, 2H), 6.86 (m, 2H), 4.33 (q, 2H, J=6.8 Hz), 3.28 (m, 2H), 3.02 (m, 2H), 1.37 (t, 3H, J=7.2 Hz).

To a solution of 3.5 (500.00 mg, 1.59 mmol) in DMSO (5.00 mL) were added ethyl 4-piperazin-1-ylbenzoate (372.52 mg, 1.59 mmol) and $K_2CO_3$ (439.51 mg, 3.18 mmol). The reaction mixture was stirred at 100° C. for 2 h and then poured into $H_2O$ (50 mL). The resulting mixture was extracted with EtOAc (2×40 mL) and the combined organic phases were dried over anhydrous $MgSO_4$, filtered and concentrated. The residue was washed with petroleum ether (2×5 mL), and dried under reduced pressure to give 3.6 (700.00 mg, 1.50 mmol, ~94% yield), which was pure enough to be used in the next step without further purification. MS (ESI) m/z=468[M+H]$^+$. $^1$H NMR (400 M, CDCl$_3$), δ 7.90 (m, 2H), 7.27 (m, 2H), 7.00 (m, 2H), 6.81 (m, 2H), 4.31 (q, 2H, J=6.8 Hz), 3.26 (m, 4H), 2.80 (m, 2H), 2.35 (m, 4H), 2.25 (m, 2H), 2.02 (m, 2H), 1.46 (m, 2H), 1.36 (t, 3H, J=6.8 Hz), 0.99 (s, 9H).

Step F: Synthesis of 3.7: To a solution of NaOH (19.70 g, 492.48 mmol) in $H_2O$ (300.00 mL) and MeOH (100.00 mL) was added 3.6 (57.50 g, 123.12 mmol) in THF (600.00 mL) at room temperature. The reaction mixture was stirred at 80° C. for 10 h. An excess of solvent was concentrated and the residue was poured into ice-water (1 L). The resulting mixture was adjusted to pH=5-6, and white solid precipitated. The solid was collected by filtration and dried to afford the 3.7 (50.00 g, 113.90 mmol, ~93% yield). MS (ESI) m/z=439[M+H]$^+$. $^1$H NMR (400 M, DMSO-d6), 10.63 (br, 1H), 7.75 (d, 2H, J=8.8 Hz), 7.38 (d, 2H, J=8.4 Hz), 7.12 (d, 2H, J=8.0 Hz, Ph), 6.91 (m, 2H, J=8.8 Hz), 3.84 (m, 2H), 3.58 (m, 2H), 3.39 (m, 2H), 2.78 (m, 2H), 2.28 (m, 2H), 2.21 (m, 2H), 1.47 (m, 2H), 1.00 (s, 6H).

Example 1.4: Synthesis of Compound 6.

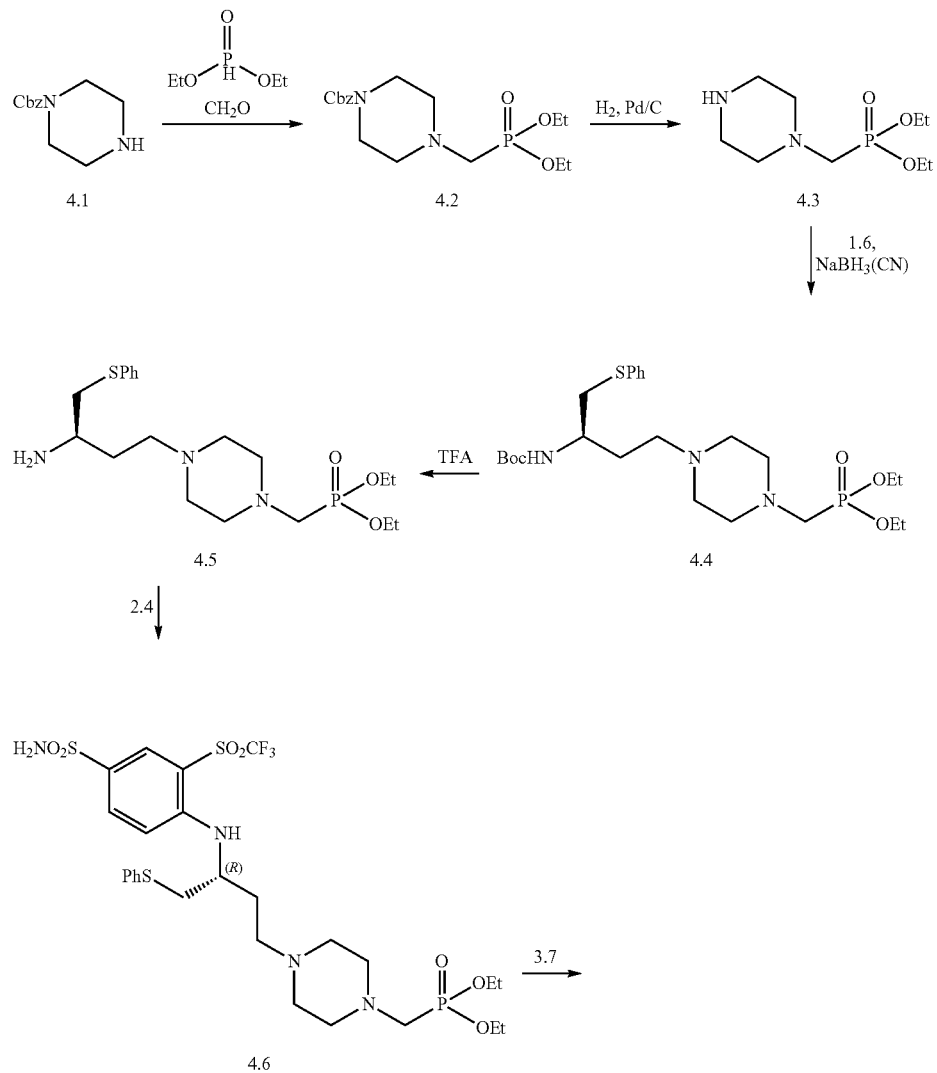

-continued

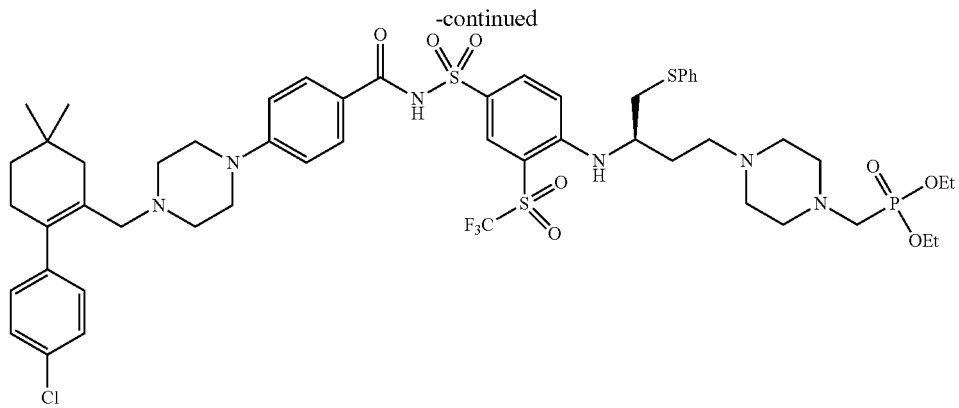

Compound 6

Step A: Synthesis of benzyl 4-((diethoxyphosphoryl)methyl)piperazine-1-carboxylate (4.2). To a solution of benzyl piperazine-1-carboxylate (500.00 mg, 2.27 mmol) in 1,4-Dioxane (30.00 mL) were added 37% HCHO (77.32 mg, 2.27 mmol) and 1-ethoxyphosphonoyloxyethane (2.27 mmol). The reaction mixture was stirred at r.t. for 30 min and then heated at 90-100° C. for 1 h. The mixture was poured into water (100 mL) and extracted with EtOAc (100 mL×3). The combined organic phases were washed with brine (100 mL), dried over anhydrous MgSO4 and concentrated. The residue was purified by flash column chromatography on silica gel (Petroleum Ether:EtOAc=1:1) to afford 4.2 (~700.00 mg, 1.89 mmol, ~83% yield). MS (ESI) m/z=371[M+H]$^+$. $^1$H NMR (400 M, CDCl$_3$), δ 7.37~7.32 (m, 5H), 5.13 (s, 2H), 4.21~4.11 (m, 4H), 3.55 (s, 4H), 2.82 (d, 2H, J=116 Hz), 2.65 (m, 4H), 1.35 (m, 6H).

Step B: Synthesis of diethyl (piperazin-1-ylmethyl)phosphonate (4.3). To a solution of 4.2 (742.00 mg, 2.00 mmol) in EtOH (20.00 mL) was added 10% Pd/C (100.33 mg). The reaction mixture was stirred at r.t. overnight under H$_2$ atmosphere. The mixture was then filtered over celite, and the filtrate was concentrated in vacuum. The residue was purified by flash column chromatography on silica gel (DCM:MeOH=10:1) to afford 4.3 (100.00 mg, 423.28 µmol, ~21% yield). MS (ESI) m/z=237[M+H]$^+$. $^1$H NMR (400 M, CDCl$_3$), δ 4.17 (m, 4H), 2.93 (m, 4H), 2.77 (d, 2H, J=116 Hz), 2.66 (m, 4H), 1.34 (m, 6H).

Step C: Synthesis of tert-Butyl (R)-(4-(4-((diethoxyphosphoryl)methyl)piperazin-1-yl)-1-(phenylthio) butan-2-yl)carbamate (4.4). To a mixture of 1.6 and 4.3 (75.00 mg, 253.89 µmol) in DCM (10.00 mL) was added Et$_3$N (102.77 mg, 1.02 mmol). The mixture was stirred at 0° C. for 10 min and then NaBH$_3$(CN) (23.93 mg, 380.84 µmol) was added. The reaction mixture was stirred at r.t. overnight and concentrated. The residue was purified by flash column chromatography on silica gel (Petroleum Ether:EtOAc=3:1) to afford 4.4 (20.00 mg, 38.79 µmol, 15% yield). MS (ESI) m/z=517[M+H]$^+$.

Step D: Synthesis of diethyl (R)-((4-(3-amino-4-(phenylthio)butyl)piperazin-1-yl)methyl)phosphonate (Compound 4.5). To a solution of 4.4 (1.00 g, 1.99 mmol) in DCM (30.00 mL) was added TFA (454.61 mg, 3.99 mmol). The reaction mixture was stirred at r.t overnight and concentrated to afford 4.5 (790.00 mg, 1.97 mmol, near quantitative), which was used in the next step without further purification. MS (ESI) m/z=416[M+H]$^+$. $^1$H NMR (400 M, DMSO-d6), δ 8.22 (br, 3H), 7.45~7.26 (m, 5H), 4.05 (m, 4H), 3.42~3.12 (m, 10H), 2.96 (m, 4H), 2.60 (m, 1H), 2.12 (m, 1H), 2.00 (m, 1H), 1.25 (m, 6H).

Step E: Synthesis of diethyl (R)-((4-(4-(phenylthio)-3-((4-sulfamoyl-2-((trifluoromethyl)sulfonyl) phenyl)amino)butyl)piperazin-1-yl)methyl)phosphonate (4.6). To a mixture of 4.5 (129.00 mg, 310.45 µmol) and 2.4 (95.38 mg, 310.45 µmol) in DCM (10.00 mL) was added DIPEA (240.74 mg, 1.86 mmol) at 0° C. The reaction mixture was heated at 40° C. overnight and then concentrated. The residue was purified by flash column chromatography on silica gel (Petroleum Ether:EtOAc=1:1) to afford 4.6 (~170.00 mg, 241.90 µmol, ~78% yield). MS (ESI) m/z=704 [M+H]$^+$.

Step F: Synthesis of Compound 6: To a mixture of 4.6 (169.69 mg, 241.46 µmol) and 3.7 (106.00 mg, 241.46 µmol) in DCM (20.00 mL) were added DMAP (59.00 mg, 482.92 µmol) and EDCI (92.72 mg, 482.92 µmol). The reaction mixture was heated at 40° C. overnight. The solvent was concentrated and the residue was purified by flash column chromatography on silica gel (DCM:MeOH=1:1) to afford a product (100 mg), which was further purified by prep-HPLC to obtain Compound 6 (25.00 mg, 22.25 µmol, 9% yield). MS (ESI) m/z=1124[M+H]$^+$. $^1$H NMR (400 M, CDCl$_3$), δ 8.33 (m, 1H), 8.06 (m, 1H), 7.74 (m, 2H), 7.36 (m, 2H), 7.32~7.21 (m, 5H), 6.97 (m, 2H), 6.92 (m, 1H), 6.76 (m, 2H), 6.62 (m, 1H), 4.15 (m, 4H), 3.86 (m, 1H), 3.29 (m, 4H), 3.04 (m, 2H), 2.91 (m, 2H), 2.80~2.44 (m, 16H), 2.26 (m, 2H), 2.14 (m, 1H), 2.02 (m, 2H), 1.72 (m, 1H), 1.46 (m, 2H), 1.33 (m, 6H), 0.97 (s, 6H).

Example 1.5: Synthesis of Compound 7.

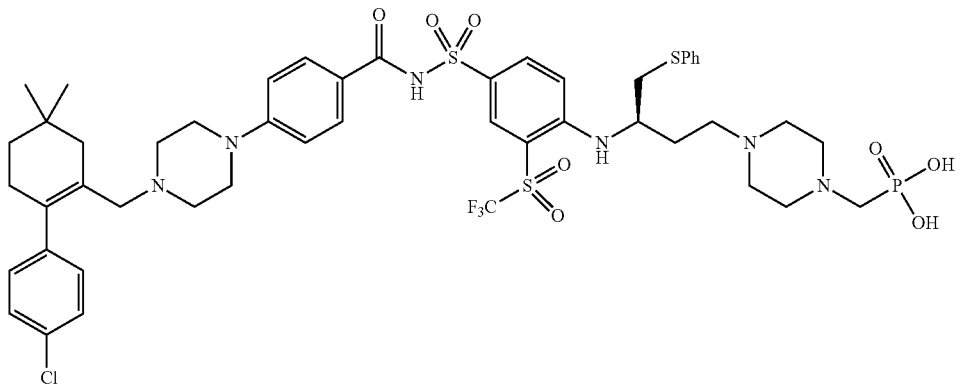

To a solution of Compound 6 (60.00 mg, 53.39 µmol) in CH$_3$CN (5.00 mL) was added TMSBr (613.93 mg, 5.34 mmol). The reaction mixture was heated at 60° C. for 3 h and then quenched with saturated NaHCO$_3$ (1.5 mL). The resulting mixture was purified by prep-HPLC to afford Compound 7 (30.00 mg, 28.10 µmol, 53% yield). MS (ESI) m/z=1068 [M+H]$^+$. $^1$H NMR (400 M, DMSO-d6), δ 8.17 (m, 1H), 8.00 (m, 1H), 7.77 (m, 2H), 7.41 (m, 2H), 7.30~7.12 (m, 8H), 6.95 (m, 3H), 4.12~2.70 (m, 26H), 2.28 (m, 2H), 2.04~1.96 (m, 4H), 1.48 (m, 2H), 0.97 (s, 6H).

Example 1.6: Synthesis of Compound 8.

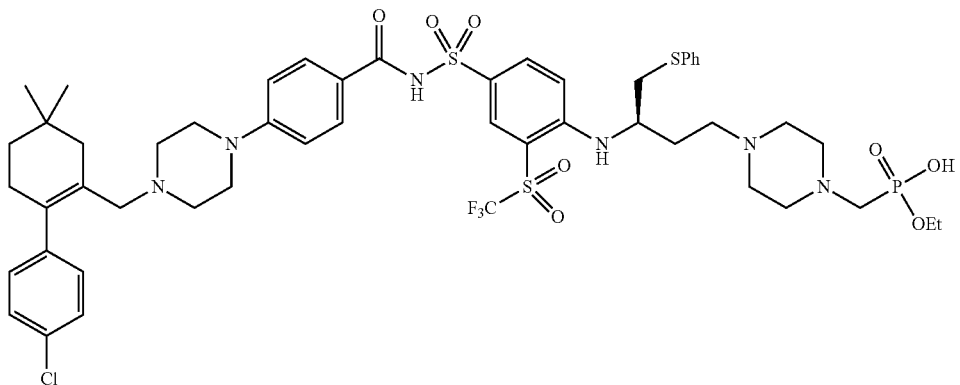

To a solution of Compound 6 (40.00 mg, 35.60 µmol) in CH$_3$CN (5 mL) was added TMSBr (204.68 mg, 1.78 mmol). The reaction mixture was stirred at r.t. for 5 h and then quenched with saturated NaHCO$_3$ (1.5 mL). The resulting mixture was directly purified by prep-HPLC to afford Compound 8 (12.00 mg, 10.95 µmol, 31% yield). MS (ESI) m/z=1096[M+H]$^+$. $^1$H NMR (400 M, MeOD-d4), δ 8.29 (m, 1H), 8.07 (m, 1H), 7.77 (m, 2H), 7.40 (m, 2H), 7.33 (m, 2H), 7.24 (m, 2H), 7.14 (m, 3H), 7.08~6.92 (m, 4H), 4.10 (m, 1H), 4.00 (m, 2H), 3.70 (m, 2H), 3.60~2.70 (m, 23H), 2.41 (m, 2H), 2.17 (m, 1H), 2.07 (m, 2H), 1.94 (m, 1H), 1.58 (m, 2H), 1.29 (m, 3H), 1.06 (s, 6H).

Example 1.7: Synthesis of Compound 9.

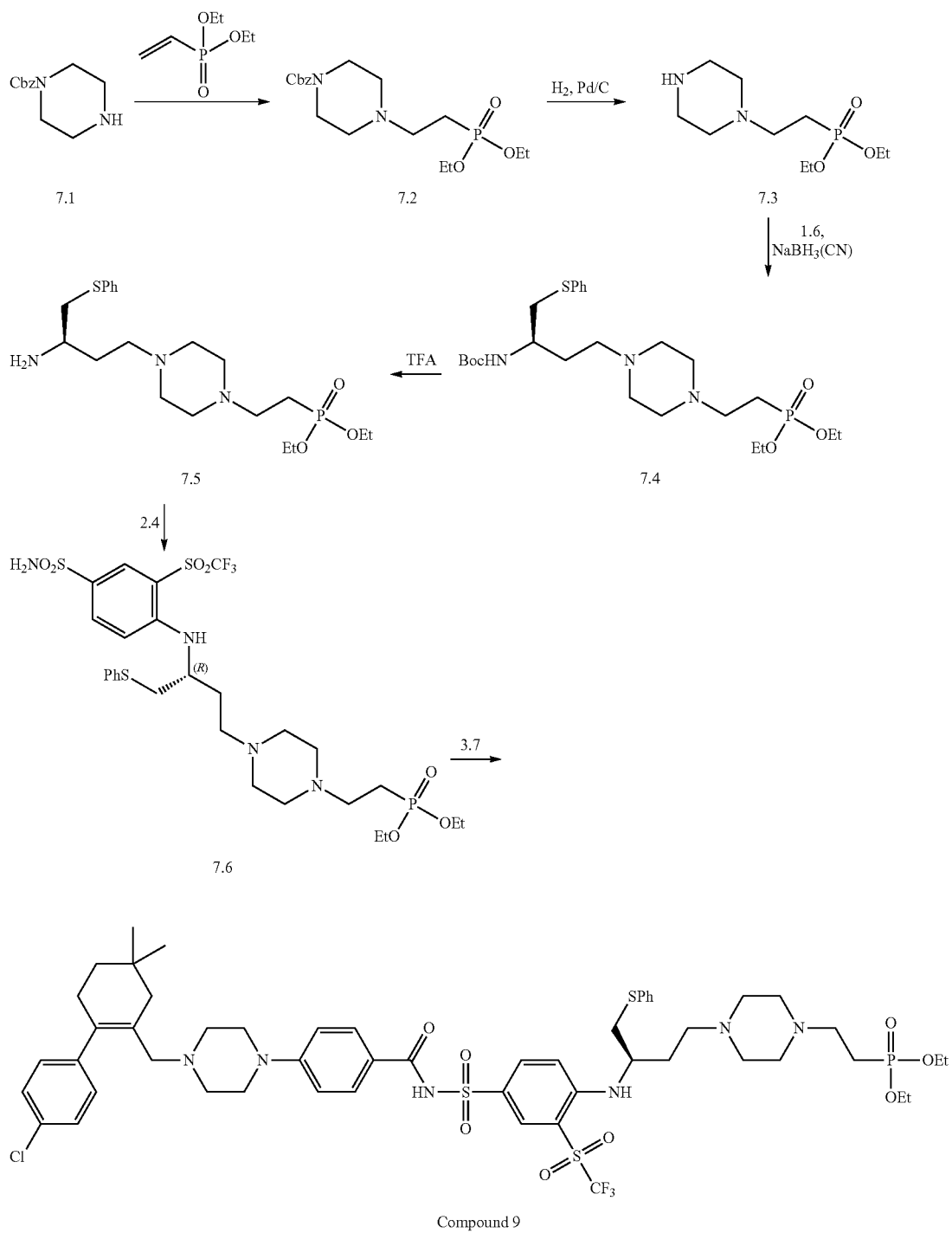

Compound 9

Step A: Synthesis of benzyl 4-(2-(diethoxyphosphoryl)ethyl)piperazine-1-carboxylate (7.2). To a solution of benzyl piperazine-1-carboxylate (1.65 g, 7.49 mmol) in EtOH (12.00 mL) was added 1-[ethoxy(vinyl)phosphoryl]oxyethane (1.48 g, 8.99 mmol). The reaction mixture was stirred at 60° C. for 24 h and then concentrated. The residue was purified by flash column chromatography on silica gel (Petroleum Ether:EtOAc=1:1) to afford 7.2 (1.88 g, 4.89 mmol, 65% yield). MS (ESI) m/z=385[M+H]$^+$. $^1$H NMR (400 M, CDCl$_3$), δ 7.35 (m, 5H), 5.13 (s, 2H), 4.12 (m, 4H), 3.53 (m, 4H), 2.68 (m, 2H), 2.44 (m, 4H), 1.98 (m, 2H), 1.31 (m, 6H).

Step B: Synthesis of diethyl (2-(piperazin-1-yl)ethyl) phosphonate (7.3). To a solution of 7.2 (1.80 g, 4.68 mmol) in EtOH was added 10% Pd/C (568.43 mg). The reaction mixture was stirred overnight under H$_2$ atmosphere and then concentrated to afford 7.3 (1.10 g, 4.40 mmol, 94% yield), which was used in the next step without further purification.

MS (ESI) m/z=251[M+H]⁺. ¹H NMR (400 M, CDCl₃), 4.12 (m, 4H), 2.90 (m, 4H), 2.65 (m, 2H), 2.46 (m, 4H), 1.98 (m, 2H), 1.32 (m, 6H).

Step C: Synthesis of tert-Butyl (R)-(4-(4-(2-(diethoxyphosphoryl)ethyl)piperazin-1-yl)—1-(phenylthio) butan-2-yl)carbamate (7.4). To a mixture of 1.6 (710.00 mg, 2.40 mmol) and 7.3 (600.65 mg, 2.40 mmol) in DCM (20.00 mL) was added Et₃N (971.42 mg, 9.60 mmol). The mixture was stirred at 0° C. for 10 min and then NaBH₃(CN) (226.22 mg, 3.60 mmol) was added. The reaction mixture was stirred at r.t. overnight. The excess solvent was concentrated and the residue was purified by flash column chromatography on silica gel (DCM:MeOH=10:1) to afford 7.4 (930.00 mg, 1.76 mmol, 73% yield). MS (ESI) m/z=530[M+H]⁺. ¹H NMR (400 M, CDCl₃), δ 7.40 (m, 2H), 7.29 (m, 2H), 7.19 (m, 1H), 5.61 (br, 1H), 4.12 (m, 4H), 3.82 (m, 1H), 3.30~2.40 (m, 14H), 2.03~1.90 (m, 4H), 1.42 (m, 9H), 1.38 (m, 3H), 1.23 (m, 3H).

Step D: Synthesis of diethyl (R)-(2-(4-(3-amino-4-(phenylthio)butyl)piperazin-1-yl)ethyl)phosphonate (7.5). To a solution of 7.4 (450.00 mg, 849.59 μmol) in DCM (20.00 mL) was added TFA (193.74 mg, 1.70 mmol). The reaction mixture was stirred at r.t. overnight and then directly concentrated to afford 7.5 (364.00 mg, 847.38 μmol, quantitative), which was used in the next step without further purification. MS (ESI) m/z=430[M+H]⁺.

Step E: Synthesis of diethyl (R)-(2-(4-(4-(phenylthio)-3-((4-sulfamoyl-2-((trifluoromethyl)sulfonyl) phenyl)amino) butyl)piperazin-1-yl)ethyl)phosphonate (7.6). To a mixture of 7.5 (350.00 mg, 814.79 μmol) and 2.4 (250.34 mg, 814.79 μmol) in DCM (20.00 mL) was added DIPEA (631.82 mg, 4.89 mmol). The reaction mixture was stirred at 40° C. overnight and then concentrated. The residue was purified by prep-HPLC to afford 7.6 (368.00 mg, 513.40 μmol, 63% yield). MS (ESI) m/z=718[M+H]⁺. ¹H NMR (400 M, CDCl₃), 8.25 (m, 1H), 7.84 (m, 1H), 7.41~7.26 (m, 5H), 7.06 (m, 1H), 6.67 (m, 1H), 4.12 (m, 4H), 3.89 (m, 1H), 3.07 (m, 2H), 2.90~2.30 (m, 12H), 2.20~2.00 (m, 4H), 1.35 (m, 6H).

Step F: Synthesis of Compound 9: To a mixture of 7.6 (637.00 mg, 888.68 μmol) and 3.7 (390.12 mg, 888.68 μmol) in DCM (40.00 mL) were added EDCI (341.25 mg, 1.78 mmol) and DMAP (217.14 mg, 1.78 mmol). The reaction mixture was heated at 40° C. for 3-4 h and then concentrated. The residue was purified by prep-HPLC and then lyophilized to afford Compound 9 (325.00 mg, 285.65 μmol, 32% yield). MS (ESI) m/z=1139[M+H]⁺. ¹H NMR (400 M, CDCl₃), δ 8.34 (s, 1H), 8.12 (m, 1H), 7.72 (m, 2H), 7.37~7.24 (m, 7H), 7.08~6.96 (m, 3H), 6.75 (m, 2H), 6.67 (m, 1H), 4.11 (m, 4H), 3.93 (m, 2H), 3.74 (m, 1H), 3.66 (m, 1H), 3.40 (m, 4H), 3.14~2.50 (m, 15H), 2.30~2.08 (m, 10H), 1.49 (m, 2H), 1.31 (m, 6H), 0.99 (m, 6H).

Example 1.8: Synthesis of Compound 13.

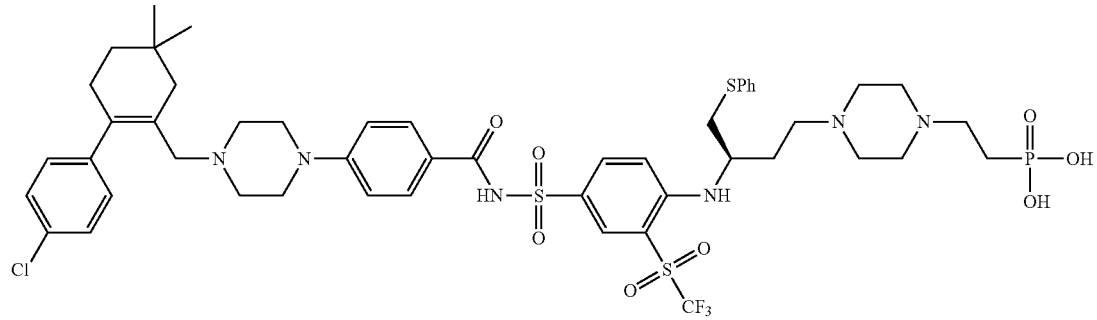

To a solution of Compound 9 (60.00 mg, 52.74 μmol) in CH₃CN (20.00 mL) was added TMSBr (606.40 mg, 5.27 mmol). The reaction mixture was stirred at 60° C. for 3-4 h and quenched with saturated NaHCO₃ (3 mL). The resulting mixture was directly purified by prep-HPLC to afford Compound 13 (20.00 mg, 18.49 μmol, 35% yield). MS (ESI) m/z=1083[M+H]⁺.

Example 1.9: Synthesis of Compound 14.

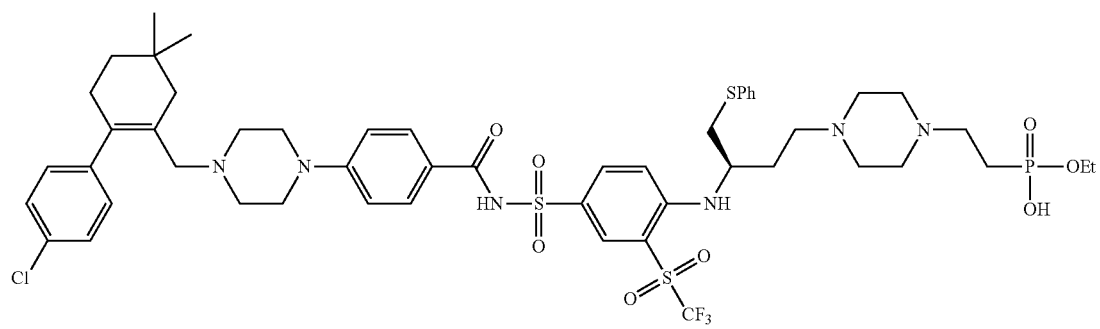

To a solution of Compound 9 (60.00 mg, 52.74 μmol) in CH₃CN (15.00 mL) was added TMSBr (181.94 mg, 1.58 mmol). The reaction mixture was stirred at r.t. for 4 h and then quenched with saturated NaHCO₃ (3 mL). The resulting mixture was directly purified by prep-HPLC to afford Compound 14 (15.00 mg, 13.52 µmol, 26% yield). MS (ESI) m/z=1111[M+H]+.

Example 1.10: Synthesis of Compound 10.

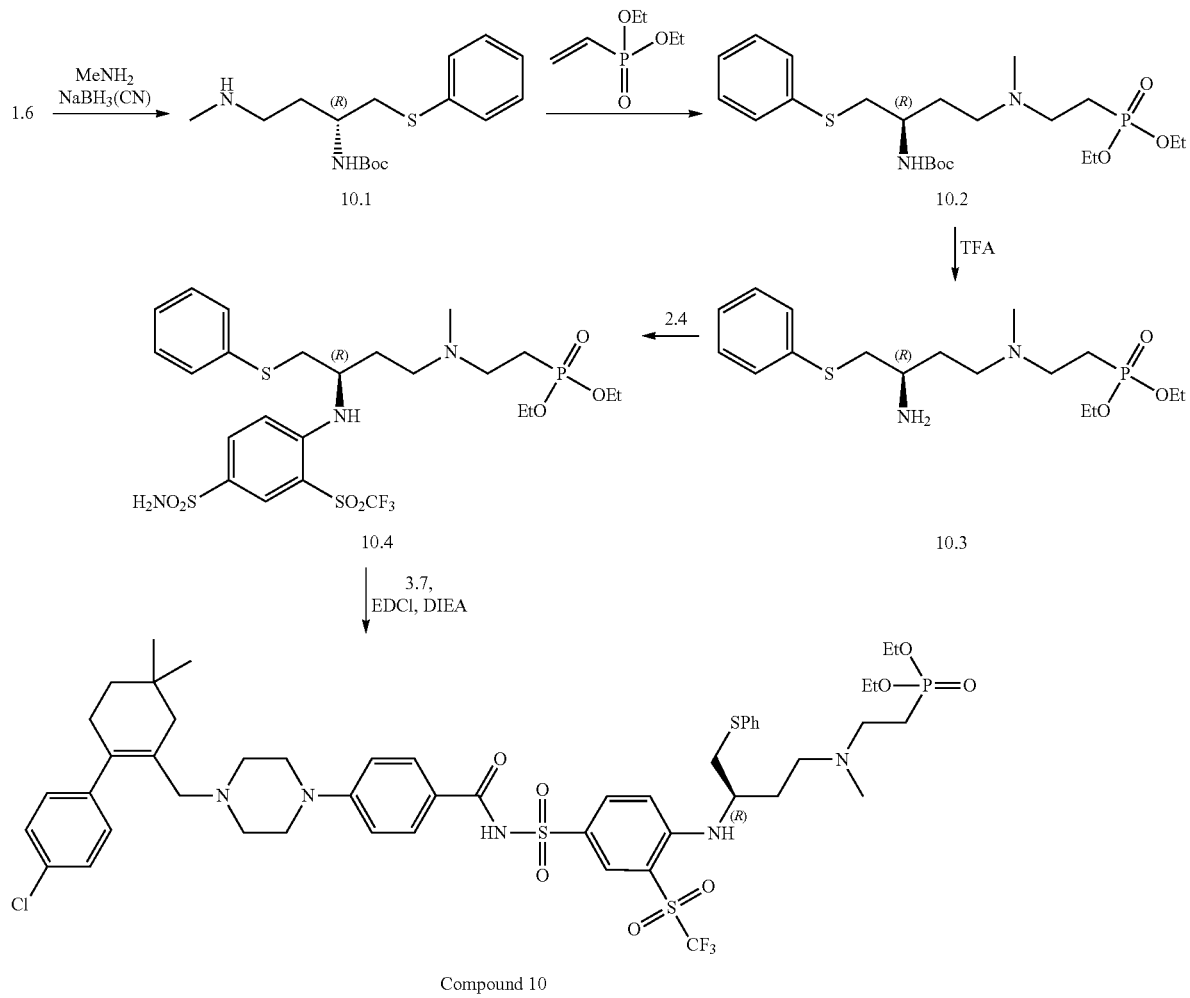

Compound 10

Step A: Synthesis of tert-Butyl (R)-(4-(methylamino)-1-(phenylthio)butan-2-yl)carbamate (10.1). To a mixture of 1.6 (1.60 g, 5.42 mmol) and methanamine (168.23 mg, 5.42 mmol) in DCM (20.00 mL) was added Et₃N (2.19 g, 21.67 mmol). The mixture was stirred at 0° C. for 10 min and then NaBH₃(CN) (510.55 mg, 8.12 mmol) was added. The reaction mixture was stirred at r.t. overnight and then concentrated to afford 10.1 (1.62 g, 5.22 mmol, 96% yield), which was used in the next step without further purification. MS (ESI) m/z=311[M+H]+.

Step B: Synthesis of tert-Butyl (R)-(4-((2-(diethoxyphosphoryl)ethyl)(methyl)amino)-1-(phenylthio) butan-2-yl)carbamate (10.2). To a solution of 10.1 (1.00 g, 3.22 mmol) in EtOH (5.00 mL) was added 1-[ethoxy(vinyl)phosphoryl] oxyethane (2.11 g, 12.88 mmol). The reaction mixture was heated at 60° C. overnight and then directly purified by prep-HPLC to afford 10.2 (100.00 mg, 210.71 µmol, ~7% yield). MS (ESI) m/z=476[M+H]+.

Step C: Synthesis of diethyl (R)-(2-((3-amino-4-(phenylthio)butyl)(methyl)amino) ethyl)phosphonate (10.3). To a solution of 10.2 (750.00 mg, 1.58 mmol) in DCM (20.00 mL) was added TFA (360.30 mg, 3.16 mmol). The reaction mixture was stirred at r.t. overnight and concentrated to afford 10.3 (590.00 mg, 1.58 mmol, near quantitative), which was used in the next step without further purification. MS (ESI) m/z=376[M+H]+.

Step D: Synthesis of diethyl (R)-(2-(methyl(4-(phenylthio)-3-((4-sulfamoyl-2-((trifluoromethyl) sulfonyl)phenyl) amino)butyl)amino)ethyl)phosphonate (10.4). To a mixture of 10.3 (590.00 mg, 1.58 mmol) and 2.4 (485.44 mg, 1.58 mmol) in DCM (30.00 mL) was added DIPEA (1.23 g, 9.48 mmol). The reaction mixture was heated at 40° C. overnight and then directly concentrated. The residue was purified by prep-HPLC to afford 10.4 (560.00 mg, 846.29 µmol, ~54% yield). MS (ESI) m/z=662[M+H]+. ¹H NMR (300 MHz, CDCl₃): δ 8.19 (m, 1H), 7.82 (m, 1H), 7.45~7.29 (m, 5H), 6.91 (m, 1H), 6.66 (m, 1H), 4.16 (m, 4H), 4.00 (m, 2H), 3.40~3.10 (m, 5H), 2.79 (s, 3H), 2.41~2.03 (m, 4H), 1.33 (m, 6H).

Step E: Synthesis of Compound 10: To a mixture of 10.4 (560.00 mg, 846.29 µmol) and 3.7 (371.51 mg, 846.29 µmol) in DCM (30.00 mL) were added EDCI (333.10 mg, 1.73 mmol) and DMAP (206.78 mg, 1.69 mmol). The reaction mixture was heated at 40° C. for 3 h and then concentrated.

The residue was purified by prep-HPLC to afford Compound 10 (350.00 mg, 323.27 µmol, ~38% yield). MS (ESI) m/z=1083[M+H]⁺.

Example 1.11: Synthesis of Compound 11.

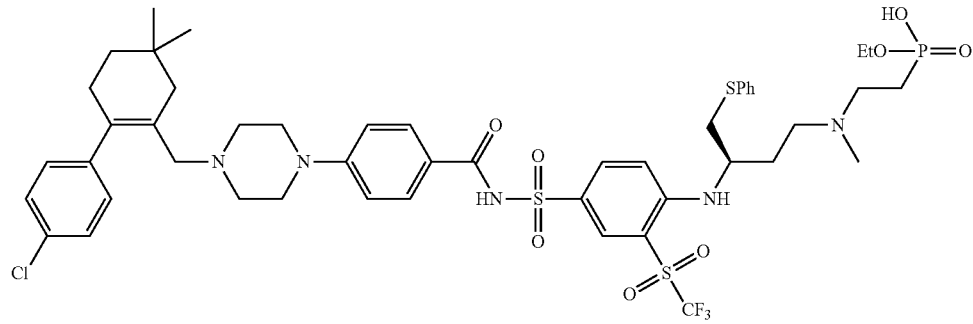

To a solution of Compound 10 (60.00 mg, 55.42 µmol) in CH₃CN (20.00 mL) was added TMSBr (191.18 mg, 1.66 mmol). The reaction mixture was stirred at r.t. for 3-4 h and quenched with saturated NaHCO₃ (3 mL). The resulting mixture was purified by prep-HPLC to afford Compound 11 (15.00 mg, 14.22 µmol, 26% yield). MS (ESI) m/z=1055 [M+H]⁺. ¹H NMR (400 MHz, MeOD-d4): δ 8.31 (m, 1H), 8.06 (m, 1H), 7.73 (m, 2H), 7.36 (m, 2H), 7.32 (m, 2H), 7.19~7.14 (m, 5H), 7.03 (m, 1H), 6.96 (m, 3H), 4.12 (m, 2H), 3.92 (m, 3H), 3.69 (m, 3H), 3.40~3.11 (m, 9H), 2.82 (s, 3H), 2.39 (m, 2H), 2.31~1.91 (m, 8H), 1.68 (m, 2H), 1.17 (t, 3H, J=7.2 Hz), 1.06 (s, 6H).

Example 1.12: Synthesis of Compound 12.

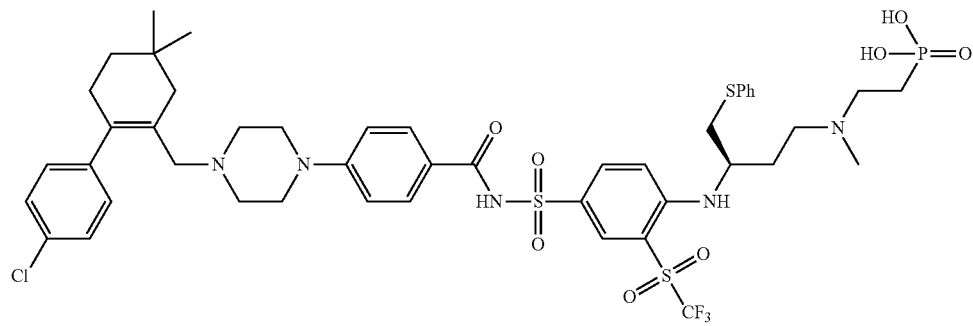

To a solution of Compound 10 (68.00 mg, 62.81 µmol) in CH₃CN (6.00 mL) was added TMSBr (722.21 mg, 6.28 mmol). The reaction mixture was stirred at 60° C. for 3 h and then quenched with saturated NaHCO₃ (2 mL). The resulting mixture was purified by prep-HPLC to afford Compound 12 (63.00 mg, 61.37 µmol, 98% yield). MS (ESI) m/z=1027 [M+H]⁺. ¹H NMR (400 MHz, MeOD-d4): δ 8.31 (m, 1H), 8.05 (m, 1H), 8.09 (m, 2H), 7.76 (m, 2H), 7.39 (m, 2H), 7.33 (m, 2H), 7.22~7.11 (m, 5H), 7.00~6.95 (m, 3H), 4.12 (m, 1H), 3.68 (m, 3H), 3.41~3.12 (m, 12H), 2.83 (s, 3H), 2.39 (m, 2H), 2.31~1.89 (m, 7H), 1.57 (m, 2H), 1.06 (s, 6H).

Example 1.13: Synthesis of Compounds 15 and 16.

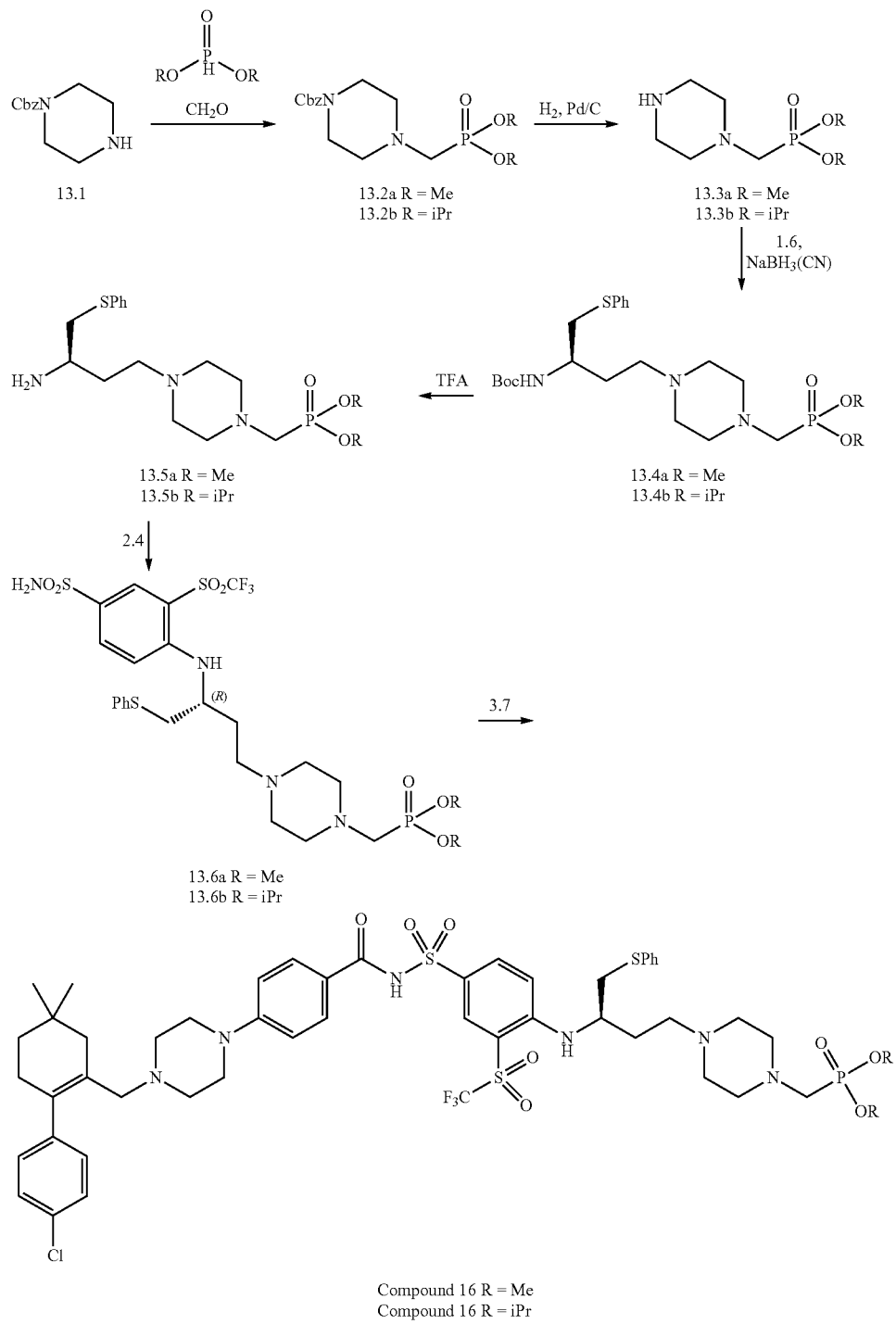

Step $A_a$: Synthesis of benzyl 4-((dimethoxyphosphoryl)methyl)piperazine-1-carboxylate (13.2a). To a solution of benzyl piperazine-1-carboxylate (2.00 g, 9.08 mmol) in 1,4-Dioxane (20.13 mL) were added 37% HCHO (7.07 mL) and methoxyphosphonoyl oxymethane (12.3 mL) at r.t. The reaction mixture was stirred for 1 h and then poured into DCM (100 mL). The two phases were separated and the organic phase was washed with $H_2O$ (2×80 mL) and 2M HCl (2×50 mL), dried over anhydrous $Na_2SO_4$ and concentrated. The residue was slurried in petroleum ether (50 mL), and then filtered. The filtration cake was collected and dried under reduced pressure to afford 13.2a (1.90 g, 5.55 mmol, 61% yield). $^1$H NMR (400 MHz, $CDCl_3$): δ 7.34 (m, 5H), 5.13 (s, 2H), 3.81 (s, 3H), 3.78 (s, 3H), 3.53 (m, 4H), 2.82 (d, 2H, J=116 Hz), 2.62 (m, 4H).

Step A$_b$: Synthesis of benzyl 4-((diisopropoxyphosphoryl)methyl)piperazine-1-carboxylate (13.2b). 13.2b was obtained following the general procedure in Step A$_a$. Yield 91%. MS (ESI) m/z=399[M+H]$^+$. $^1$H NMR (400 MHz, CDCl$_3$): 57.38 (m, 5H), 5.15 (s, 2H), 4.79 (m, 2H), 4.46~3.3 (m, 10H), 1.37 (m, 12H).

Step B$_a$: Synthesis of dimethyl (piperazin-1-ylmethyl) phosphonate (13.3a). To a solution of 13.2a (1.30 g, 3.80 mmol) in EtOH (50.00 mL) was added Pd/C (130.00 mg). The reaction mixture was stirred under H$_2$ atmosphere at r.t. overnight. The mixture was then filtered, and the filtrate was concentrated to afford the crude 13.3a (~750.00 mg, 3.60 mmol, ~95% yield), which was directly used in the next step without further purification. MS (ESI) m/z=209[M+H]$^+$. $^1$H NMR (400 MHz, CDCl$_3$): δ 3.81 (s, 3H), 3.78 (s, 3H), 2.91 (m, 4H), 2.80 (d, 2H, J=116 Hz), 2.62 (m, 4H).

Step B$_b$: Synthesis of diisopropyl (piperazin-1-ylmethyl) phosphonate (13.3b). 13.3b was obtained from 13.2b following the general procedure in Step B$_a$. Yield 91%. MS (ESI) m/z=265[M+H]$^+$. $^1$H NMR (400 MHz, CDCl$_3$): δ 4.72 (m, 2H), 3.24 (m, 4H), 3.00 (m, 4H), 2.79 (d, 2H, J=120 Hz), 1.32 (m, 12H).

Step C$_a$: Synthesis of tert-Butyl (R)-(4-(4-((dimethoxyphosphoryl)methyl)piperazin-1-yl)—1-(phenyl thio)butan-2-yl)carbamate (13.4a). To a solution of 1.6 (300.00 mg, 1.02 mmol) in DCM (15.00 mL) were added 13.3a (212.35 mg, 1.02 mmol), TEA (412.86 mg, 4.08 mmol) and NaBH$_3$(CN) (96.15 mg, 1.53 mmol) at r.t. The reaction mixture was stirred at r.t. overnight, and then concentrated directly. The residue was purified by flash column chromatography on silica gel (DCM:MeOH=10:1) to afford 13.4a (350.00 mg, 717.82 μmol, ~70% yield). MS (ESI) m/z=488[M+H]$^+$. $^1$H NMR (400 MHz, CDCl$_3$): δ 7.39 (m, 2H), 7.30 (m, 2H), 7.19 (m, 1H), 5.69 (br, 1H), 3.82 (s, 3H), 3.78 (s, 3H), 3.22 (m, 2H), 3.07 (m, 2H), 2.82 (m, 2H), 2.78~2.50 (m, 9H), 1.90 (m, 1H), 1.72 (m, 1H), 1.42 (s, 9H).

Step C$_b$: Synthesis of tert-Butyl (R)-(4-(4-((diisopropoxyphosphoryl)methyl)piperazin-1-yl)-1-(phenyl thio)butan-2-yl)carbamate (13.4b). 13.4b was obtained from 13.3b following the general procedure in Step C$_a$. Yield 76%. MS (ESI) m/z=544[M+H]$^+$. $^1$H NMR (400 MHz, CDCl$_3$): δ 7.41 (m, 2H), 7.31 (m, 2H), 7.20 (m, 1H), 5.41 (br, 1H), 4.74 (m, 2H), 3.80 (m, 1H), 3.20 (m, 1H), 3.10 (m, 1H), 2.94~2.65 (m, 12H), 2.04 (m, 1H), 1.71 (m, 1H), 1.41 (s, 9H), 1.33 (m, 12H).

Step D$_a$: Synthesis of dimethyl (R)-((4-(3-amino-4-(phenylthio)butyl)piperazin-1-yl)methyl) phosphonate (13.5a). To a solution of 13.4a (200.00 mg, 410.18 μmol) in DCM (9.00 mL) was added TFA (3.00 mL). The reaction mixture was stirred at room temperature for 5 h, and then concentrated to afford 13.5a (~150.00 mg, 387.12 μmol, ~94% yield), which was used directly in the next step without further purification. MS (ESI) m/z=388[M+H]$^+$.

Step D$_b$: Synthesis of diisopropyl (R)-((4-(3-amino-4-(phenylthio)butyl)piperazin-1-yl)methyl) phosphonate (13.5b). 13.5b was obtained from 13.4b following the general procedure in Step D$_a$. Yield 94%. MS (ESI) m/z=444 [M+H]$^+$. $^1$H NMR (400 MHz, CDCl$_3$): δ 7.40 (m, 2H), 7.33 (m, 3H), 4.76 (m, 2H), 3.47~3.20 (m, 11H), 3.17 (m, 2H), 3.10 (m, 2H), 2.30 (m, 2H), 1.36 (m, 12H).

Step E$_a$: Synthesis of dimethyl (R)-((4-(4-(phenylthio)-3-((4-sulfamoyl-2-((trifluoromethyl)sulfonyl) phenyl)amino) butyl)piperazin-1-yl)methyl)phosphonate (13.6a). To a mixture of 13.5a (150.00 mg, 387.12 μmol) and 2.4 (118.94 mg, 387.12 μmol) in acetonitrile (10.00 mL) was added DIPEA (300.19 mg, 2.32 mmol). The reaction mixture was stirred at 75° C. for 2 hours and then concentrated directly. The residue was purified by prep-TLC (EtOAc:MeOH=10:1) to afford 13.6a (120.00 mg, 177.85 μmol, 46% yield). MS (ESI) m/z=676[M+H]$^+$. $^1$H NMR (400 MHz, CDCl$_3$): δ 8.23 (m, 1H), 7.84 (m, 1H), 7.40~7.27 (m, 5H), 6.97 (m, 1H), 6.70 (m, 1H), 5.21 (br, 2H), 3.90 (m, 1H), 3.80 (m, 3H), 3.78 (m, 3H), 3.08 (m, 2H), 2.83 (d, 2H, J=112 Hz), 2.71~2.38 (m, 10H), 1.78~1.38 (m, 2H).

Step E$_b$: Synthesis of diisopropyl (R)-((4-(4-(phenylthio)-3-((4-sulfamoyl-2-((trifluoromethyl)sulfonyl) phenyl) amino)butyl)piperazin-1-yl)methyl)phosphonate (13.6b). 13.6b was obtained from 13.5b following the general procedure in Step E$_a$. Yield 76%. MS (ESI) m/z=732[M+H]$^+$. $^1$H NMR (400 MHz, CDCl$_3$): δ 8.22 (m, 1H), 7.84 (m, 1H), 7.40 (m, 2H), 7.32 (m, 3H), 6.97 (m, 1H), 6.70 (m, 1H), 4.72 (m, 2H), 3.91 (m, 1H), 3.080 (m, 2H), 2.80~2.40 (m, 12H), 2.11 (m, 1H), 1.75 (m, 1H), 1.32 (m, 12H).

Step F$_a$: Synthesis of Compound 16.

To a solution of 13.6a (200.00 mg, 296.42 μmol) in DCM (20.00 mL) were added 3.7 (130.13 mg, 296.42 μmol), DMAP (72.43 mg, 592.84 μmol) and EDCI (113.65 mg, 592.84 μmol). The reaction mixture was stirred at 40° C. overnight, and then concentrated directly. The residue was purified by flash column chromatography on silica gel (EtOAc:MeOH=10:1) to afford Compound 16 (100.00 mg, 91.27 μmol, ~31% yield). MS (ESI) m/z=1096[M+H]$^+$. $^1$H NMR (400 MHz, CDCl$_3$): δ 8.37 (m, 1H), 8.11 (m, 1H), 7.65 (m, 1H), 7.40~7.20 (m, 10H), 7.00 (m, 2H), 6.79 (m, 1H), 6.61 (m, 1H), 3.89 (m, 1H), 3.79 (m, 3H), 3.75 (m, 3H), 3.70 (m, 1H), 3.35 (m, 4H), 3.13~2.31 (m, 22H), 2.28 (m, 2H), 2.05 (m, 2H), 1.45 (m, 2H), 0.99 (s, 6H).

Step F$_b$: Synthesis of Compound 15.

Compound 15 was obtained from compound 13.6b following the general procedure of Step F$_a$. Yield 42%. MS (ESI) m/z=1152[M+H]$^+$. $^1$H NMR (400 MHz, CDCl$_3$): δ 8.36 (m, 1H), 8.09 (m, 1H), 7.65 (m, 1H), 7.36 (m, 2H), 7.32~7.20 (m, 6H), 7.00 (m, 3H), 6.79 (m, 2H), 6.61 (m, 1H), 4.72 (m, 2H), 3.87 (m, 1H), 3.71 (m, 1H), 3.30 (m, 5H), 3.09~2.31 (m, 19H), 2.27 (m, 4H), 2.01 (m, 2H), 1.44 (m, 2H), 1.32 (m, 12H), 0.99 (m, 6H).

Example 1.14: Synthesis of Compounds 14.1b, 14.1c and 14.1d.

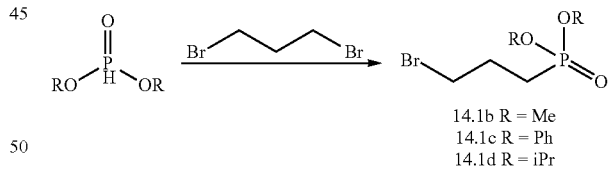

14.1b R = Me
14.1c R = Ph
14.1d R = iPr

Step A$_b$: Synthesis of 1-Bromo-3-dimethoxyphosphorylpropane (14.1b). Trimethyl phosphite (1.24 g, 9.99 mmol) was added to 1,3-dibromopropane (10.08 g, 49.95 mmol) and the reaction mixture was refluxed for 4 h. The mixture was then cooled to r.t. and directly subjected to flash column chromatography on silica gel (Petroleum Ether:EtOAc=1:1) to afford 14.1b (1.40 g, 6.06 mmol, 61% yield) as an oil. MS (ESI) m/z=233.2[M+H]$^+$. $^1$H NMR (400 M, CDCl$_3$), δ 3.77~3.75 (s, 6H), 3.48~3.46 (m, 2H), 2.24~2.16 (m, 2H), 1.97~1.90 (m, 2H).

Step A$_c$: [3-Bromopropyl(phenoxy)phosphoryl]oxybenzene (14.1c) was obtained in the same way. Yield 19%. MS (ESI) m/z=356.6[M+H]$^+$. $^1$H NMR (400 M, CDCl$_3$), δ 7.35~7.32 (m, 4H), 7.19~7.16 (m, 6H), 3.55~3.52 (m, 2H), 2.40~2.22 (m, 4H).

Step $A_d$: 1-bromo-3-diisopropoxyphosphoryl-propane (14.1d) was obtained in the same way. Yield 44%. MS (ESI) m/z=288.8[M+H]$^+$. $^1$H NMR (400 M, CDCl$_3$), 54.73 (m, 2H), 3.49~3.46 (m, 2H), 2.22~2.18 (m, 2H), 1.90~1.82 (m, 2H), 1.35~1.33 (m, 12H).
Example 1.15: Synthesis of Compounds 23, 24, 25 and 27.
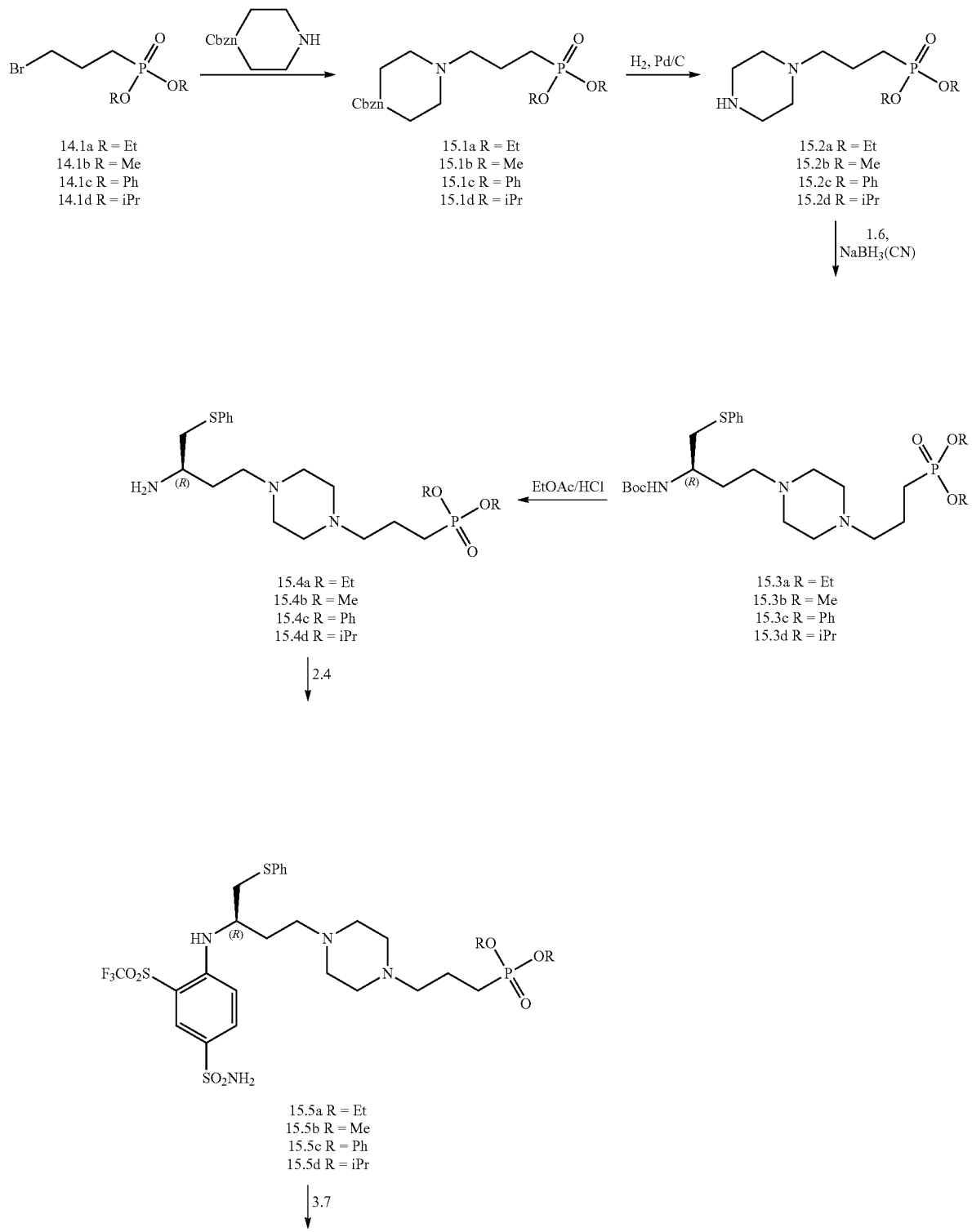

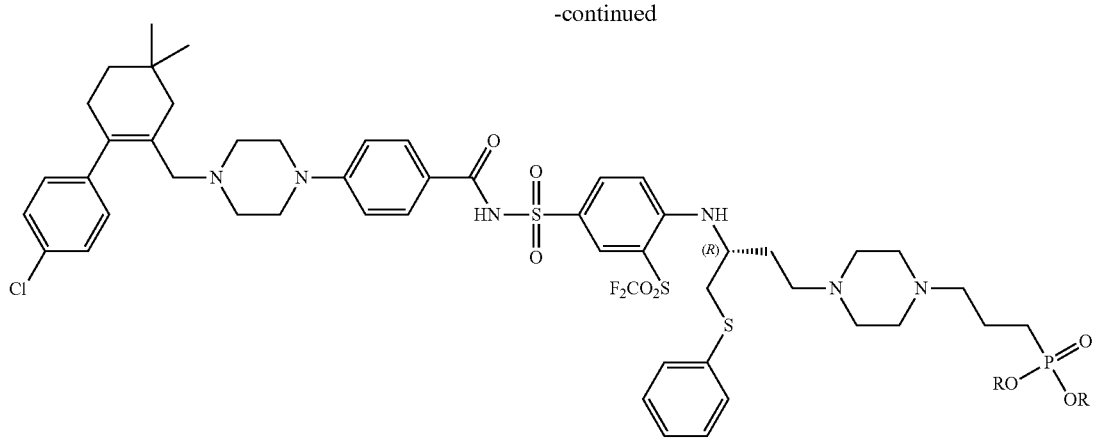

Compound 23 R = Et
Compound 24 R = Me
Compound 25 R = Ph
Compound 27 R = iPr

Step $A_a$: Synthesis of benzyl 4-(3-diethoxyphosphorylpropyl) piperazine-1-carboxylate (15.1a). To a solution of benzyl piperazine-1-carboxylate (1.10 g, 4.99 mmol) and 1-bromo-3-diethoxyphosphoryl-propane (1.29 g, 4.99 mmol) in $CH_3CN$ (40.00 mL) was added $K_2CO_3$ (1.38 g, 9.98 mmol). The reaction mixture was stirred at 75° C. overnight and then EtOAc (50 mL) and water (30 mL) were added. The layers were separated, and the aqueous phase was extracted again with EtOAc (20 mL×2). The combined organic phases were washed with brine (40 mL), dried over anhydrous $MgSO_4$, filtered and concentrated. The residue was purified by flash column chromatography on silica gel to afford Compound 15.1a (EtOAc/MeOH=50:1) to afford (1.80 g, 4.52 mmol, 91% yield) as an oil. $^1H$ NMR (400 M, $CDCl_3$), δ 7.35 (m, 5H), 5.13 (s, 2H), 4.12 (m, 4H), 3.52 (m, 4H), 2.42 (m, 6H), 1.78 (m, 4H), 1.32 (m, 6H).

Step $A_b$: Benzyl 4-(3-dimethoxyphosphorylpropyl) piperazine-1-carboxylate (15.1b) was obtained from 14.1b in the same way. Yield 87%. MS (ESI) m/z=371.4[M+H]$^+$. $^1H$ NMR (400 M, $CDCl_3$), δ 7.35 (m, 5H), 5.13 (s, 2H), 3.76 (s, 3H), 3.74 (s, 3H), 3.52 (m, 4H), 2.41 (m, 6H), 1.79 (m, 4H).

Step $A_c$: Benzyl 4-(3-diphenoxyphosphorylpropyl) piperazine-1-carboxylate (15.1c) was obtained from 14.1c in the same way. Yield 57%. MS (ESI) m/z=495.4[M+H]$^+$. $^1H$ NMR (400 M, $CDCl_3$), δ 7.37~7.30 (m, 9H), 7.19~7.15 (m, 6H), 5.13 (s, 2H), 3.50 (m, 4H), 2.48~2.30 (m, 6H), 2.15~2.11 (m, 2H), 2.00~1.91 (m, 2H).

Step $A_d$: Benzyl 4-(3-diisopropoxyphosphorylpropyl)piperazine-1-carboxylate (15.1d) was obtained from 14.1d in the same way. Yield 54%. MS (ESI) m/z=427.1[M+H]$^+$. $^1H$ NMR (400 M, $CDCl_3$), δ 7.35 (m, 5H), 5.13 (s, 2H), 4.73~4.66 (m, 2H), 3.53~3.48 (m, 4H), 2.50~2.30 (m, 6H), 1.79 (m, 4H), 1.33 (m, 12H).

Step $B_a$: Synthesis of 1-(3-diethoxyphosphorylpropyl) piperazine (15.2a). To a solution of 15.1a (1.20 g, 3.01 mmol) in EtOH (20 mL) was added 10% Pd/C (200 mg). The reaction mixture was stirred overnight under $H_2$ atmosphere and then concentrated to afford 15.2a (~700 mg, 2.65 mmol, ~88% yield), which was used in the next step without further purification. MS (ESI) m/z=265.4[M+H]$^+$. $^1H$ NMR (400 M, $CDCl_3$), δ 4.16~4.06 (m, 4H), 2.91 (m, 4H), 2.63 (m, 2H), 2.44~2.39 (m, 4H), 1.80~1.75 (m, 4H), 1.38~1.30 (m, 6H).

Step $B_b$: 1-(3-Dimethoxyphosphorylpropyl)piperazine (15.2b) was obtained from 15.1b in the same way. Yield 92%. MS (ESI) m/z=237[M+H]$^+$. $^1H$ NMR (400 M, $CDCl_3$), δ 3.74 (s, 3H), 3.71 (s, 3H), 2.93 (m, 4H), 2.45 (m, 4H), 2.38 (m, 2H), 1.76 (m, 4H).

Step $B_c$: 1-(3-Diphenoxyphosphorylpropyl)piperazine (15.2c) was obtained from 15.1c in the same way. Yield 87%. MS (ESI) m/z=361[M+H]$^+$. $^1H$ NMR (400 M, $CDCl_3$), δ 7.34~7.29 (m, 4H), 7.20~7.15 (m, 6H), 3.73 (m, 2H), 2.90 (m, 4H), 2.43 (m, 4H), 2.15 (m, 2H), 1.95 (m, 2H).

Step $B_d$: 1-(3-Diisopropoxyphosphorylpropyl)piperazine (15.2d) was obtained from 15.1d in the same way. Yield 78%. MS (ESI) m/z=293.2[M+H]$^+$. $^1H$ NMR (400 M, $CDCl_3$), δ4.71 (m, 2H), 3.76 (m, 4H), 2.62~2.50 (m, 6H), 1.80~1.66 (m, 4H), 1.30 (m, 12H).

Step $C_a$: Synthesis of tert-Butyl-N-[(1R)-3-[4-(3-diethoxyphosphorylpropyl)piperazin-1-yl]-1-(phenylsulfanylmethyl)propyl]carbamate (15.3a). To a mixture of 1.6 (1.00 g, 3.39 mmol) and 15.2a (896 mg, 3.39 mmol) in DCM (50.00 mL) was added $Et_3N$ (1.37 g, 13.56 mmol). The mixture was stirred at 0° C. for 10 min and then $NaBH_3(CN)$ (243.33 mg, 3.73 mmol) was added. The reaction mixture was stirred at r.t. overnight. An excess of solvent was concentrated and the residue was purified by flash column chromatography on silica gel (DCM:MeOH=10:1) to afford 15.3a (1.35 g, 2.48 mmol, 73% yield). MS (ESI) m/z=544.5 [M+H]$^+$. $^1H$ NMR (400 M, $CDCl_3$), δ 7.40 (m, 2H), 7.31 (m, 2H), 7.19 (m, 1H), 5.10 (br, 1H), 4.13 (m, 4H), 3.82 (m, 1H), 3.30~2.40 (m, 14H), 1.90~1.70 (m, 6H), 1.42 (m, 9H), 1.40~1.20 (m, 6H).

Step $C_b$: tert-Butyl-N-[(1R)-3-[4-(3-dimethoxyphosphorylpropyl)piperazin-1-yl]-1-(phenylsulfanylmethyl)propyl] carbamate (15.3b) was obtained from 15.2b in the same way. Yield 9%. MS (ESI) m/z=516[M+H]$^+$. $^1H$ NMR (400 M, $CDCl_3$), δ 7.40 (m, 2H), 7.32 (m, 2H), 7.20 (m, 1H), 5.42 (br, 1H), 3.75 (s, 3H), 3.74 (s, 3H), 3.82 (m, 1H), 3.30~2.40 (m, 14H), 1.90~1.70 (m, 6H), 1.42 (m, 9H).

Step $C_c$: tert-Butyl-N-[(1R)-3-[4-(3-diphenoxyphosphorylpropyl)piperazin-1-yl]-1-(phenylsulfanylmethyl)propyl] carbamate (15.3c) was obtained from 15.2c in the same way. Yield 46%. MS (ESI) m/z=640.5[M+H]$^+$. $^1H$ NMR (400 M, $CDCl_3$), δ 7.40 (m, 2H), 7.34~7.30 (m, 6H), 7.20~7.16 (m, 7H), 5.52 (br, 1H), 3.84 (m, 1H), 3.30~2.40 (m, 14H), 1.90~1.70 (m, 6H), 1.42 (m, 9H).

Step C$_d$: tert-Butyl-N-[(1R)-3-[4-(3-diisopropoxyphosphorylpropyl)piperazin-1-yl]-1-(phenylsulfanylmethyl)propyl]carbamate (15.3d) was obtained from 15.2.d in the same way. Yield 68%. MS (ESI) m/z=572.5[M+H]$^+$. $^1$H NMR (400 M, CDCl$_3$), δ 7.40 (m, 2H), 7.33 (m, 2H), 7.20 (m, 1H), 5.12 (br, 1H), 4.71 (m, 2H), 3.82 (m, 1H), 3.30~2.40 (m, 14H), 1.90~1.60 (m, 6H), 1.42 (m, 9H), 1.32 (m, 12H).

Step D$_a$: Synthesis of (2R)-4-[4-(3-Diethoxyphosphorylpropyl)piperazin-1-yl]-1-phenylsulfanyl-butan-2-amine (15.4a). To a solution of 15.3a (1.35 g, 2.48 mmol) in EtOAc (20.00 mL)/MeOH (5.0 mL) was added EtOAc/HCl (3 M) (20 mL) at 0° C. The reaction mixture was stirred at 0° C. for 4 hours and then directly concentrated to afford 15.4a (1.05 g, 2.37 mmol, quantitative), which was used in the next step without further purification. MS (ESI) m/z=444.5 [M+H]$^+$.

Step D$_b$: (2R)-4-[4-(3-Dimethoxyphosphorylpropyl)piperazin-1-yl]-1-phenylsulfanyl-butan-2-amine (15.4b) was obtained from 15.3b in the same way. Yield 90%. MS (ESI) m/z=416.5[M+H]$^+$.

Step D$_c$: (2R)-4-[4-(3-Diphenoxyphosphorylpropyl)piperazin-1-yl]-1-phenylsulfanyl-butan-2-amine (15.4c) was obtained from 15.3c in the same way. Yield 92%. MS (ESI) m/z=540.5[M+H]$^+$. $^1$H NMR (400 M, CDCl$_3$), δ 7.52 (m, 2H), 7.38~7.30 (m, 6H), 7.22~7.16 (m, 7H), 5.32 (br, 1H), 3.80 (m, 1H), 3.50~3.30 (m, 8H), 2.42~2.20 (m, 6H), 1.32 (m, 6H).

Step D$_d$: (2R)-4-[4-(3-Diisopropoxyphosphorylpropyl)piperazin-1-yl]-1-phenylsulfanyl-butan-2-amine (15.4d) was obtained from 15.3d in the same way. Yield 91%. MS (ESI) m/z=472.5[M+H]$^+$.

Step E$_a$: Synthesis of 4-[[(1R)-3-[4-(3-diethoxyphosphorylpropyl)piperazin-1-yl]-1-(phenylsulfanylmethyl)propyl]amino]-3-(trifluoromethylsulfonyl)benzenesulfonamide (15.5a). To a mixture of 15.4a (650.00 mg, 1.47 mmol) and 2.4 (540.26 mg, 1.76 mmol) in acetonitrile (20.00 mL) was added triethylamine (592.00 mg, 5.86 mmol). The reaction mixture was stirred at 80° C. for 3 hours and then concentrated. The residue was purified by flash column chromatography on silica gel (DCM:MeOH=10:1) to afford 15.5a (~800.00 mg, 1.09 mmol, ~74% yield). MS (ESI) m/z=730.9 [M+H]$^+$. $^1$H NMR (400 M, CDCl$_3$), δ 7.98 (m, 1H), 7.84 (m, 1H), 7.51~7.22 (m, 5H), 7.08 (m, 1H), 6.88 (m, 1H), 4.05 (m, 1H), 3.98 (m, 4H), 3.07 (m, 4H), 2.82 (m, 2H), 2.40~2.20 (m, 6H), 1.90~1.60 (m, 8H), 1.40 (m, 2H), 1.25 (m, 6H).

Step E$_b$: 4-[[(1R)-3-[4-(3-Dimethoxyphosphorylpropyl)piperazin-1-yl]-1-(phenylsulfanylmethyl)propyl]amino]-3-(trifluoromethylsulfonyl)benzenesulfonamide (15.5b) was obtained from 15.4b in the same way. Yield 48%. MS (ESI) m/z=703.5[M+H]$^+$. $^1$H NMR (400 M, CDCl$_3$), δ 8.24 (m, 1H), 8.09 (m, 1H), 7.53~7.27 (m, 5H), 7.08 (m, 1H), 6.74 (m, 1H), 3.92 (m, 1H), 3.77 (s, 3H), 3.75 (s, 3H), 2.82 (m, 6H), 2.60~2.40 (m, 6H), 1.90~1.60 (m, 8H), 1.40 (m, 2H).

Step E$_c$: 4-[[(1R)-3-[4-(3-Diphenoxyphosphorylpropyl)piperazin-1-yl]-1-(phenylsulfanylmethyl)propyl]amino]-3-(trifluoromethylsulfonyl)benzenesulfonamide (15.5c) was obtained from 15.4c in the same way. Yield 65%. MS (ESI) m/z=827.5[M+H]$^+$. $^1$H NMR (400 M, CDCl$_3$), δ 8.24 (m, 1H), 8.06 (m, 1H), 7.40~7.20 (m, 9H), 7.17 (m, 6H), 6.95 (m, 1H), 6.72 (m, 1H), 3.92 (m, 1H), 2.8~2.40 (m, 12H), 2.15~2.00 (m, 8H), 1.40 (m, 2H).

Step E$_d$: 4-[[(1R)-3-[4-(3-Diisopropoxyphosphorylpropyl)piperazin-1-yl]-1-(phenylsulfanylmethyl)propyl]amino]-3-(trifluoromethylsulfonyl)benzenesulfonamide (15.5d) was obtained from 15.4d in the same way. Yield 72%. MS (ESI) m/z=759.5[M+H]$^+$.

Step F$_a$: Synthesis of Compound 23.

To a mixture of 15.5a (250.00 mg, 342.08 µmol and 3.7 (150.17 mg, 342.08 µmol in DCM (40.00 mL) were added EDCI (98.52 mg, 513.12 µmol) and DMAP (62.69 mg, 513.12 µmol). The reaction mixture was heated under reflux overnight and then concentrated. The residue was purified by flash column chromatography on silica gel (EtOAc:MeOH=10:1) followed by prep-TLC to afford Compound 23 (235.00 mg, 204.03 µmol, 60% yield). MS (ESI) m/z=1151.5[M+H]$^+$. $^1$H NMR (400 M, DMSO), δ 8.07 (m, 1H), 7.95 (m, 1H), 7.71 (m, 2H), 7.38~7.24 (m, 7H), 7.18 (m, 1H), 7.12 (m, 2H), 6.94 (m, 1H), 6.82 (m, 2H), 6.77 (m, 1H), 4.03 (m, 6H), 3.32 (m, 3H), 3.17 (m, 4H), 2.70~2.60 (m, 6H), 2.30 (m, 6H), 2.24 (m, 4H), 2.00 (m, 4H), 1.73 (m, 6H), 1.43 (m, 2H), 1.23 (m, 6H), 0.96 (m, 6H).

Step F$_b$: Synthesis of Compound 24.

To a mixture of Compound 15.5b (60.00 mg, 85.38 µmol) and 3.7 (44.98 mg, 102.46 µmol) in DCM (25.00 mL) were added EDCl (24.59 mg, 128.07 µmol) and DMAP (15.65 mg, 128.07 µmol). The reaction mixture was heated under reflux overnight and then concentrated. The residue was purified by prep-TLC to afford Compound 24 (70.00 mg, 62.29 µmol, ~73% yield). MS (ESI) m/z=1123.4[M+H]$^+$. $^1$H NMR (400 M, CDCl$_3$), δ 8.31 (s, 1H), 8.10 (m, 1H), 7.81 (m, 2H), 7.37~7.24 (m, 7H), 6.99 (m, 3H), 6.75 (m, 2H), 6.58 (m, 1H), 3.83 (m, 1H), 3.75 (s, 3H), 3.74 (s, 3H), 3.32 (m, 4H), 3.08 (m, 1H), 3.02~2.90 (m, 4H), 2.85~2.60 (m, 10H), 2.57~2.40 (m, 6H), 2.30~2.20 (m, 2H), 2.18~1.85 (m, 4H), 1.77 (m, 4H), 1.46 (m, 2H), 0.97 (m, 6H).

Step F$_c$: Synthesis of Compound 25.

To a mixture of Compound 15.5c (80.00 mg, 96.75 µmol) and 3.7 (50.97 mg, 116.10 µmol) in DCM (40.00 mL) were added EDCl (27.87 mg, 145.13 µmol) and DMAP (17.73 mg, 145.13 µmol). The reaction mixture was heated under reflux overnight and then concentrated. The residue was purified by prep-TLC to afford Compound 25 (70.00 mg, 56.10 µmol, ~58% yield). MS (ESI) m/z=1247.6[M+H]$^+$. $^1$H NMR (400 M, CDCl$_3$), δ 8.34 (s, 1H), 8.07 (m, 1H), 7.73 (m, 2H), 7.39~7.16 (m, 17H), 6.98 (m, 3H), 6.69 (m, 2H), 6.54 (m, 1H), 3.83 (m, 1H), 3.30 (m, 4H), 3.08 (m, 1H), 3.02~2.90 (m, 4H), 2.85~2.60 (m, 10H), 2.57~2.40 (m, 6H), 2.30~2.20 (m, 2H), 2.18~1.98 (m, 7H), 1.77 (m, 1H), 1.46 (m, 2H), 0.97 (m, 6H).

Step F$_d$: Synthesis of Compound 27.

To a mixture of 15.5d (180.00 mg, 237.19 µmol) and 3.7 (124.95 mg, 284.63 µmol) in DCM (25.00 mL) were added EDCl (68.31 mg, 355.79 µmol) and DMAP (43.47 mg, 355.79 µmol). The reaction mixture was heated under reflux overnight and then concentrated. The residue was purified by prep-TLC to afford Compound 27 (180.00 mg, 152.56 µmol, 64% yield). MS (ESI) m/z=1179.6[M+H]$^+$. $^1$H NMR (400 M, CDCl$_3$), δ 8.32 (s, 1H), 8.12 (m, 1H), 7.78 (m, 2H), 7.39~7.24 (m, 7H), 7.08~6.94 (m, 3H), 6.75 (m, 2H), 6.55 (m, 1H), 4.71 (m, 2H), 3.83 (m, 1H), 3.32 (m, 4H), 3.12~3.06 (m, 2H), 2.96~2.90 (m, 4H), 2.75~2.60 (m, 7H), 2.57~2.40 (m, 6H), 2.25 (m, 2H), 2.18~1.85 (m, 6H), 1.77 (m, 4H), 1.46 (m, 2H), 1.35 (m, 12H), 0.97 (m, 6H).

Example 1.16: Synthesis of Compound 26.
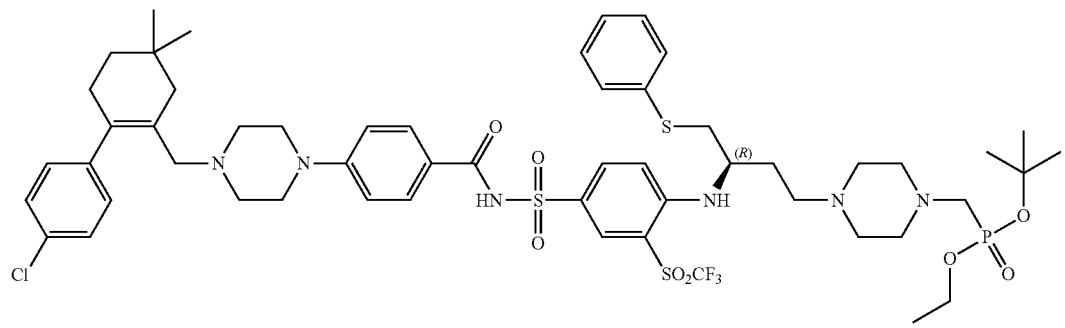
To a solution of Compound 8 (50 mg, 45.7 μmol) in DMF (5 mL) were added K$_2$CO$_3$ (139 mg, 1.01 mmol) and 2-bromo-2-methylpropane (125 mg, 913 μmol). The reaction mixture was stirred at 60° C. overnight and then concentrated. The residue was purified by prep-HPLC to afford Compound 26 (8 mg, 15% yield) as TFA salt. MS (ESI) m/z=1151.5[M+H]$^+$.
Example 1.17: Synthesis of Compound 28.
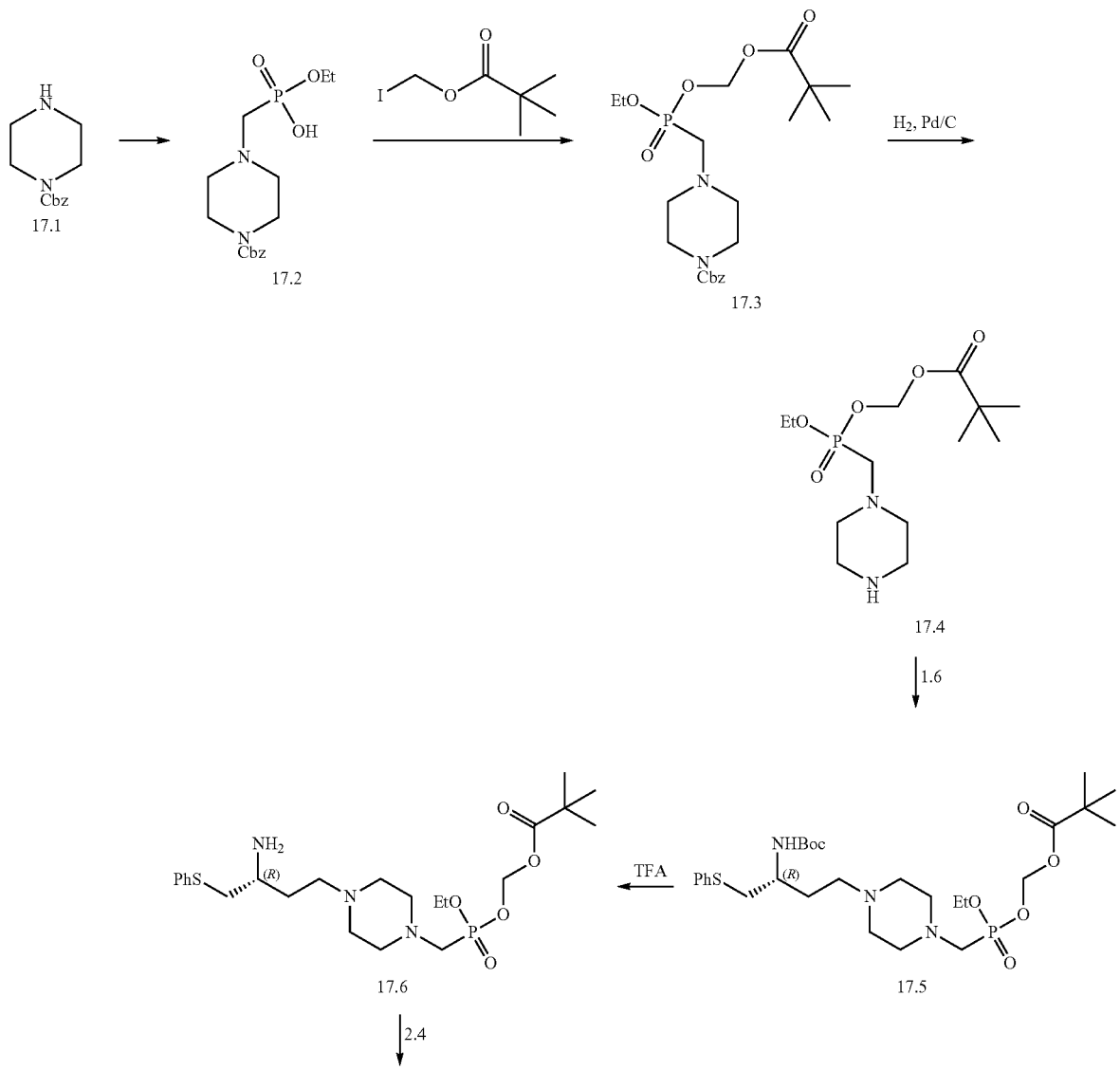

-continued

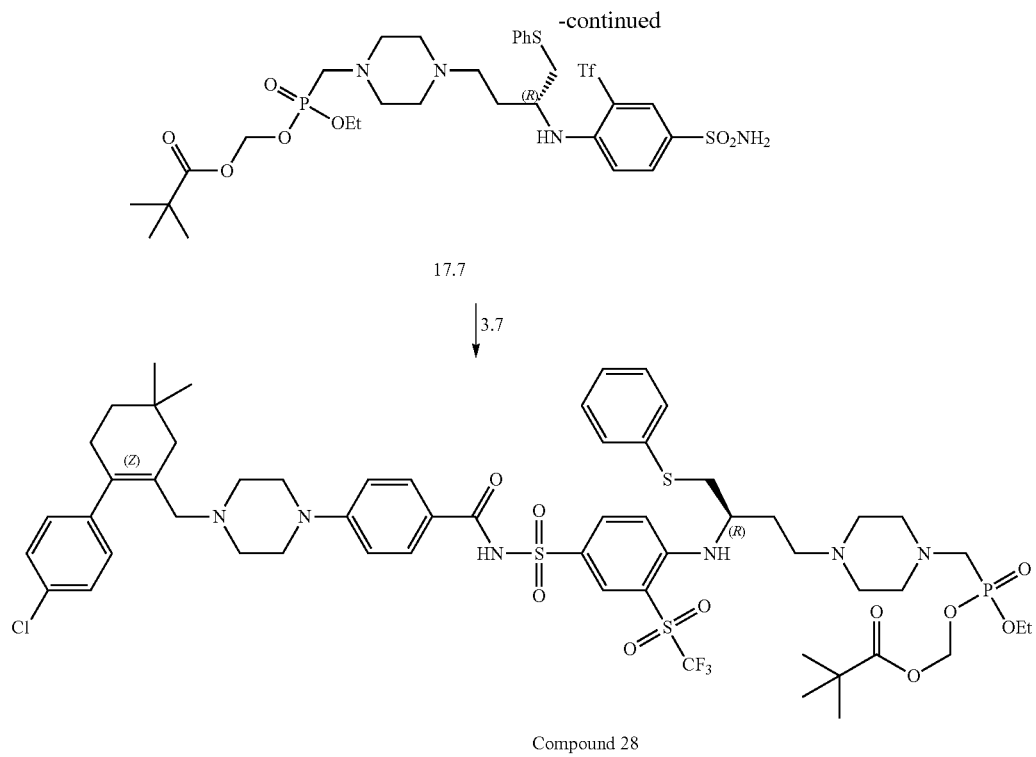

Compound 28

Step A: To a solution of 17.1 (6.02 g, 27.37 mmol) in 1,4-dioxane (100 mL) were added aqueous formaldehyde (37%, 2.47 g, 82.13 mmol) and 1-ethoxyphosphonoyl-oxy-ethane (28.35 g, 205.32 mmol). The reaction mixture was stirred at room temperature for 30 min and then at 100° C. overnight. The mixture was poured into water (300 mL), and the resulting mixture was extracted with EtOAc (100 mL×3). The water phase was directly concentrated to afford crude 17.2 (5.98 g, 62% yield). MS (ESI) m/z=343.5[M+H]$^+$.

Step B: To a solution of 17.2 (1.50 g, 4.38 mmol) in DMF (100 mL) were added $K_2CO_3$ (604 mg, 4.38 mmol) and iodomethyl 2,2-dimethylpropanoate (10.60 g, 43.80 mmol). The reaction mixture was stirred for 2 days at room temperature, and then partitioned between DCM (200 mL) and water (200 mL). The organic phase was dried over anhydrous $Na_2SO_4$ and concentrated. The residue was purified by flash column chromatography on silica gel (Petroleum Ether:EtOAc=2:1~1:1) to give 17.3 (620 mg, 31% yield). MS (ESI) m/z=457.3[M+H]$^+$. $^1$H NMR (400 MHz, $CDCl_3$): δ 7.35 (m, 5H), 5.69 (m, 2H), 5.13 (s, 2H), 4.20 (m, 2H), 3.52 (m, 4H), 2.62 (m, 4H), 1.23 (s, 9H).

Step C: To a solution of 17.3 (620 mg, 1.36 mmol) in EtOH (30 mL) was added Pd/C (250 mg). The reaction mixture was stirred at r.t. under $H_2$ atmosphere for 2 h. The mixture was then filtered and the filtrate was concentrated to give crude 17.4 (430 mg, 98% yield). MS (ESI) m/z=324.3 [M+H]$^+$. $^1$H NMR (400 MHz, $CDCl_3$): δ 5.72 (m, 2H), 4.19 (m, 2H), 3.72 (m, 1H), 3.93 (m, 2H), 3.82 (m, 2H), 3.79~3.62 (m, 4H), 2.11 (m, 2H), 1.34 (m, 3H), 1.26 (s, 9H).

Step D: To a solution of 17.4 (120 mg, 372.28 μmol) in DCM (15 mL) were added TEA (226 mg, 2.23 mmol), 1.6 (110 mg, 372.28 μmol) and $NaBH_3CN$ (47 mg, 744.56 μmol). The reaction mixture was stirred at 70° C. for 2 h and then partitioned between DCM (20 mL) and water (20 mL). The organic phase was dried over anhydrous $Na_2SO_4$ and concentrated to give crude 17.5 (202 mg, 91% yield). MS (ESI) m/z=602.3[M+H]$^+$ Step E: To a solution of 17.5 (30 mg, 49.86 μmol) in DCM (3 mL) was added TFA (34 mg, 299.14 μmol). The reaction mixture was stirred at room temperature overnight, and then concentrated to afford 17.6 (25 mg, near quantitative). MS (ESI) m/z=502.48[M+H]$^+$ Step F: To a solution of 17.6 (201 mg, 400.34 μmol) in $CH_3CN$ (15 mL) were added TEA (405 mg, 4.00 mmol) and 2.4 (123 mg, 400.34 μmol). The reaction mixture was stirred at 70° C. for 2 h and then concentrated. The residue was purified by prep-HPLC to afford 17.7 (120 mg, 38% yield) as TFA salt. MS (ESI) m/z=788.99[M+H]$^+$ Step G: Synthesis of Compound 28 ((((4-((R)-3-((4-(N-(4-(4-((4'-Chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio) butyl)piperazin-1-yl)methyl)(ethoxy)phosphoryl)oxy) methyl pivalate.

To a solution of 17.7 (120 mg, 152.12 μmol) in DCM (10 mL) were added 3.7 (70 mg, 159.73 μmol), EDCI (52 mg, 304.24 μmol) and DMAP (37 mg, 304.24 μmol). The reaction mixture was stirred at 40° C. for 5 h, and then concentrated. The residue was purified by prep-HPLC to afford Compound 28 (21 mg, 11% yield). MS (ESI) m/z=1209.6[M+H]$^+$. $^1$H NMR (400 MHz, $CDCl_3$, characteristic peaks only): δ 8.39 (m, 1H), 8.11 (m, 1H), 7.72 (m, 2H), 7.38 (m, 2H), 7.28 (m, 4H), 7.25 (m, 1H), 6.98 (m, 3H), 6.79 (m, 2H), 6.71 (m, 1H), 5.68 (m, 2H), 4.18 (m, 2H), 3.89 (m, 1H), 3.32 (m, 4H), 3.06 (m, 2H), 2.87 (m, 5H), 2.79~2.32 (m, 14H), 2.25 (m, 2H), 2.12 (m, 1H), 2.03 (m, 2H), 1.44 (m, 2H), 1.32 (m, 3H), 1.26 (s, 9H), 0.99 (s, 6H).

Example 1.18: Synthesis of Compounds 31, 32, 33, 36 and 40.

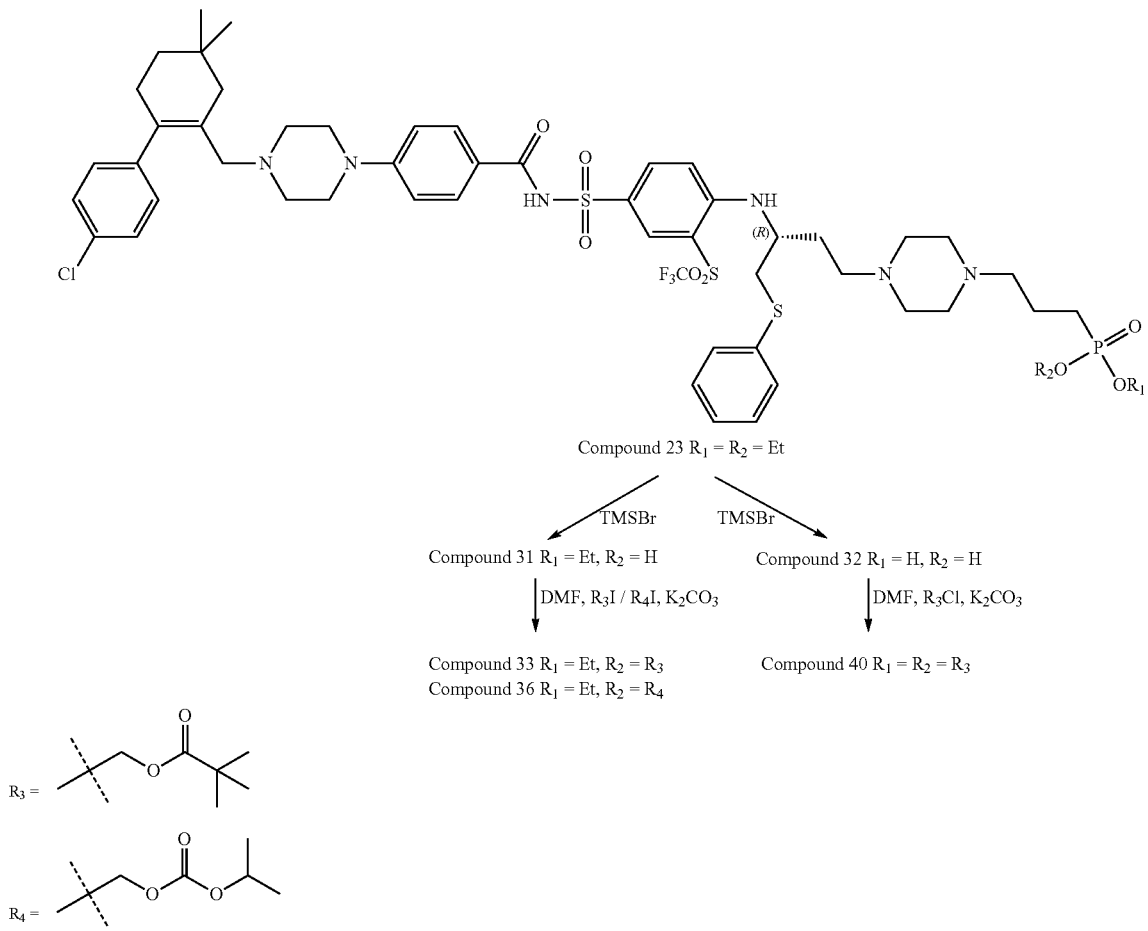

Synthesis of Compounds 31 and 32: To a solution of Compound 23 (800.00 mg, 694.57 μmol) in CH$_3$CN (25.00 mL) was added TMSBr (0.8 mL). The reaction mixture was stirred at 60° C. for 2 h and quenched with saturated NaHCO$_3$ (5 mL). The resulting mixture was directly purified by prep-HPLC (TFA) to afford Compound 31 (130.00 mg, 115.69 μmol, 17% yield). MS (ESI) m/z=1122.43[M]$^+$ and Compound 32 (160.00 mg, 146.03 μmol, 21% yield). MS (ESI) m/z=1094.35[M]$^+$.

Synthesis of Compound 33: To a solution of Compound 31 (112.00 mg, 99.67 μmol) in DMF (15.00 mL) was added K$_2$CO$_3$ (275.09 mg, 1.99 mmol). The mixture was stirred at r.t. for 30 min, and then iodomethyl 2,2-dimethylpropanoate (482.50 mg, 1.99 mmol) was added. The reaction mixture was heated at 60° C. overnight. The mixture was quenched with saturated NaHCO$_3$ (5 mL) and the resulting mixture was purified by prep-HPLC (NH$_4$HCO$_3$) to afford Compound 33 (45.00 mg, 36.35 μmol, 36% yield) as white solid. MS (ESI) m/z=1037.6[M]$^+$. $^1$H NMR (400 M, CDCl$_3$), δ 8.34 (s, 1H), 8.12 (m, 1H), 7.68 (m, 2H), 7.39~7.24 (m, 7H), 7.00~6.93 (m, 3H), 6.77 (m, 2H), 6.66 (m, 1H), 5.68 (m, 2H), 4.21~4.08 (m, 2H), 3.83 (m, 1H), 3.28 (m, 4H), 3.12~3.06 (m, 2H), 2.82~2.78 (m, 2H), 2.50~2.26 (m, 14H), 2.24 (m, 2H), 2.13~1.98 (m, 3H), 1.78~1.60 (m, 8H), 1.47 (m, 2H), 1.36 (m, 3H), 1.23 (m, 9H), 0.98 (m, 6H).

Synthesis of Compound 36: To a solution of Compound 31 (30.00 mg, 26.70 μmol) in DMF (5.00 mL) was added K$_2$CO$_3$ (73.68 mg, 533.93 μmol). The mixture was stirred at r.t. for 30 min and then iodomethyl isopropyl carbonate (130.30 mg, 533.93 μmol) was added. The reaction mixture was heated at 60° C. for 4 hours and then poured into aqueous HCl (0.2 M, 2.0 mL) to control the pH value of resulting aqueous mixture at ~7. This mixture was purified by prep-HPLC (NH$_4$HCO$_3$) to afford Compound 36 (~30.00 mg, 24.20 μmol, ~91% yield) as white solid. MS (ESI) m/z=1239.4[M]$^+$. $^1$H NMR (400 M, CDCl$_3$), δ 8.34 (m, 1H), 8.12 (m, 1H), 7.68 (m, 2H), 7.37~7.24 (m, 7H), 7.02~6.95 (m, 3H), 6.77 (m, 2H), 6.61 (m, 1H), 5.68 (m, 2H), 4.92 (m, 1H), 4.20~4.05 (m, 2H), 3.83 (m, 1H), 3.28 (m, 4H), 3.10~3.00 (m, 2H), 2.82~2.78 (m, 2H), 2.53~2.26 (m, 14H), 2.24 (m, 2H), 2.13~1.98 (m, 3H), 1.78~1.60 (m, 8H), 1.43 (m, 2H), 1.36~1.20 (m, 9H), 0.98 (m, 6H).

Synthesis of Compound 40: To a solution of Compound 32 (80.00 mg, 73.01 μmol) in DMF (4.00 mL) was added K$_2$CO$_3$ (201.52 mg, 1.46 mmol). The mixture was stirred at r.t. for 30 min and then chloromethyl 2,2-dimethylpropanoate (164.94 mg, 1.10 mmol) was added. The reaction mixture was heated at 60° C. for 4 hours and then quenched with aqueous HCl (1.0 M, 3 mL) to control the pH value of the resulting mixture at 7. This mixture was purified by prep-HPLC (NH$_4$HCO$_3$) to afford Compound 40 (15.00 mg, 11.33 μmol, 16% yield) as white solid. MS (ESI) m/z=1323.7[M]$^+$. $^1$H NMR (400 M, CDCl$_3$), δ 8.34 (m, 1H), 8.12 (m, 1H), 7.68 (m, 2H), 7.39~7.24 (m, 7H), 7.00~6.93 (m, 3H), 6.77 (m, 2H), 6.66 (m, 1H), 5.68 (m, 4H), 3.83 (m, 1H), 3.28 (m, 4H), 3.12~3.06 (m, 2H), 2.82~2.78 (m, 2H), 2.50~2.26 (m, 14H), 2.24 (m, 2H), 2.13~1.98 (m, 3H), 1.78~1.60 (m, 8H), 1.47 (m, 2H), 1.23 (m, 18H), 0.98 (m, 6H).

Example 1.19: Synthesis of Compounds 34 and 35.

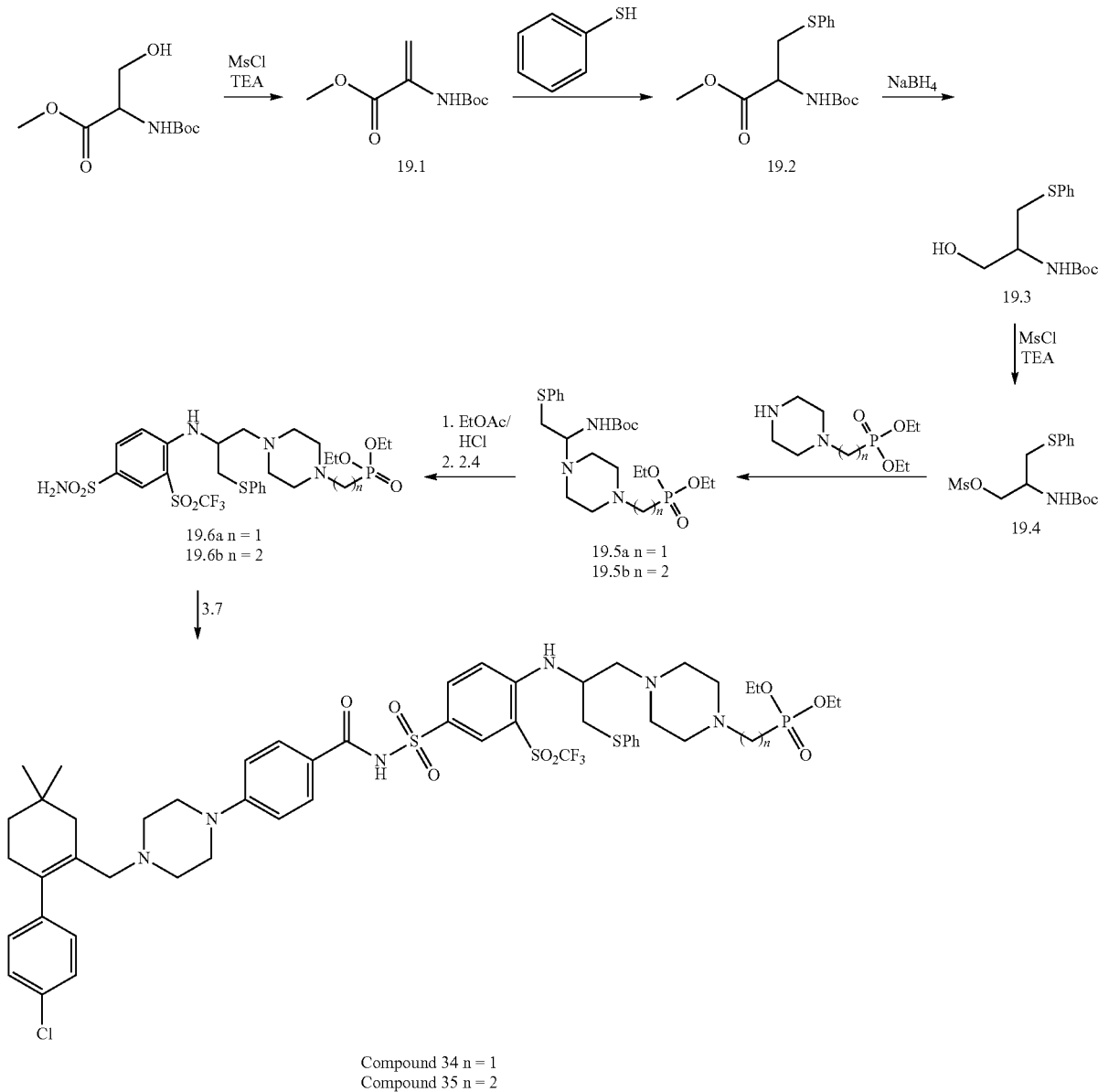

Compound 34 n = 1
Compound 35 n = 2

Step A: To a solution of methyl 2-(tert-butoxycarbonylamino)-3-hydroxy-propanoate (10.02 g, 45.6 mmol) in DCM (100 mL) was added MsCl (6.27 g, 54.73 mmol) at −50° C. under $N_2$ followed by TEA (13.85 g, 136.83 mmol). The reaction mixture was stirred at the same temperature for 45 min, and then left at room temperature overnight. The mixture was poured into water (50 mL) and the resulting mixture was extracted with DCM (3×50 mL). The combined organic phases were dried over anhydrous $MgSO_4$, and concentrated to afford crude 19.1 (9.02 g, 98% yield), which was used in the next step without further purification. $^1$H NMR (400 MHz, CDCl$_3$): δ 7.02 (m, 1H), 6.16 (m, 1H), 5.73 (d, J=1.6 Hz, 1H), 3.83 (s, 3H), 1.49 (s, 9H).

Step B: To a solution of benzenethiol (7.39 g, 67.09 mmol) in MeCN (100 mL) was added $K_2CO_3$ (12.34 g, 89.45 mmol) at room temperature. The mixture was stirred for 10 min, and then 19.1 (9.01 g, 44.73 mmol) was added. The reaction mixture was stirred overnight, and then concentrated directly. The residue was purified by flash column chromatography on silica gel (Petroleum Ether:EtOAc=10:1) to afford 19.2 (13.89 g, 99% yield). $^1$H NMR (400 MHz, CDCl$_3$): δ 7.29 (m, 2H), 7.27 (m, 2H), 7.22 (m, 1H), 4.57 (m, 1H), 3.54 (s, 3H), 3.38 (m, 2H), 1.42 (s, 9H).

Step C: To a solution of 19.2 (2.00 g, 6.42 mmol) in THF (20 mL) and $H_2O$ (20 mL) was added NaBH$_4$ (243 mg, 6.42 mmol) at room temperature. The reaction mixture was stirred at 20° C. for 2 days. The mixture was then quenched with $H_2O$ (100 mL) and the resulting mixture was extracted with EtOAc (2×100 mL). The combined organic phases were dried over anhydrous $MgSO_4$ and concentrated to afford crude 19.3 (1.51 g, 83% yield), which was used in the next step without further purification. MS (ESI) m/z=306.28 [M+Na]+. 1H NMR (400 MHz, CDCl3): δ 7.38 (m, 2H), 7.30 (m, 2H), 7.19 (m, 1H), 5.03 (m, 1H), 3.81 (m, 2H), 3.70 (m, 1H), 3.14 (m, 2H), 1.44 (s, 9H).

Step D: To a solution of 19.3 (4.40 g, 15.53 mmol) and TEA (2.36 g, 23.29 mmol) in DCM (150 mL) was added MsCl (2.13 g, 18.63 mmol) at 0° C. The reaction mixture was stirred at r.t. for 2 hours. The mixture was then washed with H2O (3×50 mL). The organic phase was dried over anhydrous MgSO4 and concentrated to afford crude 19.4 (4.52 g, 81% yield), which was used directly in the next step without further purification. MS (ESI) m/z=383.77[M+Na]+. 1H NMR (400 MHz, CDCl3): δ 7.41 (m, 2H), 7.33 (m, 2H), 7.26 (m, 1H), 4.91 (m, 1H), 4.31 (m, 1H), 4.02 (m, 1H), 3.22 (m, 1H), 3.05 (m, 1H), 2.99 (s, 3H), 1.44 (s, 9H).

Step $E_a$: To a solution of 19.4 (201 mg, 553.28 μmol) in MeCN (10 mL) was added K2CO3 (152.71 mg, 1.11 mmol) followed by 1-(diethoxyphosphorylmethyl)piperazine (222 mg, 941 μmol). The reaction mixture was stirred at 60° C. overnight and then concentrated directly. The residue was dissolved in EtOAc (20 mL) and the resulting mixture was washed with 2 N HCl (2×15 mL) and Na2CO3 (aq) (2×15 mL), sequentially. The organic phase was dried over anhydrous MgSO4 and concentrated to afford the crude 19.5a (79 mg, 28% yield), which was used in the next step without further purification. MS (ESI) m/z=501.71[M+H]+.

Step $E_b$: Intermediate 19.5b was synthesized in the same way, except diethyl (2-(piperazin-1-yl)ethyl) phosphonate was used instead of 1-(diethoxyphosphorylmethyl)piperazine. MS (ESI) m/z=517.4[M+H]+. 1H NMR (400 MHz, CDCl3): δ 7.40 (m, 2H), 7.27 (m, 2H), 7.18 (m, 1H), 4.85 (m, 1H), 4.11 (m, 4H), 3.91 (m, 1H), 3.17 (m, 2H), 2.65 (m, 3H), 2.44 (m, 9H), 1.97 (m, 2H), 1.43 (s, 9H), 1.31 (m, 6H).

Step $F_a$: To a solution of 19.5a (79 mg, 159 μmol) in EtOAc (2 mL) was added EtOAc/HCl (4 mol/L, 10 mL). The reaction mixture was stirred at room temperature for 3 hours, and then concentrated directly. The residue was dissolved in acetonitrile (10 mL). To this mixture were added 2.4 (49 mg, 159.4 μmol) and TEA (80 mg, 797 μmol) at room temperature. The reaction mixture was stirred at 70° C. for 2 hours and then concentrated. The residue was purified by prep-TLC (EtOAc:MeOH=20:1) to afford 19.6a (51 mg, 46% yield). MS (ESI) m/z=688.64[M+H]+.

Step $F_b$: Intermediate 19.6b was synthesized following the procedure of Step $F_a$. MS (ESI) m/z=702.4[M+H]+. 1H NMR (400 MHz, CDCl3): δ 8.25 (m, 1H), 7.82 (m, 1H), 7.44 (m, 3H), 7.33 (m, 2H), 6.45 (m, 1H), 5.08 (m, 1H), 4.31 (m, 1H), 4.12 (m, 4H), 3.68 (m, 1H), 3.09 (m, 2H), 2.99~2.30 (m, 12H), 1.62 (m, 2H), 1.33 (m, 6H).

Step $G_a$: Synthesis of Compound 34 ((4-(2-((4-(N-(4-(4-((4'-chloro-4,4-dimethyl-3,4,5,6-tetrahydro-[1,1'-bi phenyl]-2-yl)methyl)piperazin-1-yl)benzoyl)sulfamoyl)-2-((trifluoromethyl)sulfonyl)phenyl)amino)-3-(phenylthio) propyl)piperazin-1-yl)methyl)phosphonate. To a solution of 19.6a (45 mg, 65 μmol) in acetonitrile (10 mL) were added 3.7 (32 mg, 71.87 μmol), DMAP (16 mg, 130.68 μmol) and EDCI (25 mg, 130.68 μmol). The reaction mixture was stirred at 70° C. for 3 hours, and then concentrated directly. The residue was purified by prep-TLC (EtOAc:MeOH=15:1) to afford Compound 34 (37 mg, 51% yield). MS (ESI) m/z=1109.5[M+H]+. 1H NMR (400 MHz, CDCl3): δ 8.36 (m, 1H), 8.12 (m, 1H), 7.68 (m, 2H), 7.45 (m, 1H), 7.41 (m, 2H), 7.32~7.25 (m, 5H), 6.98 (m, 2H), 6.76 (m, 2H), 6.45 (m, 1H), 4.14 (m, 5H), 3.72 (m, 1H), 3.39 (m, 4H), 3.09 (m, 2H), 2.94 (m, 2H), 2.77 (m, 2H), 2.66 (m, 6H), 2.50 (m, 7H), 2.29 (m, 2H), 2.05 (m, 2H), 1.48 (m, 2H), 1.31 (m, 6H), 1.01 (s, 6H).

Step $G_b$: Synthesis of Compound 35 (Diethyl (2-(4-(2-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-3-(phenylthio)propyl)piperazin-1-yl)ethyl)phosphonate). Compound 35 was prepared from 19.6b following the procedure for preparing Compound 34. MS (ESI) m/z=1123.4 [M+H]+. 1H NMR (400 MHz, CDCl3): δ 8.34 (m, 1H), 8.12 (m, 1H), 7.69 (m, 2H), 7.43 (m, 3H), 7.28 (m, 5H), 6.99 (m, 2H), 6.77 (m, 2H), 6.43 (m, 1H), 4.10 (m, 4H), 3.68 (m, 1H), 3.32 (m, 4H), 3.13 (m, 2H), 2.92 (m, 2H), 2.90~2.50 (m, 10H), 2.41 (m, 2H), 2.26 (m, 2H), 2.04 (m, 2H), 1.46 (m, 2H), 1.30 (m, 6H), 0.98 (s, 6H).

Example 1.20: Synthesis of Compound 37.

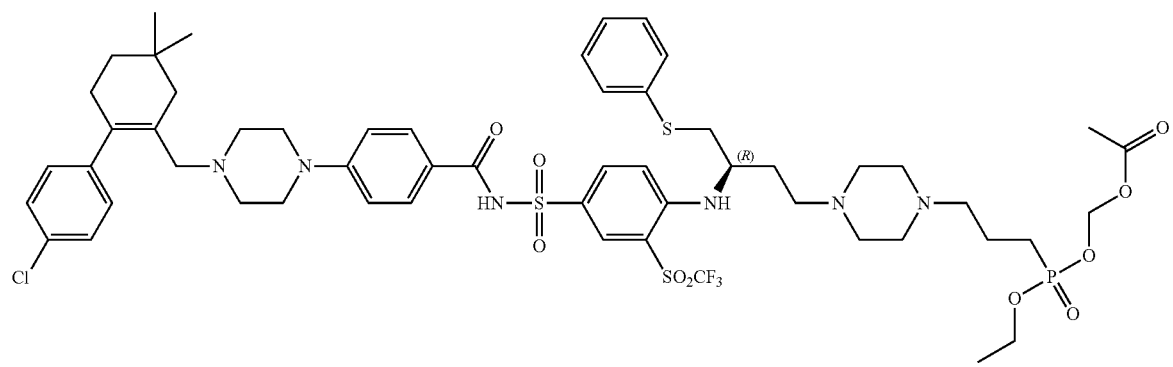

To a solution of Compound 31 (201 mg, 164 μmol) in DMF (5 mL) were added K2CO3 (98 mg, 712 μmol) and chloromethyl acetate (77 mg, 712 μmol). The reaction mixture was heated at 60° C. overnight, and then directly submitted to prep-HPLC to afford Compound 37 (6 mg, 14% yield) as TFA salt. MS (ESI) m/z=1195.8[M]+.

Example 1.21: Synthesis of Compound 38.

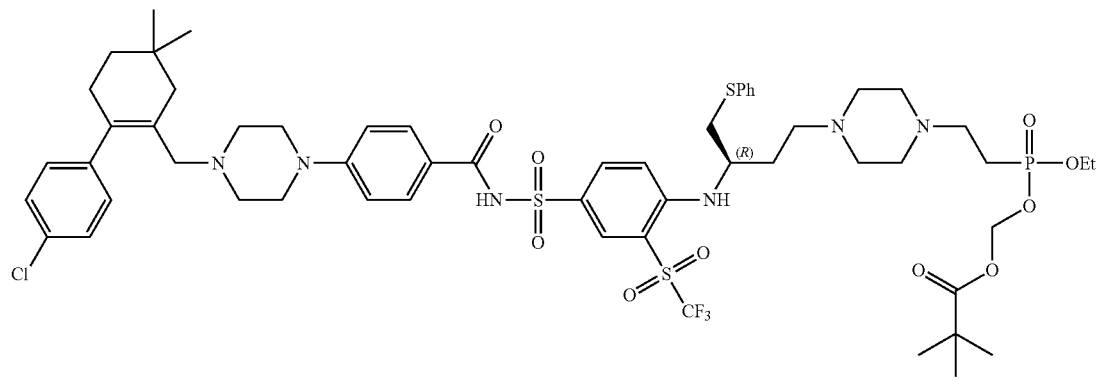

To a solution of Compound 14 (20 mg, 18.02 μmol) in DMF (5 mL) was added K$_2$CO$_3$ (49 mg, 360.40 μmol). The mixture was stirred at r.t. for about 30 min and then chloromethyl 2,2-dimethylpropanoate (54 mg, 360.40 μmol) was added. The reaction mixture was stirred at 60° C. for 5 hours and then directly submitted to prep-HPLC to afford Compound 38 (7 mg, 32% yield). MS (ESI) m/z=1225.4 [M+H]$^+$.

Example 1.22: Synthesis of Compound 39.

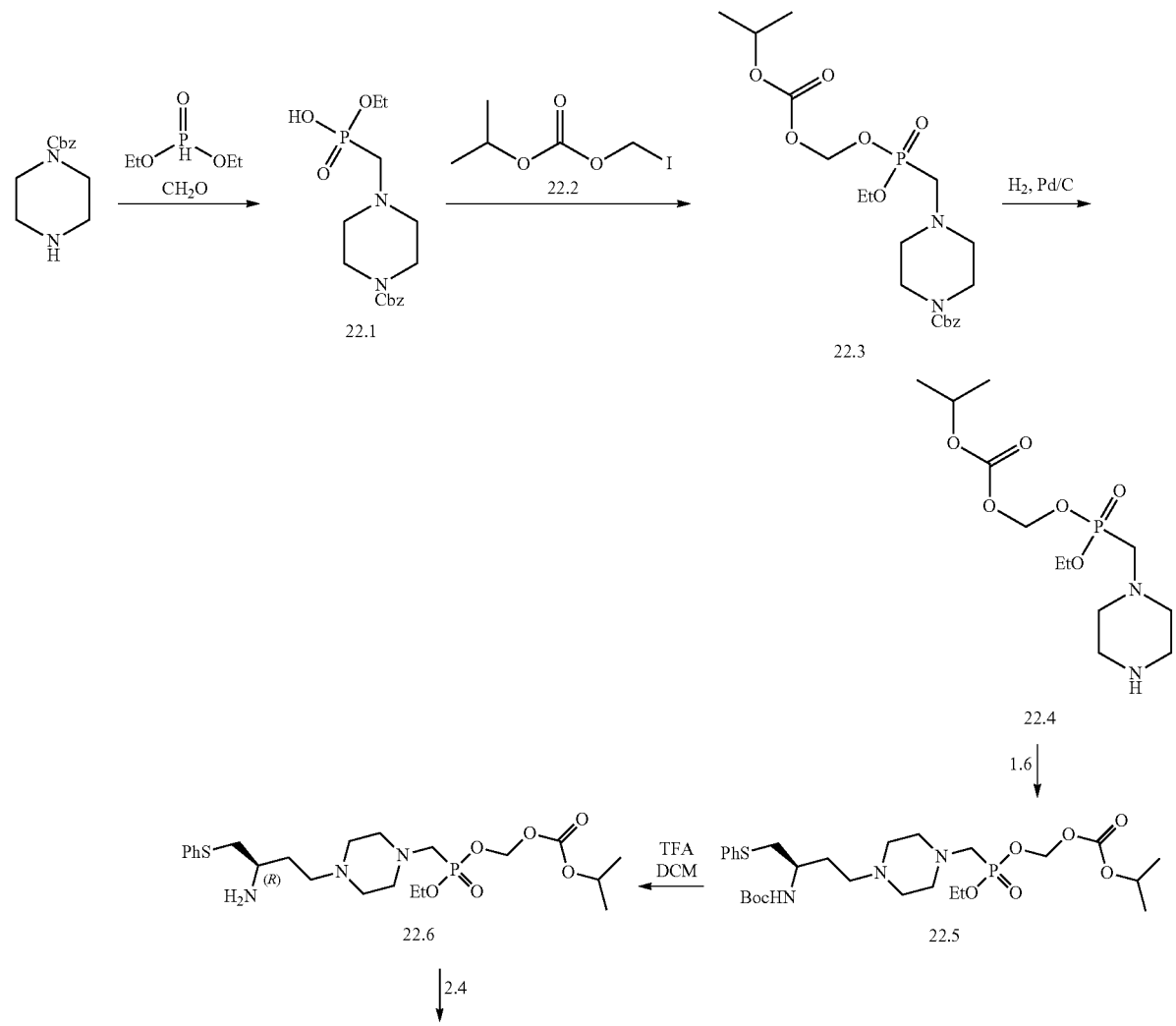

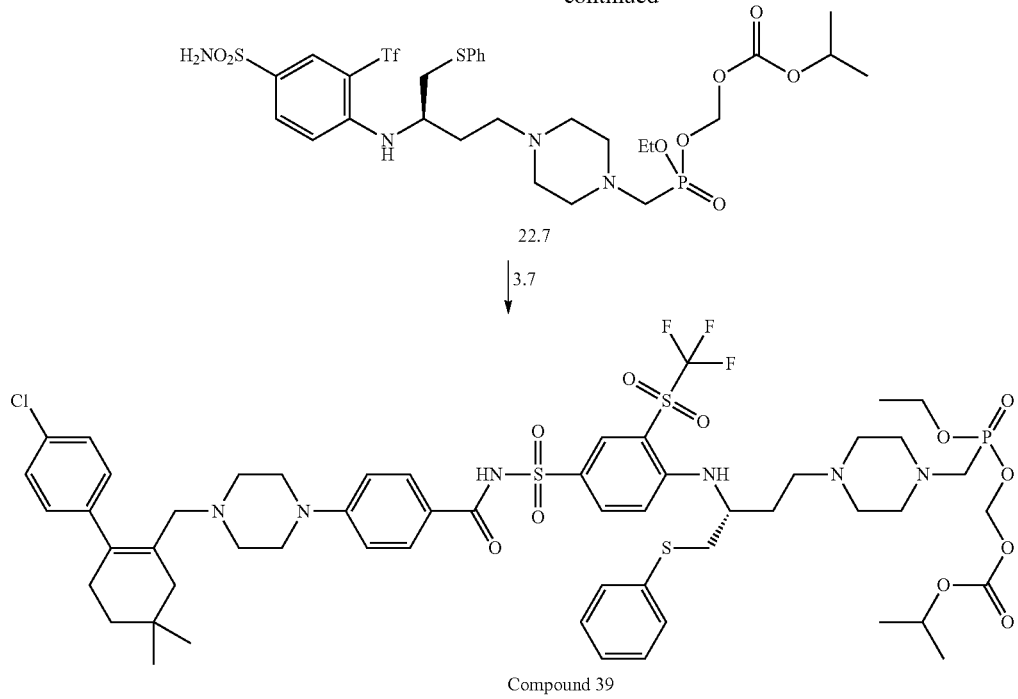

Compound 39

Step A: To a solution of benzyl piperazine-1-carboxylate (6.01 g, 27.24 mmol) in dioxane (60 mL) were added formaldehyde (16.36 g, 544.80 mmol) and diethyl phosphonate (56.43 g, 408.60 mmol). The reaction mixture was stirred at room temperature for 16 hrs and then heated at 100° C. for another 2 hr. The mixture was then concentrated and the residue was poured into water (200 mL). The resulting mixture was extracted with EtOAc (200 mL×3) and the water phase was concentrated to give crude 22.1 (8.01 g, 86% yield). MS (ESI) m/z=343.5[M+H]⁺.

Step B: To a solution of chloromethyl isopropyl carbonate (5.02 g, 32.77 mmol) in MeCN (20 mL) was added NaI (14.74 g, 98.31 mmol). The reaction mixture was stirred at 60° C. for 3 hr. The mixture was then concentrated and the residue was dissolved in DCM (300 mL). The resulting mixture was washed with sat. $Na_2S_2O_3$ (100 mL×2), and the organic phase was dried and concentrated to give 22.2 (7.90 g, 99% yield). ¹H NMR (400 MHz, $CDCl_3$): δ 5.95 (s, 2H), 4.96 (m, 1H), 1.33 (d, J=6.4 Hz, 6H).

Step C: To a solution of 22.1 (803 mg, 2.34 mmol) in DMF (10 mL) were added $K_2CO_3$ (3.88 g, 28.08 mmol) and 22.2 (5.71 g, 23.40 mmol). The reaction mixture was heated at 60° C. for 48 hr. The mixture was then filtered and the filtrate was poured into water (50 mL). The resulting mixture was extracted with EtOAc (100 mL×2). The combined organic phases were dried over anhydrous $MgSO_4$ and concentrated. The residue was purified by prep-HPLC to give 22.3 (61 mg, 6% yield). MS (ESI) m/z=459.3[M+H]⁺. ¹H NMR (400 MHz, $CDCl_3$): δ 7.35 (m, 5H), 5.69 (m, 2H), 5.13 (s, 2H), 4.93 (m, 1H), 4.19 (m, 2H), 3.52 (m, 4H), 2.85 (m, 2H), 2.62 (m, 4H), 1.36 (s, 3H), 1.31 (s, 9H).

Step D: To a solution of 22.3 (49 mg, 109.07 μmol) in EtOH (10 mL) was added Pd/C (13 mg, 109.07 μmol) under $H_2$ atmosphere. The reaction mixture was stirred at room temperature overnight and then filtered. The filtrate was concentrated to give crude 22.4 (31 mg, 85% yield), which was used for next step without further purification. MS (ESI) m/z=325.3[M+H]⁺.

Step E: To a solution of 1.6 (164 mg, 555.18 μmol) in DCM (15 mL) were added 22.4 (135 mg, 416.38 μmol) and $NaBH_3CN$ (69 mg, 1.11 mmol). The reaction mixture was stirred at room temperature overnight. The mixture was concentrated and the residue was purified by prep-HPLC to give 22.5 (48 mg, 14% yield). MS (ESI) m/z=604.1[M+H]⁺.

Step F: A solution of 22.5 (45 mg, 74.54 μmol) in TFA (980 μL)/DCM (6 mL) was stirred at room temperature for 3 hours. The mixture was concentrated to give crude 22.6 (35 mg, 93% yield), which was used in the next step without further purification. MS (ESI) m/z=504.4[M+H]⁺.

Step G: To a solution of 22.6 (41 mg, 79.43 μmol) in MeCN (2 mL) were added $Et_3N$ (24 mg, 238.29 μmol) and 2.4 (27 mg, 87.37 μmol). The reaction mixture was stirred at 80° C. for 3 hr. The mixture was concentrated and the residue was purified by prep-HPLC to give 22.7 (10 mg, 16% yield). MS (ESI) m/z=791.4[M+H]⁺.

Step H: Synthesis of Compound 39 [[4-[(3R)-3-[4-[[4-[[2-(4-Chlorophenyl)-5,5-dimethyl-cyclohexen-1-yl]methyl]piperazin-1-yl]benzoyl]sulfamoyl]-2-(trifluoromethylsulfonyl)anilino]-4-phenylsulfanyl-butyl]piperazin-1-yl]methyl-ethoxy-phosphoryl]oxymethyl isopropyl carbonate. To a solution of 22.7 (20 mg, 25.29 μmol) and 3.7 (11 mg, 25.29 μmol) in DCM (10 mL) were added EDCI (9 mg, 50.58 μmol) and DMAP (6 mg, 50.58 μmol). The reaction mixture was heated at 40° C. for 3 hrs and then concentrated. The residue was purified by prep-HPLC to give Compound 39 (4 mg, 13% yield). MS (ESI) m/z=1211.4[M+H]⁺.

Example 1.23: Synthesis of Compound 41.

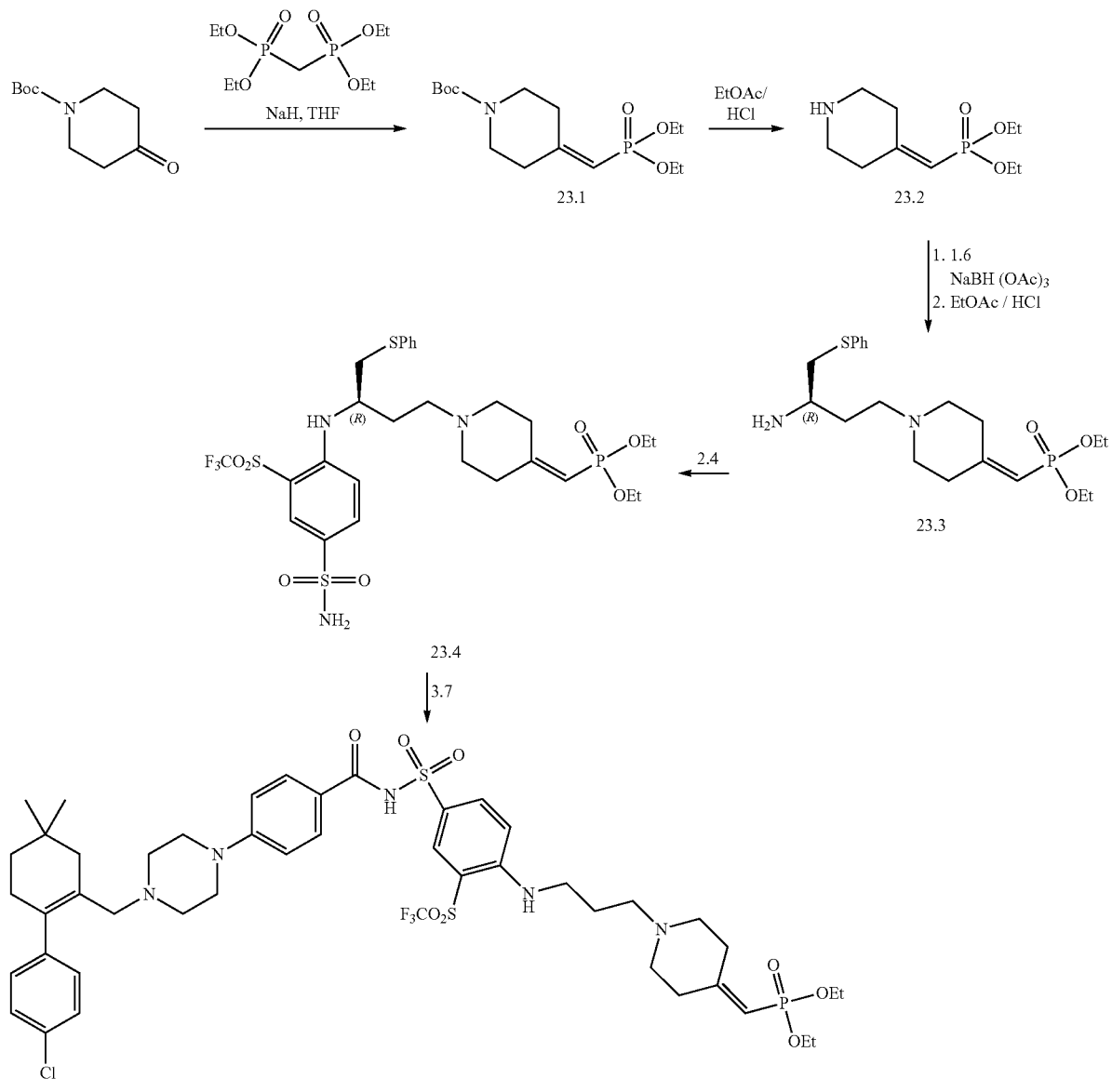

Compound 41

Step A: To a solution of 1-[diethoxyphosphorylmethyl(ethoxy)phosphoryl]oxyethane (1.45 g, 5.02 mmol) in THF (25 mL) was added NaH (120 mg, 5.02 mmol) at room temperature. The mixture was stirred at room temperature for 40 min, and then tert-butyl 4-oxopiperidine-1-carboxylate (1.00 g, 5.02 mmol) was added. The reaction mixture was stirred for another 2 hours. Water (50 mL) was added and the resulting mixture was extracted with EtOAc (3×50 mL). The combined organic phases were dried over anhydrous $Na_2SO_4$ and concentrated. The residue was purified by flash column chromatography on silica gel (Petroleum Ether:EtOAc=1:2) to afford 23.1 (859 mg, 51% yield). $^1$H NMR (400 MHz, $CDCl_3$): δ 5.58 (m, 1H), 4.12 (m, 4H), 3.90 (m, 2H), 3.49 (m, 2H), 2.56 (m, 2H), 2.23 (m, 2H), 1.47 (s, 9H), 1.32 (m, 6H).

Step B: To a solution of 23.1 (402 mg, 1.20 mmol) in EtOAc (5 mL) was added EtOAc/HCl (0.6 mol/L, 10 mL) at 0° C. The reaction mixture was stirred at 0° C. for 2 hours, and then concentrated to afford crude 23.2 (251 mg, 89% yield). $^1$H NMR (400 MHz, $CDCl_3$): δ 5.62 (m, 1H), 4.12 (m, 4H), 3.72 (m, 2H), 3.33 (m, 2H), 2.58 (m, 2H), 2.05 (m, 2H), 1.32 (m, 6H).

Step C: To a mixture of 1.6 (253 mg, 857.49 μmol) and 23.2 (200 mg, 857.49 μmol) in DCM (20 mL) was added $Et_3N$ (346 mg, 3.43 mmol) at room temperature. $NaCNBH_3$ (80 mg, 1.29 mmol) was added, and the reaction mixture was stirred overnight. The mixture was concentrated, and the residue was purified by flash column chromatography on silica gel (EtOAc:MeOH=20:1) to afford Boc-23.3. MS (ESI) m/z=513.06[M+H]$^+$.

Step D: To a solution of Boc-23.3 in EtOAc (10 mL) was added EtOAc/HCl (3 mol/L, 10 mL) at 0° C. The reaction mixture was stirred at the same temperature for 2 hours and then concentrated to afford crude 23.3 (181 mg, 51%). MS (ESI) m/z=412.93[M+H]$^+$.

Step E: To a solution of 23.3 (270 mg, 654.50 μmol) in CH₃CN (20 mL) were added 2.4 (201 mg, 654.50 μmol) and Et₃N (264 mg, 2.62 mmol) at room temperature. The reaction mixture was stirred at 70° C. for 3 hours and then concentrated directly. The residue was purified by flash column chromatography on silica gel (EtOAc:MeOH=20:1) to afford 23.4 (179 mg, 39% yield). MS (ESI) m/z=699.61 [M+H]⁺. ¹H NMR (400 MHz, CDCl₃): δ 8.20 (m, 1H), 7.94 (m, 1H), 7.39 (m, 2H), 7.27 (m, 3H), 6.98 (m, 2H), 5.61 (m, 1H), 4.12 (m, 4H), 3.92 (m, 1H), 3.12 (m, 2H), 3.10 (m, 2H), 2.80~2.45 (m, 8H), 2.27 (m, 2H), 1.30 (m, 6H).

Step F: Synthesis of Compound 41 (Diethyl (R)-((1-(3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperidin-4-ylidene)methyl)phosphonate). To a solution of 3.7 (169 mg, 385.85 μmol) and 23.4 (180 mg, 257.23 μmol) in MeCN (4 mL) were added EDCI (74 mg, 385.85 μmol) and DMAP (47 mg, 385.85 μmol). The reaction mixture was stirred at 70° C. for 6 hours and concentrated. The residue was purified by prep-TLC to afford Compound 41 (33 mg, 11% yield). MS (ESI) m/z=1120.6[M+H]⁺. ¹H NMR (400 MHz, CDCl₃): δ 8.37 (m, 1H), 8.08 (m, 1H), 7.69 (m, 2H), 7.36 (m, 2H), 7.25 (m, 5H), 7.00 (m, 1H), 6.98 (m, 2H), 6.77 (m, 2H), 6.71 (m, 1H), 5.30 (m, 1H), 4.12 (m, 4H), 3.92 (m, 1H), 3.29 (m, 4H), 3.09 (m, 2H), 2.84 (m, 2H), 2.80~2.40 (m, 8H), 2.38 (m, 4H), 2.26 (m, 4H), 2.02 (m, 2H), 1.75 (m, 2H), 1.46 (m, 2H), 1.33 (m, 6H), 0.98 (m, 6H).

Example 1.24: Synthesis of Compound 43 and 45.

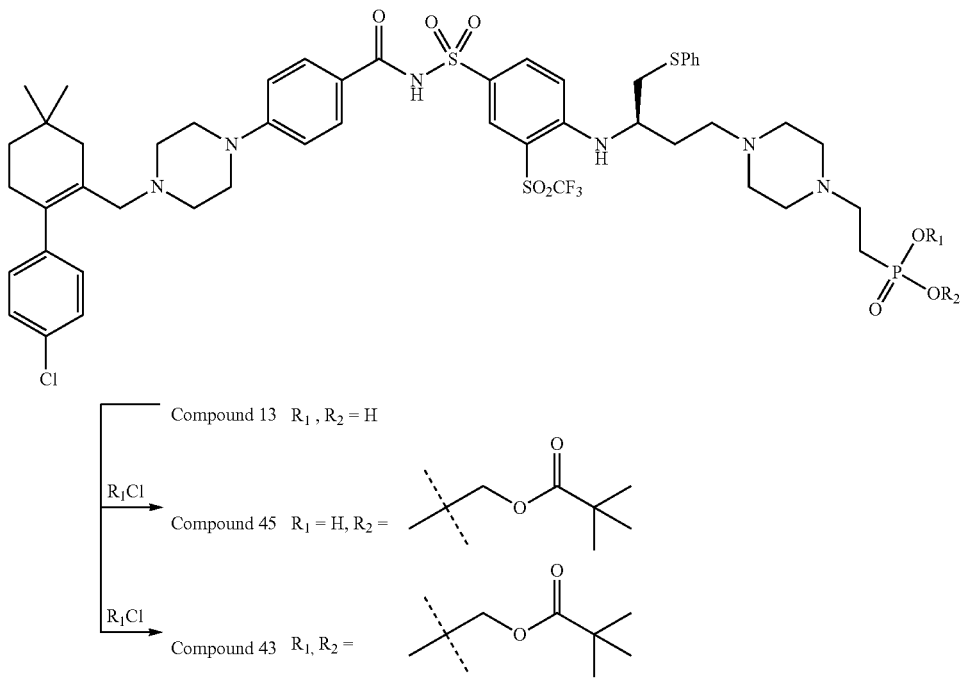

Synthesis of Compound 45. (((2-(4-((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)ethyl)(hydroxy)phosphoryl)oxy)methyl pivalate. To a solution of Compound 13 (50 mg, 46.23 μmol) in DMF (7 mL) was added K₂CO₃ (64 mg, 462.30 μmol). The reaction mixture was stirred at room temperature for 1 hour and then chloromethyl 2,2-dimethylpropanoate (70 mg, 462.30 μmol) was added. The reaction mixture was stirred at 60° C. overnight. The mixture was purified by prep-HPLC to afford Compound 45 (3.7 mg, 7% yield). MS (ESI) m/z=1195.6[M+H]⁺.

Synthesis of Compound 43 (R)-(((2-(4-(3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)ethyl)phosphoryl)bis(oxy))bis(methylene) bis(2,2-dimethylpropanoate). To a solution of Compound 13 (20 mg, 18.49 μmol) in DMF (10 mL) was added K₂CO₃ (51 mg, 369.80 μmol). The reaction mixture was stirred at room temperature for 30 min and then chloromethyl 2,2-dimethylpropanoate (55 mg, 369.80 μmol) was added. The reaction mixture was stirred at 60° C. overnight and then purified by prep-HPLC to afford Compound 43 (2.6 mg, 11% yield). MS (ESI) m/z=1309.6[M+H]⁺.

Example 1.25: Synthesis of Compound 44.

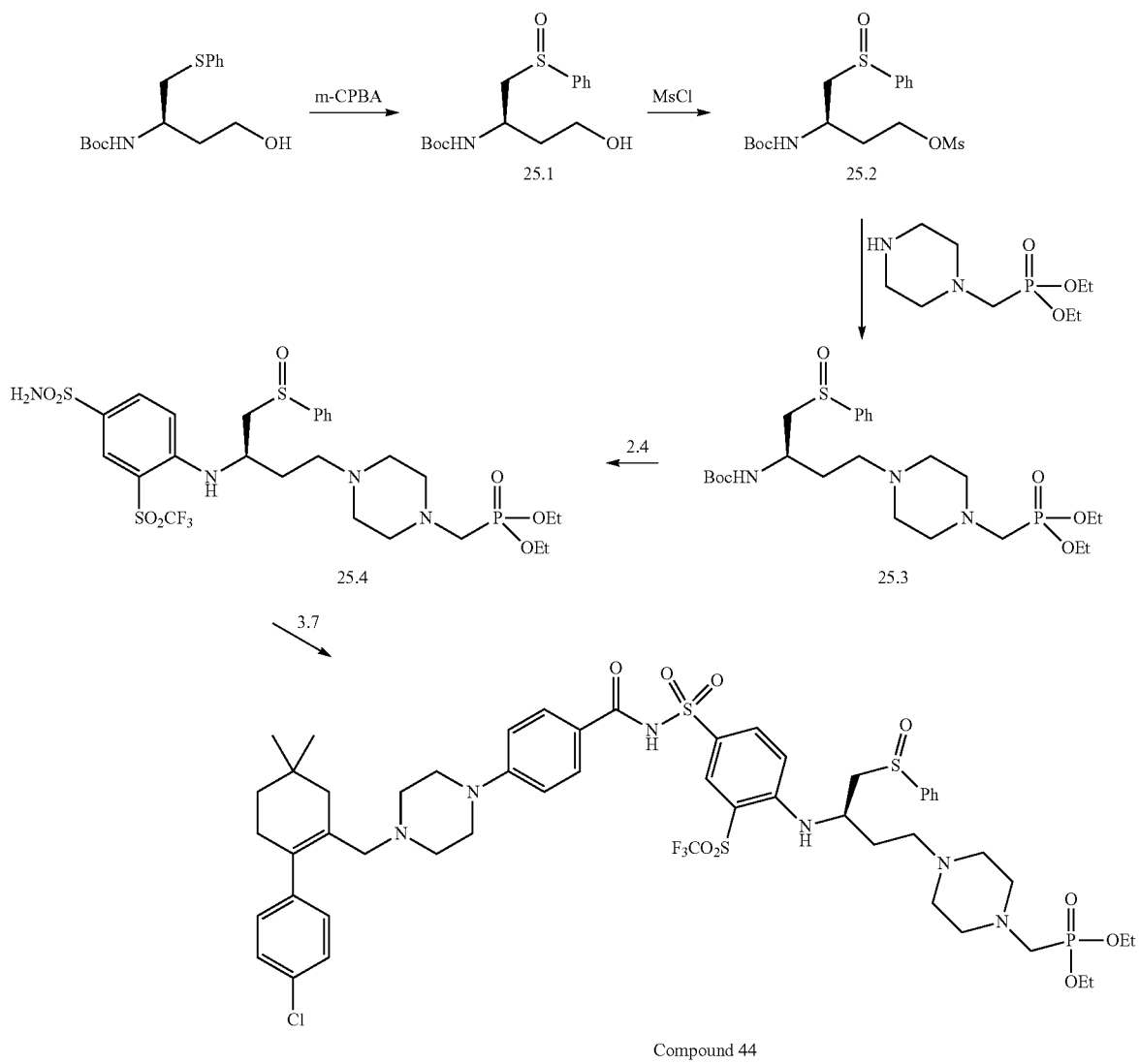

Compound 44

Step A: To a solution of tert-butyl N-[(1R)-3-hydroxy-1-(phenylsulfanylmethyl)propyl]carbamate (502 mg, 1.68 mmol) in DCM (20 mL) was added m-CPBA (290 mg, 1.68 mmol). The reaction mixture was stirred at room temperature for 4 hours. The mixture was washed with aqueous NaOH (1 mol/L, 15 mL) and aqueous HCl (1 mol/L, 15 mL), sequentially. The organic phase was dried over anhydrous MgSO$_4$ and concentrated. The residue was purified by flash column chromatography on silica gel (EtOAc:Petroleum ether=5:1) to afford 25.1 (430 mg, 82% yield). MS (ESI) m/z=314.41[M+H]$^+$.

Step B: To a solution of 25.1 (420 mg, 1.34 mmol) in DCM (50 mL) were added TEA (407 mg, 4.02 mmol) and MsCl (230 mg, 2.01 mmol). The reaction mixture was stirred at room temperature for 1 hour. The mixture was then washed with aqueous NaOH (1 mol/L, 50 mL). The organic phase was dried over anhydrous MgSO$_4$ and concentrated to afford crude 25.2 (461 mg, 88% yield), which was used in the next step without further purification. MS (ESI) m/z=392.29[M+H]$^+$. $^1$H NMR (400 MHz, CDCl$_3$): δ 7.65 (m, 2H), 7.55 (m, 3H), 5.31 (m, 0.5H), 5.04 (m, 0.5H), 4.37 (m, 1H), 4.30 (m, 1H), 4.15 (m, 1H), 3.11 (m, 2H), 3.04 (s, 3H), 2.15 (m, 2H), 1.43 (s, 9H).

Step C: To a solution of 25.2 (302 mg, 766.28 μmol) in MeCN (20 mL) were added diethyl (piperazin-1-ylmethyl)phosphonate (181 mg, 766.28 μmol) and K$_2$CO$_3$ (212 mg, 1.53 mmol). The reaction mixture was stirred at 70° C. overnight and then concentrated directly. The residue was dissolved in aqueous HCl (1 mol/L, 30 mL) and the resulting mixture was washed with DCM (3×30 mL). The water phase was adjusted to pH=9~10, and extracted with DCM (3×30 mL). The combined organic phases were dried over anhydrous MgSO$_4$ and concentrated to afford crude 25.3 (268 mg, 66% yield), which was used in the next step without further purification. MS (ESI) m/z=532.42[M+H]$^+$.

Step D: To a solution of 25.3 (201 mg, 376.19 μmol) in DCM (9 mL) was added TFA (3 mL). The reaction mixture was stirred at room temperature for 1 hour and then concentrated directly. The residue was dissolved in MeCN (10 mL), and to the resulting mixture were added 2.4 (114 mg, 370.77 μmol) and TEA (225 mg, 2.22 mmol). The reaction mixture was stirred at 70° C. for 2 hours and then concentrated directly. The residue was purified by prep-TLC (EtOAc:MeOH=5:1) to afford 25.4 (141 mg, 53% yield). MS (ESI) m/z=719.18[M+H]+.

Step E: Synthesis of Compound 44 (Diethyl ((4-((3R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylsulfinyl)butyl)piperazin-1-yl)methyl)phosphonate).

To a solution of 25.4 (80 mg, 111.30 μmol) in MeCN (5 mL) were added 3.7 (49 mg, 111.30 μmol), DMAP (27 mg, 222.60 μmol) and EDCl (43 mg, 222.60 μmol). The reaction mixture was stirred at 70° C. for 2 hours and then concentrated directly. The residue was purified by prep-TLC (DCM:MeOH=10:1) to afford Compound 44 (71 mg, 56% yield). MS (ESI) m/z=1139.57[M+H]+.

Example 1.26: Synthesis of Compounds 26.5 and 26.7.

Step C: To a solution of 26.2 (51 mg, 231.0 μmol) in THF (10 mL) was slowly added NaBH$_4$ (26 mg, 692.33 μmol) at 0° C. The reaction mixture was stirred at r.t. for 1 hour. The mixture was poured into water (30 mL) and the resulting mixture was extracted with DCM (40 mL×2). The combined organic phases were dried over anhydrous MgSO$_4$ and concentrated to afford crude product [2-(4-chlorophenyl)phenyl]methanol (49 mg, 99% yield), which was used in the next step without further purification. $^1$H NMR (400 M, CDCl$_3$), δ 7.55 (m, 1H), 7.42~7.7.32 (m, 6H), 7.25 (m, 1H), 4.59 (s, 2H).

To a solution of [2-(4-chlorophenyl)phenyl]methanol (1.01 g, 4.57 mmol) in DCM (30 mL) was slowly added PBr$_3$ (928 mg, 3.43 mmol) at −10° C. The reaction mixture was stirred at the same temperature for 30 min. The mixture was poured into ice water (100 mL), and saturated aq.

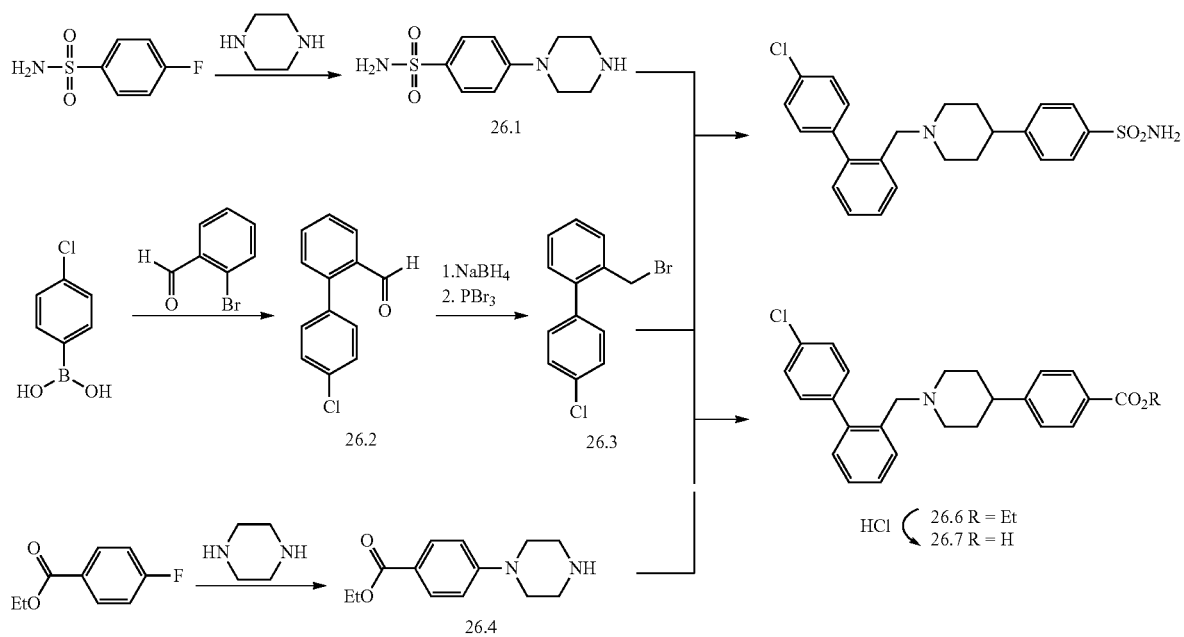

Step A: To a solution of 4-fluorobenzenesulfonamide (1.02 g, 5.71 mmol) in H$_2$O (10 mL) was added piperazine (2.46 g, 28.55 mmol). The reaction mixture was stirred at 100° C. overnight. The mixture was cooled to room temperature and filtered. The filtration cake was washed with H$_2$O (20 mL), toluene (30 mL) and ether (30 mL) to give 26.1 (401 mg, 29% yield). MS (ESI) m/z=242.0[M+H]+. $^1$H NMR (400 M, DMSO-d6), δ 7.60 (d, J=8.8 Hz, 2H), 7.05 (m, 2H), 7.00 (d, J=8.8 Hz, 2H), 3.17 (m, 4H), 2.80 (m, 4H), 2.33 (m, 1H).

Step B: To a solution of 2-bromobenzaldehyde (185 mg, 999.89 μmol) in dioxane (20 mL) and H$_2$O (1 mL) were added (4-chlorophenyl)boronicacid (235 mg, 1.50 mmol), CH$_3$COOK (295 mg, 3.00 mmol) and Pd(dppf)Cl$_2$(20 mg). The reaction mixture was heated at 90° C. for 2 hours under N$_2$ atmosphere. The mixture was poured into water (40 mL) and the resulting mixture was extracted with EtOAc (50 mL×2). The combined organic phases were dried over anhydrous MgSO$_4$ and concentrated. The residue was purified by flash chromatography on silica gel (Hexane/EtOAc=50:1) to afford 26.2 (150 mg, 69% yield). $^1$H NMR (400 M, CDCl$_3$), δ 9.97 (s, 1H), 8.03 (m, 1H), 7.65 (m, 1H), 7.54 (m, 1H), 7.45 (m, 2H), 7.42 (m, 1H), 7.32 (m, 2H).

Na$_2$CO$_3$(50 mL) was added to adjust pH to 8. The resulting mixture was extracted with DCM (100 mL×2). The organic phases were dried over anhydrous MgSO$_4$ and concentrated. The residue was purified by flash column chromatography on silica gel (Petroleum Ether:EtOAc=50:1) to afford 26.3 (521 mg, 40% yield). $^1$H NMR (400 M, CDCl$_3$), δ 7.53 (m, 1H), 7.44~7.35 (m, 6H), 7.23 (m, 1H), 4.42 (s, 2H).

Step D: Synthesis of Compound 26.5. To a mixture of 26.3 (100 mg, 355.14 μmol) and 26.1 (86 mg, 355.14 μmol) in DMSO (4 mL) was added K$_2$CO$_3$ (98 mg, 710.28 μmol). The reaction mixture was stirred at 100° C. for 3 h. The mixture was cooled to r.t. and poured into water (30 mL). The resulting mixture was extracted with EtOAc (50 mL×3). The combined organic phases were dried over anhydrous MgSO$_4$ and concentrated to afford crude 26.5 (140 mg, 89% yield). $^1$H NMR (400 M, DMSO-d6), δ 7.59 (m, 2H), 7.51 (m, 1H), 7.36 (m, 4H), 7.26 (m, 2H), 7.05 (m, 1H), 6.97 (m, 2H), 3.40 (m, 2H), 3.22 (m, 4H), 2.54 (m, 2H), 2.42 (m, 4H).

Step E: To a solution of ethyl 4-fluorobenzoate (51 g, 297.34 mmol) in DMSO (500 mL) were added piperazine (76.84 g, 892.02 mmol) and K$_2$CO$_3$ (82.19 g, 594.68 mmol). The reaction mixture was stirred at 100° C. overnight. The mixture was poured into H$_2$O (2 L), and the resulting mixture was extracted with EtOAc (3×500 mL). The combined phases were washed with brine (2×800 mL), dried over anhydrous MgSO$_4$, and concentrated to afford crude 26.4 (43 g, 62% yield), which was used in the next step without further purification. MS (ESI) m/z=235.18[M+H]$^+$. $^1$H NMR (400 M, CDCl$_3$), δ 7.92 (m, 2H), 6.87 (m, 2H), 4.32 (m, 2H), 3.28 (m, 4H), 3.03 (m, 4H), 1.37 (m, 4H).

Step F: To a solution of 26.3 (3.47 g, 12.32 mmol) in DMSO (25 mL) were added 26.4 (3.34 g, 12.32 mmol) and K$_2$CO$_3$ (5.11 g, 36.96 mmol). The reaction mixture was stirred at 90° C. for 3 hours. The mixture was poured into ice water (200 mL) and extracted with EtOAc (2×200 mL). The combined organic phases were dried over anhydrous Na$_2$SO$_4$, filtered and concentrated to afford crude 26.6 (5.33 g, near quantitative). MS (ESI) m/z=435.52[M+H]$^+$.

Step G: Synthesis of Compound 26.7. To a solution of 26.6 (6.10 g, 14.02 mmol) in THF (10 mL) was added diluted HCl (6 mol/L, 100 mL) at room temperature. The reaction mixture was stirred at 80° C. for 3 hours. The mixture was cooled to 5° C. and filtered. The filtration cake was washed with DCM (50 mL) and Petroleum Ether (100 mL) to afford 26.7 (5.21 g, 92% yield). MS (ESI) m/z=407.48[M+H]$^+$.

Example 1.27: Synthesis of Compounds 42, 50, 52, 55 and 57.

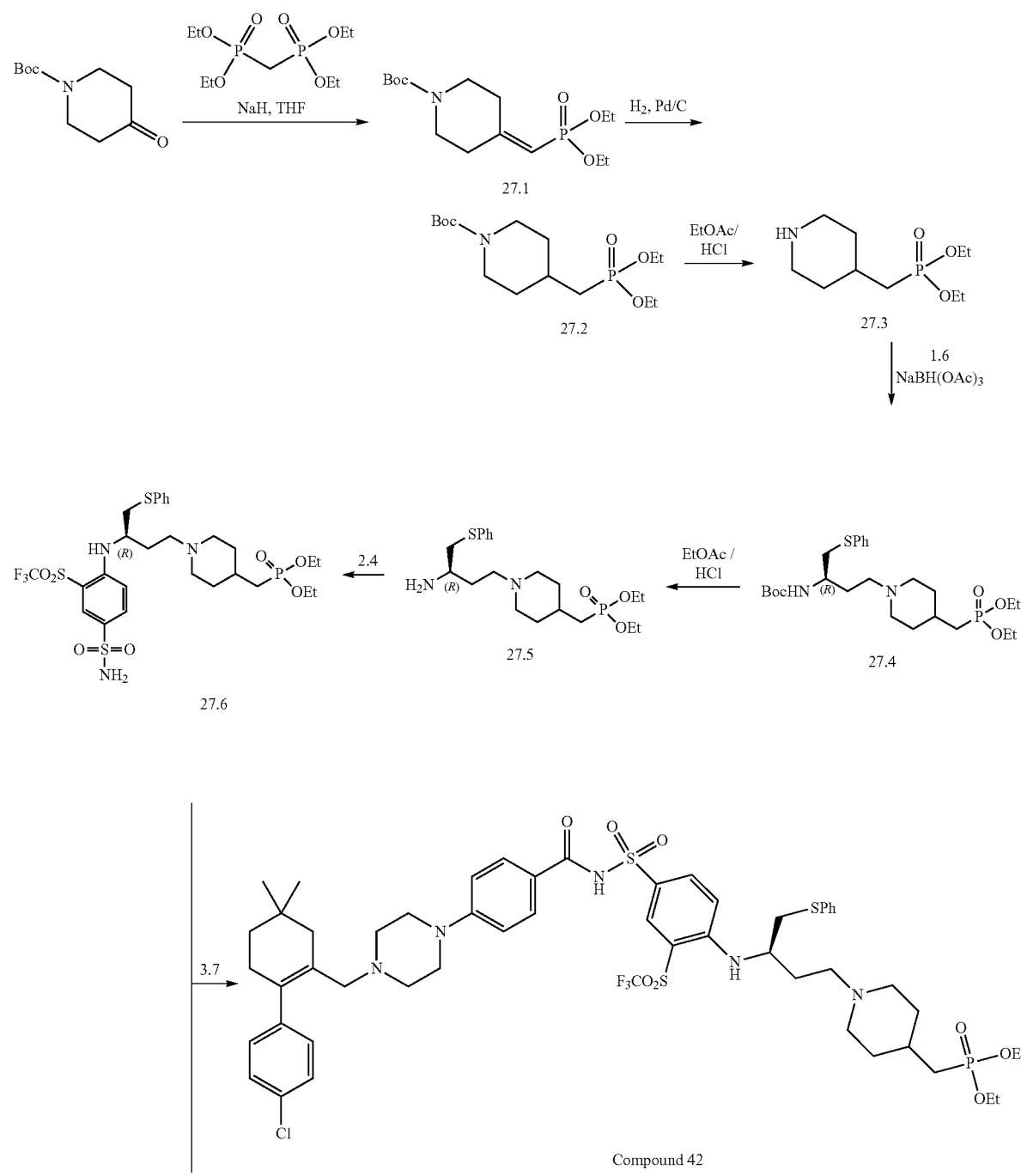

Compound 42

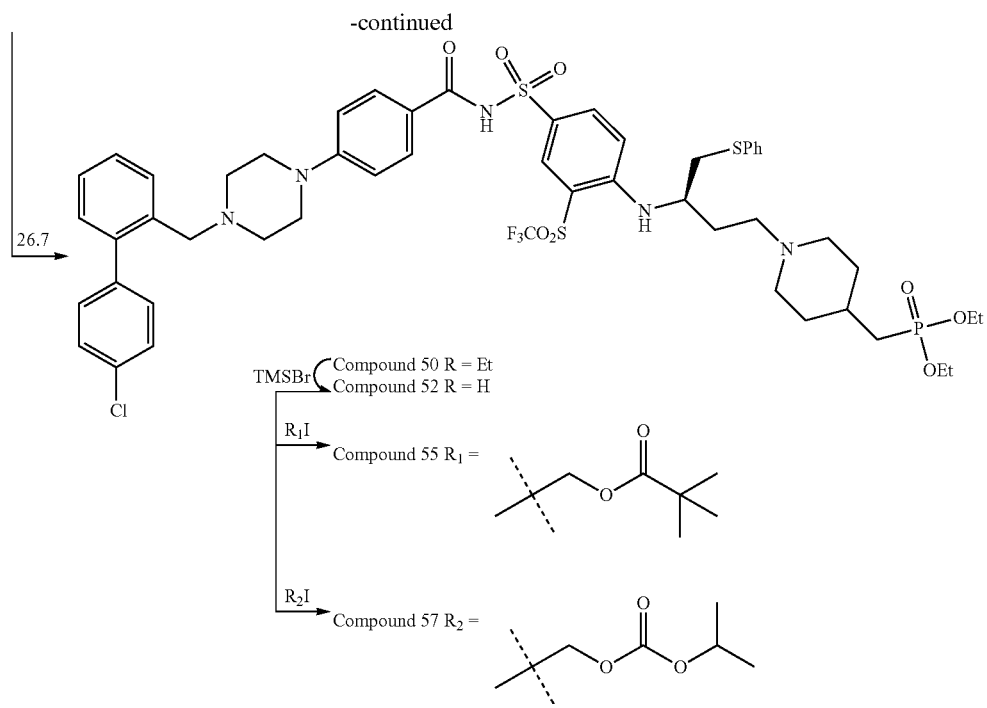

Step A: To a solution of 1-[diethoxyphosphorylmethyl(ethoxy)phosphoryl]oxyethane (1.45 g, 5.02 mmol) in THF (25 mL) was added NaH (120 mg, 5.02 mmol) at room temperature. The mixture was stirred at room temperature for 40 min, and then tert-butyl 4-oxopiperidine-1-carboxylate (1.00 g, 5.02 mmol) was added. The reaction mixture was stirred for another 2 hours. Water (50 mL) was added and the resulting mixture was extracted with EtOAc (3×50 mL). The combined organic phases were dried over anhydrous $Na_2SO_4$ and concentrated. The residue was purified by flash column chromatography on silica gel (Petroleum Ether:EtOAc=1:2) to afford 27.1 (859 mg, 51% yield). $^1$H NMR (400 MHz, $CDCl_3$): δ 5.58 (m, 1H), 4.12 (m, 4H), 3.90 (m, 2H), 3.49 (m, 2H), 2.56 (m, 2H), 2.23 (m, 2H), 1.47 (s, 9H), 1.32 (m, 6H).

Step B: To a solution of 27.1 (650 mg, 1.95 mmol) in EtOH (50 mL) was added Pd/C (237 mg, 585 μmol) at room temperature. Then the reaction mixture was stirred under $H_2$ atmosphere at room temperature overnight. The mixture was filtered and concentrated to afford crude 27.2 (631 mg, 96% yield). $^1$H NMR (400 MHz, $CDCl_3$): δ 4.12 (m, 4H), 4.08 (m, 2H), 3.72 (m, 2H), 1.84 (m, 3H), 1.69 (m, 2H), 1.47 (s, 9H), 1.32 (m, 6H), 1.21 (m, 2H).

Step C: To a solution of 27.2 (601 mg, 1.79 mmol) in EtOAc (5 mL) was added EtOAc/HCl (6 mol/L, 10 mL) at 0° C. The reaction mixture was stirred at 0° C. for 2 hours and then concentrated to afford crude 27.3 (403 mg, 95% yield). $^1$H NMR (400 MHz, $CDCl_3$): 4.12 (m, 4H), 3.48 (m, 2H), 2.89 (m, 2H), 2.02 (m, 1H), 1.77 (m, 4H), 1.33 (m, 6H), 1.21 (m, 2H).

Step D: To a mixture of 27.3 (301 mg, 1.02 mmol) and 1.6 (240 mg, 1.02 mmol) in DCM (15 mL) was added $Et_3N$ (412 mg, 4.08 mmol) at room temperature. $NaBH_3CN$ (94.86 mg, 1.53 mmol) was then added and the reaction mixture was stirred overnight. The mixture was then concentrated and the residue was purified by flash column chromatography on silica gel (EtOAc:MeOH=20:1) to afford 27.4 (281 mg, 53% yield).

Step E: To a solution of 27.4 (302 mg, 582.91 μmol) in EtOAc (10 mL) was added EtOAc/HCl (3 mol/L, 10 mL) at 0° C. The reaction mixture was stirred at the same temperature for 2 hours and then concentrated to afford crude 27.5 (232 mg, 95% yield).

Step F: To a solution of 27.5 (250 mg, 603.08 μmol) in MeCN (13 mL) were added 2.4 (204 mg, 663.39 μmol) and $Et_3N$ (244 mg, 2.41 mmol) at room temperature. The reaction mixture was heated at 70° C. for 3 hours and then concentrated. The residue was purified by flash column chromatography on silica gel (EtOAc:MeOH=20:1) to afford 27.6 (281 mg, 66% yield). $^1$H NMR (400 MHz, $CDCl_3$): δ 8.23 (m, 1H), 7.88 (m, 1H), 7.40 (m, 2H), 7.31 (m, 3H), 7.00 (m, 1H), 6.77 (m, 1H), 5.91 (m, 2H), 4.11 (m, 4H), 4.01 (m, 1H), 3.11 (m, 2H), 2.62 (m, 2H), 2.21 (m, 2H), 2.06 (m, 2H), 1.94 (m, 3H), 1.72 (m, 2H), 1.61 (m, 2H), 1.27 (m, 6H), 0.88 (m, 2H).

Step G: Synthesis of Compound 42 (Diethyl (R)-((4-(3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)methyl)phosphonate) To a mixture of 3.7 (235 mg, 535.91 μmol) and 27.6 (250 mg, 357.27 μmol) in MeCN (5 mL) were added EDCl (137 mg, 714.54 μmol) and DMAP (87 mg, 714.54 μmol). The reaction mixture was heated at 70° C. for 6 hours and then concentrated. The residue was purified by prep-TLC to afford Compound 42 (42 mg, 10%). MS (ESI) m/z=1122.4 [M+H]$^+$. $^1$H NMR (400 MHz, $CDCl_3$): δ 8.33 (m, 1H), 8.03 (m, 1H), 7.76 (m, 2H), 7.35 (m, 2H), 7.26 (m, 5H), 7.00 (m, 2H), 6.98 (m, 1H), 6.79 (m, 2H), 6.61 (m, 1H), 4.08 (m, 4H), 3.92 (m, 1H), 3.28 (m, 4H), 3.07 (m, 2H), 2.84 (m, 2H), 2.76 (m, 2H), 2.40 (m, 4H), 2.26 (m, 4H), 2.15~1.80 (m, 7H), 1.74 (m, 2H), 1.69 (m, 2H), 1.47 (m, 2H), 1.33 (m, 6H), 1.26 (m, 2H), 0.98 (m, 6H).

Step G: Synthesis of Compound 50 (Diethyl (R)-((4-(3-((4-(N-(4-(4-((4'-chloro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)methyl)phosphonate). To a solution of 26.7 (230 mg, 565.25 µmol) in MeCN (20 mL) were added 27.6 (397 mg, 565.25 µmol), DMAP (138 mg, 1.13 mmol) and EDCl (216 mg, 1.13 mmol). The reaction mixture was stirred at 70° C. for 2 hours and then concentrated. The residue was purified by flash column chromatography on silica gel (DCM:MeOH=20:1) to afford desired product. It was then partitioned between aqueous HCl (2 mol/L, 100 mL) and DCM (100 mL). The organic phase was dried over $Na_2SO_4$ and concentrated to afford Compound 50 (328 mg, 52% yield) as HCl salt. MS (ESI) m/z=1090.7[M+H]$^+$. $^1$H NMR (400 MHz, CDCl$_3$): δ 8.34 (m, 1H), 8.21 (m, 1H), 8.04 (m, 1H), 7.82 (m, 2H), 7.56 (m, 5H), 7.32 (m, 2H), 7.19 (m, 3H), 7.00~6.81 (m, 5H), 4.40 (m, 2H), 4.21 (m, 1H), 4.07 (m, 4H), 3.84 (m, 2H), 3.71 (m, 2H), 3.45 (m, 4H), 3.30~2.80 (m, 6H), 2.77 (m, 2H), 2.45 (m, 2H), 2.21 (m, 2H), 2.02 (m, 3H), 1.77 (m, 2H), 1.31 (m, 6H).

Step H: Synthesis of Compound 52 (Ethyl hydrogen ((4-((R)-3-((4-(N-(4-(4-((4'-chloro-[1,1'-biphenyl]-2-yl)methyl) piperazin-1-yl)benzoyl)sulfamoyl)-2-((trifluoromethyl)sulfonyl)phenyl)amino)-4-(phenylthio)butyl)piperazin-1-yl)methyl)phosphonate). To a solution of Compound 50 (51 mg, 46 µmol) in MeCN (2.50 mL) was added TMSBr (400 µL) at room temperature. The reaction mixture was stirred for 3 hours and then quenched with aqueous $Na_2CO_3$ (5 mL). The resulting mixture was purified by prep-HPLC to afford Compound 52 (15 mg, 28% yield) as TFA salt. MS (ESI) m/z=1062.6[M+H]$^+$.

Step I: Synthesis of Compound 55 (((((4-((R)-3-((4-(N-(4-(4-((4'-chloro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)methyl)(ethoxy)phosphoryl)oxy)methyl pivalate. To a solution of Compound 52 (20 mg, 18.82 µmol) in DMF (2 mL) was added $K_2CO_3$ (52 mg, 376.21 µmol). The mixture was stirred for 30 min and then iodomethyl 2,2-dimethylpropanoate (91 mg, 376.02 µmol) was added. The reaction mixture was stirred at 60° C. for 2 hours, and then submitted to prep-HPLC to afford Compound 55 (11 mg, 50% yield). MS (ESI) m/z=1176.7[M+H]$^+$.

Step I: Synthesis of Compound 57 (((((4-((R)-3-((4-(N-(4-(4-((4'-chloro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)methyl)(ethoxy)phosphoryl)oxy)methyl isopropyl carbonate. To a solution of Compound 52 (40 mg, 37.64 µmol) in DMF (4 mL) was added $K_2CO_3$ (104 mg, 753.62 µmol). The mixture was stirred for 30 min and then iodomethyl isopropyl carbonate (183 mg, 749.91 µmol) was added. The reaction mixture was stirred at 65° C. for 2 hours and then submitted to prep-HPLC to afford Compound 57 (12 mg, 27% yield). MS (ESI) m/z=1178.8[M+H]$^+$. $^1$H NMR (400 MHz, DMSO): δ 8.05 (m, 1H), 7.88 (m, 1H), 7.72 (m, 2H), 7.50 (m, 5H), 7.42~7.17 (m, 8H), 6.79 (m, 3H), 6.61 (m, 1H), 5.55 (m, 2H), 4.81 (m, 1H), 3.99 (m, 2H), 3.96 (m, 1H), 3.45 (m, 2H), 3.29 (m, 2H), 3.13 (m, 4H), 2.78 (m, 1H), 2.58 (m, 1H), 2.40 (m, 4H), 2.56 (m, 2H), 1.90 (m, 1H), 1.85~1.60 (m, 7H), 1.52 (m, 1H), 1.22 (m, 6H), 1.20 (m, 3H), 1.16 (m, 2H).

Example 1.28: Synthesis of Compound 46.

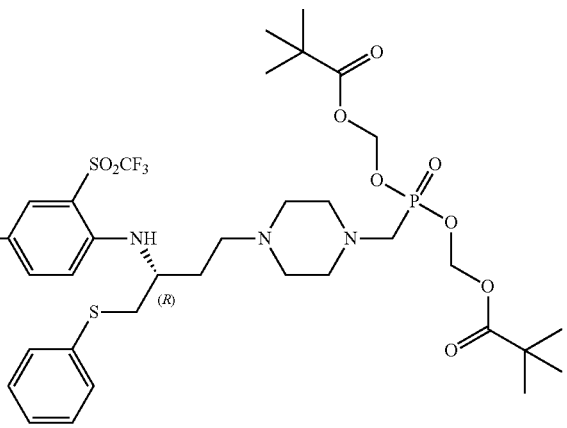

To a solution of Compound 7 (18 mg, 16.88 µmol) in DMF (5 mL) were added $K_2CO_3$ (47 mg, 340.58 µmol) and iodomethyl pivalate (82 mg, 338.78 µmol). The reaction mixture was heated at 60° C. overnight, and then submitted directly to prep-HPLC to afford Compound 46 (4 mg, 18% yield). MS (ESI) m/z=1294.9[M+H]$^+$.

Example 1.29: Synthesis of Compounds 47, 48 and 49

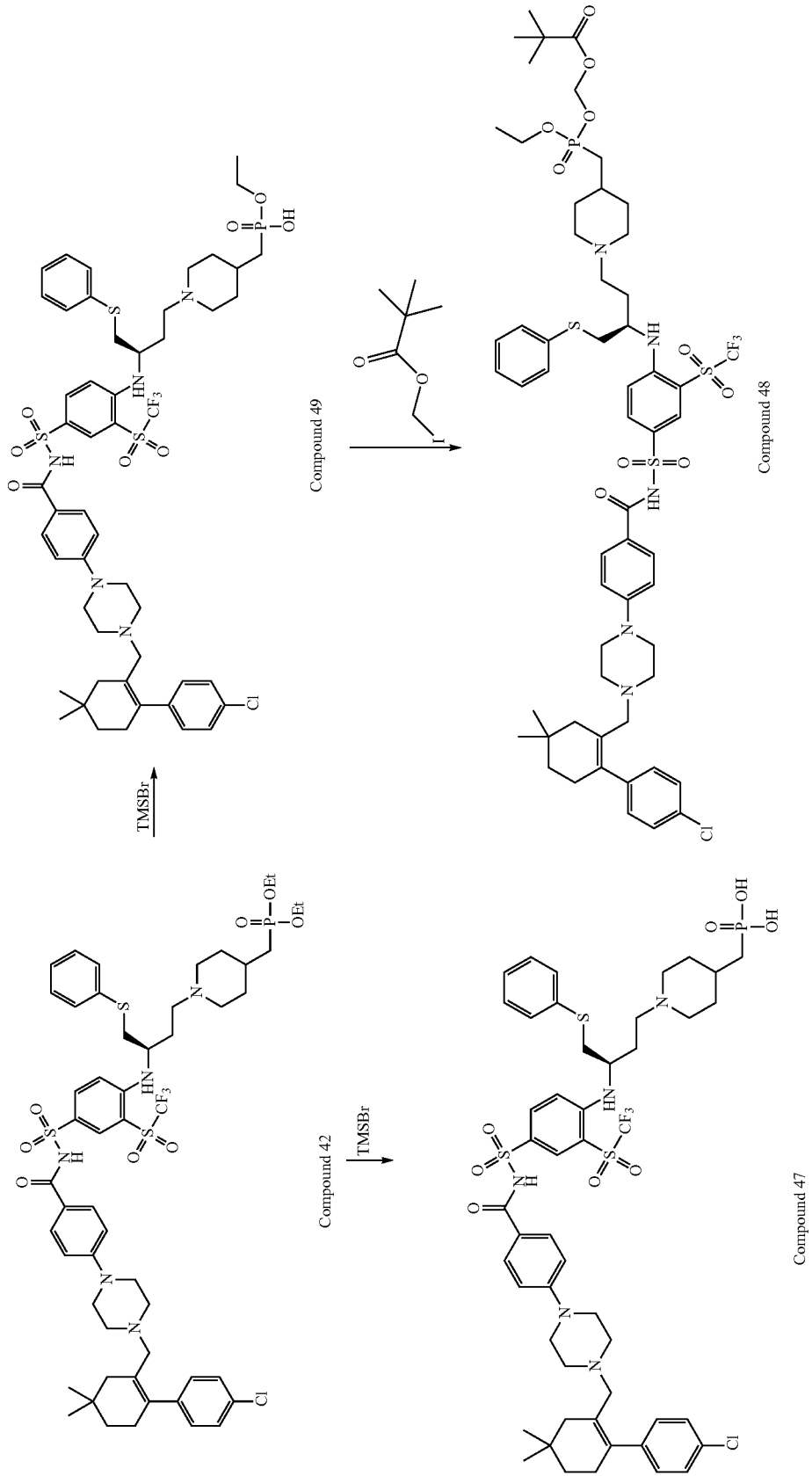

Synthesis of Compound 47 (Diethyl (R)-((1-(3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperidin-4-yl)methyl)phosphonate). To a solution of Compound 42 (139 mg, 123 mmol) in MeCN (3 mL) was added TMSBr (2 mL) at room temperature. The reaction mixture was stirred overnight, and then quenched with sat. $Na_2CO_3$ (5 mL). White solid precipitated out and was collected to afford Compound 47 (128 mg, 97% yield). MS (ESI) m/z=1066.5[M+H]$^+$.

Synthesis of Compound 49 (Ethylhydrogen((1-((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperidin-4-yl)methyl)phosphonate). To a solution of Compound 42 (85 mg, 75.6 mmol) in MeCN (8 mL) was added TMSBr (1 mL) at room temperature. The reaction mixture was stirred overnight, and then quenched with saturated $Na_2CO_3$ (5 mL). The resulting mixture was filtered, and the filtration cake was collected and purified by prep-HPLC to afford Compound 49 (41 mg, 50% yield). MS (ESI) m/z=1094.5[M+H]$^+$.

Synthesis of Compound 48 (((((1-((R)-3-((4-(N-(4-(4-((4'-chloro-4,4-dimethyl-3,4,5,6-tetrahydro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperidin-4-yl)methyl)(ethoxy)phosphoryl)oxy)methyl pivalate). To a solution of Compound 49 (50 mg, 45.7 mmol) in DMF (5 mL) were added $K_2CO_3$ (126 mg, 91.4 mmol) and iodomethyl pivalate (221 mg, 91.4 mmol). The reaction mixture was stirred at 60° C. overnight and then submitted to prep-HPLC to afford Compound 48 (12 mg, 22% yield). MS (ESI) m/z=1208.8[M+H]$^+$ Example 1.30: Synthesis of Compounds 51, 53, 54 and 56.

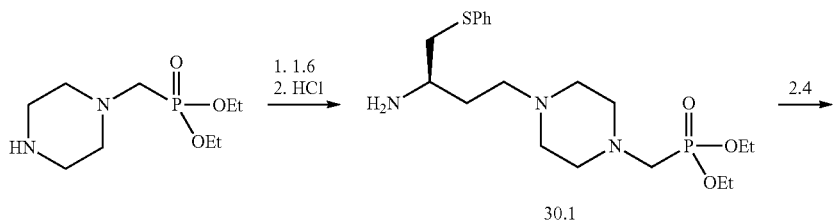

30.1

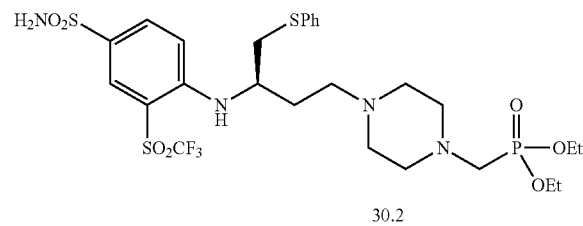

30.2

-continued

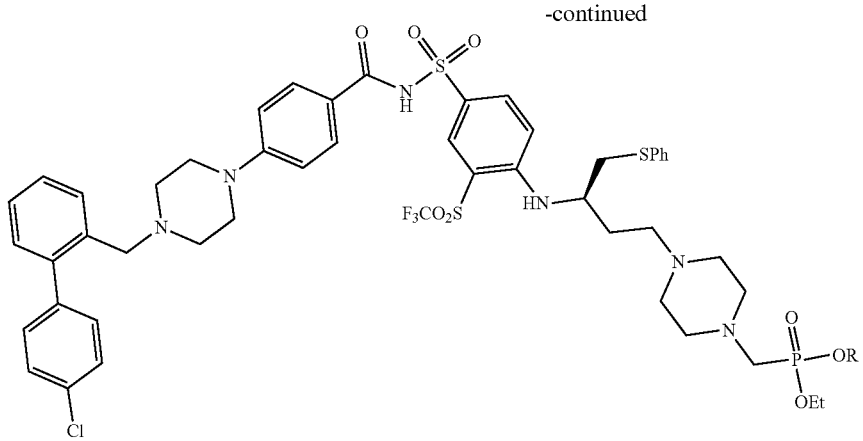

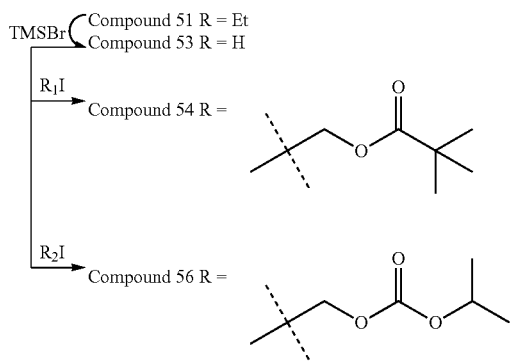

Step A: To a solution of 1.6 (4.50 g, 15.23 mmol) in DCM (100 mL) were added TEA (6.17 g, 60.93 mmol), 1-(diethoxyphosphorylmethyl)piperazine (3.60 g, 15.23 mmol) and NaBH(OAc)$_3$ (4.84 g, 22.85 mmol). The reaction mixture was stirred at room temperature overnight. The mixture was concentrated directly and the residue was dissolved in EtOAc (150 mL). The resulting mixture was washed with H$_2$O (50 mL) and 1N HCl (150 mL) respectively. The organic phase was dried over anhydrous Na$_2$SO$_4$ and concentrated to afford Boc-30.1 (7.18 g, 85% yield), which was used in the next step without further purification. MS (ESI) m/z=515.63[M+H]$^+$.

To a solution of Boc-30.1 (12.70 g, 24.63 mmol) in EtOAc (100 mL) was added EtOAc/HCl (6 mol/L, 100 mL). The reaction mixture was stirred at room temperature for 2 hours and then concentrated directly to afford crude 30.1 (10.02 g, 98% yield). MS (ESI) m/z=415.96[M+H]$^+$. $^1$H NMR (400 MHz, DMSO): 8.54 (br, 2H), 7.47 (m, 2H), 7.37 (m, 2H), 7.27 (m, 1H), 4.06 (m, 4H), 3.47 (m, 2H), 3.31 (m, 2H), 3.26 (m, 5H), 3.10 (m, 4H), 2.86 (m, 2H), 2.22 (m, 1H), 2.11 (m, 1H), 1.25 (m, 6H).

Step B: To a solution of 30.1 (5.20 g, 12.51 mmol) in MeCN (100 mL) were added TEA (7.60 g, 75.06 mmol) and 2.4 (3.84 g, 12.51 mmol). The reaction mixture was stirred at 70° C. for 2 hours and then concentrated directly. The residue was poured into H$_2$O (200 mL), and the resulting mixture was extracted with EtOAc (3×150 mL). The combined organic phases were dried over anhydrous Na$_2$SO$_4$ and concentrated to afford crude 30.2 (7.90 g, 90% yield), which was used in the next step without further purification. MS (ESI) m/z=702.87[M+H]$^+$.

Step C: Synthesis of Compound 51 (Diethyl (R)-((4-(3-((4-(N-(4-(4-((4'-chloro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)methyl) phosphonate). To a solution of 26.7 (115 mg, 282.62 µmol) in MeCN (10 mL) were added 30.2 (200 mg, 285.45 µmol), DMAP (69 mg, 565.24 µmol) and EDCl (108 mg, 562.41 µmol). The reaction mixture was stirred at 70° C. for 2 hours and then concentrated. The residue was purified by flash column chromatography on silica gel (DCM:MeOH=20:1) to afford the product. It was then partitioned between aqueous HCl (2 mol/L, 100 mL) and DCM (100 mL). The organic phase was dried over anhydrous Na$_2$SO$_4$ and concentrated to afford Compound 51 (196 mg, 61% yield) as HCl salt. MS (ESI) m/z=1091.8[M+H]$^+$.

Synthesis of Compound 53 (Ethyl hydrogen ((4-((R)-3-((4-(N-(4-(4-((4'-chloro-[1,1'-biphenyl]-2-yl)methyl) piperazin-1-yl)benzoyl)sulfamoyl)-2-((trifluoromethyl)sulfonyl)phenyl)amino)-4-(phenylthio)butyl)piperazin-1-yl)methyl) phosphonate). To a solution of Compound 51 (50 mg, 45.80 µmol) in MeCN (2.50 mL) was added TMSBr (400 uL). The reaction mixture was stirred at room temperature for 3 hours and then quenched by aqueous Na$_2$CO$_3$(5 mL). The resulting mixture was submitted to prep-HPLC to afford Compound 53 (19 mg, 35% yield) as TFA salt. MS (ESI) m/z=1063.7 [M+H]$^+$.

Synthesis of Compound 54 (((((4-((R)-3-((4-(N-(4-(4-((4'-chloro-[1,1'-biphenyl]-2-yl)methyl)piperazin-1-yl)benzoyl) sulfamoyl)-2-((trifluoromethyl)sulfonyl)phenyl)amino)-4-(phenylthio)butyl)piperazin-1-yl)methyl)(ethoxy) phosphoryl)oxy)methyl pivalate. To a solution of Compound 53 (20 mg, 18.80 µmol) in DMF (2 mL) was added K$_2$CO$_3$ (52 mg, 376.19 µmol). The mixture was stirred for 30 min and then iodomethyl 2,2-dimethylpropanoate (91 mg, 376.00 µmol) was added. The reaction mixture was stirred at 60° C. for 2 hours and then directly submitted to prep-HPLC to afford Compound 54 (11 mg, 50% yield). MS (ESI) m/z=1177.73[M+H]⁺.

Synthesis of Compound 56 (((((4-((R)-3-((4-(N-(4-(4-((4'-chloro-[1,1'-biphenyl]-2-yl)methyl)piperazin-1-yl)benzoyl)sulfamoyl)-2-((trifluoromethyl)sulfonyl)phenyl)amino)-4-(phenylthio)butyl)piperazin-1-yl)methyl)(ethoxy)phosphoryl)oxy)methyl isopropyl carbonate. To a solution of Compound 53 (20 mg, 18.80 μmol) in DMF (2 mL) was added K$_2$CO$_3$ (52 mg, 376.19 μmol). The mixture was stirred for 30 min and then iodomethyl isopropyl carbonate (92 mg, 376.94 μmol) was added. The reaction mixture was stirred at 60° C. for 2 hours and then quenched with aqueous HCl (0.2N, 5 mL). The resulting mixture was purified by prep-HPLC to afford Compound 56 (4 mg, 18% yield). MS (ESI) m/z=1180.03[M+H]⁺

Example 1.31: Alternative synthesis of Compound 6.

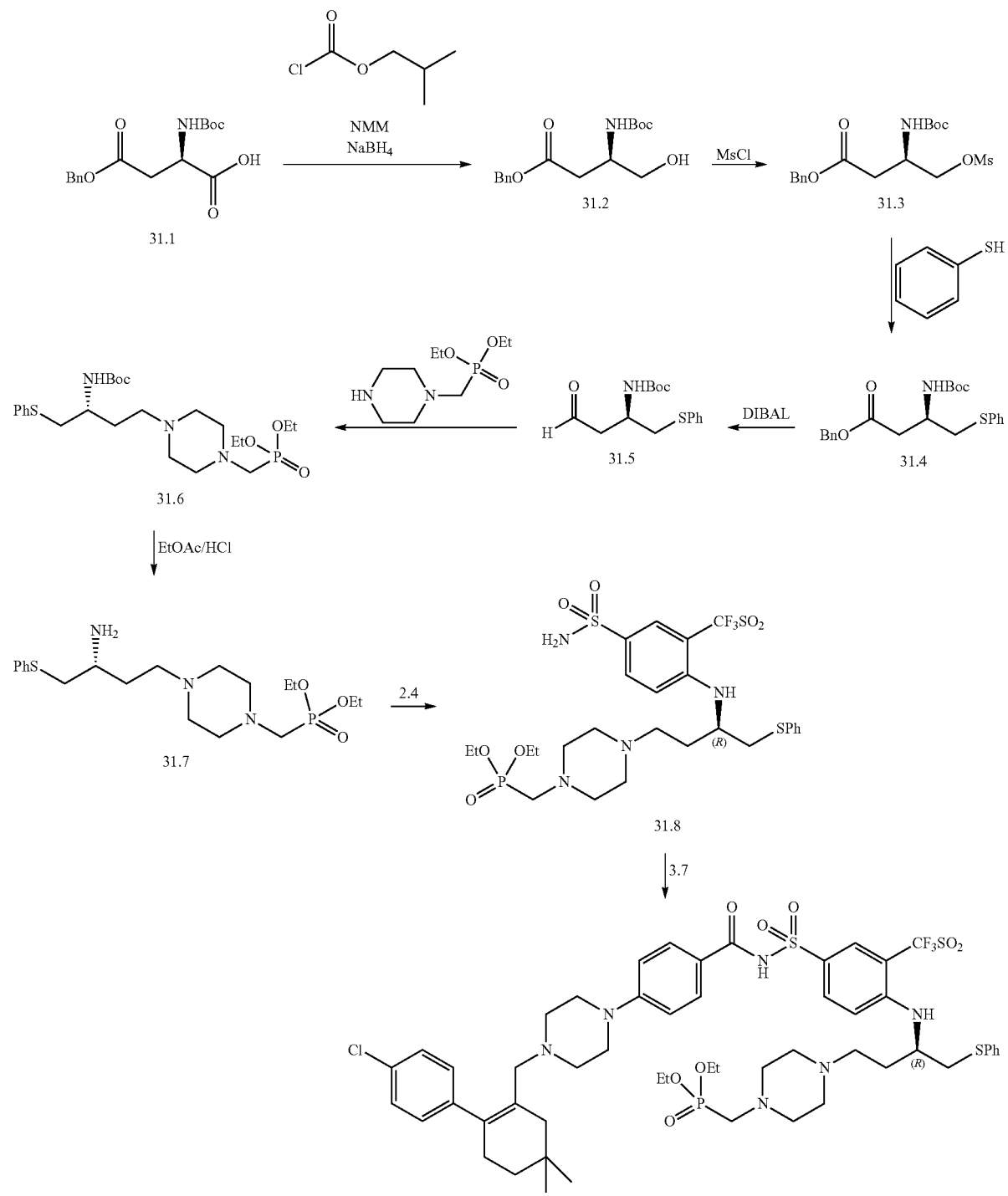

Compound 6

Step A: Synthesis of benzyl (R)-3-((tert-butoxycarbonyl)amino)-4-hydroxybutanoate (31.2). To a solution of (2R)-4-benzyloxy-2-(tert-butoxycarbonylamino)-4-oxo-butanoic acid (20.00 g, 61.85 mmol) in THF (200.00 mL) were added NMM (7.51 g, 74.22 mmol) and isobutyl carbonochloridate (10.14 g, 74.22 mmol) at −10° C. The mixture was stirred at −10° C. for 1 hour and then filtered. The filtrate was cooled to −10° C., and NaBH$_4$. (3.51 g, 92.78 mmol) was added. The reaction mixture was stirred at room temperature for 4 hours and then quenched with H$_2$O (300 mL). The resulting mixture was extracted with EtOAc (3×300 mL), and the combined organic phases were dried over anhydrous Na$_2$SO$_4$, filtered and concentrated to afford the crude 31.2 (19.00 g, 61.42 mmol, 99% yield), which was used in the next step without further purification. MS (ESI) m/z=331.9 [M+Na]$^+$. $^1$H NMR (400 M, CDCl$_3$), δ 7.36~7.32 (m, 5H), 5.23 (br, 1H), 5.11 (s, 2H), 4.02 (m, 1H), 3.69 (m, 2H), 2.68 (m, 2H), 1.44 (m, 9H).

Step B: Synthesis of benzyl (R)-3-((tert-butoxycarbonyl)amino)-4-((methylsulfonyl)oxy)butanoate (31.3). To a solution of 31.2 (30.00 g, 96.97 mmol) in DCM (300.00 mL) were added TEA (19.62 g, 193.94 mmol) and MsCl (13.33 g, 116.36 mmol). The reaction mixture was stirred at room temperature for 3 hours and then washed with H$_2$O (200 mL) and 1N HCl (150 mL) sequentially. The organic phase was dried over anhydrous Na$_2$SO$_4$, filtered and concentrated. The residue was purified by flash column chromatography on silica gel (DCM:MeOH=20:1) to afford 31.3 (34.00 g, 87.75 mmol, 91% yield). MS (ESI) m/z=409.9[M+Na]$^+$. $^1$H NMR (400 M, CDCl$_3$), δ 7.38~7.34 (m, 5H), 5.18 (br, 1H), 5.14 (s, 2H), 4.33~4.28 (m, 3H), 3.05 (s, 3H), 2.70 (m, 2H), 1.44 (s, 9H).

Step C: Synthesis of benzyl (R)-3-((tert-butoxycarbonyl)amino)-4-(phenylthio)butanoate (31.4). To a solution of 31.3 (34.00 g, 87.75 mmol) in toluene (300.00 mL) and H$_2$O (996.01 μL) were added Bu$_4$NI (3.24 g, 8.78 mmol), K$_2$CO$_3$ (24.26 g, 175.50 mmol) and benzenethiol (9.67 g, 87.75 mmol). The reaction mixture was stirred at 55° C. for 2 h and then concentrated directly. The residue was dissolved in water (500 mL), and then extracted with EtOAc (2×300 mL). The combined organic phases were dried over anhydrous Na$_2$SO$_4$, filtered and concentrated. The residue was purified by flash column chromatography on silica gel (Petroleum ether/EtOAc=10:1) to afford 31.4 (25.00 g, 62.26 mmol, 71% yield). MS (ESI) m/z=424.3[M+Na]$^+$. $^1$H NMR (400 M, CDCl$_3$), δ 7.38~7.25 (m, 9H), 7.20~7.16 (m, 1H), 5.19 (br, 1H), 5.09 (s, 2H), 4.12 (m, 1H), 3.27~3.22 (m, 1H), 3.12~3.00 (m, 1H), 2.83~2.78 (m, 1H), 2.70~2.65 (m, 1H), 1.42 (m, 9H).

Step D: Synthesis of tert-Butyl (R)-(4-oxo-1-(phenylthio) butan-2-yl)carbamate (31.5). To a solution of 31.4 (10.00 g, 24.91 mmol) in toluene (100.00 mL) was added DIBAL-H (33.2 mL, 49.82 mmol) at −78° C. The reaction mixture was stirred at −78° C. for 2 h and then quenched with saturated aqueous NH$_4$Cl (16 mL) at −70° C. The resulting mixture was poured into DCM (500 mL), dried over anhydrous MgSO$_4$ and concentrated. The residue was purified by flash column chromatography on silica gel (EtOAc:MeOH=10:1) to afford 31.5 (4.40 g, 14.90 mmol, 60% yield).

Step E: Synthesis of tert-Butyl (R)-(4-(4-((diethoxyphosphoryl)methyl)piperazin-1-yl)—1-(phenylthio) butan-2-yl)carbamate (31.6). To a solution of 31.5 (4.50 g, 15.23 mmol) in DCM (100.00 mL) were added TEA (6.17 g, 60.93 mmol), 1-(diethoxyphosphorylmethyl)piperazine (3.60 g, 15.23 mmol) and NaBH(OAc)$_3$ (4.84 g, 22.85 mmol). The reaction mixture was stirred at room temperature overnight and then concentrated directly. The residue was dissolved in EtOAc (150 mL), quenched with H$_2$O (50 mL) and 1N HCl (150 mL). The water phase was collected, and extracted with DCM (3×200 mL). The combined DCM phases were dried over Na$_2$SO$_4$, filtered and concentrated to afford 31.6 (7.18 g, 13.00 mmol, 85% yield, NCl), which was used in the next step without further purification.

Step F: Synthesis of Diethyl (R)-((4-(3-amino-4-(phenylthio)butyl)piperazin-1-yl)methyl)phosphonate (31.7). To a solution of 31.6 (6.48 g, 11.74 mmol, HCl salt) in EtOAc (60.00 mL) was added 6M EtOAc/HCl (60.00 mL). The reaction mixture was stirred at room temperature for 2 hours and then concentrated directly to afford crude 31.7 (4.80 g, 11.55 mmol, 98% yield), which was used in the next step without further purification.

Step G: Synthesis of 4-[[(1R)-3-[4-(3-Dimethoxyphosphorylpropyl)piperazin-1-yl]-1-(phenylsulfanylmethyl)propyl]amino]-3-(trifluoromethylsulfonyl)benzenesulfonamide (31.8). To a solution of 31.7 (5.20 g, 12.51 mmol) in acetonitrile (100.00 mL) were added TEA (7.60 g, 75.06 mmol) and 2.4 (3.84 g, 12.51 mmol). The reaction mixture was stirred at 70° C. for 2 hours and then concentrated directly. The residue was dissolved in H$_2$O (200 mL), and extracted with EtOAc (3×150 mL). The combined organic phases were dried over anhydrous Na$_2$SO$_4$, filtered and concentrated to afford crude 31.8 (7.90 g, 11.24 mmol, 90% yield), which was used in the next step without further purification.

Step G: Synthesis of Compound 6 (HCl salt). To a solution of 31.8 (4.00 g, 5.69 mmol) in acetonitrile (100.00 mL) were added 3.7 (2.75 g, 6.26 mmol), DMAP (1.39 g, 11.38 mmol) and EDCI (2.18 g, 11.38 mmol). The reaction mixture was stirred at 70° C. for 2 hours and then concentrated directly. The residue was purified by flash column chromatography on silica gel (EtOAc:MeOH=10:1) to afford crude product, which was then dissolved in DCM (200 mL), washed with 1 N HCl (150 mL), dried over anhydrous MgSO$_4$ and concentrated. The residue was further purified by flash column chromatography on silica gel (DCM:MeOH=10:1) to afford Compound 6-HCl salt (3.80 g, 3.28 mmol, 58% yield, HCl salt).

Step H: Synthesis of Compound 6 (free base). To a solution of Compound 31.8 (4.00 g, 5.69 mmol) in acetonitrile (50.00 mL) were added 3.7 (2.75 g, 6.26 mmol), DMAP (1.39 g, 11.38 mmol) and EDCI (2.18 g, 11.38 mmol). The reaction mixture was stirred at 70° C. for 2 hours and then concentrated directly. The residue was purified by flash column chromatography on silica gel (EtOAc:MeOH=10:1) to afford crude product, which was dissolved in DCM (200 mL), washed with 1 N HCl (150 mL), dried over MgSO$_4$ and concentrated. The residue was further purified by flash column chromatography on silica gel (DCM:MeOH=10:1) to afford the HCl salt in 95% purity. The HCl salt was dissolved in DCM (200 mL), and washed with 2M K$_2$CO$_3$ (2×200 mL). The DCM phase was dried over MgSO$_4$, filtered and concentrated. The residue was further purified by flash column chromatography on silica gel (DCM:MeOH=10:1) to afford Compound 6 in free base form (4.10 g, 3.65 mmol, 64% yield).

Example 2

BCL-Binding Assay

Compounds were prepared as 400× DMSO stock solutions in a 1:4 dilution series then diluted 1:100 in assay buffer (25 mM HEPES pH 7.5, 100 mM NaCl, 0.1% BSA, 0.005% Tween) immediately before use. Aliquots of 400 nM 6xHis-tagged BCL-xL, BCL-2, and BCL-w were thawed on ice and diluted to 0.4 (BCL-XL) or 0.8 (BCL-W and 2) nM in assay buffer. Aliquots of biotinylated BIM and BAD peptides were diluted in assay buffer to 120 and 60 nM respectively. Ten microliters of biotinylated peptide were added to wells of a 96-well PCR plate, followed by ten microliters of inhibitor, then ten microliters of BCL protein, BCL-XL with BAD and BCL-W/2 with BIM. The plates were sealed and incubated at room temperature. After 24 hr, 0.16 µg Anti-His conjugated AlphaLISA acceptor beads were added in 5 µL assay buffer. After one hour at room temperature, 0.16 µg AlphaScreen streptavidin donor beads were added in 5 µL assay buffer and plates were incubated an additional 30 min in the dark. Two 17 µL aliquots of each reaction were plated in a Perkin Elmer 384-well proxiplate, and plates were scanned for using a Perkin Elmer Enspire plate reader. Kd values were calculated in Prism Graph Pad using a one site competitive binding model and previously determined Kd values for each protein peptide pair. Compounds of the disclosure with Bcl-binding (Kd) of less than 1 nM have "A" activity, from 1 nM to 10 nM have "B" activity, from greater than 10 nM to 50 nM have "C" activity, and of greater than 50 nM have "D" activity. Results from this assay are seen in Table 1.

TABLE 1

BCL-BINDING DATA

| Compound # | Structure | Bcl-xL | Bcl-2 | Bcl-w |
|---|---|---|---|---|
| 6 | 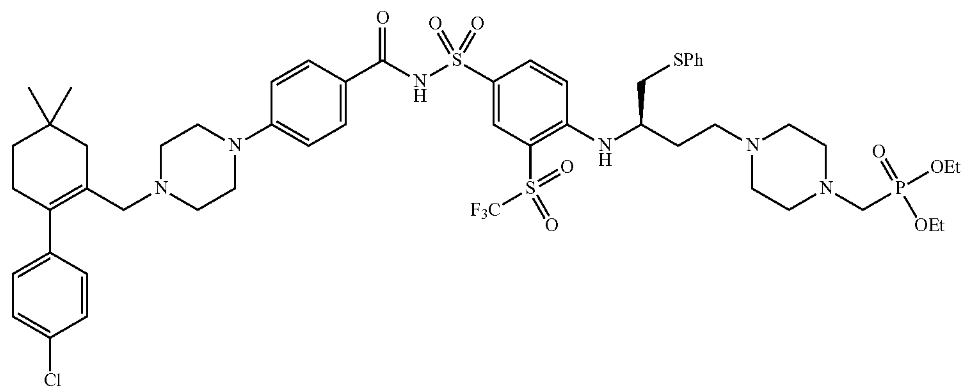 | A | A | B |
| 7 | 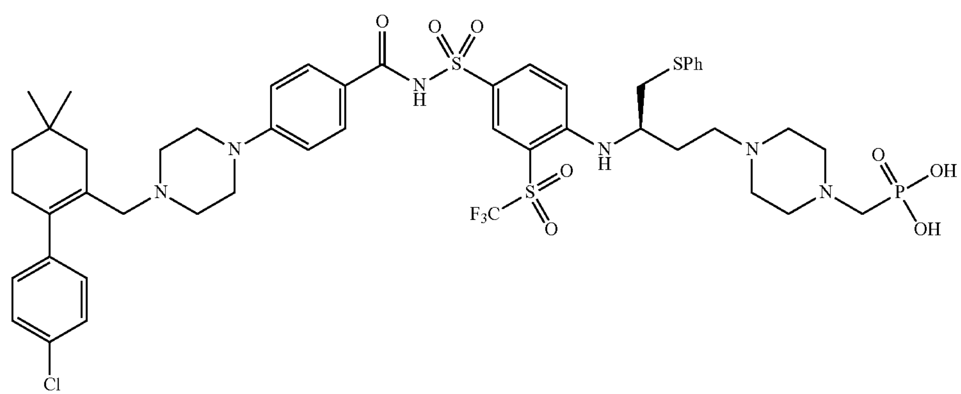 | A | A | C |

TABLE 1-continued
BCL-BINDING DATA
| Compound # | Structure | Bcl-xL | Bcl-2 | Bcl-w |
|---|---|---|---|---|
| 8 | 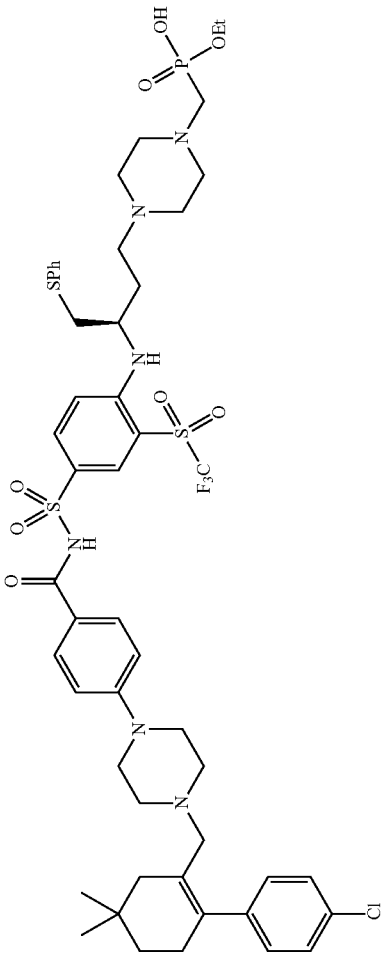 | | | |
| 9 | 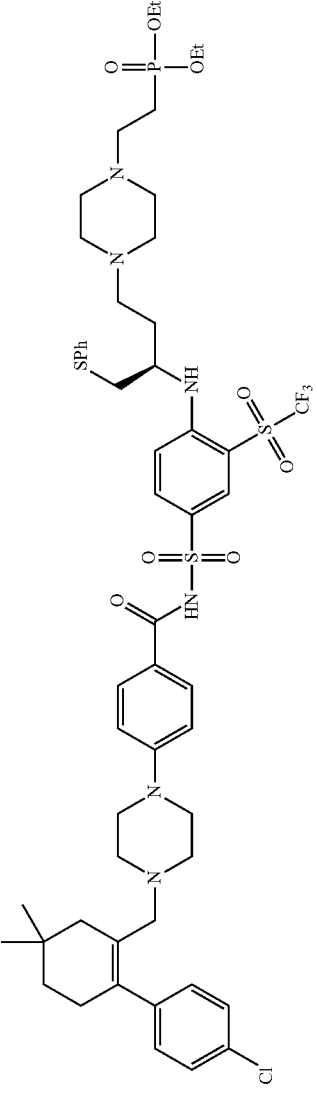 | A | A | B |

TABLE 1-continued

BCL-BINDING DATA

| Compound # | Structure | Bcl-xL | Bcl-2 | Bcl-w |
|---|---|---|---|---|
| 10 | 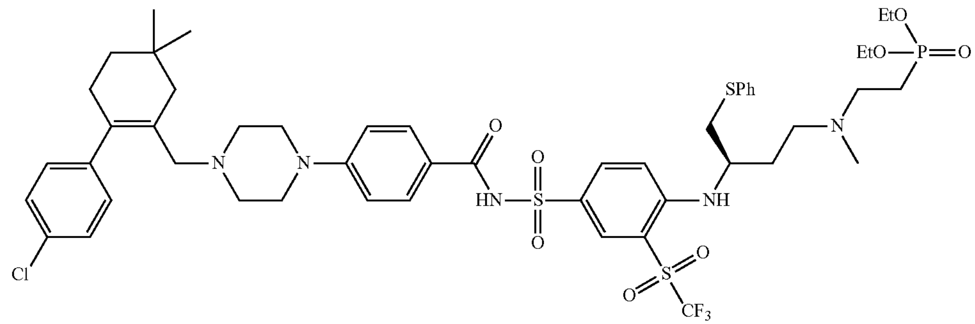 | A | A | B |
| 11 | 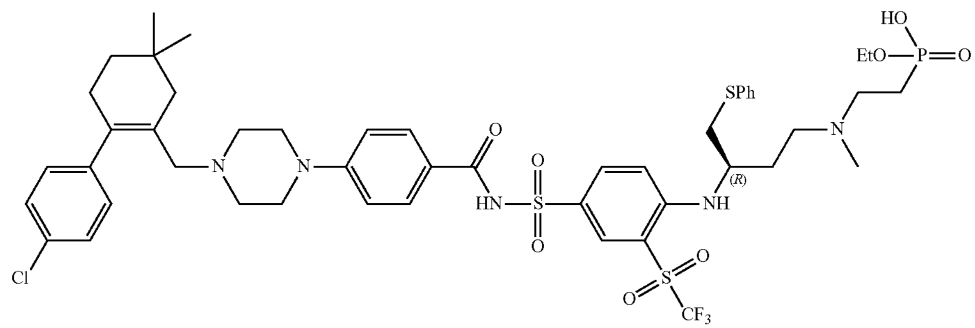 | A | A | B |
| 12 | 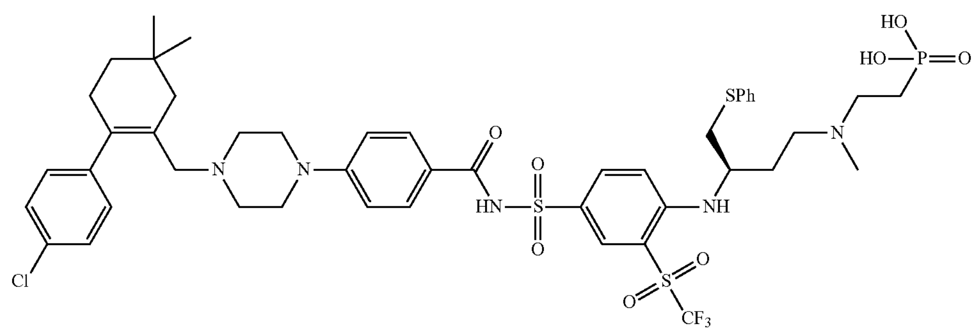 | A | A | C |

TABLE 1-continued

BCL-BINDING DATA

| Compound # | Structure | Bcl-xL | Bcl-2 | Bcl-w |
|---|---|---|---|---|
| 13 | 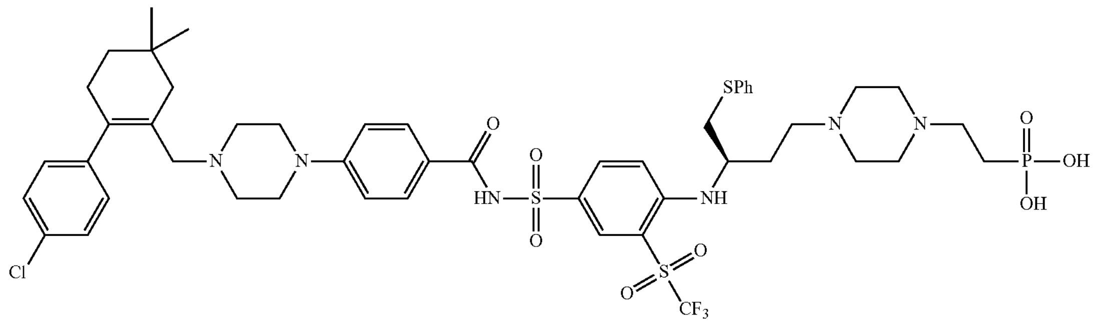 | A | A | B |
| 14 | 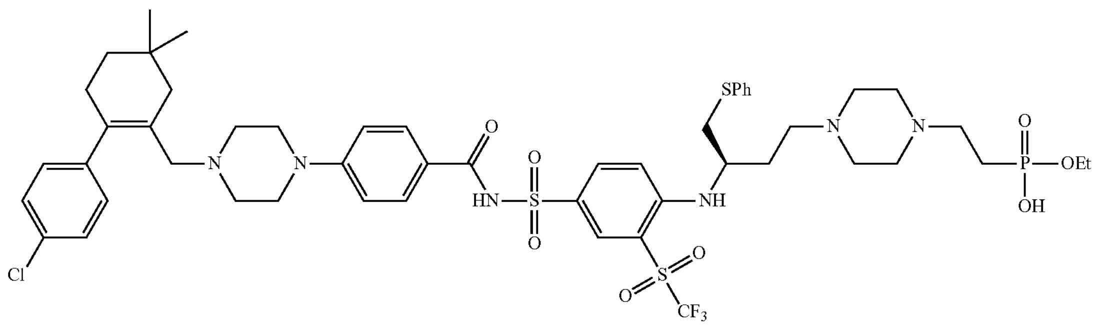 | A | A | B |
| 15 | 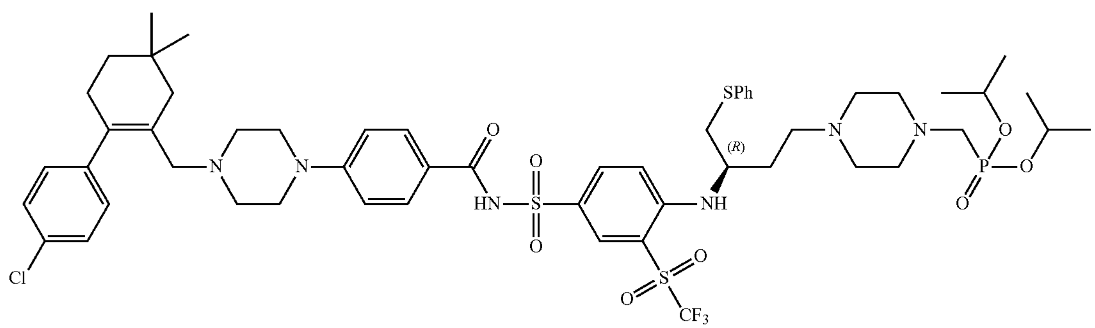 | A | A | C |

TABLE 1-continued
BCL-BINDING DATA
| Compound # | Structure | Bcl-xL | Bcl-2 | Bcl-w |
|---|---|---|---|---|
| 16 | 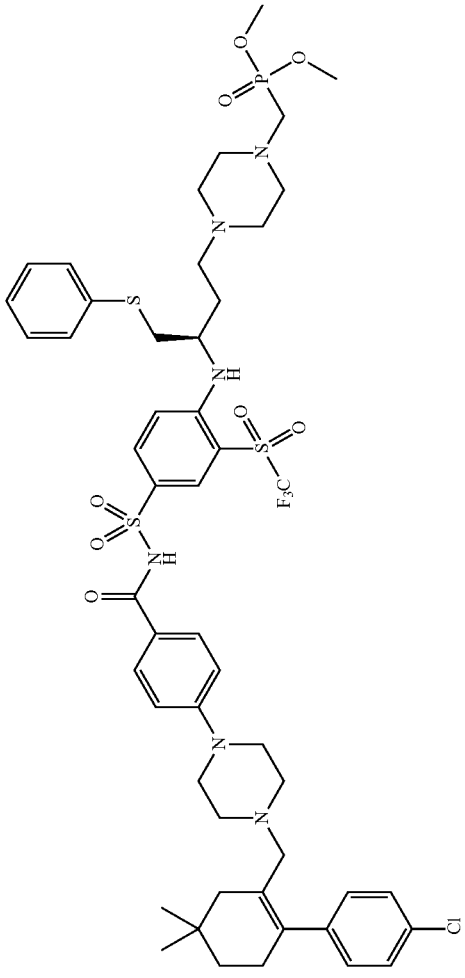 | A | A | B |
| 23 | 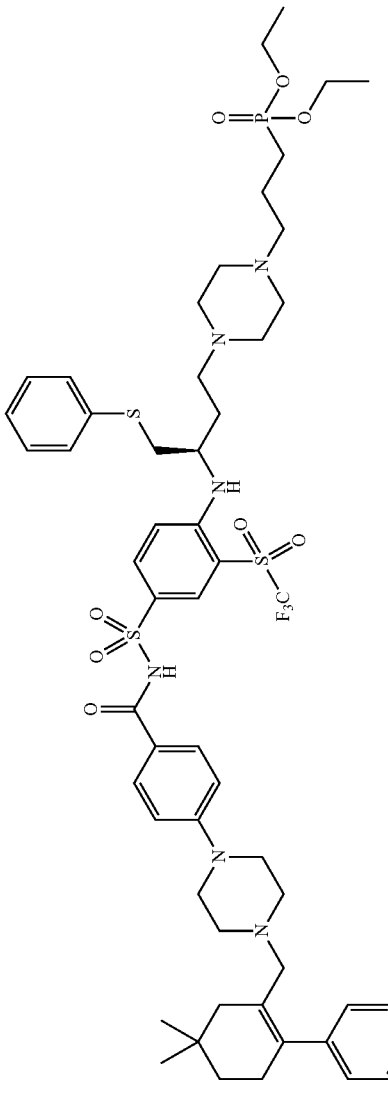 | A | A | B |

TABLE 1-continued
| Compound # | Structure | Bcl-xL | Bcl-2 | Bcl-w |
|---|---|---|---|---|
| 24 | 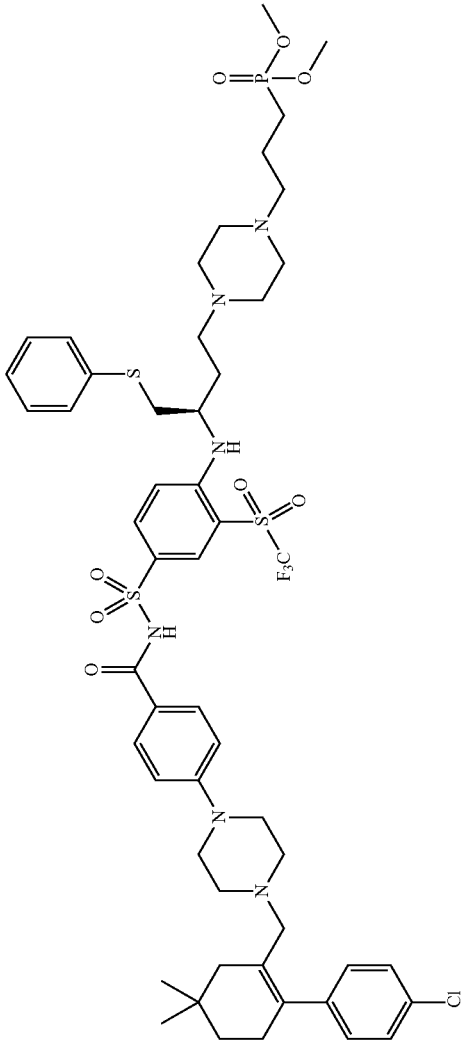 | A | A | B |
| 25 | 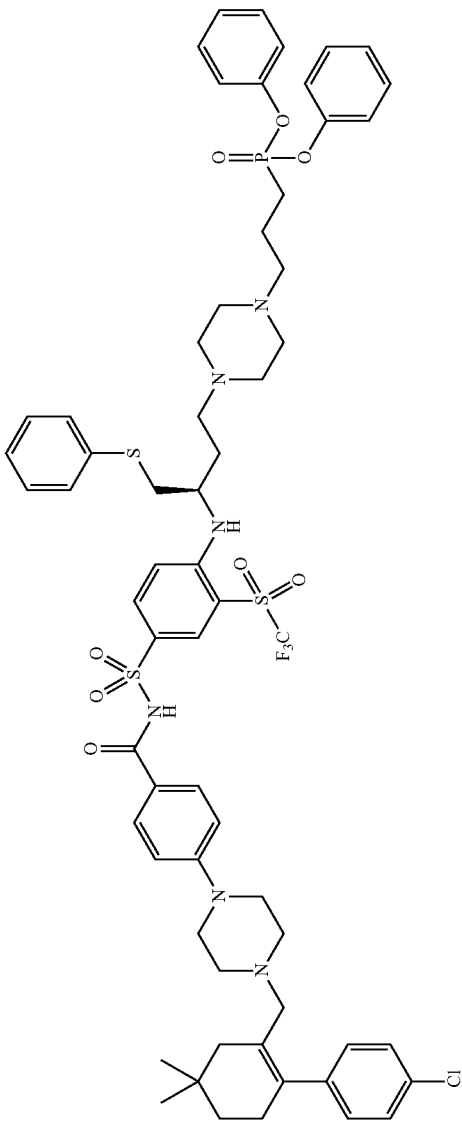 | B | A | D |

TABLE 1-continued
BCL-BINDING DATA
| Compound # | Structure | Bcl-xL | Bcl-2 | Bcl-w |
|---|---|---|---|---|
| 26 | 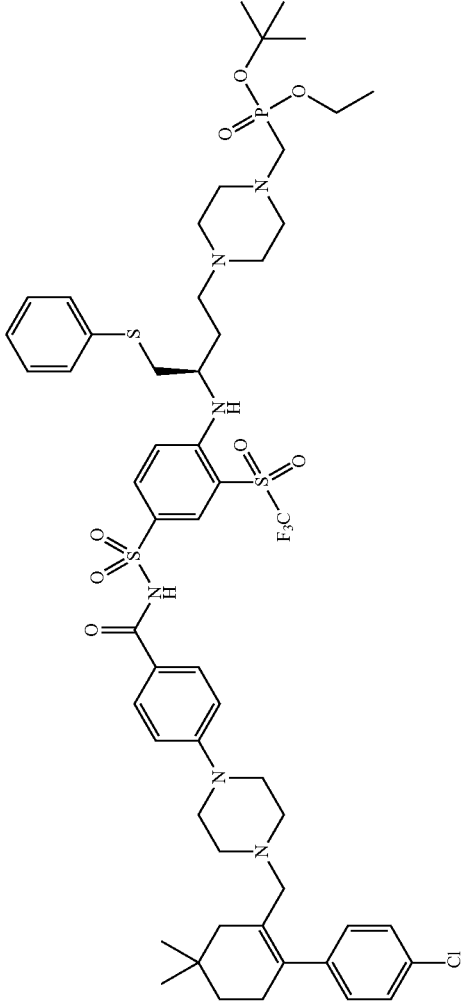 | C | D | D |
| 27 | 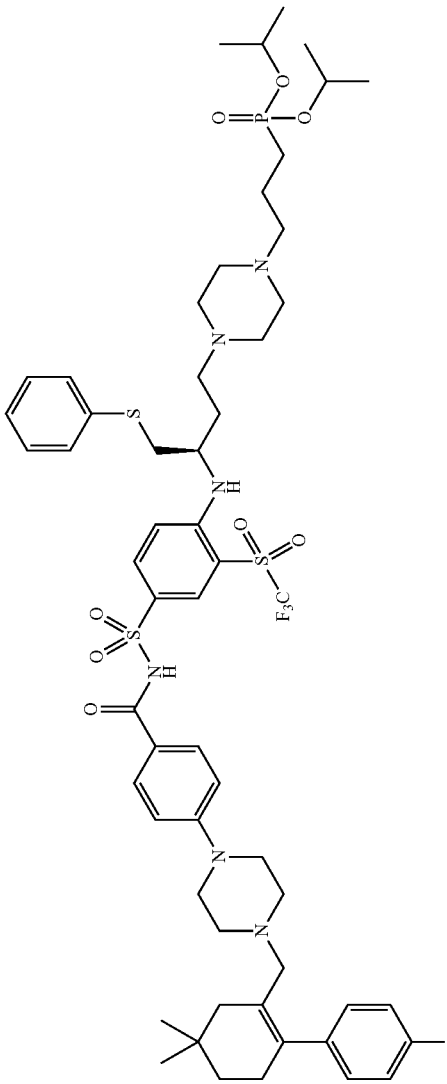 | A | A | B |

TABLE 1-continued

BCL-BINDING DATA

| Compound # | Structure | Bcl-xL | Bcl-2 | Bcl-w |
|---|---|---|---|---|
| 28 | 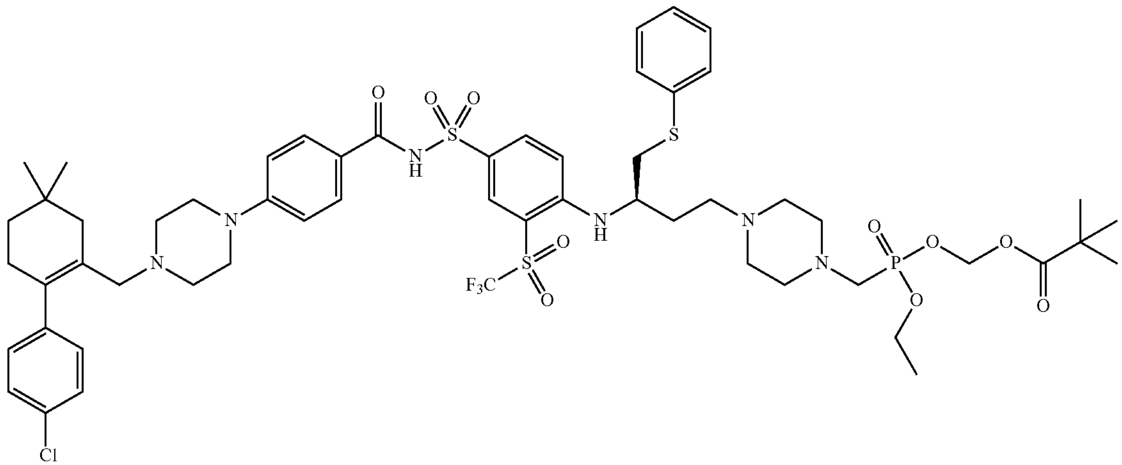 [SMILES: CCOP(=O)(CN1CCN(CC[C@H](CSc2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OCOC(=O)C(C)(C)C] | B | A | C |
| 29 | 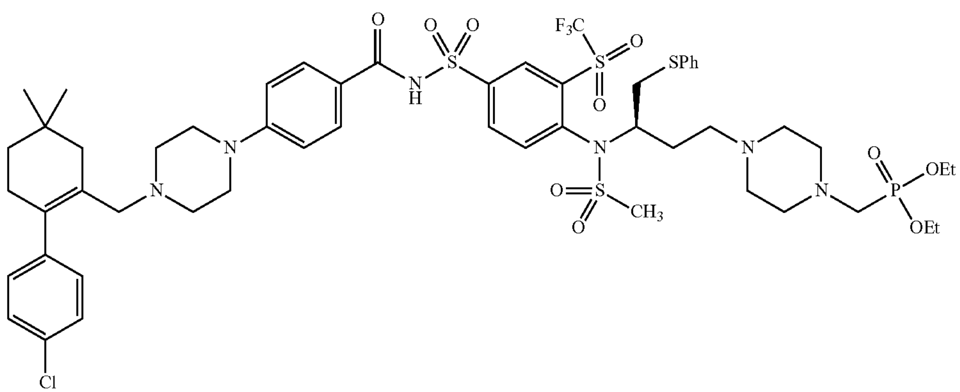 | C | C | D |

TABLE 1-continued
BCL-BINDING DATA
| Compound # | Structure | Bcl-xL | Bcl-2 | Bcl-w |
|---|---|---|---|---|
| 30 | 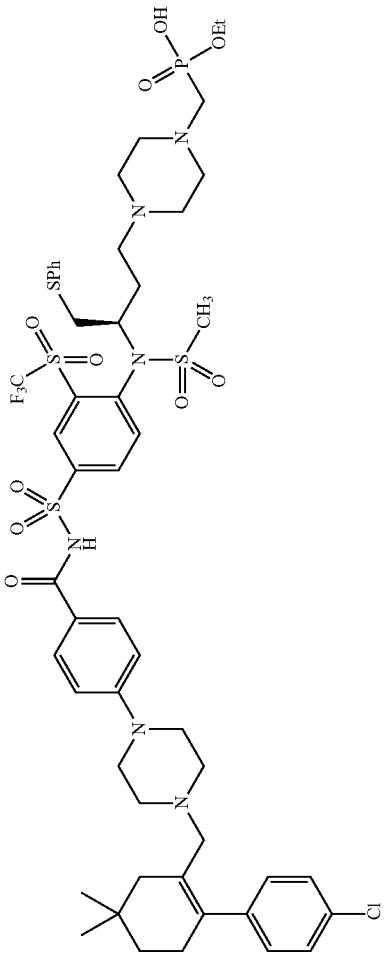 | B | B | D |
| 31 | 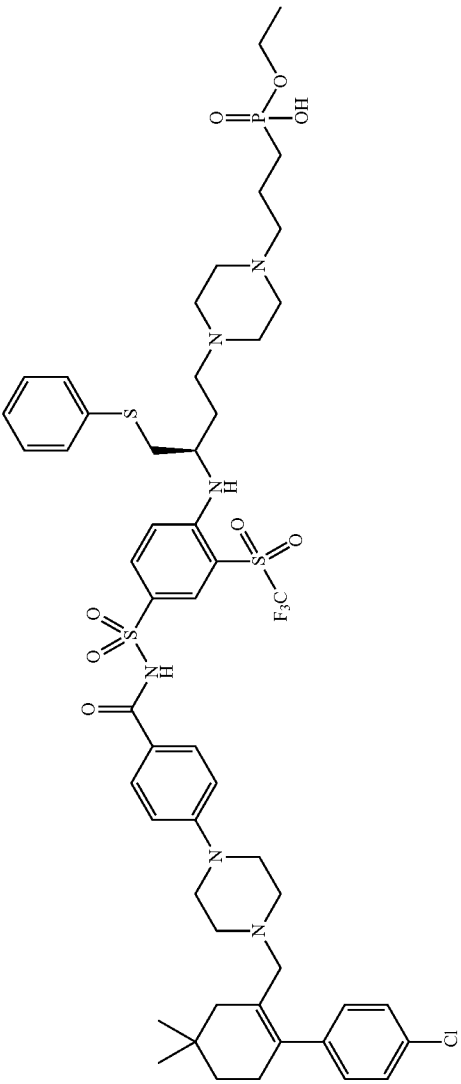 | A | A | B |

TABLE 1-continued
BCL-BINDING DATA
| Compound # | Structure | Bcl-xL | Bcl-2 | Bcl-w |
|---|---|---|---|---|
| 32 | 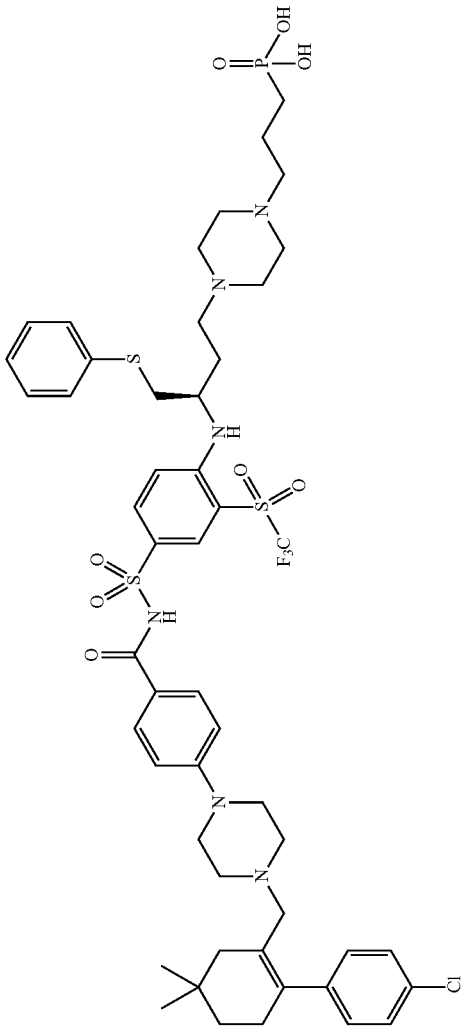 | A | A | C |
| 33 | 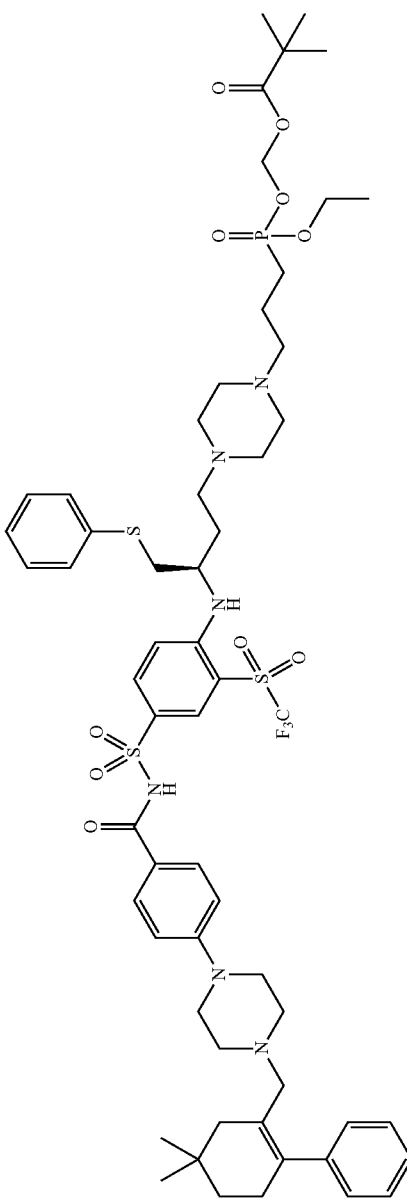 | A | A | B |

TABLE 1-continued

| Compound # | Structure | BCL-BINDING DATA | | |
|---|---|---|---|---|
| | | Bcl-xL | Bcl-2 | Bcl-w |
| 34 | 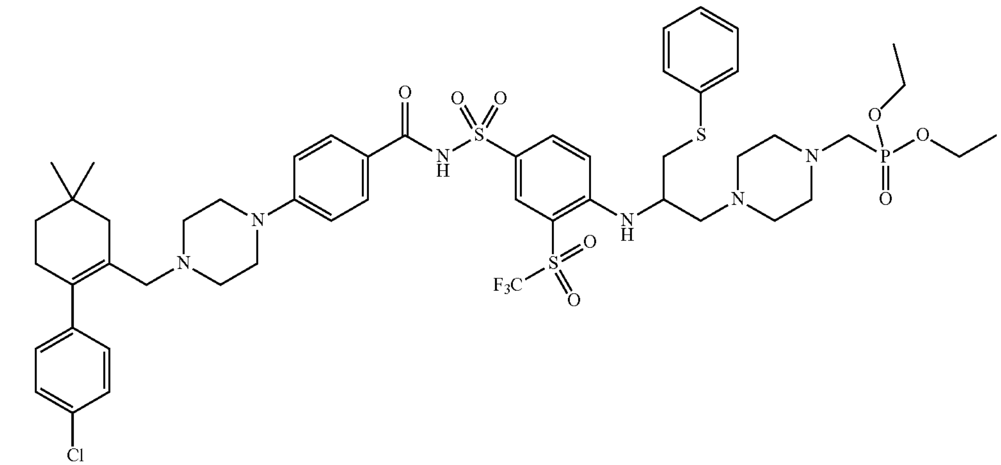 [SMILES: CCOP(=O)(CN1CCN(CC(CSc2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OCC] | B | A | D |
| 35 | 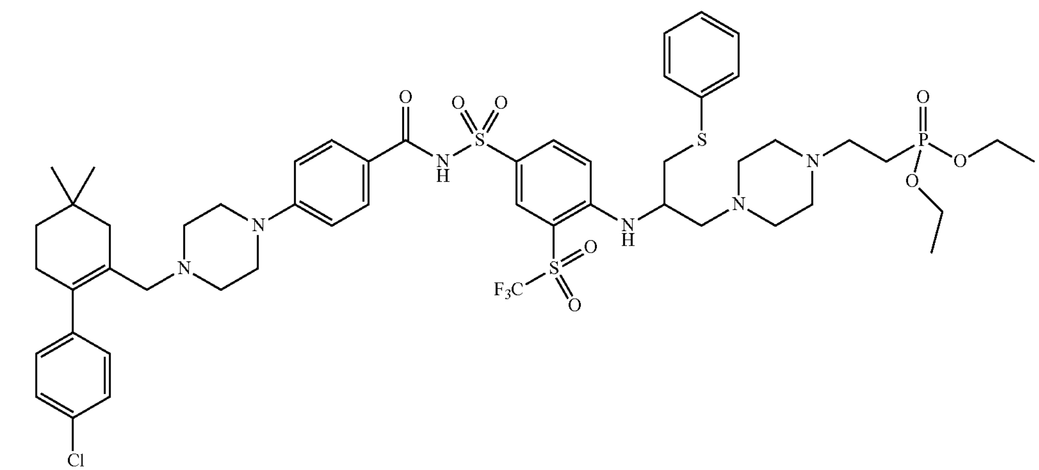 [SMILES: CCOP(=O)(CCN1CCN(CC(CSc2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OCC] | B | A | D |

TABLE 1-continued

BCL-BINDING DATA

| Compound # | Structure | Bcl-xL | Bcl-2 | Bcl-w |
|---|---|---|---|---|
| 36 | 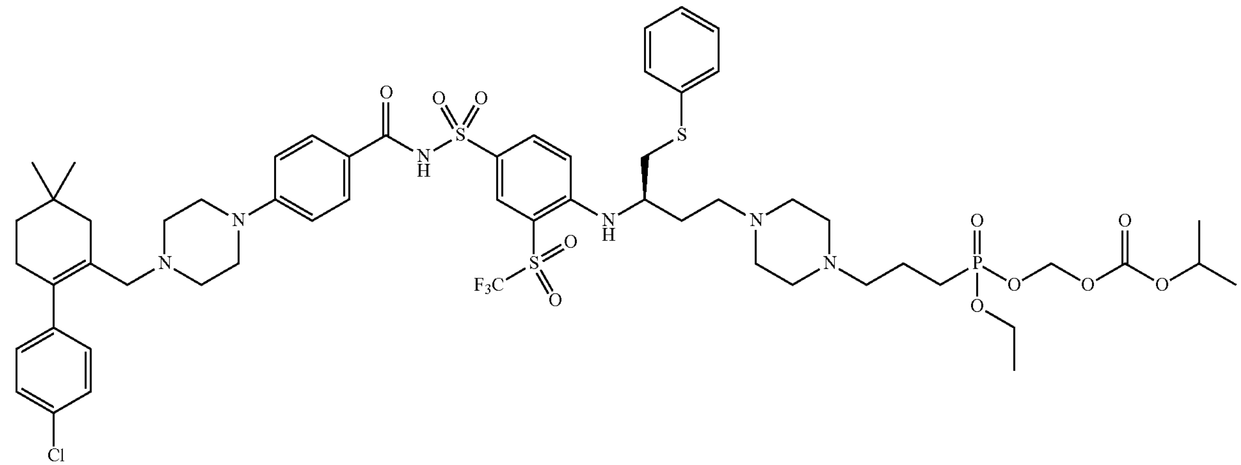 [SMILES: CCOP(=O)(CCCN1CCN(CC[C@H](CSc2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OCOC(=O)OC(C)C] | A | A | C |
| 37 | 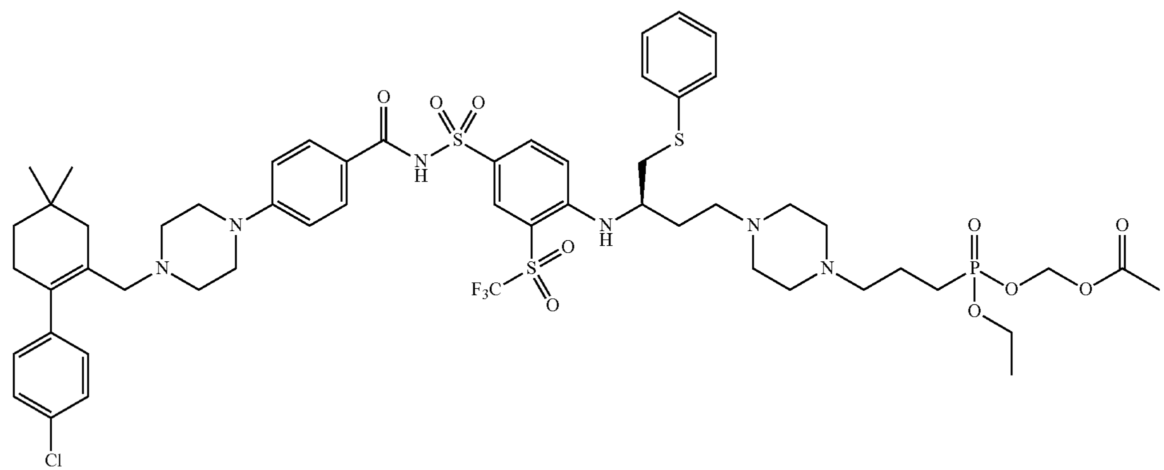 [SMILES: CCOP(=O)(CCCN1CCN(CC[C@H](CSc2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OCOC(C)=O] | A | A | B |

TABLE 1-continued
BCL-BINDING DATA
| Compound # | Structure | Bcl-xL | Bcl-2 | Bcl-w |
|---|---|---|---|---|
| 38 | 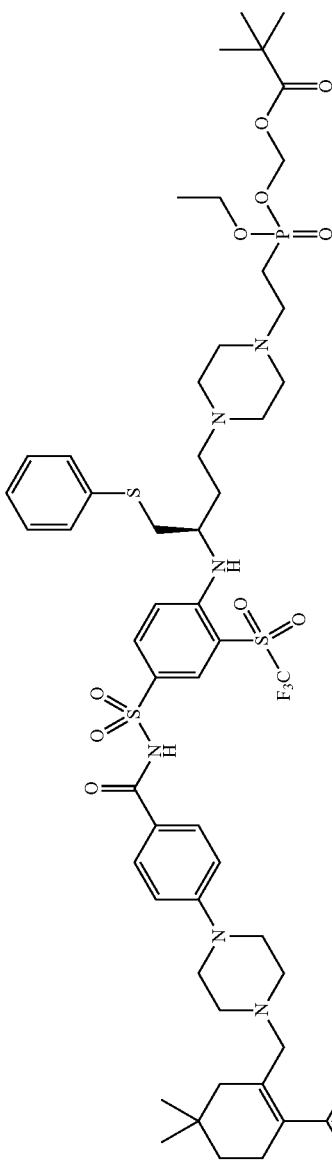 | A | A | C |
| 39 | 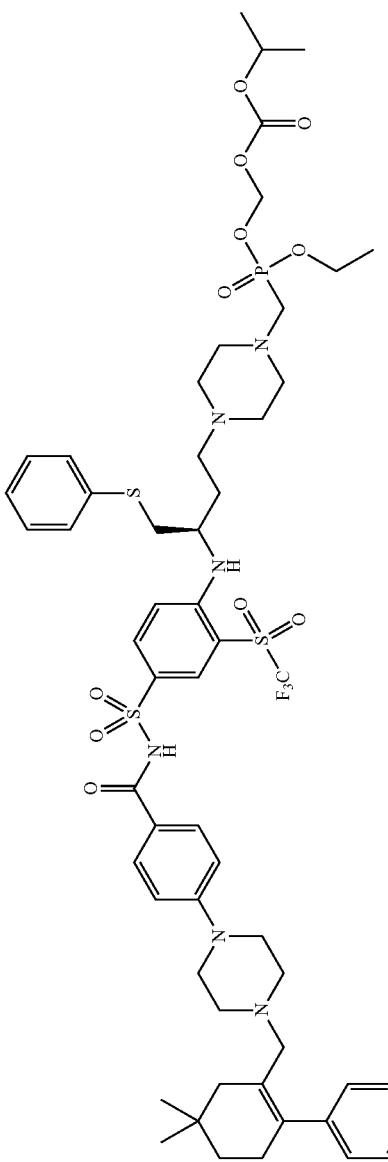 | A | A | C |

TABLE 1-continued
BCL-BINDING DATA
| Compound # | Structure | Bcl-xL | Bcl-2 | Bcl-w |
|---|---|---|---|---|
| 40 | 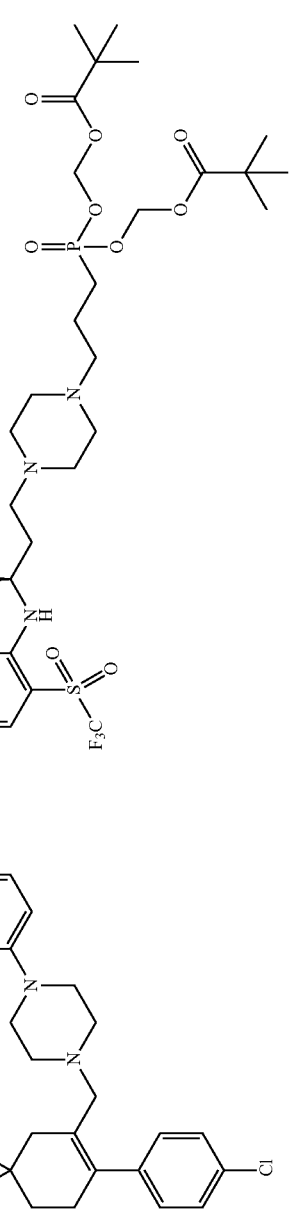 | A | A | C |
| 41 | 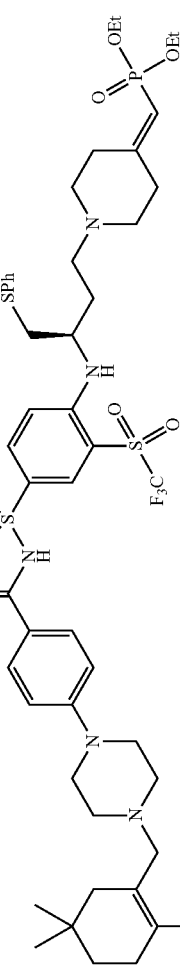 | A | A | B |

TABLE 1-continued
BCL-BINDING DATA
| Compound # | Structure | Bcl-xL | Bcl-2 | Bcl-w |
|---|---|---|---|---|
| 42 | 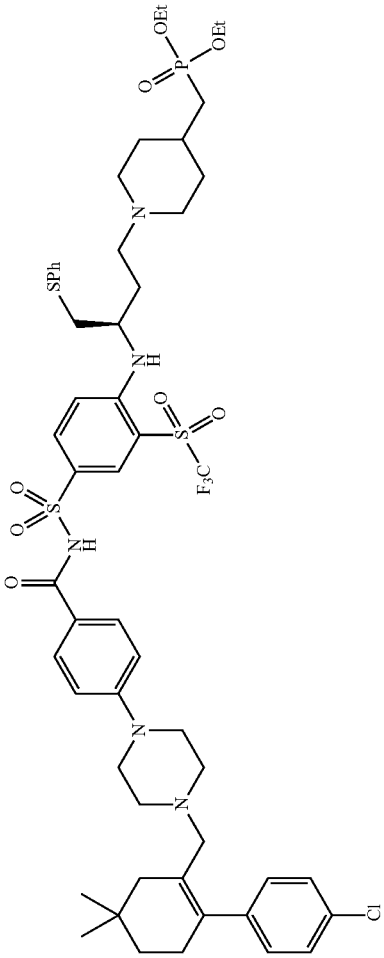 | A | A | B |
| 43 | 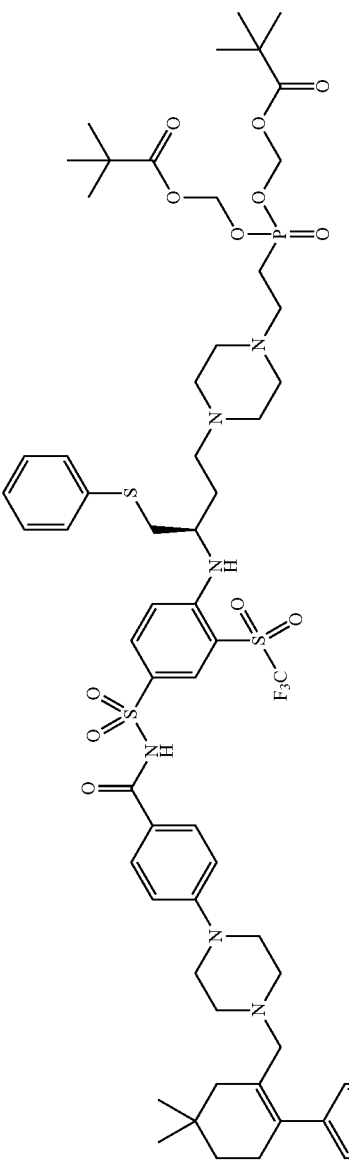 | B | A | C |

TABLE 1-continued
BCL-BINDING DATA
| Compound # | Structure | Bcl-xL | Bcl-2 | Bcl-w |
|---|---|---|---|---|
| 44 | 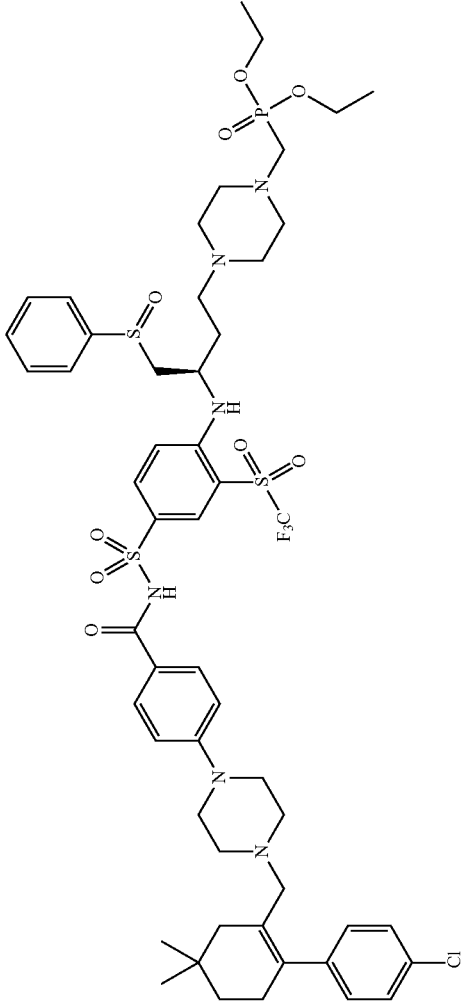 | A | A | C |
| 45 | 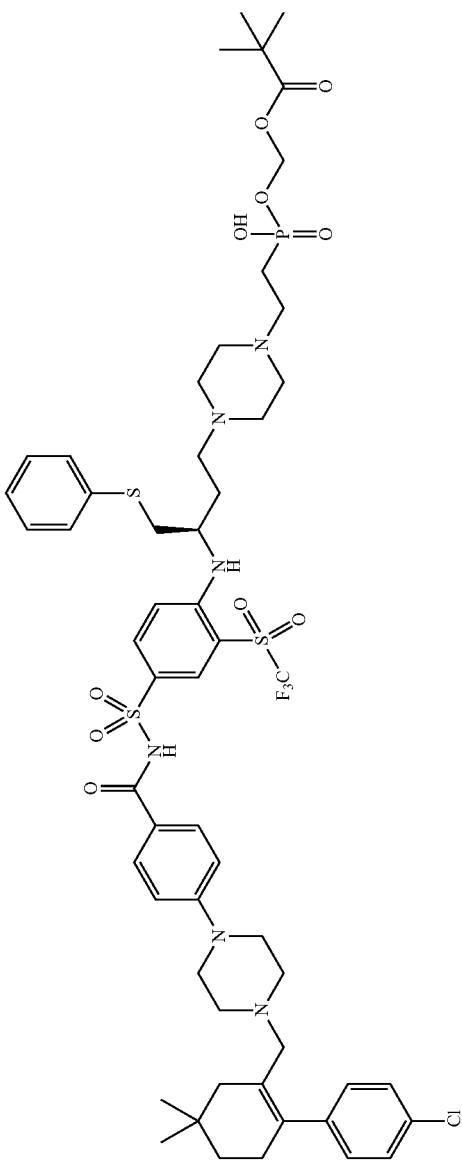 | A | A | B |

TABLE 1-continued

BCL-BINDING DATA

| Compound # | Structure | Bcl-xL | Bcl-2 | Bcl-w |
|---|---|---|---|---|
| 46 | 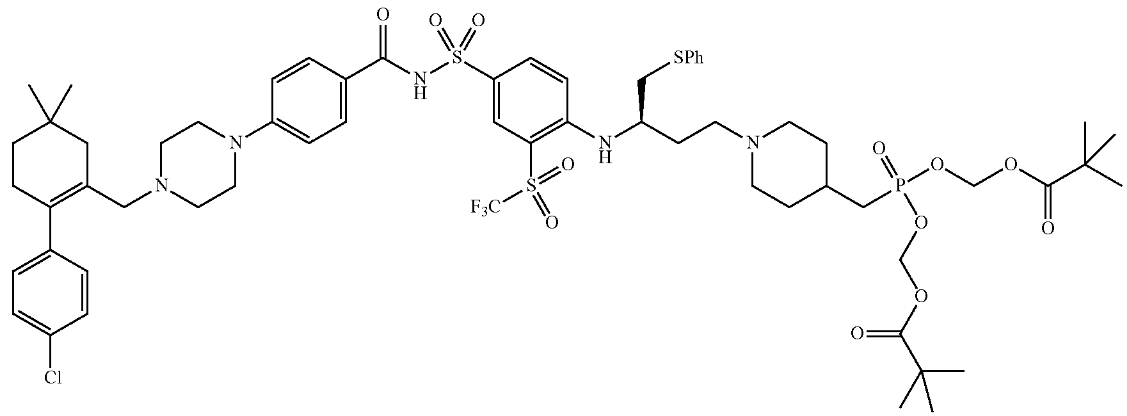 | B | B | D |
| 47 | 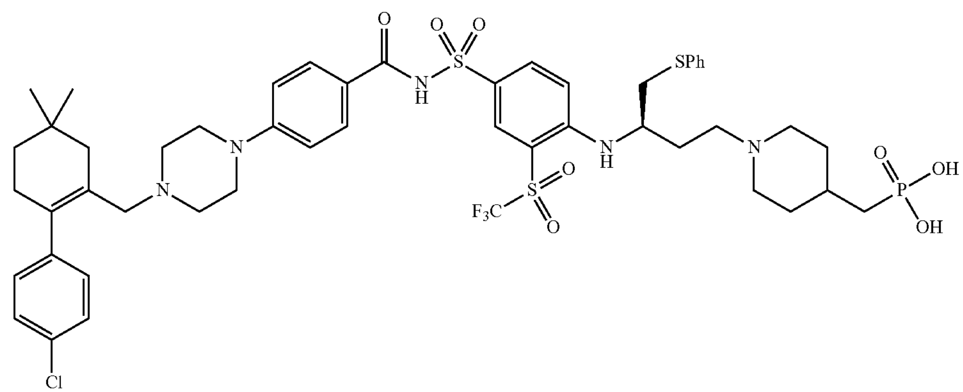 | A | A | B |

TABLE 1-continued
BCL-BINDING DATA
| Compound # | Structure | Bcl-xL | Bcl-2 | Bcl-w |
|---|---|---|---|---|
| 48 | 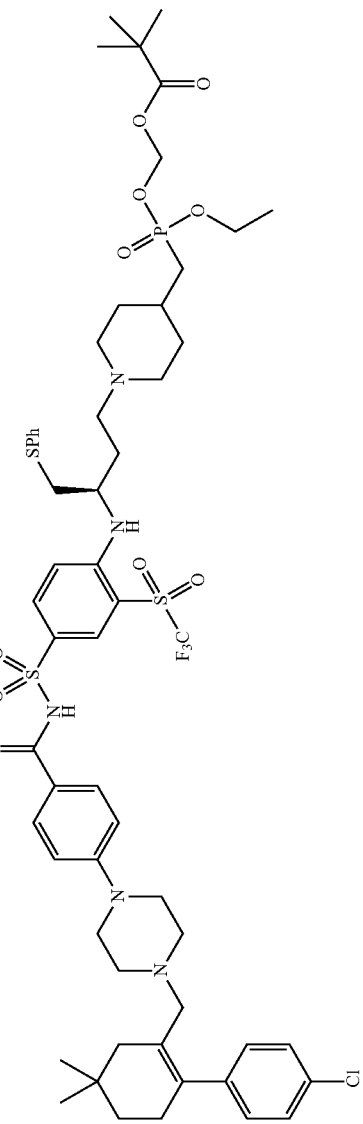 | A | A | B |
| 49 | 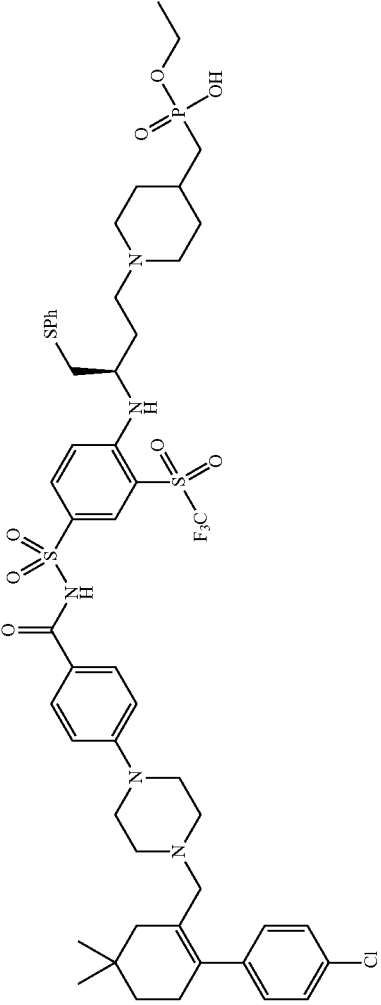 | A | A | B |

TABLE 1-continued
BCL-BINDING DATA
| Compound # | Structure | Bcl-xL | Bcl-2 | Bcl-w |
|---|---|---|---|---|
| 50 | 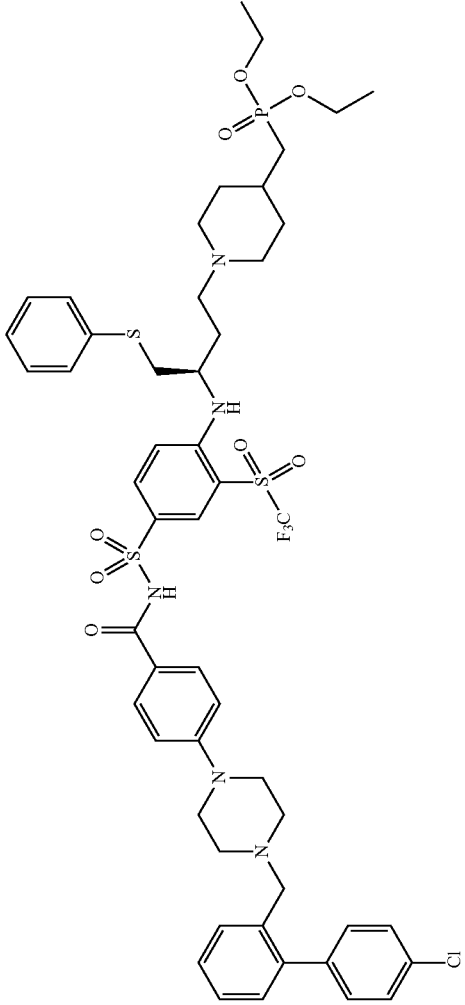 | A | A | A |
| 51 | 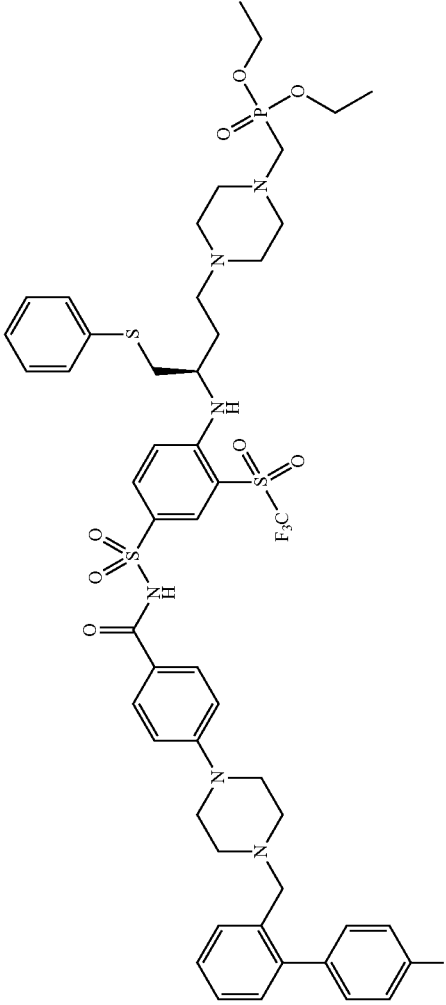 | A | A | B |

TABLE 1-continued
BCL-BINDING DATA
| Compound # | Structure | Bcl-xL | Bcl-2 | Bcl-w |
|---|---|---|---|---|
| 52 | 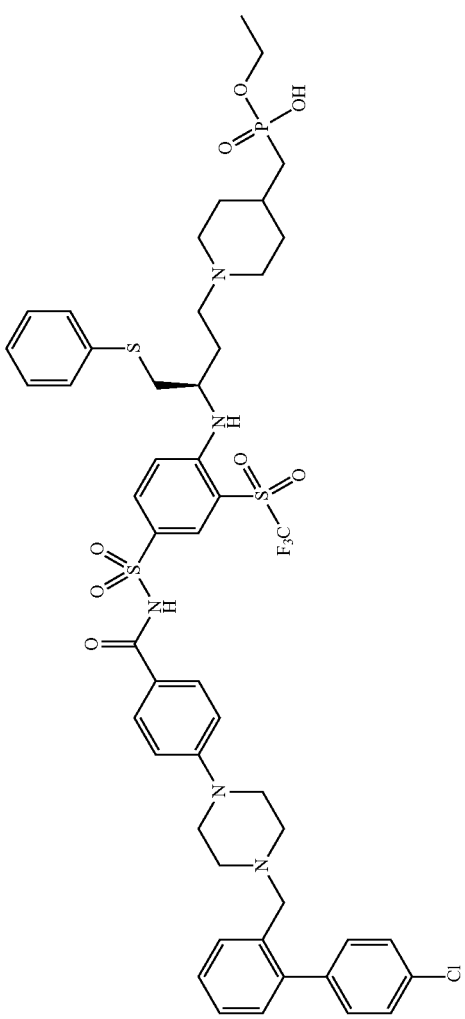 | A | A | A |
| 53 | 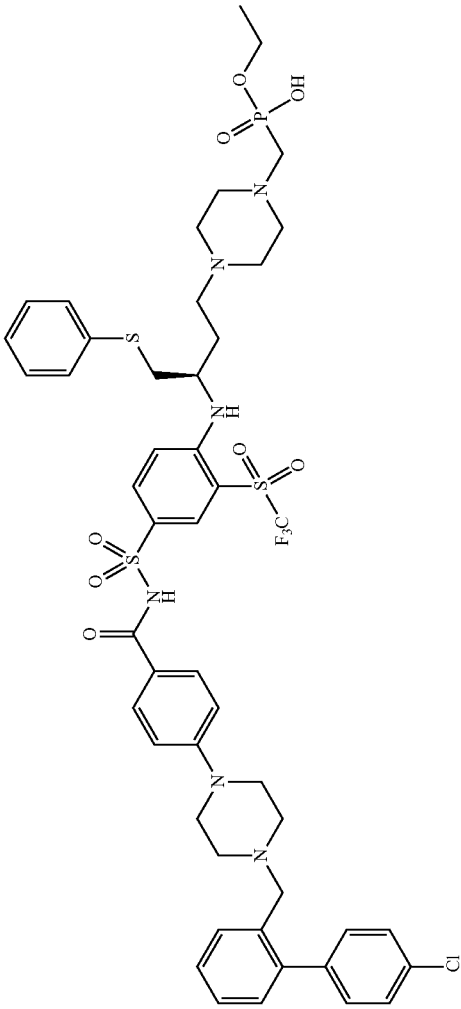 | A | A | A |

TABLE 1-continued

BCL-BINDING DATA

| Compound # | Structure | Bcl-xL | Bcl-2 | Bcl-w |
|---|---|---|---|---|
| 54 | 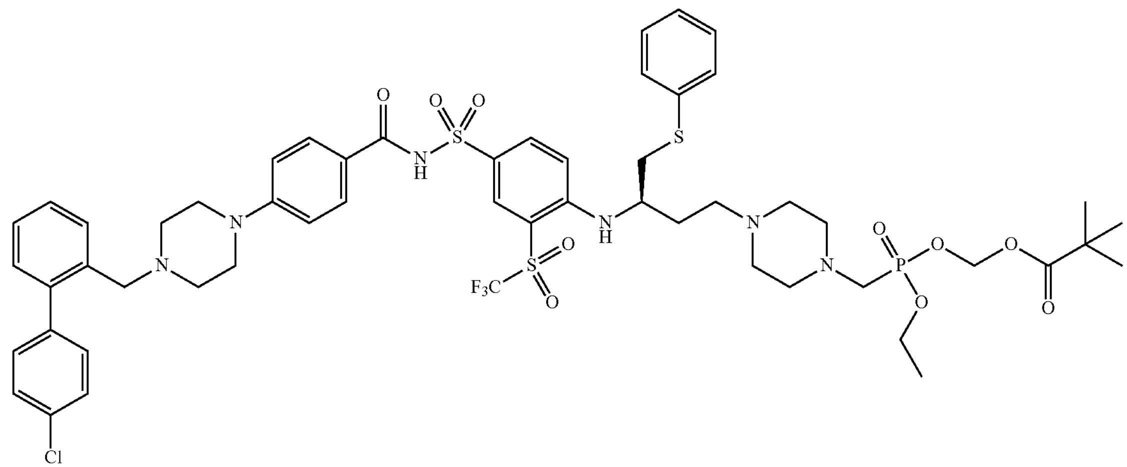 [SMILES: CCOP(=O)(CN1CCN(CC[C@H](CSc2ccccc2)Nc2ccc(S(=O)(=O)NC(=O)c3ccc(N4CCN(Cc5ccccc5-c5ccc(Cl)cc5)CC4)cc3)cc2S(=O)(=O)C(F)(F)F)CC1)OCOC(=O)C(C)(C)C] | A | A | B |
| 55 | 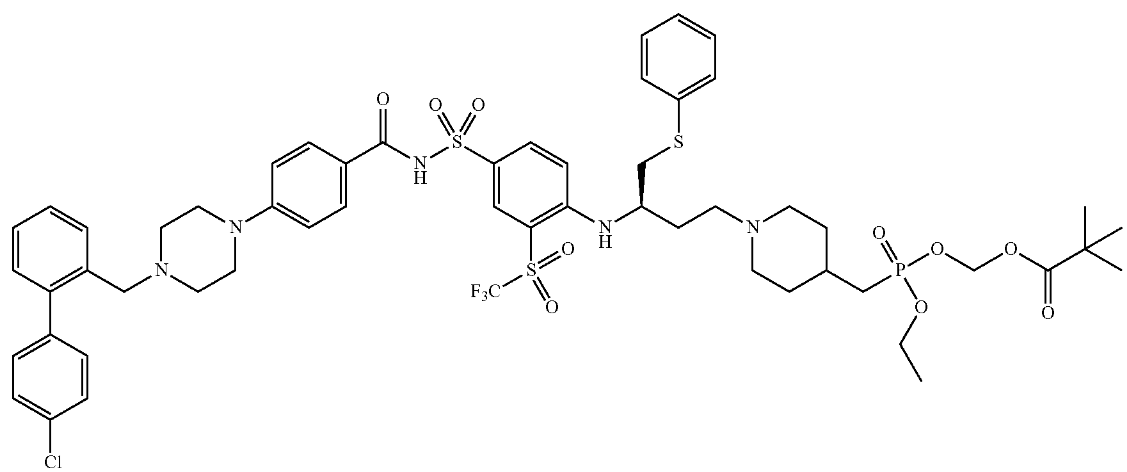 [SMILES: CCOP(=O)(CC1CCN(CC[C@H](CSc2ccccc2)Nc2ccc(S(=O)(=O)NC(=O)c3ccc(N4CCN(Cc5ccccc5-c5ccc(Cl)cc5)CC4)cc3)cc2S(=O)(=O)C(F)(F)F)CC1)OCOC(=O)C(C)(C)C] | A | A | B |

TABLE 1-continued
| Compound # | Structure | Bcl-xL | Bcl-2 | Bcl-w |
|---|---|---|---|---|
| 56 | 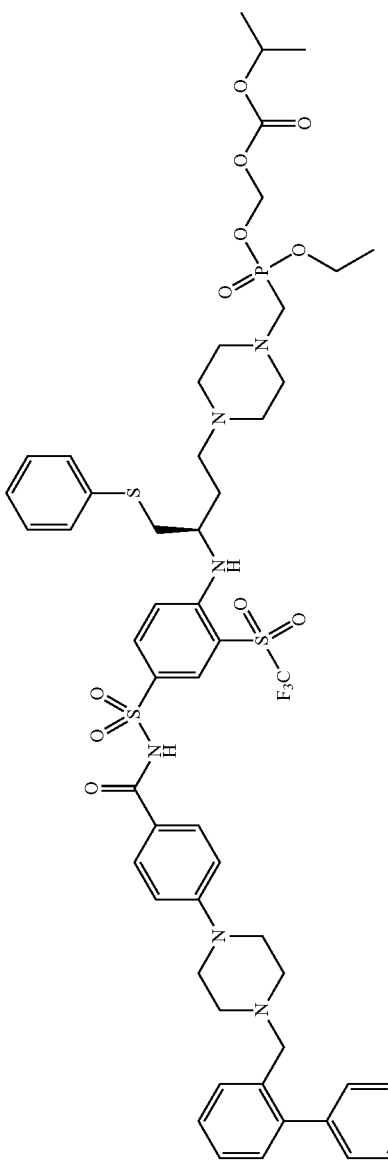 | A | A | B |
| 57 | 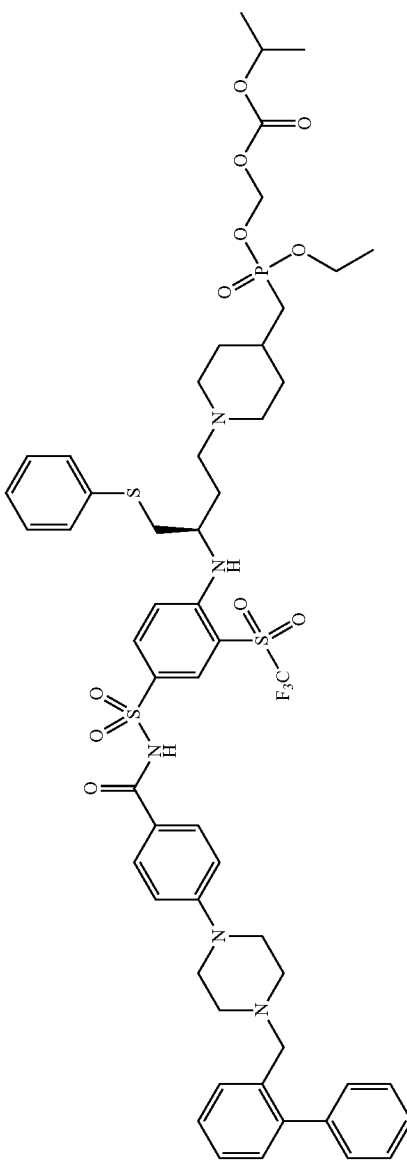 | A | A | B |

Example 3

Senolysis Assay

In certain embodiments, any of the assays described herein or others available in the art may be used to screen a compound or salt of Formula (I) or (II) for senolytic activity.

IMR90 cells are maintained in DMEM supplemented with 10% FBS. To prepare a senescent population, cells were trypsinized, diluted to 50,000 per mL, and irradiated with 10-15 Gy of X-ray irradiation. Irradiated cells were plated at 5000 cells per well in one third of a 96-well plate and maintained for two weeks prior to the assay. Four days prior to the assay, non-senescent IMR90s were plated at 2500 per well in the second third of the plate. One day prior to the assay, 2500 non-senescent cells were plated in the final third of the plate. Compounds were prepared as a 200×DMSO dilution series then diluted to 1× in media immediately before adding to cells. Three days after compound addition, cell viability was measured using CellTiter-Glo reagent from Promega. Viability was calculated relative to a DMSO control and EC50 values are calculated in Prism GraphPad. Compounds of the disclosure with an $EC_{50}$ value for senolytic cells of less than 1 µM have "A" activity, from 1 µM to 10 µM have "B" activity and greater than 10 µM have "C" activity. The selectivity (SI) of the compounds described herein is a ratio of the $EC_{50}$ of non-senescent cells to the $EC_{50}$ of senescent cells. The SI of the compounds described herein is 10 or above for "A" selectivity, between 2 and 10 for "B" selectivity or 2 or less for "C" selectivity. Results from this assay are seen in Table 2.

TABLE 2

SENOLYTIC ACTIVITY

| Compound # | IMR-90 SnC | SI |
|---|---|---|
| 6 | A | A |
| 7 | C | B |
| 8 | | |
| 9 | A | A |
| 10 | B | A |
| 11 | C | C |
| 12 | C | N/A |
| 13 | C | N/A |
| 14 | C | N/A |
| 15 | B | B |
| 16 | A | A |
| 23 | A | A |
| 24 | A | A |
| 25 | C | C |
| 26 | C | N/A |
| 27 | C | C |
| 28 | A | B |
| 29 | B | C |
| 30 | B | N/A |
| 31 | C | N/A |
| 32 | C | N/A |
| 33 | C | B |
| 34 | C | C |
| 35 | B | C |
| 36 | B | B |
| 37 | B | B |
| 38 | B | A |
| 39 | A | A |
| 40 | C | B |
| 41 | A | A |
| 42 | A | A |
| 43 | C | N/A |
| 44 | B | B |
| 45 | C | N/A |
| 46 | C | N/A |
| 47 | C | N/A |
| 48 | A | A |
| 49 | | |
| 50 | A | B |
| 51 | B | B |
| 52 | C | N/A |
| 53 | C | N/A |
| 54 | B | B |
| 55 | B | B |
| 56 | C | N/A |
| 57 | B | B |

Example 4

In Vitro Cell Assays for Determining Senolytic Activity of a Pharmaceutical Agent Described Herein Foreskin fibroblast cell lines HCA2 and BJ, lung fibroblast cell line IMR90, and mouse embryonic fibroblasts are seeded in six-well plates and induced to senesce with 10 Gy of ionizing radiation (IR) or a 24 hr treatment with doxorubicin (Doxo). Senescent phenotype is allowed to develop for at least 7 days, at which point a cell count is made to determine the baseline number of cells. Treatment is then initiated for a period of at least 9 days. Media alone or media with drug as appropriate is refreshed at least every three days. At the end of the assay time period, cells are counted. Each condition is seeded in three plate wells and counted independently. Initial cell count serves as a control to determine the induction of senescence, as compared to the last day count without treatment. Initial non-senescent cell count serves as a proxy to determine toxicity of the pharmaceutical agent described herein.

Foreskin fibroblast cell lines HCA2 and BJ, lung fibroblast cell line IMR90, and mouse embryonic fibroblasts are exposed to 10 Gy of ionizing radiation (IR) to induce senescence. Seven days following irradiation, the cells are treated with varying concentrations of a pharmaceutical agent (0, 2.5 µM, and 10 µM) for a period of 9 days, with the drug refreshed at least every 3 days. Percent survival is calculated as a ratio of cell count on day 9 of treatment to initial cell count on first day of treatment.

Foreskin fibroblasts (HCA2) and aortic endothelial cells (Endo Aort) are treated with doxorubicin (250 nM) for one day (24 hours) to induce senescence. Eight days following doxorubicin treatment, treatment with a pharmaceutical agent is initiated. HCA2 cells are exposed to the pharmaceutical agent for 9 days, and aortic endothelial cells are exposed to the pharmaceutical agent for 11 days. Media containing the pharmaceutical agent or control media is refreshed at least every 3 days. Percent survival is calculated as a ratio of cell count on the last day of pharmaceutical agent treatment to initial cell count on first day of treatment.

Non-senescent foreskin fibroblasts (HCA2), lung fibroblasts (IMR90), and mouse embryonic fibroblasts (MEF) are treated with varying concentrations (0, 2.5 µM, and 10 µM) of the pharmaceutical agent for a period of 9 days to assess toxicity. Cell counts are taken at the start (NS start) and end of treatment. The difference between counts of cells not treated with a pharmaceutical agent on day 9 (NS 0) and cell counts determined at day zero (NS start) reflects the cell growth over the indicated time period.

Non-senescent aortic endothelial (Endo Aort) cells and pre-adipocytes (Pread) are also treated with varying concentrations (0, 2.5 µM, and 10 µM) of a pharmaceutical agent for a period of 11 days to assess toxicity, as described above. Cell counts are taken at the start at Day 0 (NS start) and at the end of treatment (NS 0). The difference between counts of cells not treated with the pharmaceutical agent on day 11 (NS 0) and cell counts from NS start reflects the cell growth over the indicated time period.

Example 5

Treatment of P16-3MR Transgenic Mice with a Pharmaceutical Agent Described Herein The promoter, $p16^{Ink4a}$, which is transcriptionally active in senescent cells but not in non-senescent cells (see, e.g., Wang et al., *J. Biol. Chem.* 276:48655-61 (2001); Baker et al., *Nature* 479:232-36 (2011)), is engineered into a nucleic acid construct. 3MR (tri-modality reporter) is a fusion protein containing functional domains of a synthetic Renilla luciferase (LUC), monomeric red fluorescence protein (mRFP), and truncated herpes simplex virus (HSV)-1 thymidine kinase (tTK), which allows killing by ganciclovir (GCV) (see, e.g., Ray et al., *Cancer Res.* 64:1323-30 (2004)). The 3MR cDNA is inserted in frame with p16 in exon 2, creating a fusion protein containing the first 62 amino acids of p16, but not a full-length wild-type p16 protein. Insertion of the 3MR cDNA also resulted in the occurrence of a stop codon in the $p19^{ARF}$ reading frame in exon 2, thereby preventing full-length $p19^{ARF}$ expression from the BAC as well. The $p16^{Ink4a}$ gene promoter (approximately 100 kilobase pairs) is introduced upstream of a nucleotide sequence encoding a trimodal reporter fusion protein. Alternatively, a truncated $p16^{Ink4a}$ promoter may be used (see, e.g., Baker et al., *Nature, supra*; International Application Publication No. WO2012/177927; Wang et al., supra). Thus, the expression of 3MR is driven by the $p16^{Ink4a}$ promoter in senescent cells only. The detectable markers, LUC and mRFP permitted detection of senescent cells by bioluminescence and fluorescence, respectively. The expression of tTK permitted selective killing of senescent cells by exposure to the pro-drug ganciclovir (GCV), which is converted to a cytotoxic moiety by tTK. Transgenic founder animals, which have a C57Bl6 background, are established and bred using known procedures for introducing transgenes into animals (see, e.g., Baker et al., *Nature* 479:232-36 (2011)).

Female C57/BL6 p16-3MR mice are randomized into doxorubicin+pharmaceutical agent treated or doxorubicin only treated groups. Senescence is induced by intraperitoneal administration of doxorubicin at 10 mg/kg to the mice ten days prior to administration of the pharmaceutical agent (Day –10). Pharmaceutical agent (25 mg/kg) is administered intraperitoneally daily from day 10 to day 24 post-doxorubicin treatment (Group=9 mice). Control mice (doxorubicin treated) are injected with equal volumes of PBS (Group=3 mice). Luminescence imaging (Xenogen Imaging system) is performed at Day 0 (i.e., 10 days post-doxorubicin treatment) as a baseline for each mouse (100% intensity).

Luminescence imaging of the mice is performed on day 7, 14, 21, 28, and 35 following the initiation of treatment with a pharmaceutical agent. Reduction of luminescence (L) is calculated as: L=(Imaging post-treatment with a pharmaceutical agent)/(Baseline Imaging) %. If L is greater than or equal to 100%, the number of senescent cells is not reduced. If L is less than 100%, then the number of senescent cells is reduced. Every mouse is calculated independently, and background is subtracted from each sample.

Experiments are performed to determine the effect of treatment with a pharmaceutical agent on expression of genes associated with senescence. Groups of female C57/BL6 p16-3MR are treated as described above. Three weeks after the end of treatment (day 35), the doxorubicin treated mice (control) (N=3) and doxorubicin+pharmaceutical agent-treated mice (N=6) are sacrificed. Skin and fat biopsies are collected for RNA extraction; fat biopsies are collected for detection of senescence-associated β-galactosidase; and lungs are flash frozen in cryoprotectant OCT media for cryostat sectioning.

RNA is analyzed for mRNA levels of endogenous senescence markers (p21, $p16^{INK4a}$ (p16), and p53) and SASP factors (mmp-3 and IL-6) relative to actin mRNA (control for cDNA quantity) using the Roche Universal Probe Library for real-time PCR assay.

The frozen lung tissue are sectioned to 10 µm thickness and stained with primary rabbit polyclonal antibody against γH2AX (Novus Biologicals, LLC), which is a marker for double-strand breaks in cells (DNA damage). The sections are then stained with ALEXA FLUOR® dye-labeled secondary goat anti-rabbit antibody (Life Technologies) and counterstained with 4',6-diamidino-2-phenylindole (DAPI) (Life Technologies). The number of positive cells is calculated using ImageJ image processing program (National Institutes of Health, see Internet at imagej.nih.gov/ij/index-.html) and represented as a percentage of the total number of cells.

Upon collection, fat biopsies are immediately fixed in 4% formalin and then stained with a solution containing X-gal to detect the presence of senescence-associated β-galactosidase (β-gal). Fat biopsies are incubated overnight at 37° C. in X-gal solution and are photographed the next day. Fat biopsies from untreated animals are used as a negative control.

Example 6

Pharmaceutical Agent Removes Senescent Cells With Established SASP

Primary human fibroblast (IMR90) cells are induced to senesce by applying 10 Gy of irradiation. Seven days after irradiation (Day 0), cells are treated with 10 µM of a pharmaceutical agent described herein or vehicle (DMSO) for nine days (Day 9). The agent or vehicle is refreshed every three days. The agent or vehicle is removed at Day 9 and the cells are cultured for an additional three days (Day 12). Cells are then fixed with 4% paraformaldehyde and stained by immunofluorescence with a specific anti-IL-6 antibody (R&D, AF-206-NA). Cells are counterstained with DAPI for nuclear visualization. IL-6 positive cells are determined in an unbiased manner using CellProfiler software.

In another experiment, IMR90 cells are induced to senesce by irradiation (10 Gy). Seven days after irradiation, cells are treated with 10 µM of the pharmaceutical agent or vehicle (DMSO) for nine days (Day 9). The drug or vehicle is refreshed every three days. The drug or vehicle is removed at Day 9 and the cells are cultured for an additional six days. Conditioned media from the treated cells is collected, and IL-6 measurement by ELISA is performed (Perkin Elmer, AL223F). IL-6 levels in culture media are determined by ELISA using a kit according to manufacturer's instructions (AL223F, Perkin Elmer). Cells are fixed with 4% paraformaldehyde and stained by immunofluorescence with a specific anti-IL-6 antibody (R&D, AF-206-NA). The IL-6 level determined by ELISA is normalized to the number of cells in each well.

Example 7

Effect of a Pharmaceutical Agent Described Herein on SASP Factor Expression

Primary human fibroblast (IMR90) cells are induced to senesce by applying 10 Gy of irradiation. Seven days after irradiation (Day 0), cells are treated with 10 µM of the pharmaceutical agent described herein or vehicle (DMSO) for nine days (Day 9). The drug or vehicle is refreshed every three days. The drug or vehicle is removed at Day 9 and the cells are cultured for an additional three days (Day 12) in media without drug or DMSO. Cells are then collected, mRNA extracted, and cDNA prepared. Quantitative PCR (qPCR) is then performed to detect expression of various genes. Cells are also collected at Day 12 after drug/vehicle had been removed for three days.

Example 8

Selective Toxicity of a Pharmaceutical Agent Described Herein for Senescent Cells Using a Cell Counting Assay To determine whether a pharmaceutical agent described herein is selectively toxic to senescent cells compared to non-senescent cells, a cell counting assay is used to determine cell survival following treatment with a pharmaceutical agent. IMR90 cells (human primary lung fibroblasts (IMR90) (IMR-90 (ATCC® CCL-186TM, Mannassas, Va.) are seeded in six well plates, and cells are induced to senescence with 10 Gy of ionizing radiation (IR) (Day 0). The media is refreshed every 3 days. The senescent phenotype is allowed to develop for 7 days at which point a cell count is made to determine the baseline number of cells. In the senescent cells (irradiated) and the non-senescent cells (the non-radiated cells), 3 µM of a pharmaceutical agent is introduced into the media. Some cells are administered a media that did not contain any pharmaceutical agent described herein as a control to account for any toxicity. Each condition is seeded in three wells and counted independently. Cells are counted after a 24 hour exposure to the pharmaceutical agent (or control culture).

Example 9

Selective Toxicity of a Pharmaceutical Agent Described Herein for Senescent Cells Using a Celltiter-Glo® Cell Viability Assay To determine whether a pharmaceutical agent described herein is selectively toxic to senescent cells compared to non-senescent cells, a cell viability assay is used to assess cell survival following treatment with the pharmaceutical agent. IMR90 cells (human primary lung fibroblasts (IMR90) (IMR-90 (ATCC® CCL-186TM, Mannassas, Va.) are seeded in six well plates, and cells are induced to senescence with 10 Gy of ionizing radiation (IR) (Day 0). The media is refreshed every 3 days. The senescent phenotype is allowed to develop for 7 days at which point a cell count is made to determine the baseline number of cells followed by seeding into 96-well plates. On day 8, the senescent cells (irradiated) and the non-senescent cells (the non-radiated cells), are exposed to serial dilutions of a pharmaceutical agent described herein for a period of 3 days. Pharmaceutical agent concentrations ranged from 0.5 nM to 3 µM. Each condition is seeded in triplicate.

After three days of treatment (Day 11), cells are assayed for cell survival using the commercially available CellTiter-Glo® (CTG) Luminescent Cell Viability Assay (Promega Corporation, Madison, Wis.). The assay determines the number of viable cells in culture based on the quantitation of ATP present which is an indicator of metabolically active cells.

Example 10

Assessment of Selective Toxicity of a Pharmaceutical Agent Described herein for Senescent Cells of Various Cell Types The methods of Example 6 are repeated in other cell strains. Cell strains included Primary Renal Cortical Cells, ATCC Cat #PCS-400-011, HCA2 foreskin fibroblast cells, Primary Small Airway Epithelial Cells, ATCC Cat #PCS-301-010 (lung), human pooled Preadipocyte from patients (Pread), Mouse embryonic fibroblast extracted from C57Bl6 mice (MEF), Primary Coronary Artery Smooth Muscle, and ATCC Cat #PCS-100-021 (Smth Mscl).

The experiments performed in these other cell strains are performed as described in Example 6.

Example 11

An Animal Study for Determining the Senolytic Effect of a Pharmaceutical Agent Described herein in Mice The senolytic effect of a pharmaceutical agent described herein can be assessed in animal models of senescence. An example of such an animal study is described here. Senescence in animals can be induced through the administration of doxorubicin followed by treatment of a pharmaceutical agent. On day 35, mice are sacrificed, and fat and skin are collected for RNA analysis, while lungs are collected and flash frozen for immunomicroscopy analysis. RNA is analyzed for expression of SASP factors (mmp3, IL-6) and senescence markers (p21, p16, and p53). Frozen lung tissue is analyzed for DNA damage marker (γH2AX).

The mice to be tested contain a transgene insertion of p16-3MR. 3MR (tri-modality reporter) is a fusion protein containing functional domains of a synthetic Renilla luciferase (LUC), monomeric red fluorescent protein (mRFP), and truncated herpes simplex virus (HSV)-1 thymidine kinase (tTK), which allows killing by ganciclovir (GCV). The 3MR cDNA is inserted in frame with p16 in exon 2, creating a fusion protein containing the first 62 amino acids of p16, but does not include the full-length wild-type p16 protein. Insertion of the 3MR cDNA also introduces a stop codon in the $p19^{ARF}$ reading frame in exon 2.

The effect of the pharmaceutical agent is analyzed by the reduction of luminescence intensity. Female C57/Bl6 p16-3MR mice are treated with Doxorubicin. Luminescence is measured 10 days later and used as baseline for each mouse (100% intensity). The pharmaceutical agent is administered intraperitoneally daily from day 10 to day 24 post-doxorubicin treatment. Luminescence is then measured at day 7, 14, 21, 28, 35 post-treatments, and final values calculated as % of the baseline values. Control animals (DOXO) are injected with equal volume of PBS.

The level of mRNA of endogenous mmp-3, IL-6, p21, p16, and p53 in the skin and fat from animals after treatment with doxorubicin alone (DOXO) or doxorubicin plus the pharmaceutical agent is plotted. The values represent the fold induction of the particular mRNA compared with untreated control animals.

Immunofluorescence microscopy of lung sections from doxorubicin treated animals (DOXO) and doxorubicin plus pharmaceutical agent-treated animals can be detected by binding to a primary rabbit polyclonal antibody specific for γH2AX followed by incubation with a secondary goat anti-rabbit antibody, and then counterstained with DAPI. The percent positive cells from immunofluorescence microscopy are calculated and can be represented as percentage of the total number of cells. Data can be obtained from doxorubicin-treated mice (Doxo), and doxorubicin+pharmaceutical agent–treated mice.

The pharmaceutical agent can be analyzed for reduced senescence-associated (SA) β-galactosidase ((β-gal) intensity of fat biopsies from animals first treated with doxorubicin. Female C57/BL6 p16-3MR mice are treated with doxorubicin. A portion of the doxorubicin treated animals receive the pharmaceutical agent or PBS (DOXO) daily from day 10 to day 24 post-doxorubicin treatment. Three weeks after the pharmaceutical agent treatment, mice are sacrificed and fat biopsies immediately fixed and stained with a solution containing X-Gal. Untreated animals are used as negative control.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

What is claimed is:
1. A compound represented by Formula (I):

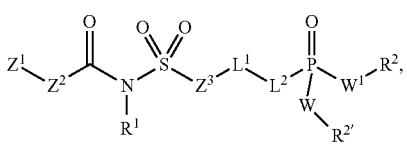

or a salt thereof, wherein:
- $Z^1$ is a piperidine or piperazine substituted with —X—$C_{1-6}$ alkyl-$R^3$ and $Z^1$ is further optionally substituted with one or more $R^6$;
- $Z^2$ is $C_{3-12}$ carbocycle optionally substituted with one or more $R^6$;
- $R^1$ is hydrogen;
- $Z^3$ is $C_{3-12}$ carbocycle optionally substituted with one or more $R^6$;
- $L^1$ is selected from —$(CH_2)_s$—$X^{10}$—$(CH_2)_r$—, —$(CH_2)_r$—$X^{10}$—$(CH_2)_r$—$X^{10}$—$(CH_2)_r$—, and —$(CH_2)_r$—$X^{10}$—$(CH_2)_r$—$X^{10}$—$(CH_2)_r$—$X^{10}$—$(CH_2)_r$—, wherein s is selected from 0 to 3, each r is selected from 1 to 6, each $X^{10}$ is selected from —O—, —S—, or —N($R^4$)—, and $L^1$ may be optionally substituted with one or more $R^6$;
- $L^2$ is Y-alkylene;
- Y is 3- to 12-membered heterocycle;
- W and $W^1$ are independently selected from —O—, —S— and —$NR^{10}$—;
- $R^2$ and $R^{2*}$ are independently selected from $R^7$, or $R^2$ and $R^{2*}$ are taken together with the atoms to which they are attached to form a heterocycle, optionally substituted with one or more $R^6$;
- $R^3$ is $C_{3-12}$ carbocycle or 3- to 12-membered heterocycle, each of which is optionally substituted with one or more $R^6$;
- $R^4$ is independently selected at each occurrence from hydrogen, —C(O)$R^{10}$, —C(O)O$R^{10}$ and —C(O)N($R^4$)—; $C_{1-6}$ alkyl, $C_{2-6}$ alkenyl, and $C_{2-6}$ alkynyl, each of which is independently optionally substituted at each occurrence with one or more substituents selected from halogen, —$NO_2$, —CN, —O$R^{10}$, —S$R^{10}$, —N($R^{10}$)$_2$, —S(=O)$R^{10}$, —S(=O)$_2R^{10}$, —S(=O)$_2$N($R^{10}$)$_2$, —$NR^{10}$S(=O)$_2R^{10}$, —C(O)$R^{10}$, —C(O)O$R^{10}$, —OC(O)$R^{10}$, —OC(O)O$R^{10}$, —OC(O)N($R^{10}$)$_2$, —$NR^{10}$C(O)$R^{10}$, —C(O)N($R^{10}$)$_2$, =O, =S, =N($R^{10}$), —P(O)(O$R^7$)$_2$, —OP(O)(O$R^7$)$_2$, $C_{3-10}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^4$ is independently optionally substituted with one or more substituents selected from halogen, —$NO_2$, —CN, —O$R^{10}$, —S$R^{10}$, —N($R^{10}$)$_2$, —S(=O)$R^{10}$, —S(=O)$_2R^{10}$, —S(=O)$_2$N($R^{10}$)$_2$, —$NR^{10}$S(=O)$_2R^{10}$, —C(O)$R^{10}$, —C(O)O$R^{10}$, —OC(O)$R^{10}$, —OC(O)O$R^{10}$, —OC(O)N($R^{10}$)$_2$, —$NR^{10}$C(O)$R^{10}$, —C(O)N($R^{10}$)$_2$, =O, =S, =N($R^{10}$), —P(O)(O$R^7$)$_2$, —OP(O)(O$R^7$)$_2$, $C_{1-6}$ alkyl, $C_{1-6}$ haloalkyl, $C_{2-6}$ alkenyl, and $C_{2-6}$ alkynyl;
- $R^6$ is independently selected at each occurrence from halogen, —$NO_2$, —CN, —O$R^{10}$, —S$R^{10}$, —N($R^{10}$)$_2$, —S(=O)$R^{10}$, —S(=O)$_2R^{10}$, —S(=O)$_2$N($R^{10}$)$_2$, —$NR^{10}$S(=O)$_2R^{10}$, —C(O)$R^{10}$, —C(O)O$R^{10}$, —OC(O)$R^{10}$, —OC(O)O$R^{10}$, —OC(O)N($R^{10}$)$_2$, —$NR^{10}$C(O)$R^{10}$, —C(O)N($R^{10}$)$_2$, =O, =S, =N($R^{10}$), —P(O)(O$R^7$)$_2$, —OP(O)(O$R^7$)$_2$; $C_{1-10}$ alkyl, $C_{2-10}$ alkenyl, and $C_{2-10}$ alkynyl, each of which is independently optionally substituted at each occurrence with one or more substituents selected from halogen, —$NO_2$, —CN, —O$R^{10}$, —S$R^{10}$, —N($R^{10}$)$_2$, —S(=O)$R^{10}$, —S(=O)$_2R^{10}$, —S(=O)$_2$N($R^{10}$)$_2$, —$NR^{10}$S(=O)$_2R^{10}$, —C(O)$R^{10}$, —C(O)O$R^{10}$, —OC(O)$R^{10}$, —OC(O)O$R^{10}$, —OC(O)N($R^{10}$)$_2$, —$NR^{10}$C(O)$R^{10}$, —C(O)N($R^{10}$)$_2$, =O, =S, =N($R^{10}$), —P(O)(O$R^{10}$)$_2$, —OP(O)(O$R^{10}$)$_2$, $C_{3-12}$ carbocycle and 3- to 12-membered heterocycle; and $C_{3-12}$ carbocycle and 3- to 12-membered heterocycle, wherein each $C_{3-12}$ carbocycle and 3- to 12-membered heterocycle in $R^6$ is independently optionally substituted with one or more substituents selected from halogen, —$NO_2$, —CN, —O$R^{10}$, —S$R^{10}$, —N($R^{10}$)$_2$, —S(=O)$R^{10}$, —S(=O)$_2R^{10}$, —S(=O)$_2$N($R^{10}$)$_2$, —$NR^{10}$S(=O)$_2R^{10}$, —C(O)$R^{10}$, —C(O)O$R^{10}$, —OC(O)$R^{10}$, —OC(O)O$R^{10}$, —OC(O)N($R^{10}$)$_2$, —$NR^{10}$C(O)$R^{10}$, —C(O)N($R^{10}$)$_2$, =O, =S, =N($R^{10}$), —P(O)(O$R^7$)$_2$, —OP(O)(O$R^7$)$_2$, $C_{1-6}$ alkyl, $C_{1-6}$ haloalkyl, $C_{2-6}$ alkenyl, and $C_{2-6}$ alkynyl;
- $R^7$ is independently selected at each occurrence from hydrogen, —C(O)$R^{10}$, —C(O)O$R^{10}$ and —C(O)N($R^4$)—; $C_{1-6}$ alkyl, $C_{2-6}$ alkenyl, $C_{2-6}$ alkynyl, and $C_{3-12}$ carbocycle, each of which is independently optionally substituted at each occurrence with one or more substituents selected from halogen, —$NO_2$, —CN, —OR$^{10}$, —SR$^{10}$, —S—S—R$^{10}$, —N(R$^{10}$)$_2$, —S(=O)R$^{10}$, —S(=O)$_2$R$^{10}$, —S(=O)$_2$N(R$^{10}$)$_2$, —NR$^{10}$S(=O)$_2$R$^{10}$, —S—C(O)R$^{10}$, —C(O)R$^{10}$, —C(O)OR$^{10}$, —OC(O)R$^{10}$, —OC(O)OR$^{10}$, —OC(O)N(R$^{10}$)$_2$, —NR$^{10}$C(O)R$^{10}$, —C(O)N(R$^{10}$)$_2$, =O, =S, =N(R$^{10}$), —P(O)(OR$^{10}$)$_2$, —OP(O)(OR$^{10}$)$_2$, C$_{3-12}$ carbocycle and 3- to 12-membered heterocycle; and C$_{3-12}$ carbocycle and 3- to 12-membered heterocycle, wherein each C$_{3-12}$ carbocycle and 3- to 12-membered heterocycle in R$^7$ is independently optionally substituted with one or more substituents selected from halogen, —NO$_2$, —CN, —OR$^{10}$, —SR$^{10}$, —N(R$^{10}$)$_2$, —S(=O)R$^{10}$, —S(=O)$_2$R$^{10}$, —S(=O)$_2$N(R$^{10}$)$_2$, —NR$^{10}$S(=O)$_2$R$^{10}$, —C(O)R$^{10}$, —C(O)OR$^{10}$, —OC(O)R$^{10}$, —OC(O)OR$^{10}$, —OC(O)N(R$^{10}$)$_2$, —NR$^{10}$C(O)R$^{10}$, —C(O)N(R$^{10}$)$_2$, =O, =S, =N(R$^{10}$), —P(O)(OR$^{10}$)$_2$, —OP(O)(OR$^{10}$)$_2$, C$_{1-6}$ alkyl, C$_{1-6}$ haloalkyl, C$_{2-6}$ alkenyl, and C$_{2-6}$ alkynyl;

R$^{10}$ at each occurrence is independently selected from hydrogen; and C$_{1-20}$ alkyl, C$_{2-20}$ alkenyl, C$_{2-20}$ alkynyl, C$_{3-12}$ carbocycle and 3- to 12-membered heterocycle, each of which may be optionally substituted by halogen, —CN, —NO$_2$, —OH and —OCH$_3$; and X at each occurrence is independently selected from bond, —O—, —S—, —N(R$^4$)—, —C(O)—, —C(O)O—, —OC(O)—, —OC(O)O—, —C(O)N(R$^4$)—, —C(O)N(R$^4$)C(O)—, —C(O)N(R$^4$)C(O)N(R$^4$)—, —N(R$^4$)C(O)—, —N(R$^4$)C(O)N(R$^4$)—, —N(R$^4$)C(O)O—, —OC(O)N(R$^4$)—, —C(NR$^4$)—, —N(R$^4$)C(NR$^4$)—, —C(NR$^4$)N(R$^4$)—, —N(R$^4$)C(NR$^4$)N(R$^4$)—, —S(O)$_2$—, —OS(O)—, —S(O)O—, —S(O)—, —OS(O)$_2$—, —S(O)$_2$O—, —N(R$^4$)S(O)$_2$—, —S(O)$_2$N(R$^4$)—, —N(R$^4$)S(O)—, —S(O)N(R$^4$)—, —N(R$^4$)S(O)$_2$N(R$^4$)—, and —N(R$^4$)S(O)N(R$^4$)—.

2. The compound or salt of claim 1, wherein —W—R$^{2*}$ and —W$^1$—R$^2$ are each —O—CH$_3$, —O—CH$_2$CH$_3$, —O—CH$_2$-Ph, —O-Ph,

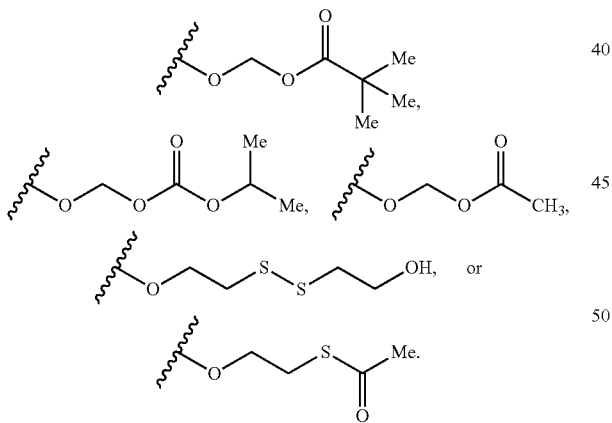

3. The compound or salt of claim 1, wherein L$^1$ is selected from:

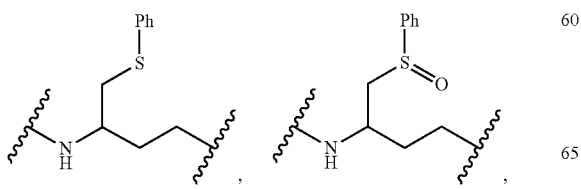

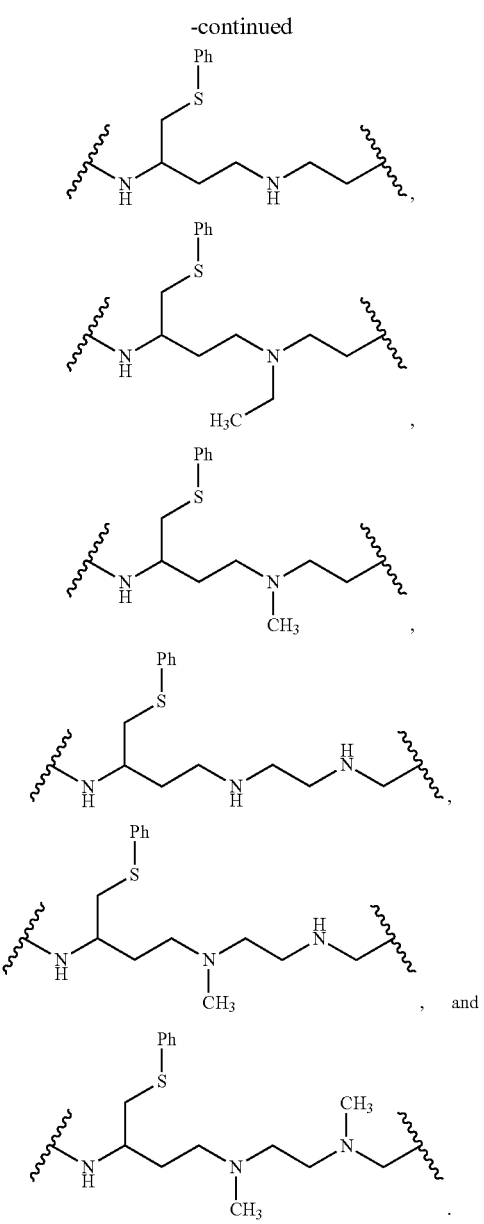

4. The compound of or salt of claim 1, wherein L$^2$ is selected from:

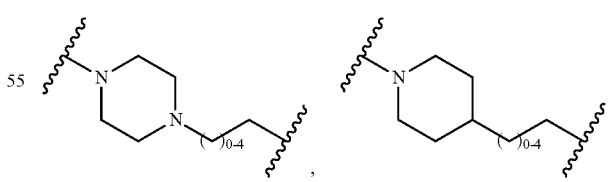

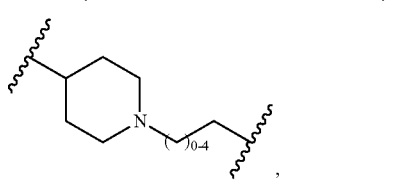

-continued

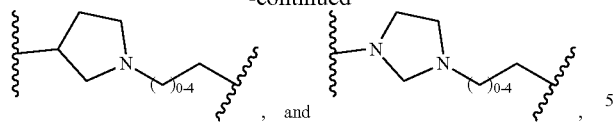

, and any one of which is optionally substituted by one or more $R^6$.

5. The compound or salt of claim 1, wherein $Z^3$ is:

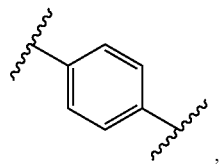 [SMILES: *c1ccc(*)cc1]

optionally substituted by one or more $R^6$.

6. The compound or salt of claim 5, wherein $Z^3$ is substituted by —SO$_2$CF$_3$.

7. The compound or salt of claim 1, wherein $Z^2$ is:

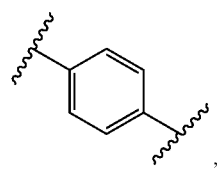 [SMILES: *c1ccc(*)cc1]

optionally substituted by one or more $R^6$.

8. The compound or salt of claim 1, wherein $R^3$ is

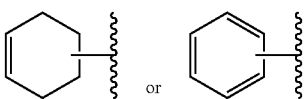

substituted with one or more $R^6$.

9. The compound or salt of claim 8, wherein $R^3$ is

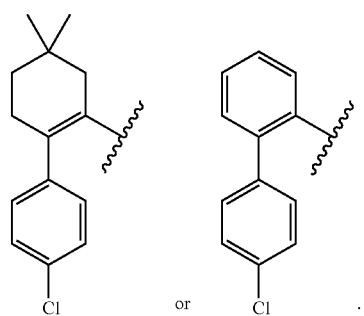 [SMILES: *C1=C(c2ccc(Cl)cc2)CCC(C)(C)C1 ; *c1ccccc1-c1ccc(Cl)cc1]

10. The compound or salt of claim 1, wherein:
$Z^2$ is $C_{5-6}$ carbocycle optionally substituted with one or more $R^6$;
$R^1$ is hydrogen;
$Z^3$ is $C_{5-6}$ carbocycle optionally substituted with one or more $R^6$;

$L^1$ is selected from:

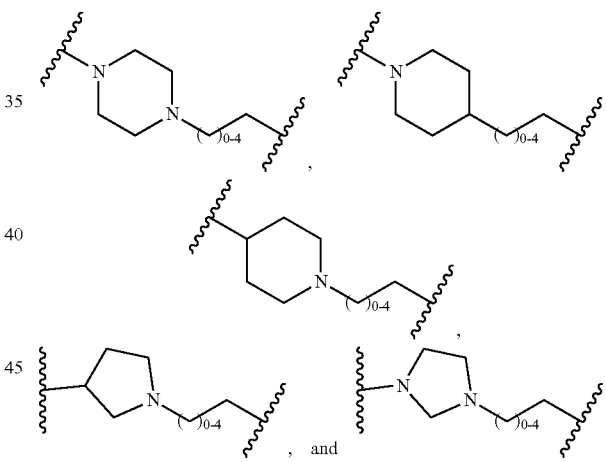

$L^2$ is Y-alkylene;
Y is 3- to 12-membered heterocycle;
W and $W^1$ are independently selected from —O—, —S— and —NR$^{10}$—;
$R^2$ and $R^{2*}$ are independently selected from $R^7$, or $R^2$ and $R^{2*}$ are taken together with the atoms to which they are attached to form a heterocycle, optionally substituted with one or more $R^6$; and
$R^3$, $R^4$, $R^6$, $R^7$, $R^{10}$ and X are as described for Formula (I).

11. The compound or salt of claim 9, wherein $L^2$ is selected from:

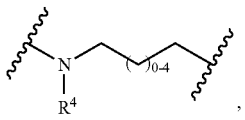

any one of which is optionally substituted by one or more $R^6$.

12. The compound or salt of claim 1, wherein:
X is a bond;
$R^3$ is $C_{5-6}$ carbocycle optionally substituted with one or more $R^6$;
$Z^2$ is phenyl optionally substituted with one or more $R^6$;
$R^1$ is hydrogen;
$Z^3$ is phenyl optionally substituted with one or more $R^6$;
$L^1$ is selected from:

-continued

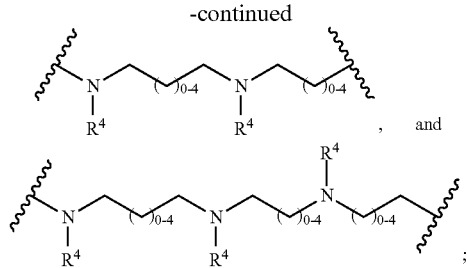

, and any one of which is optionally substituted with one or more $R^6$;

$L^2$ is Y-methylene, Y-ethylene, or Y-propylene;

Y is 5- to 6-membered heterocycle optionally substituted with one or more $R^6$;

W and $W^1$ are independently selected from —O—, —S— and —$NR^{10}$—;

$R^2$ and $R^{2*}$ are independently selected from $R^7$, or $R^2$ and $R^{2*}$ are taken together with the atoms to which they are attached to form a heterocycle, optionally substituted with one or more $R^6$; and $R^4$, $R^6$, $R^7$, and $R^{10}$ are as described for Formula (I).

13. The compound or salt of claim 1, represented by Formula (VI):

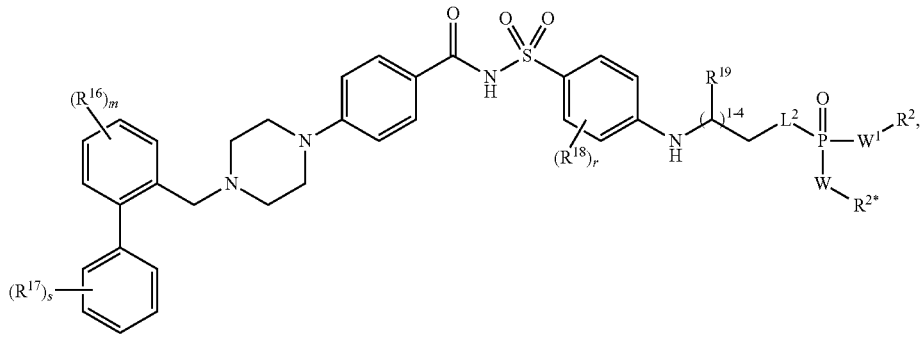

wherein:
$L^2$, W, $W^1$, $R^2$, and $R^{2*}$ are as defined for Formula (I);
$R^{16}$, $R^{17}$ and $R^{18}$ are independently selected at each occurrence from $R^6$;
$R^{19}$ is selected at each occurrence from hydrogen and $R^6$; and
m, s, and r are independently selected from 0 to 6.

14. The compound of claim 1, which is selected from the following table:

| Compound # | Structure |
|---|---|
| 6 | ![structure] |
| 7 | ![structure] |

| Compound # | Structure |
|---|---|
| 8 | 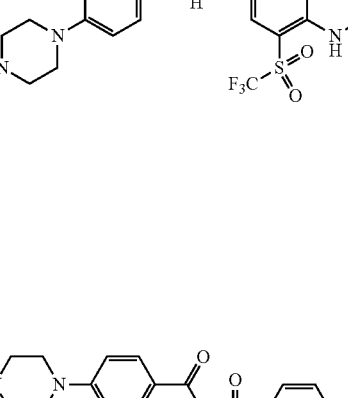 |
| 9 | 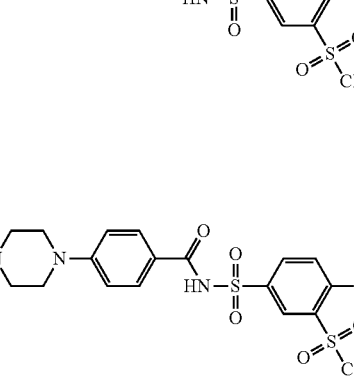 |
| 13 | 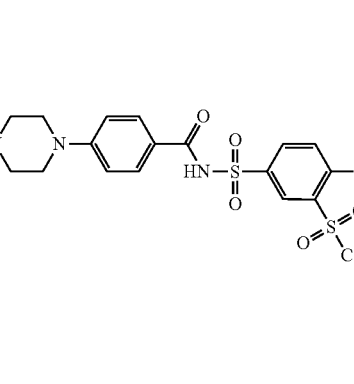 |
| 14 | 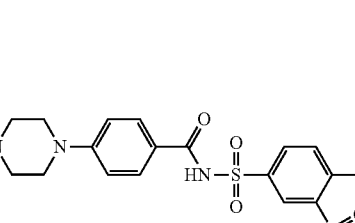 |
| 15 | 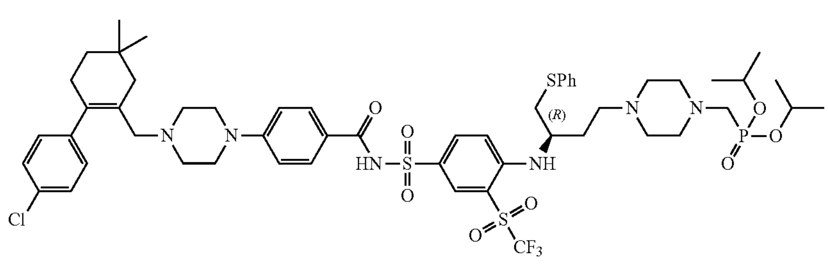 |

| Com- pound # | Structure |
|---|---|
| 16 | 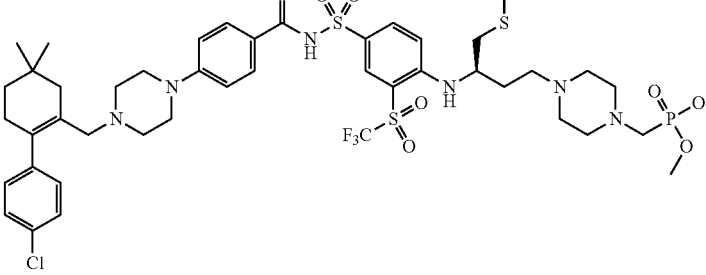 |
| 23 | 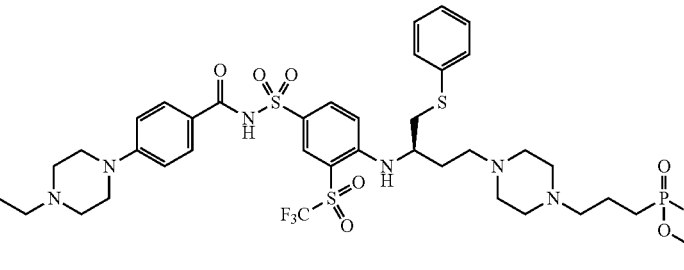 |
| 24 | 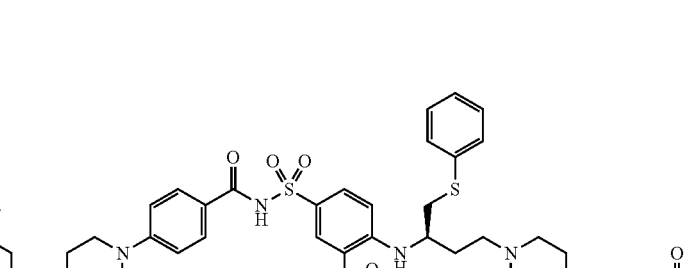 |
| 25 | 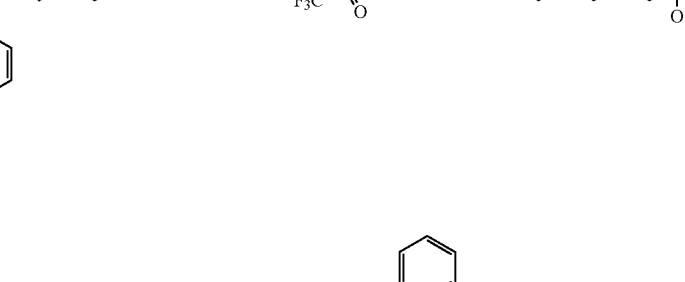 |

| Compound # | Structure |
|---|---|
| 26 | 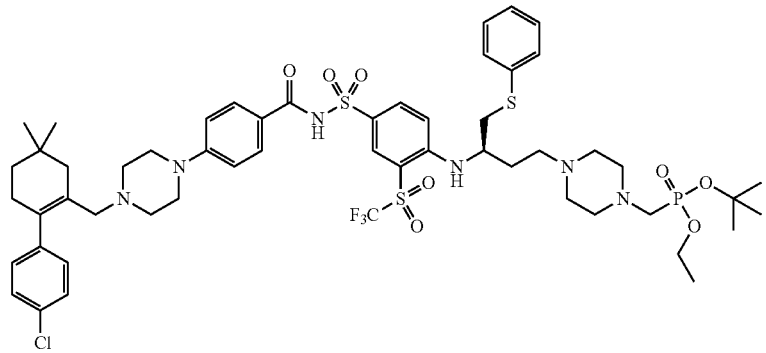 [SMILES: CCOP(=O)(CN1CCN(CC[C@H](CSc2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OC(C)(C)C] |
| 27 | 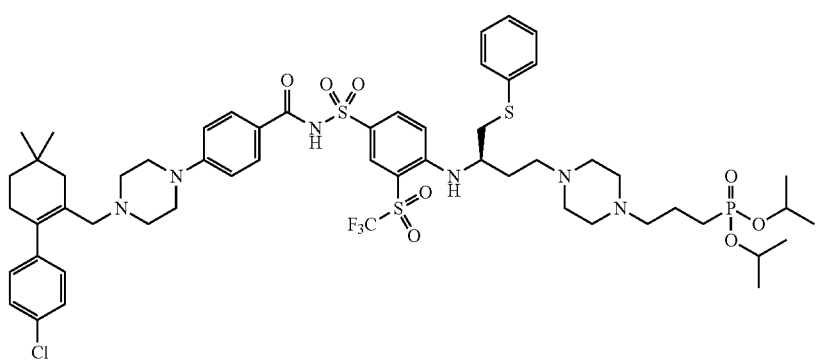 [SMILES: CC(C)OP(=O)(CCCN1CCN(CC[C@H](CSc2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OC(C)C] |
| 28 | 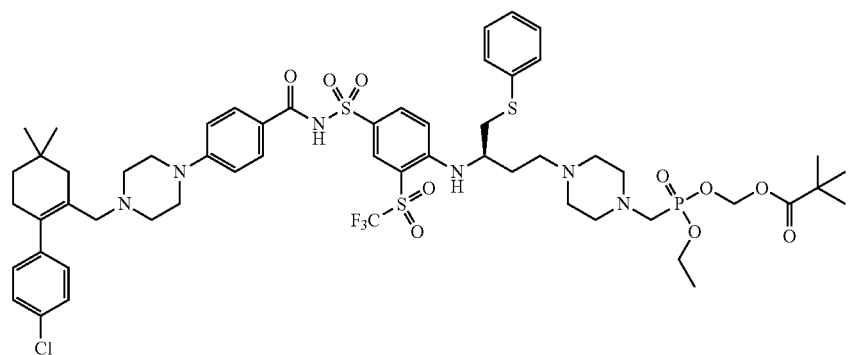 [SMILES: CCOP(=O)(CN1CCN(CC[C@H](CSc2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OCOC(=O)C(C)(C)C] |
| 29 | 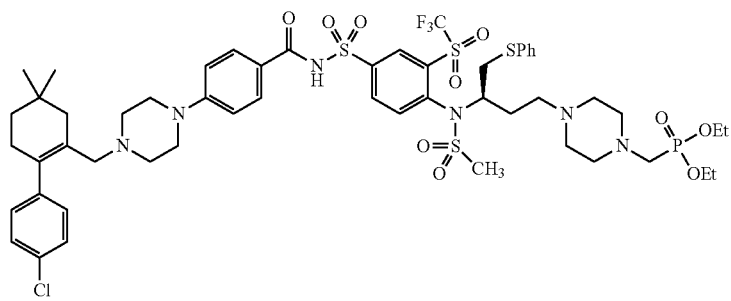 |

| Compound # | Structure |
|---|---|
| 30 | 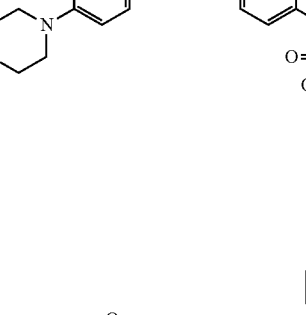 |
| 31 | 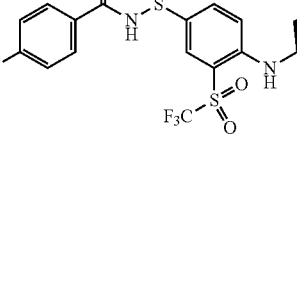 |
| 32 | 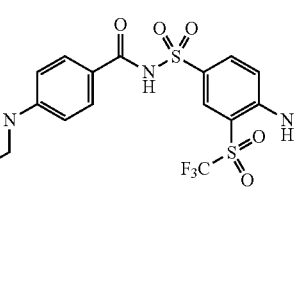 |
| 33 | 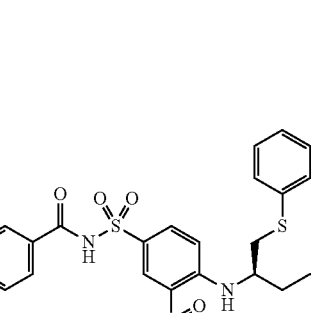 |

| Compound # | Structure |
|---|---|
| 34 | 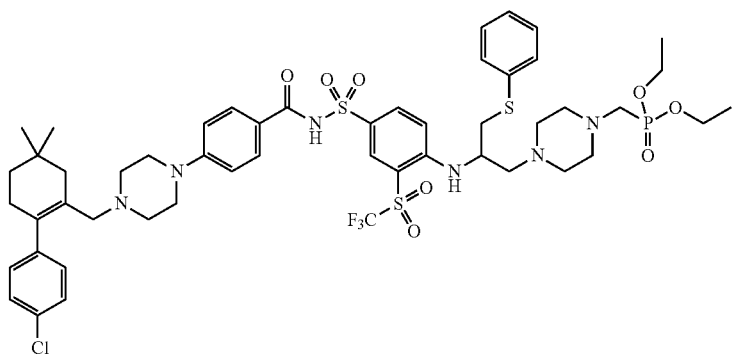 [SMILES: CCOP(=O)(CN1CCN(CC(CSc2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OCC] |
| 35 | 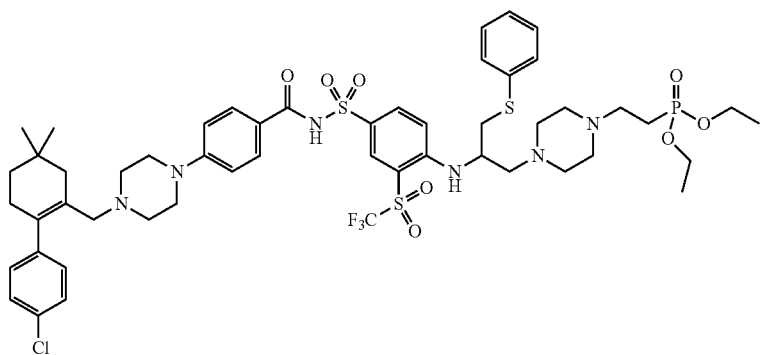 [SMILES: CCOP(=O)(CCN1CCN(CC(CSc2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OCC] |
| 36 | 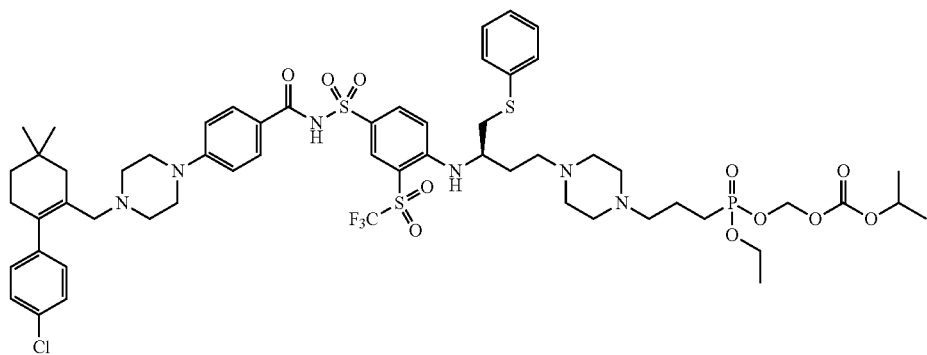 [SMILES: CCOP(=O)(CCCN1CCN(CC[C@H](CSc2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OCOC(=O)OC(C)C] |
| 37 | 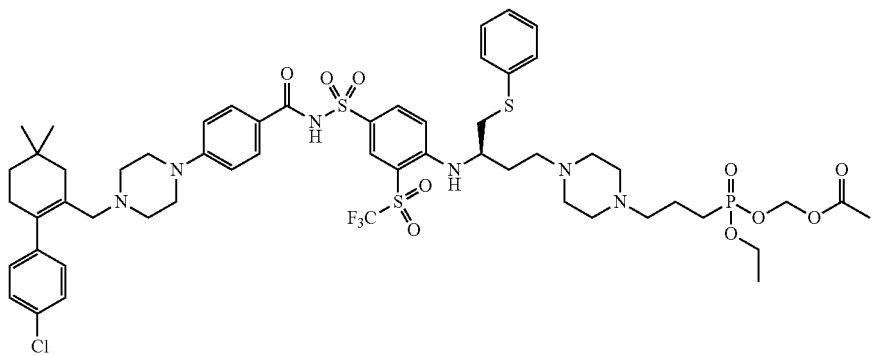 [SMILES: CCOP(=O)(CCCN1CCN(CC[C@H](CSc2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OCOC(C)=O] |

| Compound # | Structure |
|---|---|
| 38 | 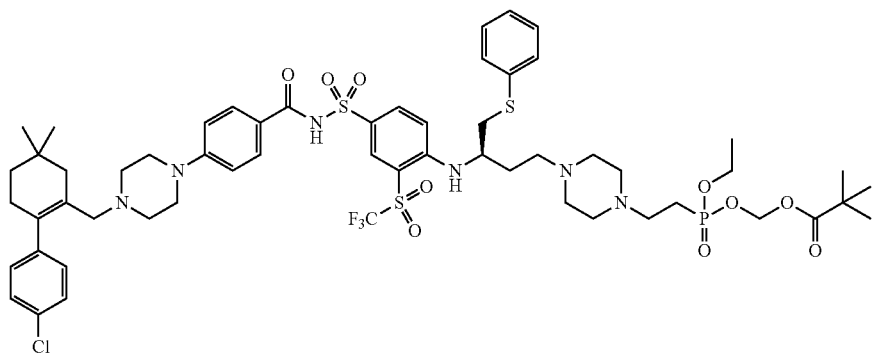 [SMILES: CCOP(=O)(CCN1CCN(CC[C@H](CSc2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OCOC(=O)C(C)(C)C] |
| 39 | 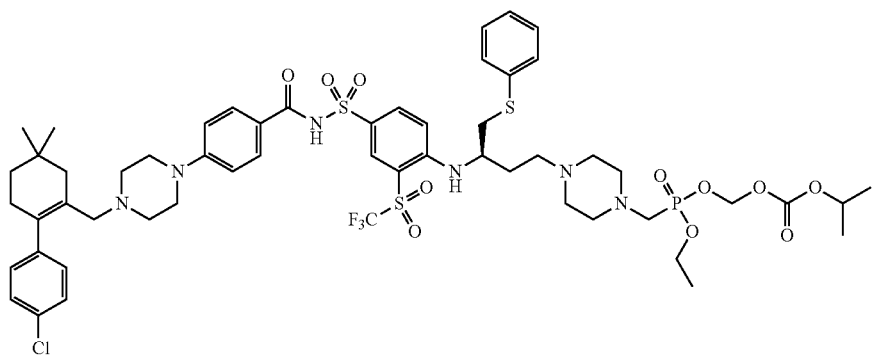 [SMILES: CCOP(=O)(CN1CCN(CC[C@H](CSc2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OCOC(=O)OC(C)C] |
| 40 | 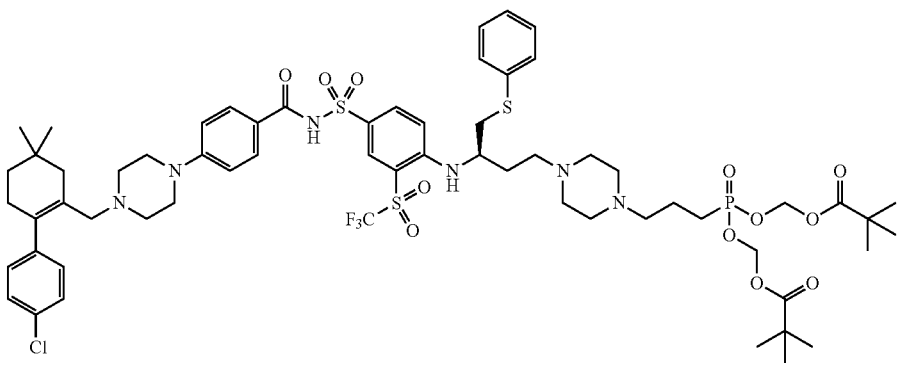 [SMILES: CC1(C)CCC(c2ccc(Cl)cc2)=C(CN2CCN(c3ccc(C(=O)NS(=O)(=O)c4ccc(N[C@H](CCN5CCN(CCCP(=O)(OCOC(=O)C(C)(C)C)OCOC(=O)C(C)(C)C)CC5)CSc5ccccc5)c(S(=O)(=O)C(F)(F)F)c4)cc3)CC2)C1] |
| 41 | 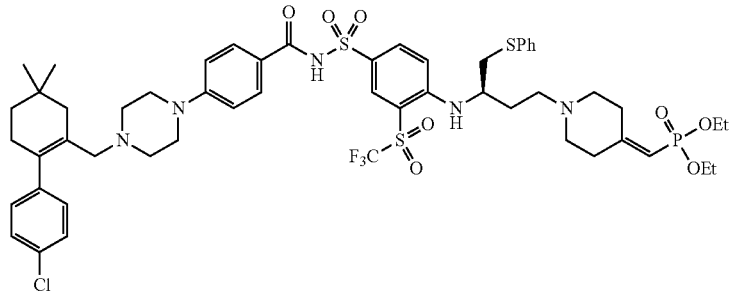 |

| Compound # | Structure |
|---|---|
| 42 | 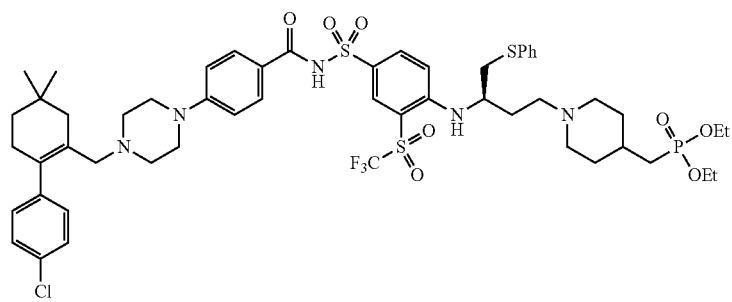 |
| 43 | 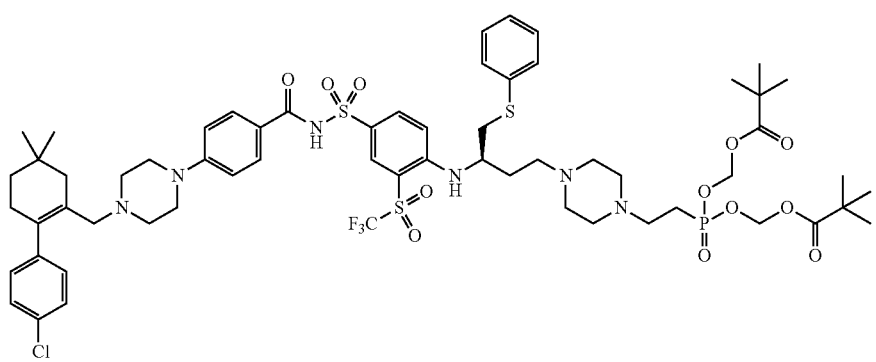 [SMILES: CC1(C)CCC(c2ccc(Cl)cc2)=C(CN2CCN(c3ccc(C(=O)NS(=O)(=O)c4ccc(N[C@H](CCN5CCN(CCP(=O)(OCOC(=O)C(C)(C)C)OCOC(=O)C(C)(C)C)CC5)CSc5ccccc5)c(S(=O)(=O)C(F)(F)F)c4)cc3)CC2)C1] |
| 44 | 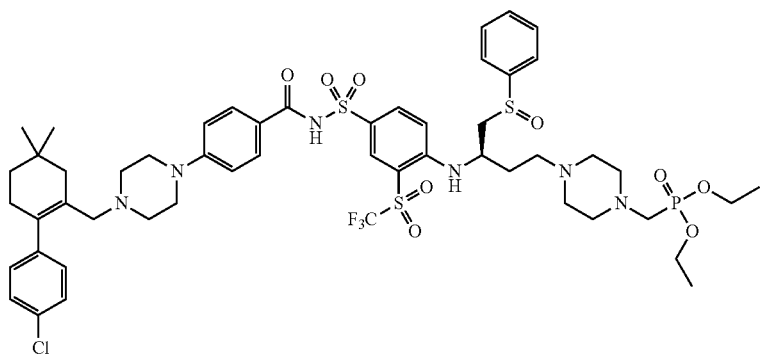 [SMILES: CCOP(=O)(CN1CCN(CC[C@H](CS(=O)c2ccccc2)Nc2ccc(S(=O)(=O)NC(=O)c3ccc(N4CCN(CC5=C(c6ccc(Cl)cc6)CCC(C)(C)C5)CC4)cc3)cc2S(=O)(=O)C(F)(F)F)CC1)OCC] |
| 45 | 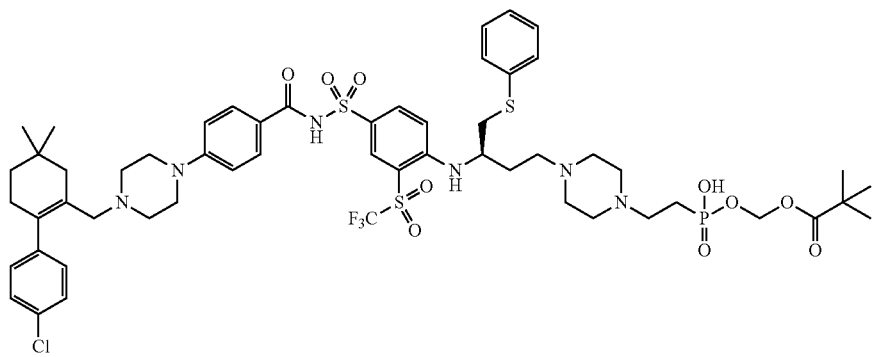 [SMILES: CC1(C)CCC(c2ccc(Cl)cc2)=C(CN2CCN(c3ccc(C(=O)NS(=O)(=O)c4ccc(N[C@H](CCN5CCN(CCP(=O)(O)OCOC(=O)C(C)(C)C)CC5)CSc5ccccc5)c(S(=O)(=O)C(F)(F)F)c4)cc3)CC2)C1] |

| Compound # | Structure |
|---|---|
| 46 | 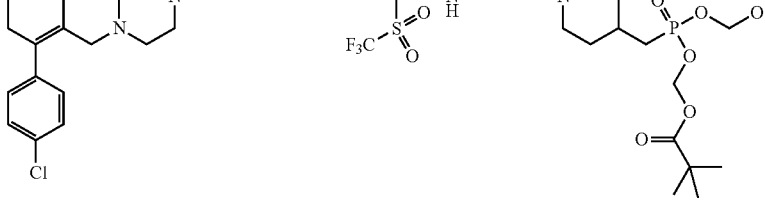 |
| 47 | 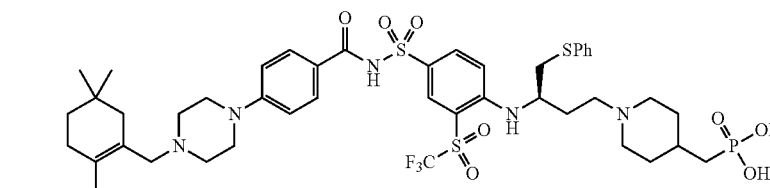 |
| 48 | 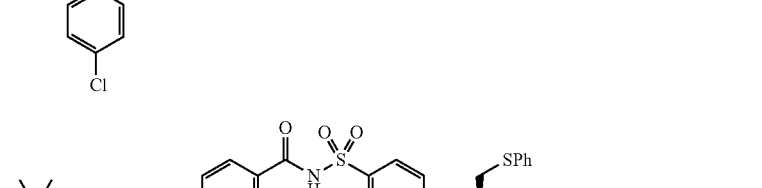 |
| 49 | 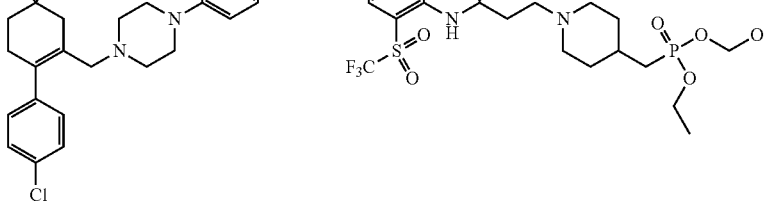 |
| 50 | 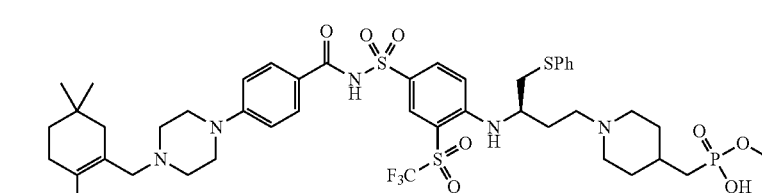 |

| Compound # | Structure |
|---|---|
| 51 | 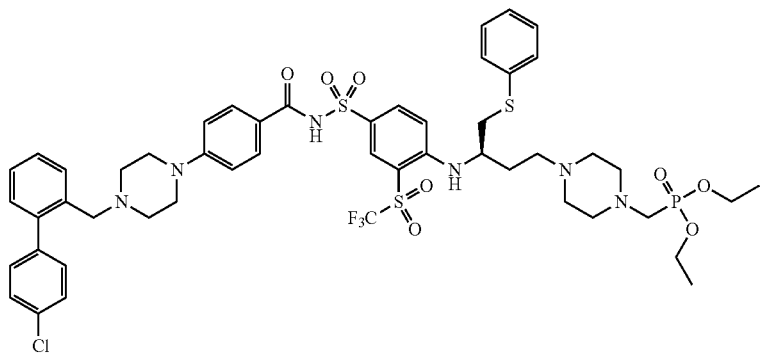 [SMILES: CCOP(=O)(CC1CCN(CC[C@H](CSc2ccccc2)Nc2ccc(S(=O)(=O)NC(=O)c3ccc(N4CCN(Cc5ccccc5-c5ccc(Cl)cc5)CC4)cc3)cc2S(=O)(=O)C(F)(F)F)CC1)OCC] |
| 52 | 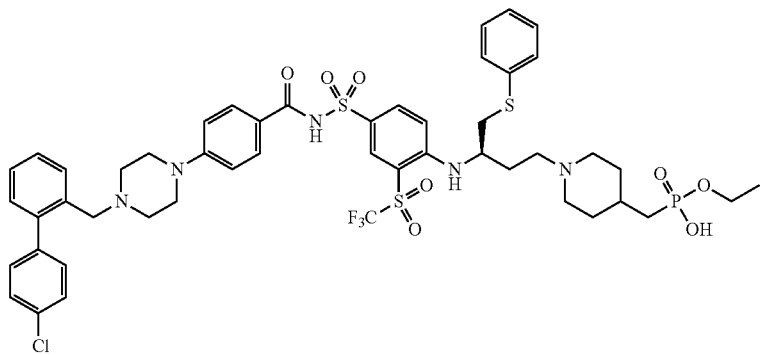 [SMILES: CCOP(=O)(O)CC1CCN(CC[C@H](CSc2ccccc2)Nc2ccc(S(=O)(=O)NC(=O)c3ccc(N4CCN(Cc5ccccc5-c5ccc(Cl)cc5)CC4)cc3)cc2S(=O)(=O)C(F)(F)F)CC1] |
| 53 | 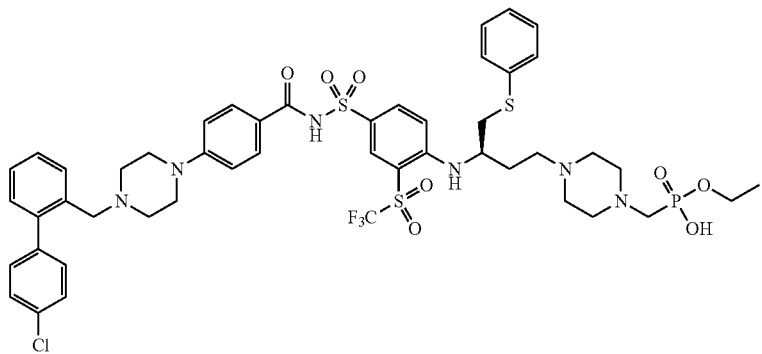 [SMILES: CCOP(=O)(O)CN1CCN(CC[C@H](CSc2ccccc2)Nc2ccc(S(=O)(=O)NC(=O)c3ccc(N4CCN(Cc5ccccc5-c5ccc(Cl)cc5)CC4)cc3)cc2S(=O)(=O)C(F)(F)F)CC1] |
| 54 | 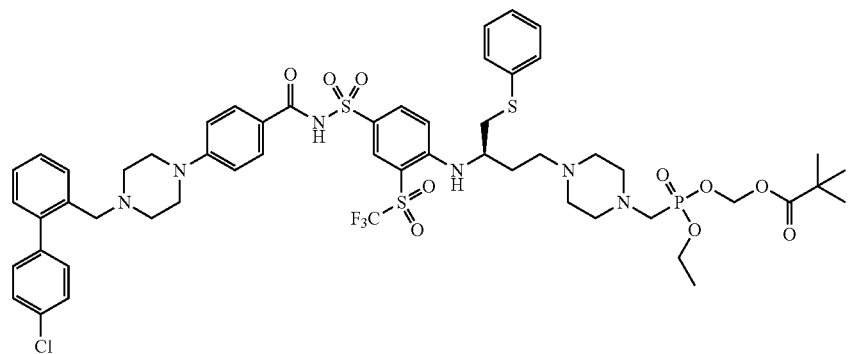 [SMILES: CCOP(=O)(CN1CCN(CC[C@H](CSc2ccccc2)Nc2ccc(S(=O)(=O)NC(=O)c3ccc(N4CCN(Cc5ccccc5-c5ccc(Cl)cc5)CC4)cc3)cc2S(=O)(=O)C(F)(F)F)CC1)OCOC(=O)C(C)(C)C] |

| Compound # | Structure |
|---|---|
| 55 | 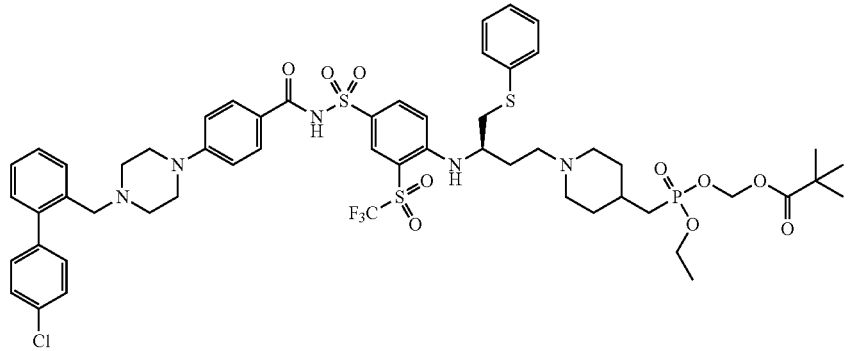 |
| 56 | 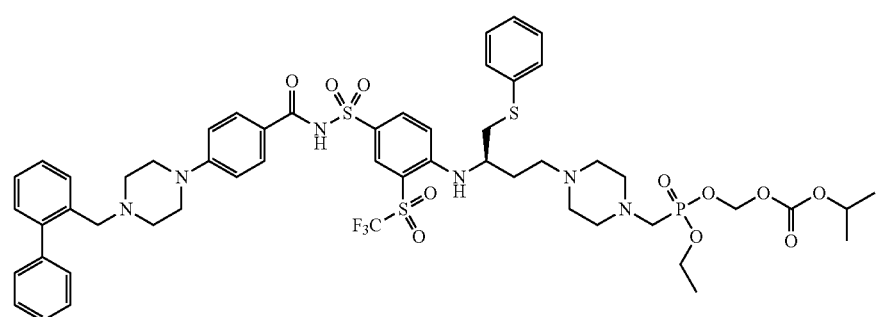 |
| 57 | 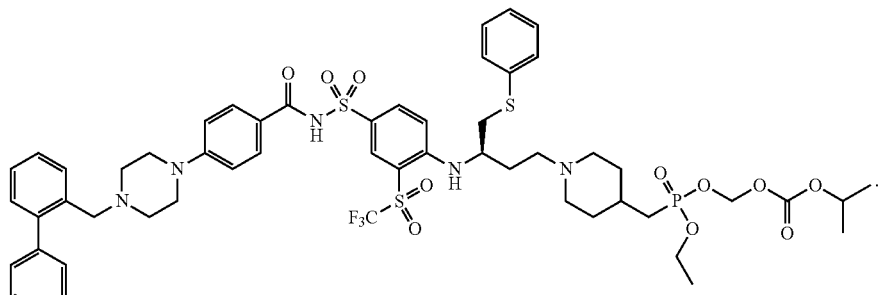 |

15. The compound or salt of claim 1, which has a binding dissociation constant (Kd) of less than 1 nM for Bcl-2 and/or Bcl-xL.

16. The compound or salt of claim 1, which has a selectivity index (SI) defined as an EC$_{50}$ value for irradiated IMR90 fibroblasts compared with non-irradiated IMR90 fibroblasts of 10 or above.

17. A method of selectively killing senescent cells, wherein the senescent cells are defined as p16 positive cells that are not cancer cells, the method comprising contacting the senescent cells with a compound or salt according to claim 1.

18. The method of claim 17, wherein the senescent cells are contacted with said compound or salt when cultured in vitro.

* * * * *